US012761555B2

(12) United States Patent
Hatakeyama

(10) Patent No.: US 12,761,555 B2
(45) Date of Patent: Oct. 13, 2026

(54) POSITIVE RESIST MATERIAL AND PATTERNING PROCESS

(71) Applicant: SHIN-ETSU CHEMICAL CO., LTD., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 446 days.

(21) Appl. No.: 18/380,475

(22) Filed: Oct. 16, 2023

(65) Prior Publication Data

US 2024/0168379 A1 May 23, 2024

(30) Foreign Application Priority Data

Oct. 17, 2022 (JP) ................................ 2022-165990

(51) Int. Cl.

*G03F 7/004* (2006.01)
*C07C 269/04* (2006.01)
*C07C 271/24* (2006.01)
*G03F 7/039* (2006.01)

(52) U.S. Cl.

CPC .......... *G03F 7/0045* (2013.01); *C07C 269/04* (2013.01); *C07C 271/24* (2013.01); *G03F 7/0392* (2013.01)

(58) Field of Classification Search

CPC ............................ C07C 269/04; C07C 271/24
See application file for complete search history.

(56) References Cited

U.S. PATENT DOCUMENTS

| | | | | |
|---|---|---|---|---|
| 10,508,078 | B2 * | 12/2019 | Terada | C07C 271/24 |
| 10,539,870 | B2 * | 1/2020 | Williams, III | C07C 269/04 |
| 11,415,887 | B2 * | 8/2022 | Hatakeyama | G03F 7/0382 |
| 2005/0214674 | A1 | 9/2005 | Sui et al. | |
| 2010/0009284 | A1 | 1/2010 | Shiono et al. | |
| 2014/0356785 | A1 | 12/2014 | Williams, III et al. | |
| 2020/0040125 | A1 | 2/2020 | Hatakeyama et al. | |
| 2020/0050105 | A1 * | 2/2020 | Hatakeyama | C07C 217/06 |
| 2020/0223796 | A1 | 7/2020 | Fukushima et al. | |

FOREIGN PATENT DOCUMENTS

| | | | | | |
|---|---|---|---|---|---|
| CN | 111440104 | A | | 7/2020 | |
| JP | 2000-327633 | A | | 11/2000 | |
| JP | 3790649 | B2 | | 6/2006 | |
| JP | 2006-347974 | A | | 12/2006 | |
| JP | 2007-145797 | A | | 6/2007 | |
| JP | 2007-297590 | A | | 11/2007 | |
| JP | 2008-106045 | A | | 5/2008 | |
| JP | 2008-111103 | A | | 5/2008 | |
| JP | 2008-122932 | A | | 5/2008 | |
| JP | 2008-158339 | A | | 7/2008 | |
| JP | 2009-007327 | A | | 1/2009 | |
| JP | 2009-258695 | A | | 11/2009 | |
| JP | 2010-215608 | A | | 9/2010 | |
| JP | 2011007937 | A | * | 1/2011 | |
| JP | 2012-041320 | A | | 3/2012 | |
| JP | 2012-048203 | A | | 3/2012 | |
| JP | 2012-106986 | A | | 6/2012 | |
| JP | 2012-153644 | A | | 8/2012 | |
| JP | 2012-208200 | A | | 10/2012 | |
| JP | 2014-133723 | A | | 7/2014 | |
| JP | 2017-026980 | A | | 2/2017 | |
| JP | 2017-219836 | A | | 12/2017 | |
| JP | 2018010280 | A | * | 1/2018 | |
| JP | 2018-197853 | A | | 12/2018 | |
| JP | 2020-023668 | A | | 2/2020 | |
| TW | 201502707 | A | | 1/2015 | |
| WO | WO-2015080257 | A1 | * | 6/2015 | C08F 2/48 |
| WO | WO-2020202944 | A1 | * | 10/2020 | C07D 11/12 |

OTHER PUBLICATIONS

Andre, et al.; Phenolic Molecular Glasses as Resists for Next Generation Lithography; Proceedings of SPIE vol. 6519 65194B-1; published Mar. 15, 2007.
Hattori, et al.; Novel Molecular Resist Based on an Amorphous Truxene Derivative; Proceedings of SPIE vol. 6923 69230J-1; published Apr. 17, 2008.
Taiwanese Office Action and Search Report in application No. 112139283 issued on Sep. 5, 2024.
Japanese Notice of Reason for Refusal in application No. 2023-156655 dated Jun. 23, 2026.

* cited by examiner

*Primary Examiner* — Amanda C. Walke

(57) ABSTRACT

The present invention is a positive resist material containing a compound having two or more urethane groups and having two or more carboxy groups that are each substituted with an acid-labile group and are bonded to the urethane groups via a linking group. This provides: a positive resist material that has higher sensitivity and higher resolution than conventional positive resist materials and smaller edge roughness and CDU, and allows excellent pattern profile after exposure to light; and a patterning process.

14 Claims, No Drawings

POSITIVE RESIST MATERIAL AND PATTERNING PROCESS

TECHNICAL FIELD

The present invention relates to: a positive resist material; and a patterning process.

BACKGROUND ART

As LSIs advance toward higher integration and higher processing speed, miniaturization of pattern rule is progressing rapidly. This is because the spread of high-speed communication of 5 G and artificial intelligence (AI) has progressed, and high-performance devices for processing these are needed. As a cutting-edge technology for miniaturization, 5-nm node devices have been mass-produced by extreme ultraviolet ray (EUV) lithography at a wavelength of 13.5 nm. Furthermore, studies are also in progress on employing EUV lithography in next-generation 3-nm node and the following-generation 2-nm node devices. IMEC of Belgium has announced a road map to the development of devices of up to 2 angstroms.

The wavelength of an EUV, which is 13.5 nm, is 1/10 or shorter than that of ArF lithography, which is 193 nm. Thus, high contrast light and high resolution are expected from EUV. However, since EUV has a short wavelength and high energy density, an acid generator is sensitized with a small amount of photons. The number of the photons in EUV exposure is said to be 1/14 of that of ArF exposure. Thus, phenomena in which variations of the photons degrade line edge roughness (LER and LWR) and hole critical dimension uniformity (CDU) are considered as a problem in EUV exposure.

In order to reduce edge roughness, studies have been made on chemically-amplified molecular resist materials that contain a low molecular weight compound as a base (Non Patent Documents 1 and 2 and Patent Document 1). This is based on the idea that when the molecular weight is lower, there is less risk of edge roughness increasing due to the solubility of a resist film to a developer being uneven. However, there has been a problem that edge roughness is degraded because of insufficient control of acid diffusion. Conventional polymer-type resist materials have smaller edge roughness, and the advantage of molecular resist materials that the molecular weight is low has not yet been brought out.

CITATION LIST

Patent Literature

Patent Document 1: JP 2006-347974 A

Non Patent Literature

Non Patent Document 1: SPIE Vol. 6519 65194B-1 (2007)

Non Patent Document 2: SPIE Vol. 6923 69230J-1 (2008)

SUMMARY OF INVENTION

Technical Problem

The present invention has been made in view of the above circumstances. An object of the present invention is to provide: a positive resist material that has higher sensitivity and higher resolution than conventional positive resist materials and smaller edge roughness and CDU, and allows excellent pattern profile after exposure to light; and a patterning process.

Solution to Problem

To achieve the object, the present invention provides a positive resist material comprising a compound having two or more urethane groups and having two or more carboxy groups that are each substituted with an acid-labile group and are bonded to the urethane groups via a linking group.

Such a positive resist material has higher sensitivity and higher resolution than conventional positive resist materials and smaller edge roughness and CDU, and allows excellent pattern profile after exposure to light.

In the present invention, the compound is preferably represented by the following formula (1), (1)

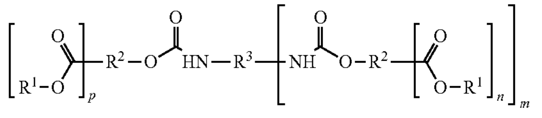

wherein $R^1$'s are identical to or different from each other and each represent an acid-labile group; $R^2$'s each represent a linking group, are identical to or different from each other, and represent a hydrocarbylene group having 1 to 20 carbon atoms, having a valency of n+1 or p+1, and optionally containing an oxygen atom, a sulfur atom, a nitrogen atom, or a halogen atom; $R^3$ represents a hydrocarbylene group having 2 to 33 carbon atoms, having a valency of m+1, and optionally containing an oxygen atom, a sulfur atom, a nitrogen atom, or a halogen atom; "m" represents an integer satisfying $1 \le m \le 6$; and "n" and "p" represent 1 or 2.

Such a compound can improve the advantageous effects of the present invention further.

In this event, the $R^1$ preferably satisfies one of the following 1) to 3):

1) a carbon atom bonded to an ester group is a tertiary carbon atom, and an alkyl group bonded to the tertiary carbon atom does not contain a halogen atom, a cyano group, or a nitro group;
2) a carbon atom bonded to an ester group is a secondary carbon atom and has a cyclic structure, does not contain a heteroatom, and has a double bond, a triple bond, or an aromatic group on a carbon atom other than the secondary carbon atom bonded to the ester group;
3) an acetal group having an ether group adjacent to a carbon atom bonded to an ester group.

Such acid-labile groups are preferable as the acid-labile groups in the compound contained in the inventive positive resist material.

The inventive positive resist material preferably further comprises a base polymer.

Such a positive resist material can improve the advantageous effects of the present invention further.

In this event, the base polymer preferably comprises: a repeating unit having an acid-labile group substituting a hydrogen atom of a carboxy group; and/or a repeating unit having an acid-labile group substituting a hydrogen atom of a phenolic hydroxy group.

Such a positive resist material can enhance dissolution contrast.

In this event, the repeating unit having an acid-labile group substituting a hydrogen atom of a carboxy group and the repeating unit having an acid-labile group substituting a hydrogen atom of a phenolic hydroxy group are preferably respectively a repeating unit represented by the following formula (a1) and a repeating unit represented by the following formula (a2), (a1)

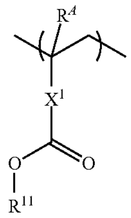

(a2)

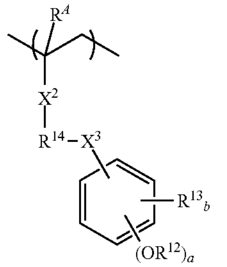

wherein each $R^A$ independently represents a hydrogen atom or a methyl group; $X^1$ represents a single bond or a linking group having 1 to 14 carbon atoms and containing a phenylene group, a naphthylene group, an ester bond, an ether bond, or a lactone ring; $X^2$ represents a single bond, an ester bond, or an amide bond; $X^3$ represents a single bond, an ether bond, or an ester bond; $R^{11}$ and $R^{12}$ represent an acid-labile group; $R^{13}$ represents a fluorine atom, a trifluoromethyl group, a cyano group, or a saturated hydrocarbyl group having 1 to 6 carbon atoms; $R^{14}$ represents a single bond or a saturated hydrocarbylene group having 1 to 6 carbon atoms, part of the carbon atoms optionally being substituted with an ether bond or an ester bond; and "a" represents 1 or 2 and "b" represents an integer of 0 to 4, provided that $1 \leq a+b \leq 5$.

When the base polymer contains such repeating units, the dissolution contrast can be enhanced further.

In the present invention, the base polymer preferably further comprises a repeating unit-b having an adhesive group selected from a hydroxy group, a carboxy group, a lactone ring, a carbonate group, a thiocarbonate group, a carbonyl group, a cyclic acetal group, an ether bond, an ester bond, a sulfonic acid ester bond, a cyano group, an amide bond, —O—C(=O)—S—, and —O—C(=O)—NH—.

The inventive positive resist material can contain a base polymer having such a repeating unit.

In the present invention, the base polymer preferably further comprises a repeating unit-c represented by one or more of the following formulae (c1) to (c3), (c1)

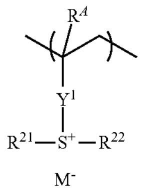

(c2)

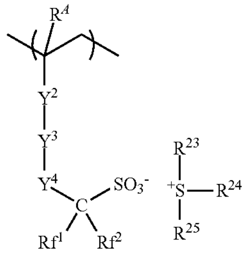

(c3)

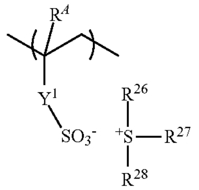

wherein each $R^A$ independently represents a hydrogen atom or a methyl group; $Y^1$ represents a single bond, a phenylene group, a naphthylene group, —O—$Y^{11}$—, —C(=O)—O—$Y^{11}$—, or —C(=O)—NH—$Y^{11}$—; $Y^{11}$ represents an aliphatic hydrocarbylene group having 1 to 6 carbon atoms, a phenylene group, a naphthylene group, or a group having 7 to 18 carbon atoms derived from a combination of these groups, $Y^{11}$ optionally containing a carbonyl group, an ester bond, an ether bond, or a hydroxy group; $Y^2$ represents a single bond or an ester bond; $Y^3$ represents a single bond, —$Y^{31}$—C(=O)—O—, —$Y^{31}$—O—, or —$Y^{31}$—O—C(=O)—; $Y^{31}$ represents a hydrocarbylene group having 1 to 12 carbon atoms, a phenylene group, or a group having 7 to 18 carbon atoms derived from a combination of these groups, $Y^{31}$ optionally containing a carbonyl group, an ester bond, an ether bond, an iodine atom, or a bromine atom; $Y^4$ represents a single bond, a methylene group, or a 2,2,2-trifluoro-1,1-ethanediyl group; $Y^5$ represents a single bond, a methylene group, an ethylene group, a phenylene group, a fluorinated phenylene group, —O—$Y^{51}$—, —C(=O)—O—$Y^{51}$—, or —C(=O)—NH—$Y^{51}$—; $Y^{51}$ represents an aliphatic hydrocarbylene group having 1 to 6 carbon atoms, a phenylene group, or a group having 7 to 18 carbon atoms derived from a combination of these groups, $Y^{51}$ optionally containing a carbonyl group, an ester bond, an ether bond, or a hydroxy group; $Rf^1$ and $Rf^2$ each independently represent a hydrogen atom, a fluorine atom, or a trifluoromethyl group, provided that at least one of $Rf^1$ and $Rf^2$ is a fluorine atom; $R^{21}$ to $R^{28}$ each independently represent a hydrocarbyl group having 1 to 20 carbon atoms and optionally containing a fluorine atom, a chlorine atom, a bromine atom, an iodine atom, or a heteroatom; $R^{23}$ and $R^{24}$ or $R^{26}$ and $R^{27}$ are optionally bonded with each other to form a ring together with a sulfur atom bonded to $R^{23}$ and $R^{24}$ or $R^{26}$ and $R^{27}$; and $M^-$ represents a non-nucleophilic counter ion.

The inventive positive resist material can contain a base polymer having such a repeating unit.

The inventive positive resist material preferably further comprises an acid generator.

The inventive positive resist material preferably further comprises an organic solvent.

The inventive positive resist material preferably further comprises a quencher.

The inventive positive resist material preferably further comprises a surfactant.

The inventive positive resist material can contain such additives.

In addition, the present invention provides a patterning process comprising the steps of:

forming a resist film on a substrate by using the above-described positive resist material;

exposing the resist film to a high-energy beam; and developing the exposed resist film by using a developer.

Such a patterning process can achieve an excellent pattern profile after exposure.

In this event, the high-energy beam is preferably an i-line beam, a KrF excimer laser beam, an ArF excimer laser beam, an electron beam, or an extreme ultraviolet ray having a wavelength of 3 to 15 nm.

Such high-energy beams can be used in the inventive patterning process.

Advantageous Effects of Invention

The inventive positive resist material is a chemically-amplified molecular resist. Since the inventive positive resist material is a low molecular weight compound-based material and not a polymer-based material, the influence of cohesion and swelling in a developer is small. In the case of conventional molecular resists, pattern collapse occurs due to low rigidity and edge roughness is large due to inadequate acid diffusion control. However, the inventive positive resist material has high rigidity due to the hydrogen bond of urethane groups, and urethane groups have a high ability of controlling acid diffusion. Thus, the above problems can be solved. Because of these excellent properties, the inventive positive resist material is quite highly practical and very useful as a material for forming fine patterns particularly for manufacturing very LSI circuits or for photomask in EB drawing, or as a material for forming patterns for EB or EUV exposure. The inventive positive resist material is applicable to not only lithography in forming, for example, semiconductor circuits, but also formations of mask circuit patterns, micro-machines, and thin-film magnetic head circuits.

DESCRIPTION OF EMBODIMENTS

As noted above, there have been demands for the development of a positive resist material and a patterning process which result in higher sensitivity, higher resolution, smaller edge roughness, and smaller CDU than conventional positive resist materials, and which result in excellent pattern profile after exposure.

The present inventor has earnestly studied to obtain a positive resist material having high resolution and small edge roughness and dimensional variation as recently demanded. Consequently, the inventor has considered that it is necessary to reduce molecular size while reducing the influence of diffusion including acid diffusion to achieve this. Thus, the inventor has found out that a compound having carboxy groups substituted with an acid-labile group, the carboxy groups being bonded with urethane groups, can minimize acid diffusion by the glass transition point of the resin being high due to hydrogen bonds between urethane groups, and that the effect on the compound of swelling in an alkaline developer is small because of the small molecular weight. The inventor has found out that such a compound is extremely effective particularly when contained as a base in a chemically amplified positive resist material.

The present inventor has also found out that it is possible to obtain a positive resist material suitable particularly as a material for manufacturing very LSI circuits or for forming a fine pattern in a photomask, the positive resist material having high sensitivity, considerably high alkaline dissolution rate contrast between before and after exposure, high resolution, and excellent pattern profile, edge roughness, and CDU after exposure. The inventor has found that this can be achieved by a base polymer contained together with the above compound, the base polymer containing a repeating unit having an acid-labile group substituting a hydrogen atom of a carboxy group or a phenolic hydroxy group, and by a hybrid of polymer-type and monomer-type chemically amplified resists for enhancing dissolution contrast. Thus, the present invention has been completed.

That is, the present invention is a positive resist material comprising a compound having two or more urethane groups and having two or more carboxy groups that are each substituted with an acid-labile group and are bonded to the urethane groups via a linking group.

Hereinafter, the present invention will be described in detail, but the present invention is not limited thereto.

[Positive Resist Material]

The inventive positive resist material contains a compound having two or more urethane groups and having two or more carboxy groups that are each substituted with an acid-labile group and are bonded to the urethane groups via a linking group.

[Compound]

As the compound, those represented by the following formula (1) are preferable.

(1)

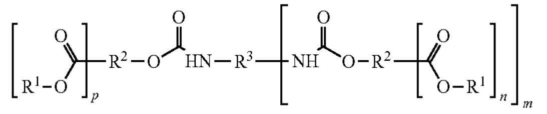

In the formula (1), $R^1$'s are identical to or different from each other and each represent an acid-labile group. $R^2$'s each represent a linking group, are identical to or different from each other, and represent a hydrocarbylene group having 1 to 20 carbon atoms, having a valency of n+1 or p+1, and optionally containing an oxygen atom, a sulfur atom, a nitrogen atom, or a halogen atom. $R^3$ represents a hydrocarbylene group having 2 to 33 carbon atoms, having a valency of m+1, and optionally containing an oxygen atom, a sulfur atom, a nitrogen atom, or a halogen atom. "m" represents an integer satisfying $1 \le m \le 6$. "n" and "p" represent 1 or 2.

Examples of the compound include the following, but are not limited thereto.

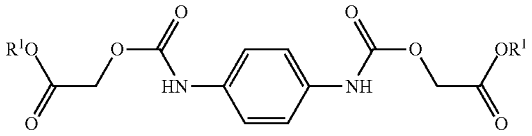
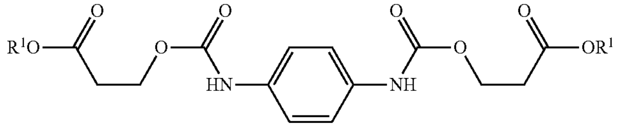
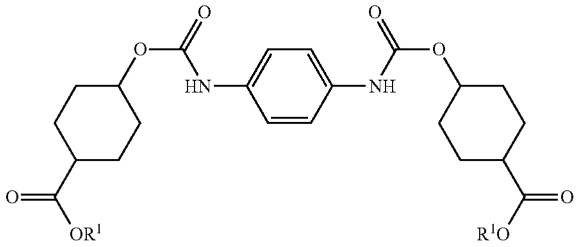
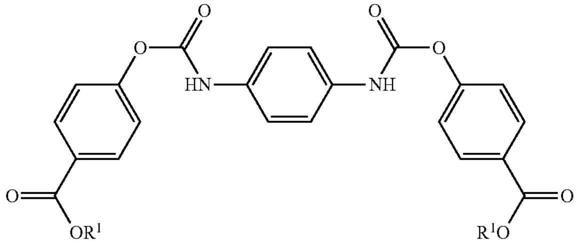
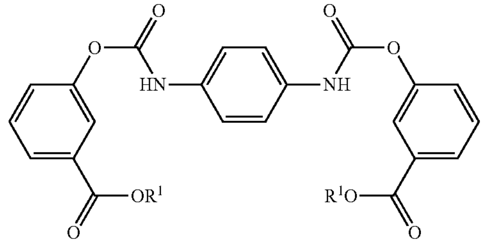
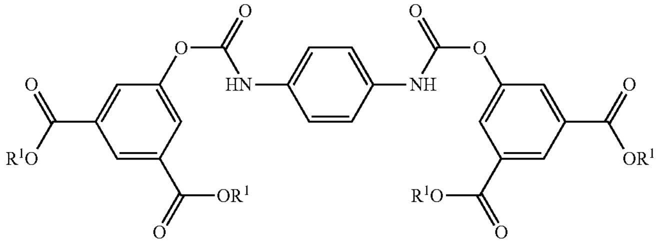
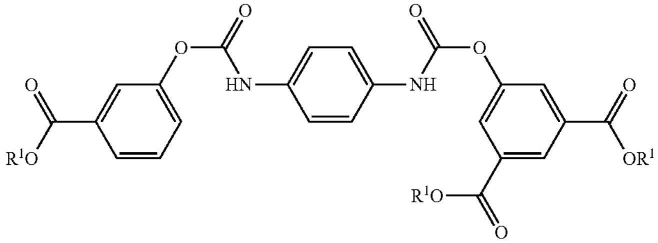
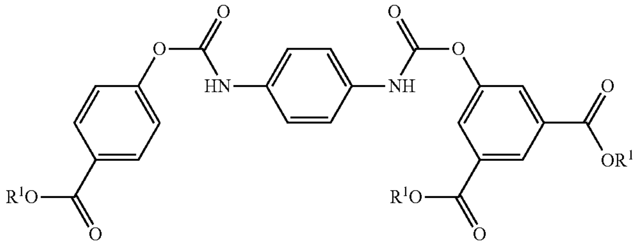
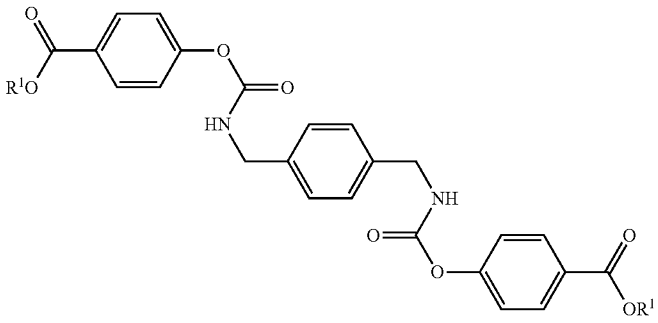

-continued
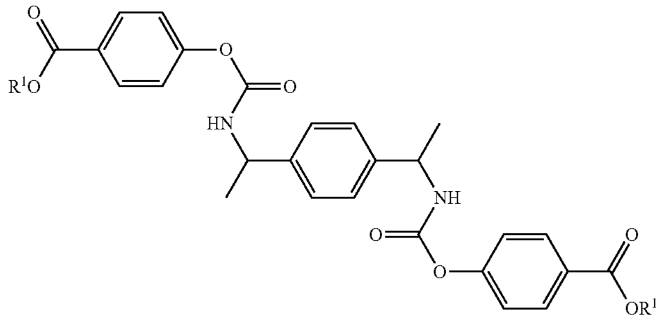
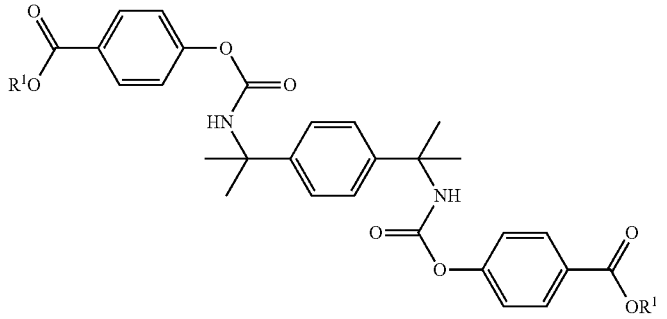
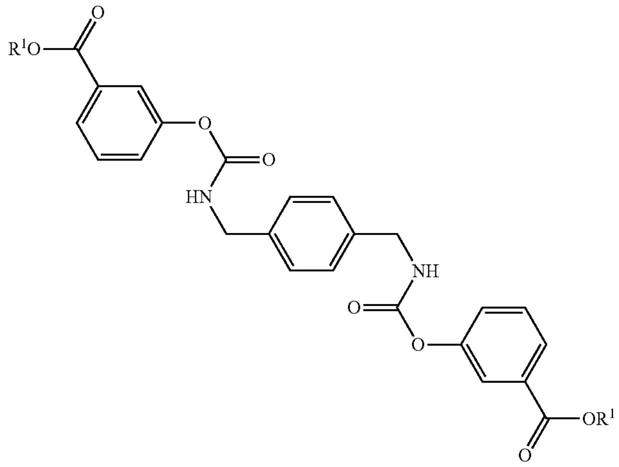
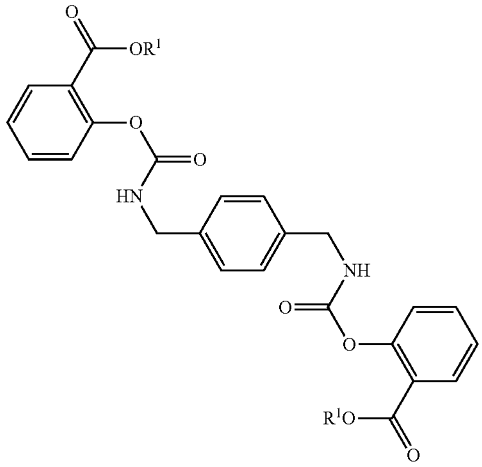
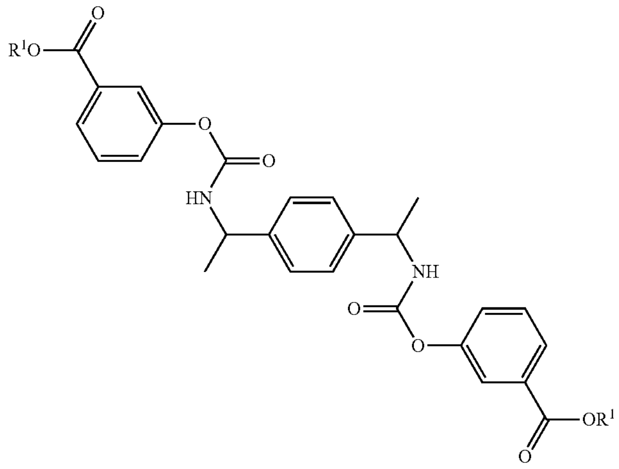

-continued
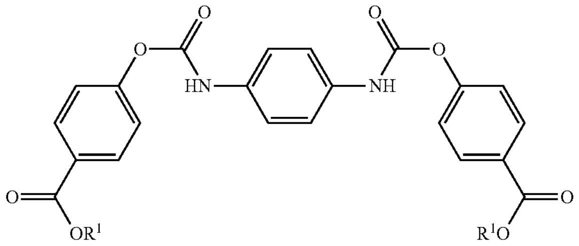
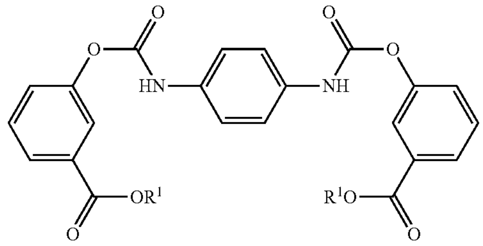
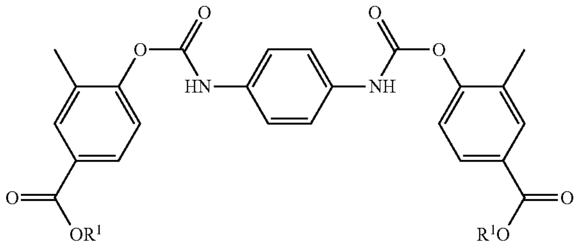
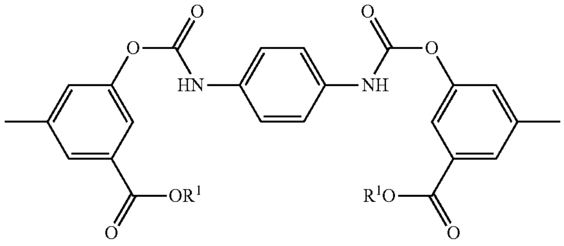
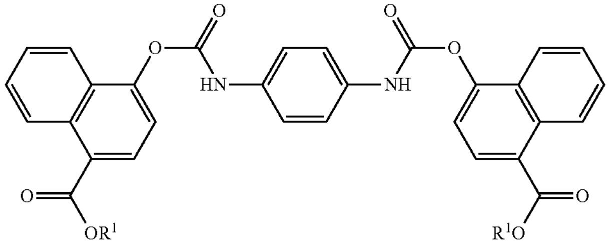
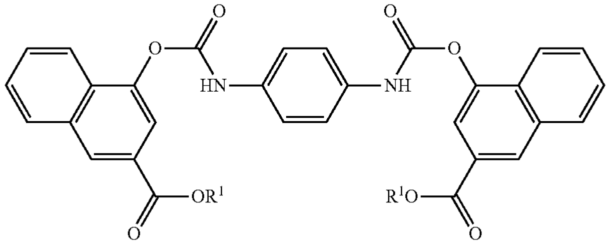
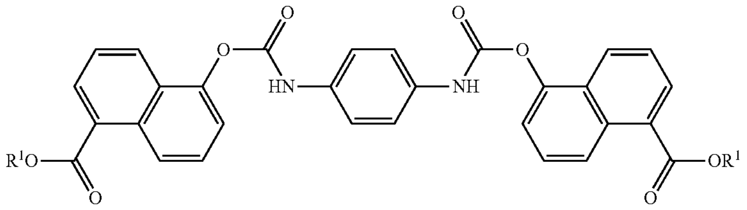
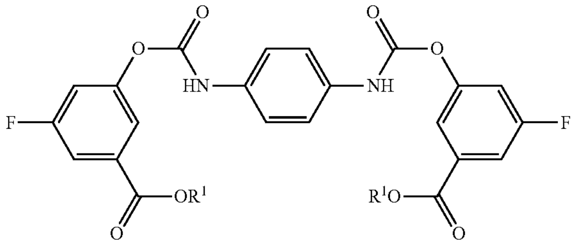
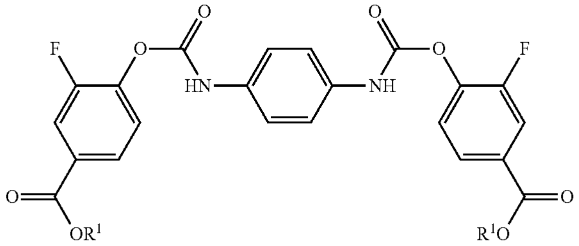

-continued
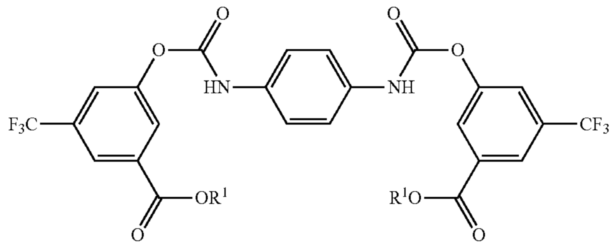
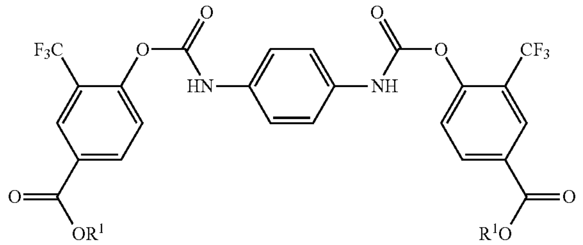
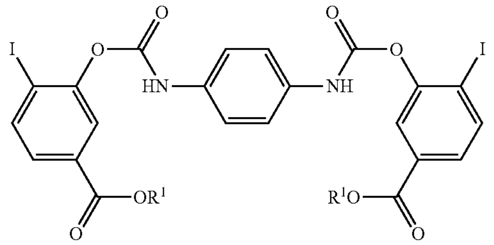
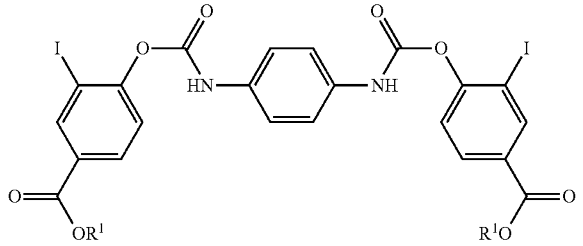
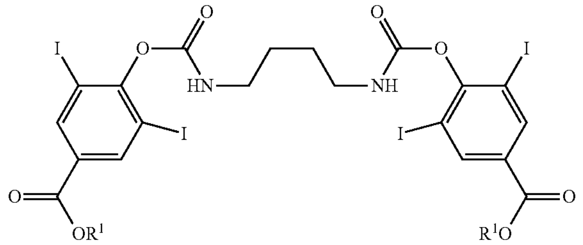
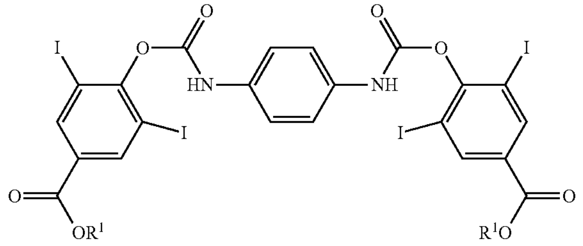
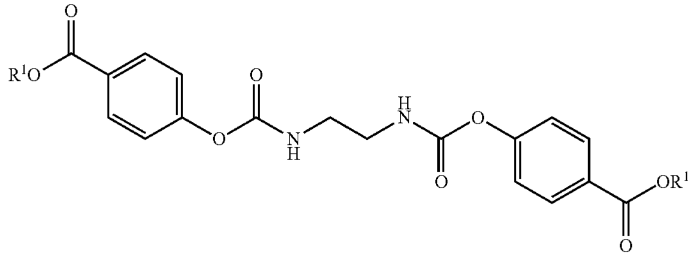
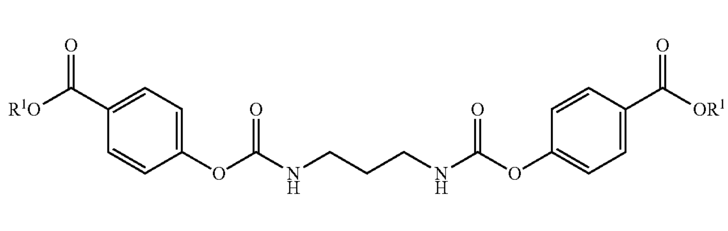

-continued
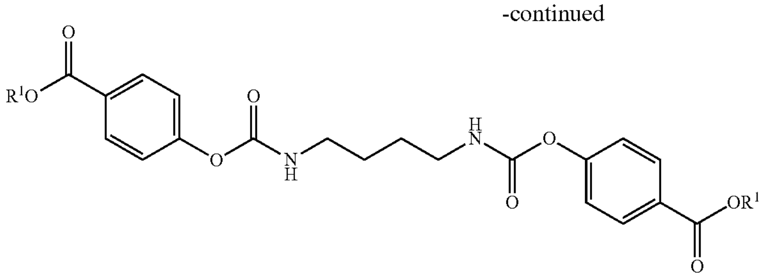
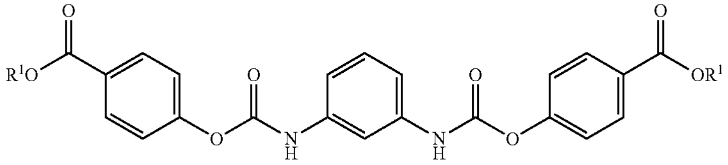
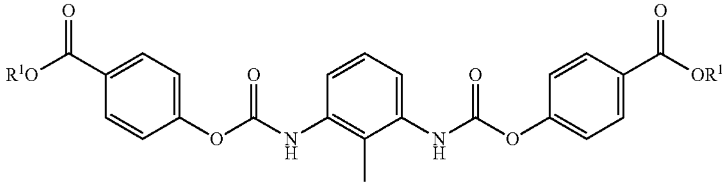
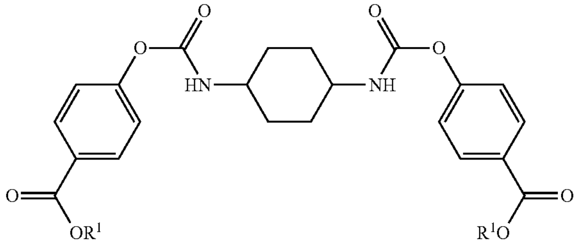
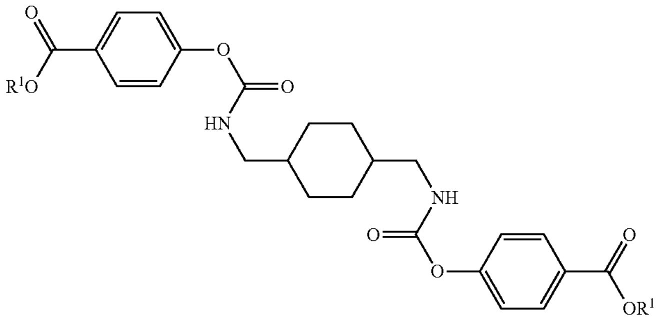
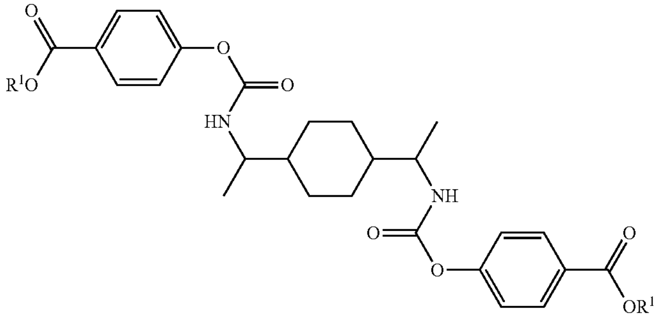

-continued
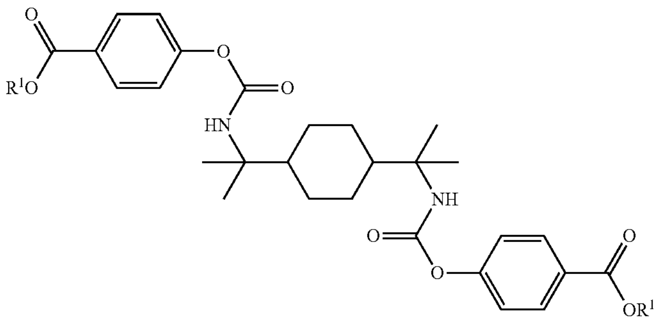
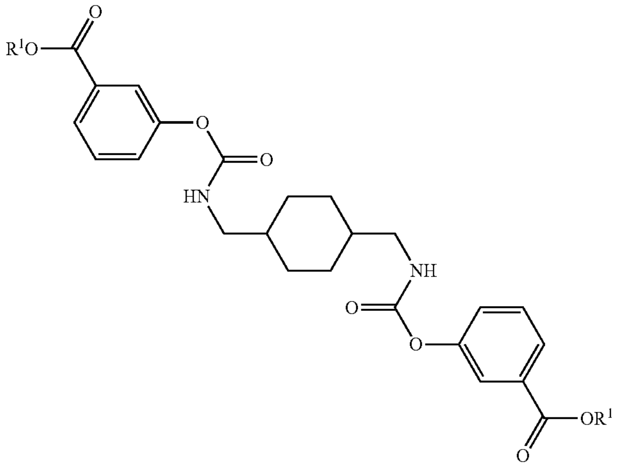
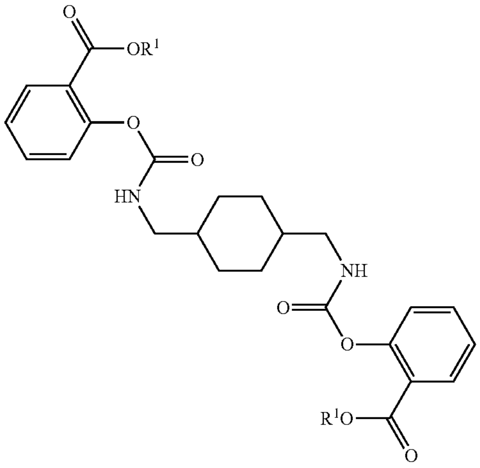
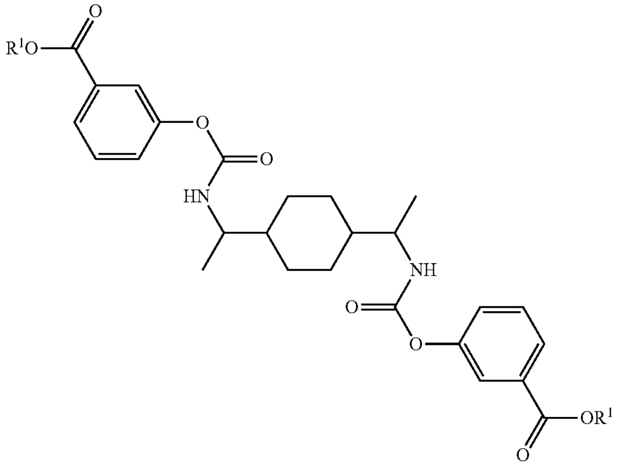

-continued
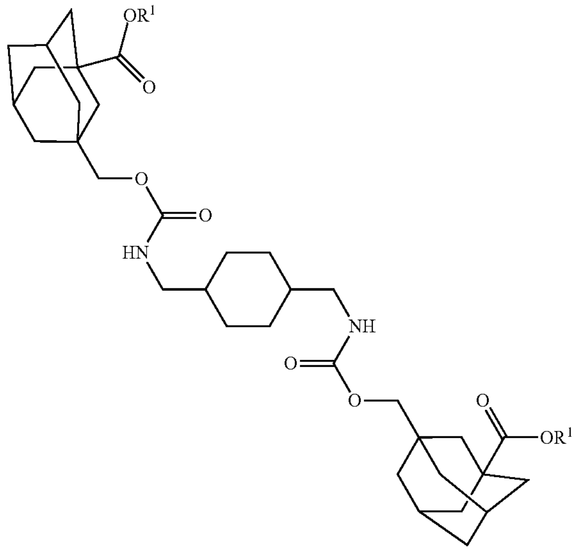
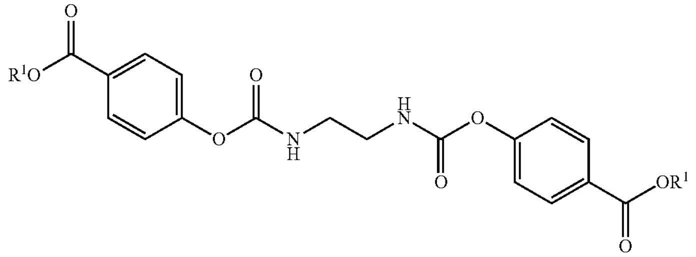
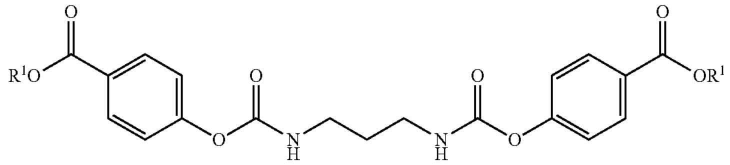
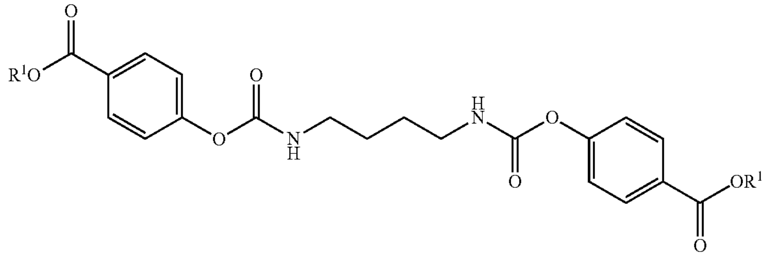
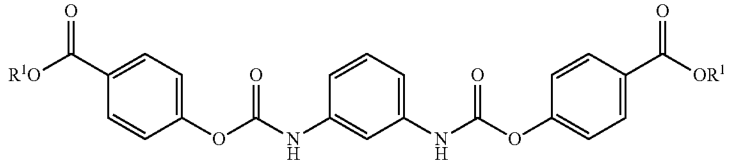
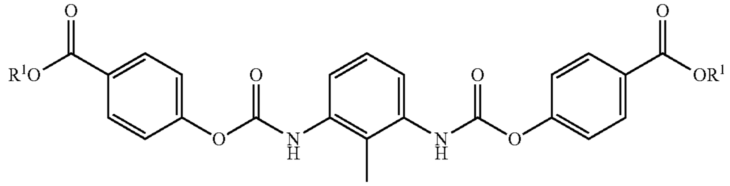

-continued
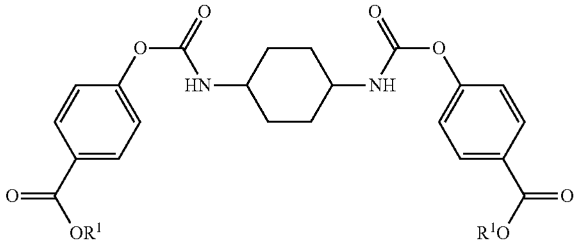
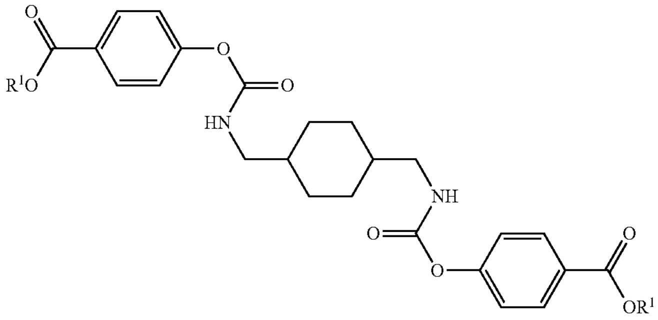
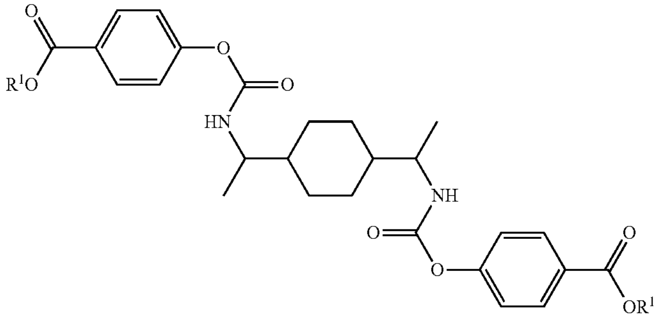
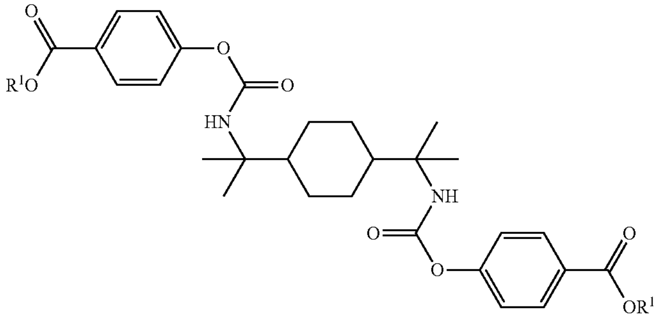
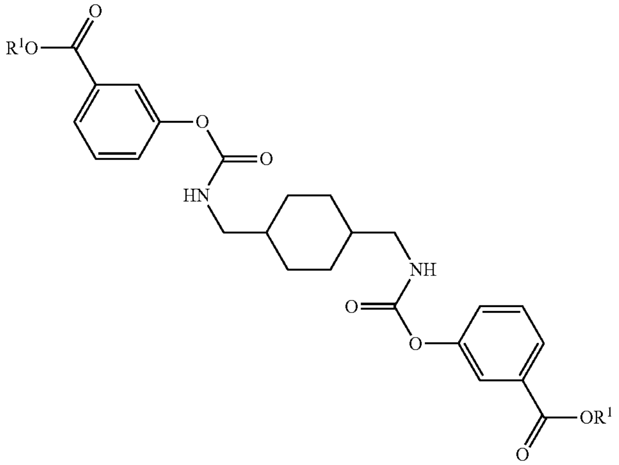
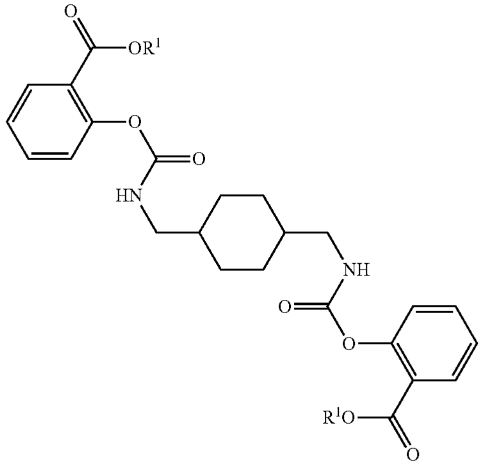

-continued
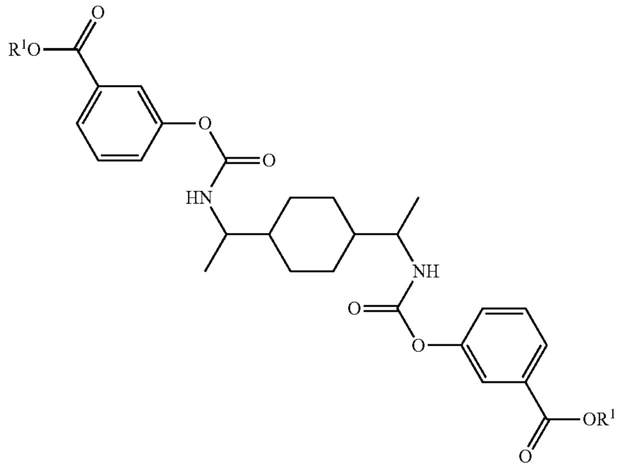
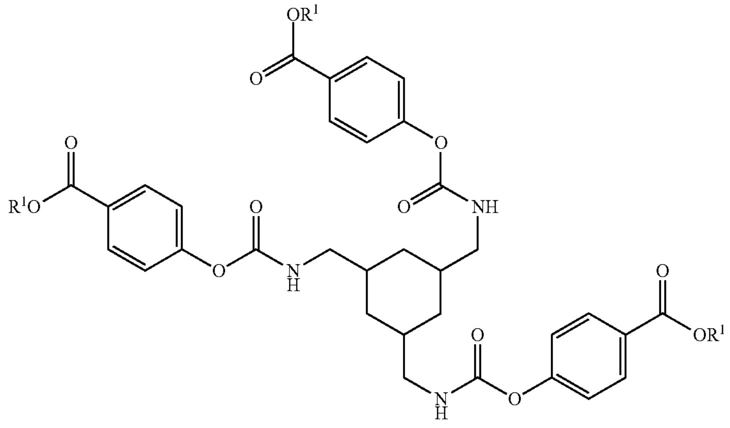
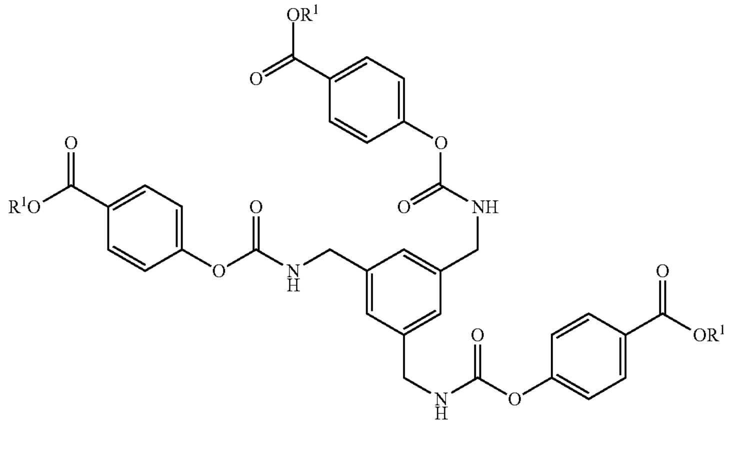

-continued
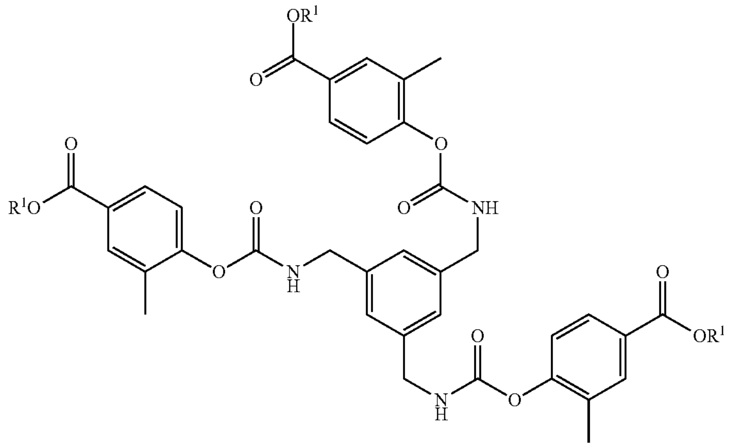
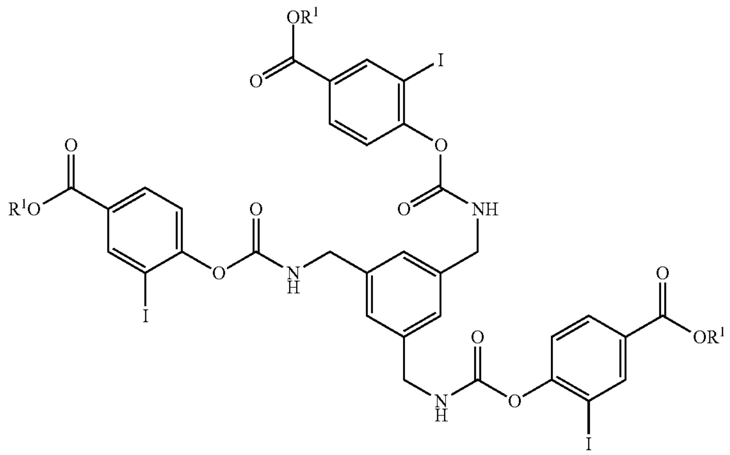
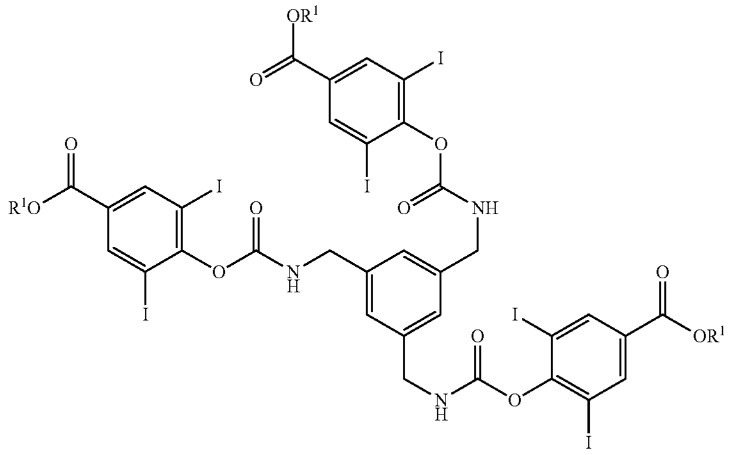

-continued
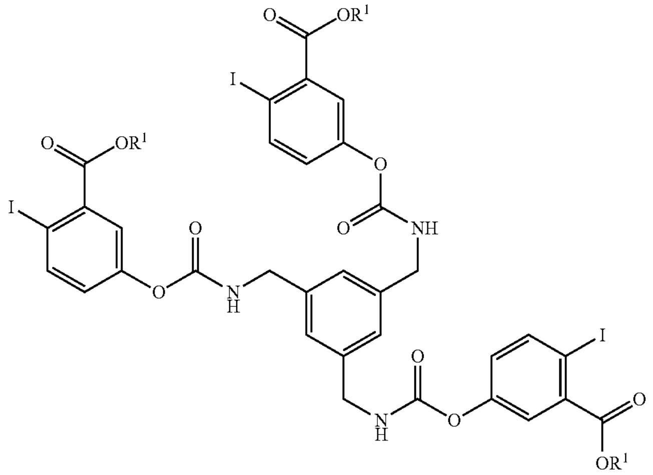
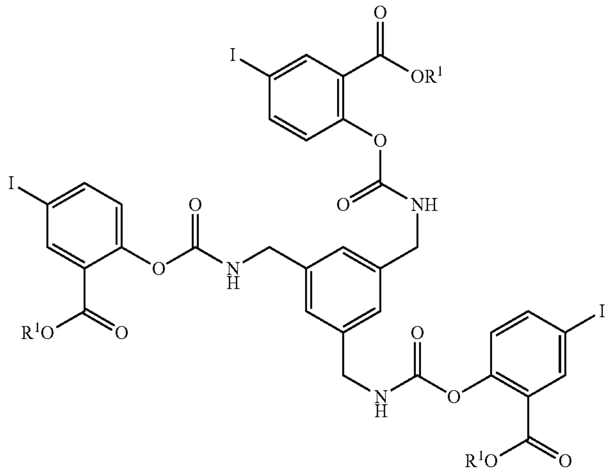
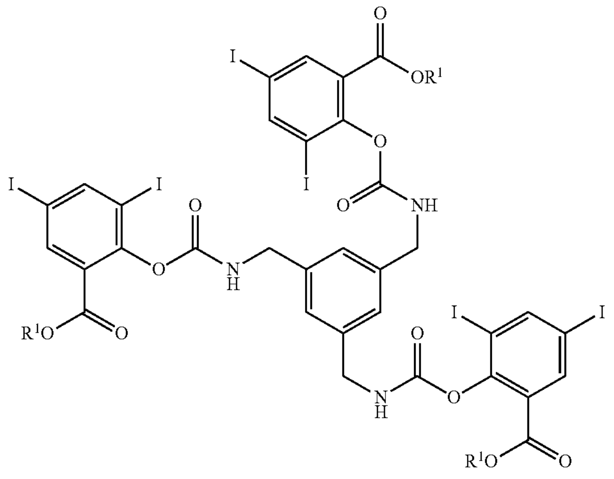

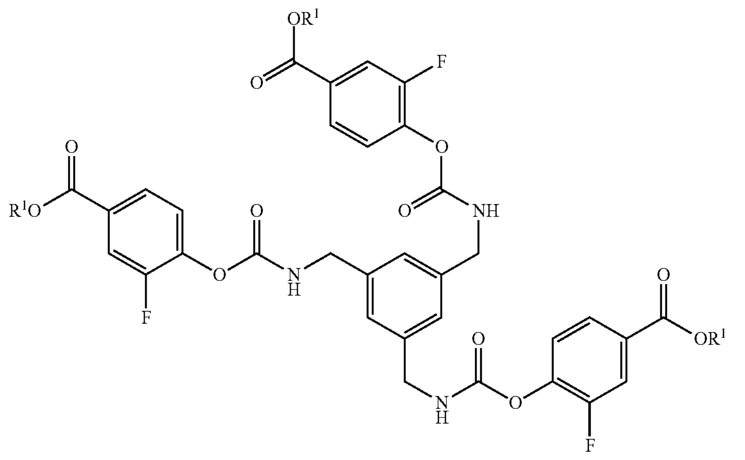
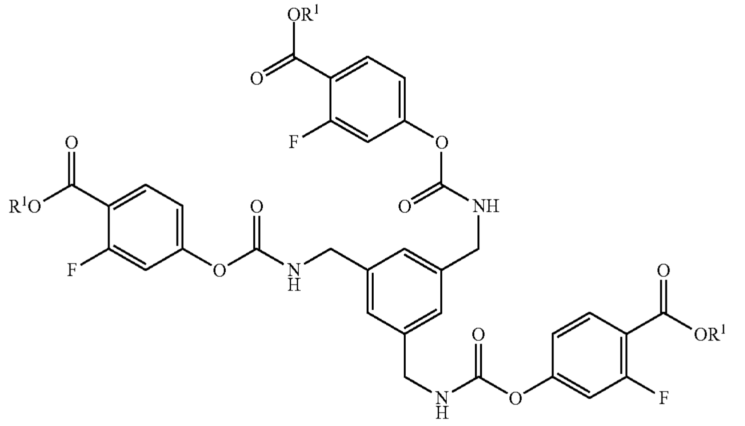
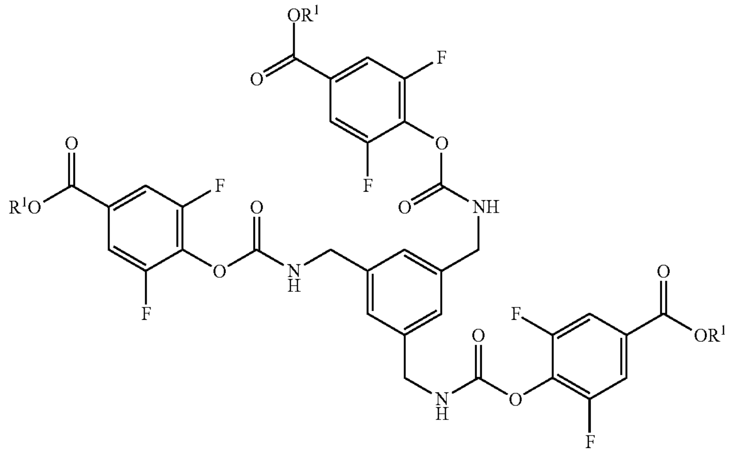

-continued
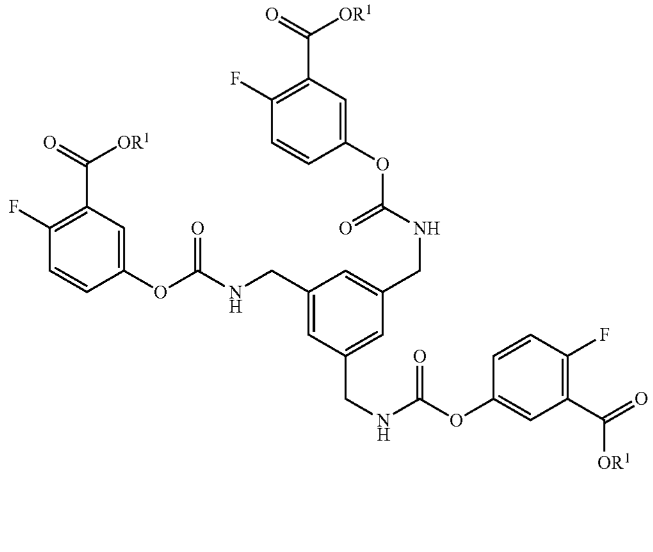
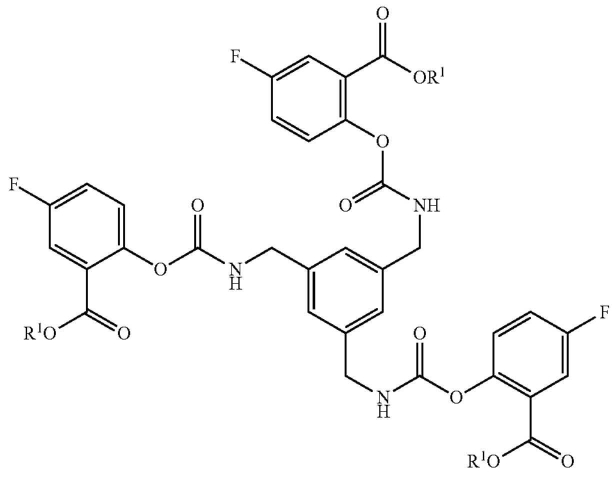
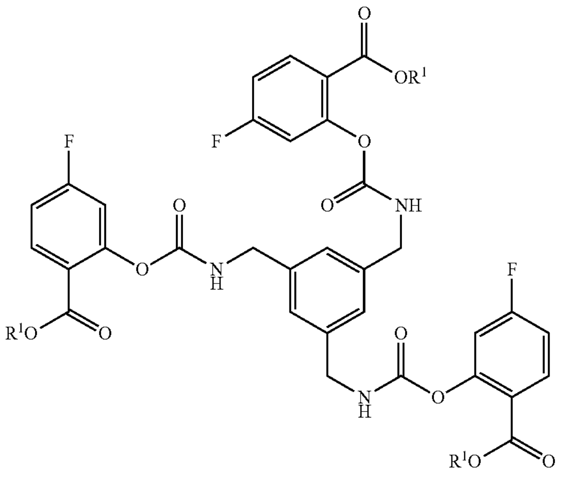
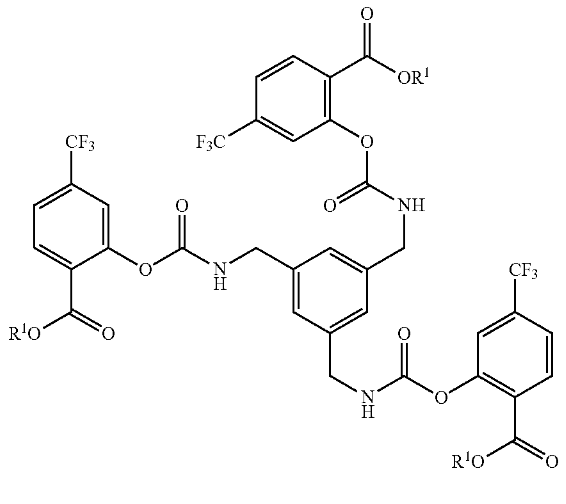

-continued
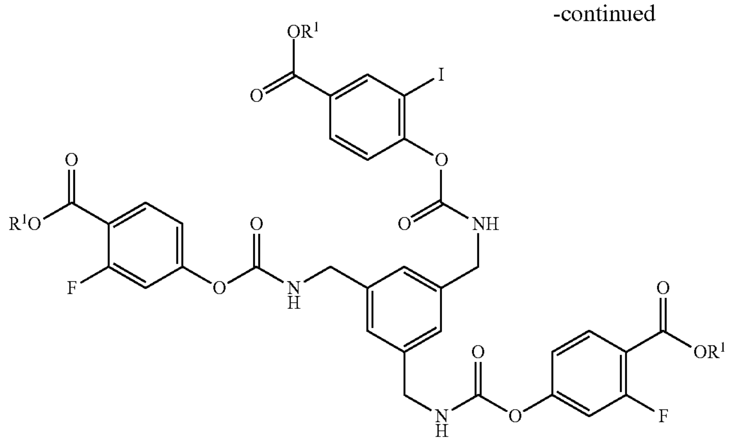
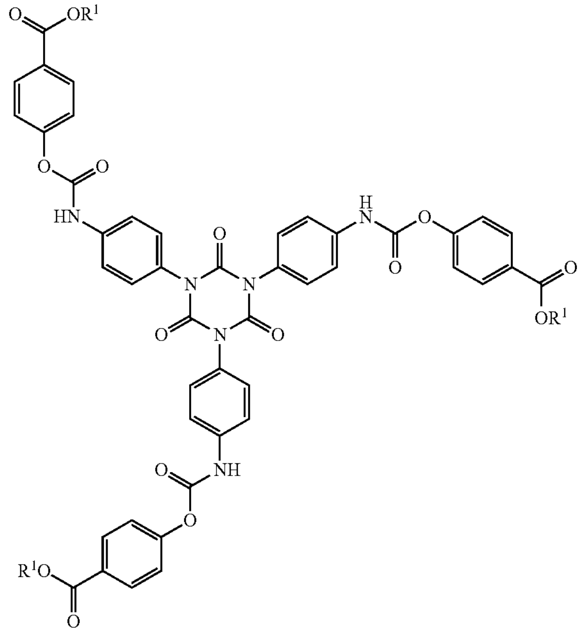
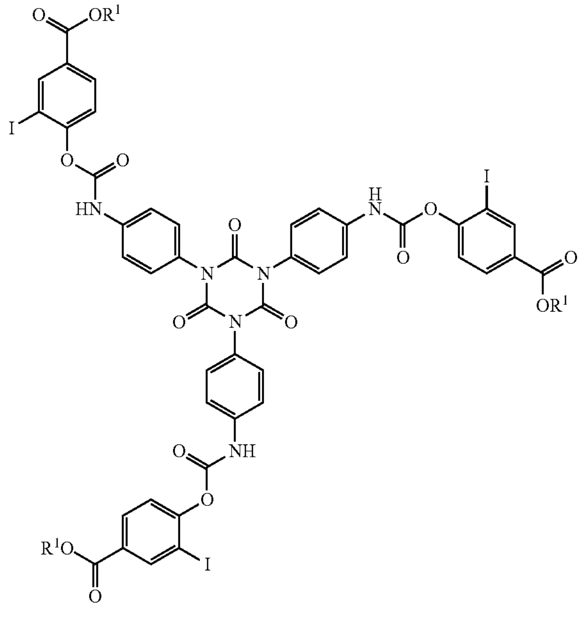

-continued
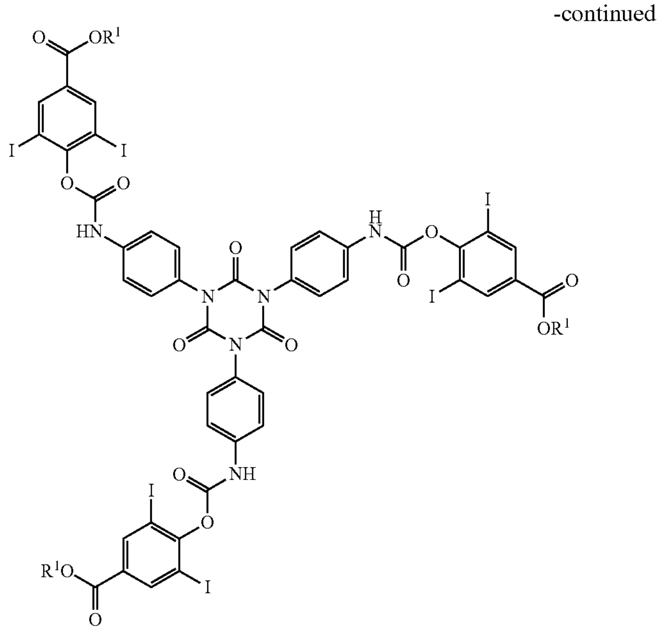
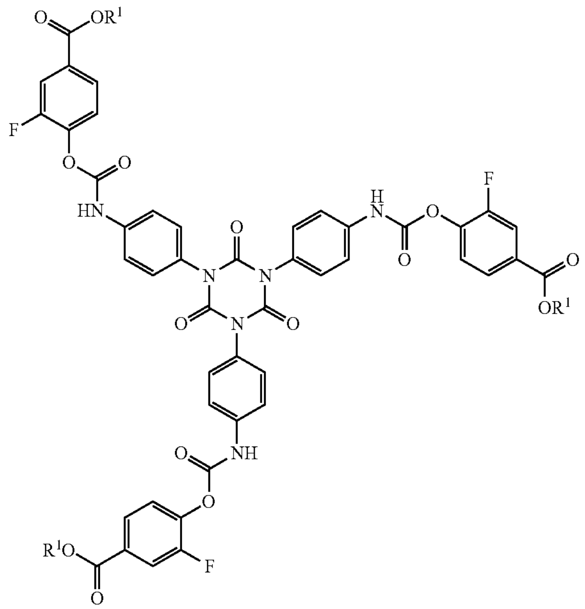

-continued
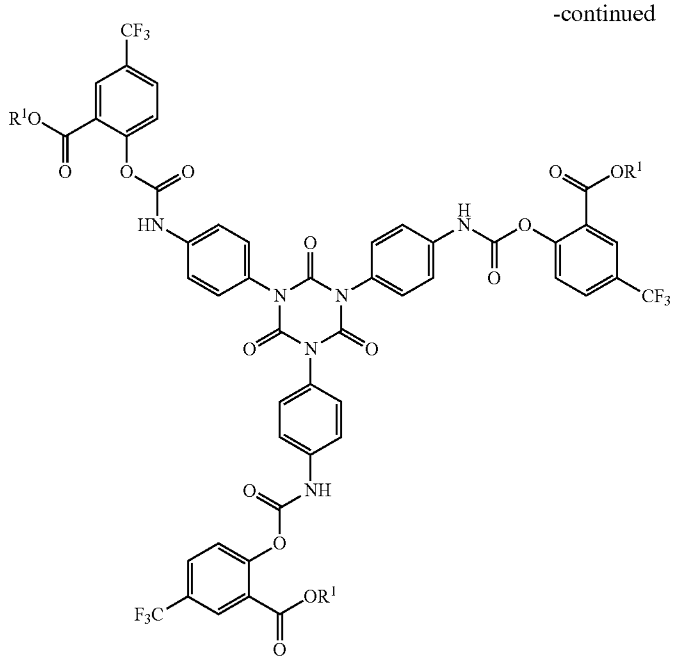
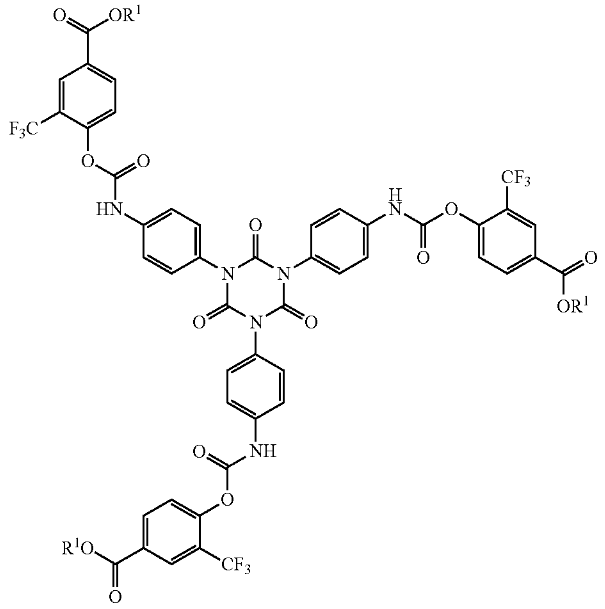

-continued
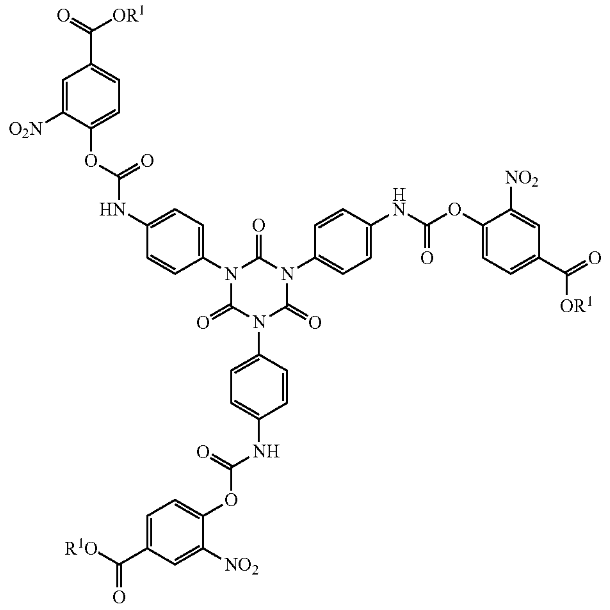
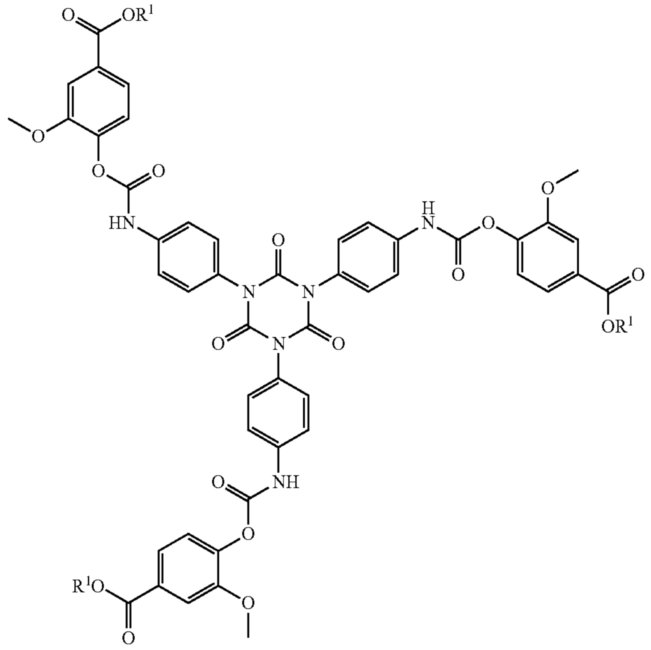

-continued
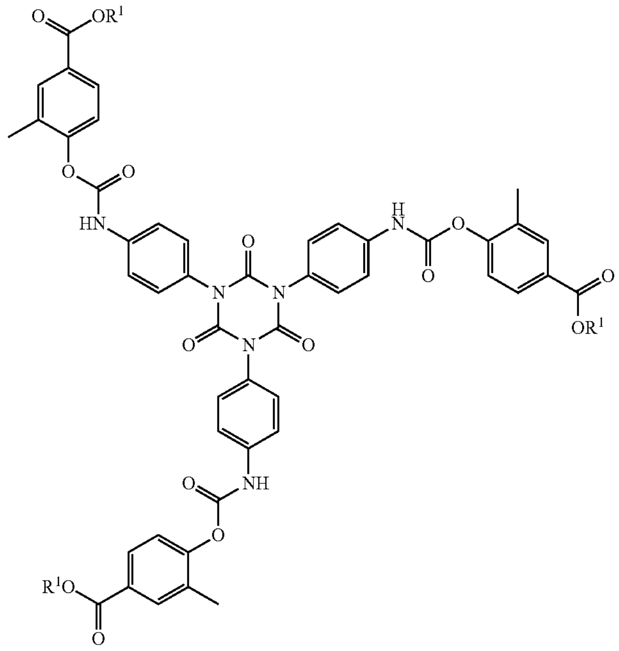
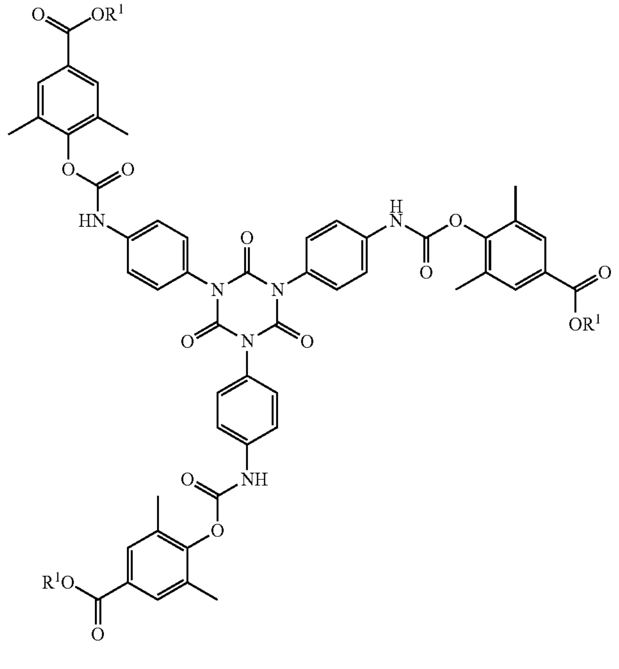

-continued
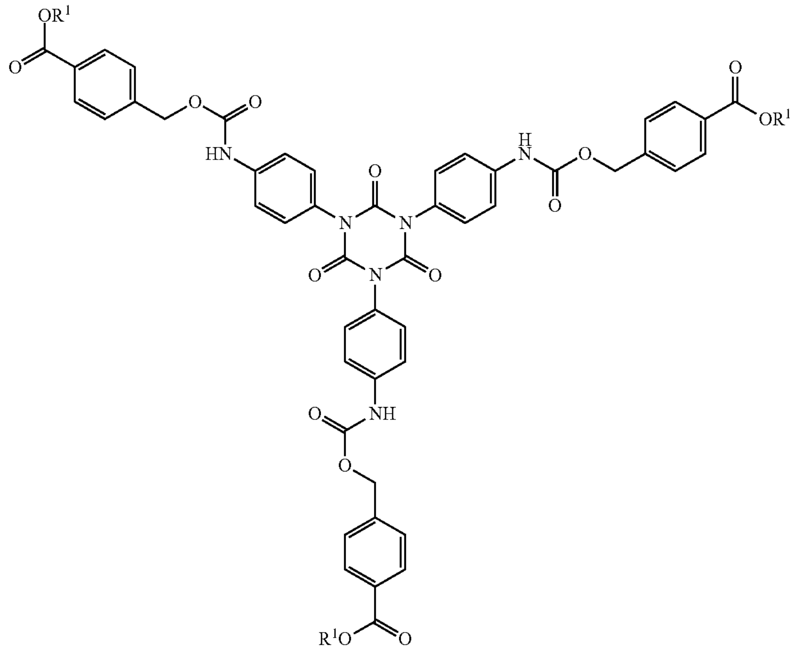
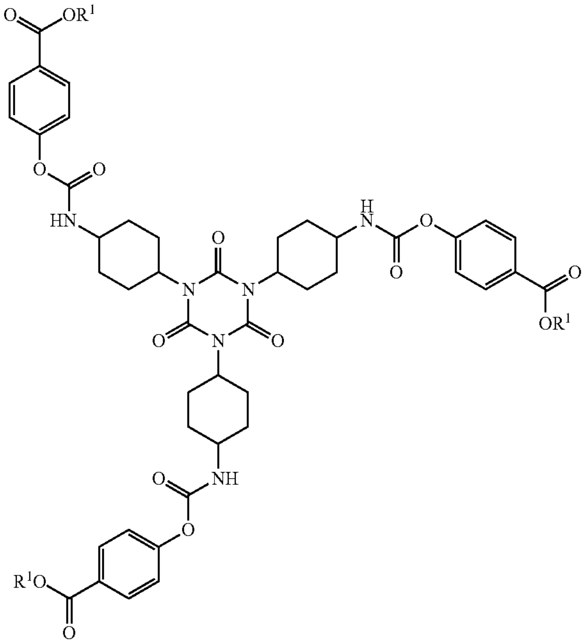

-continued
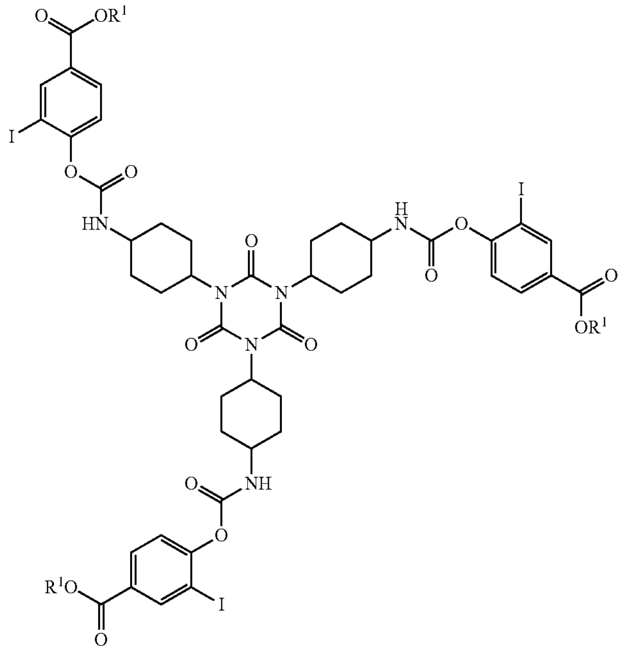
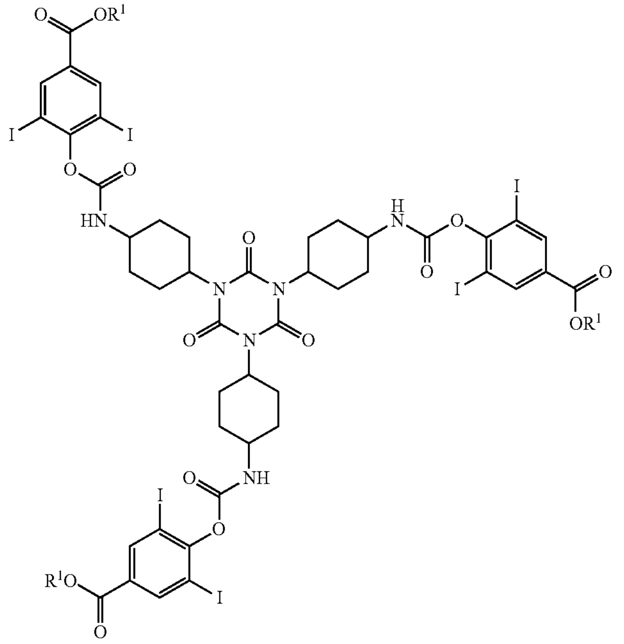

-continued
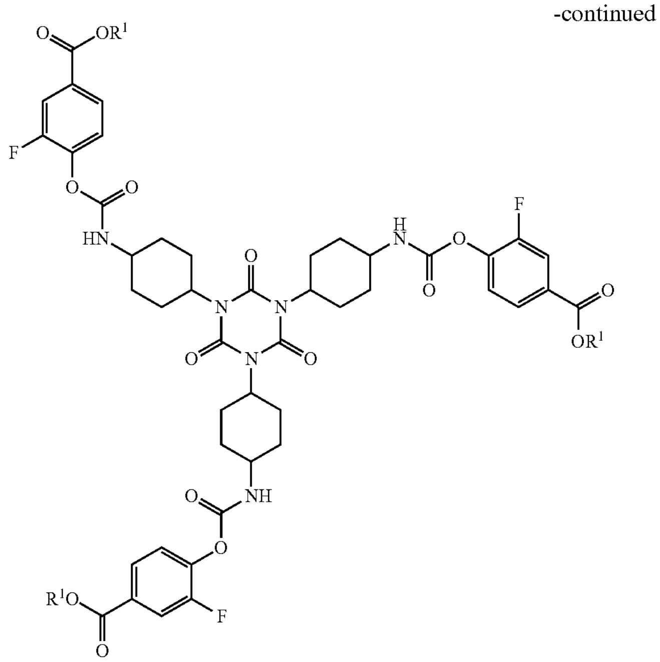
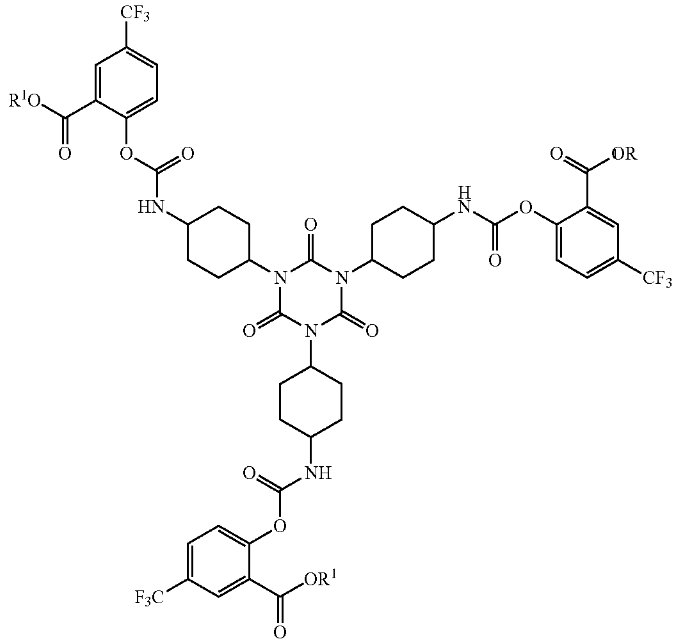

-continued
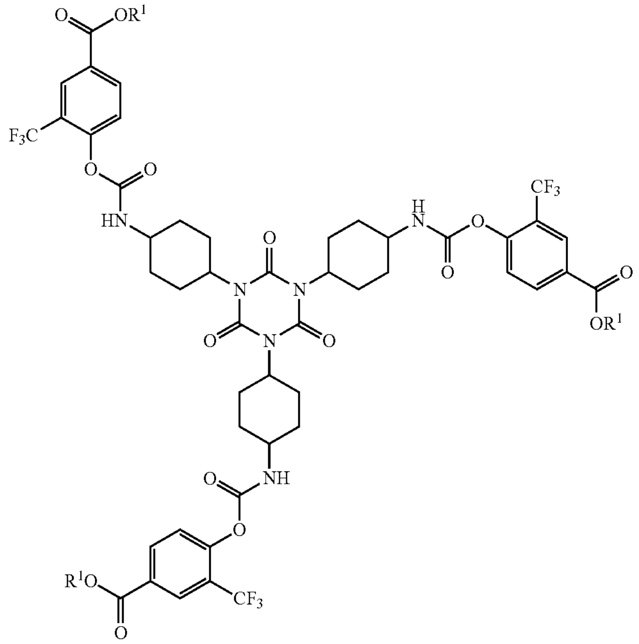
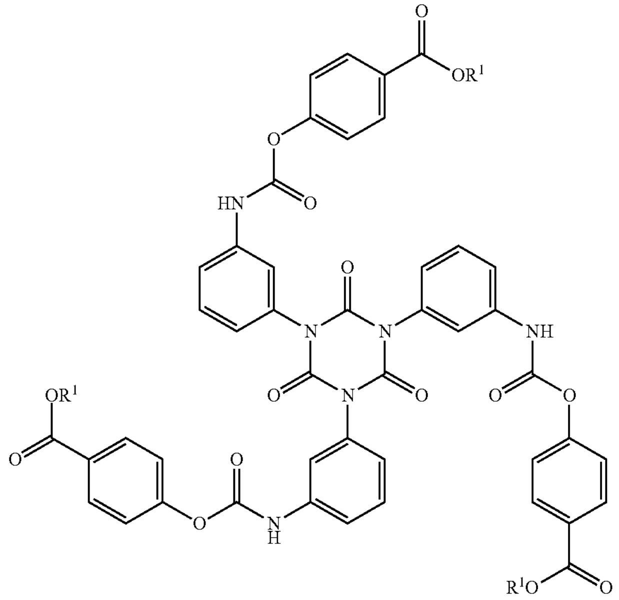

-continued
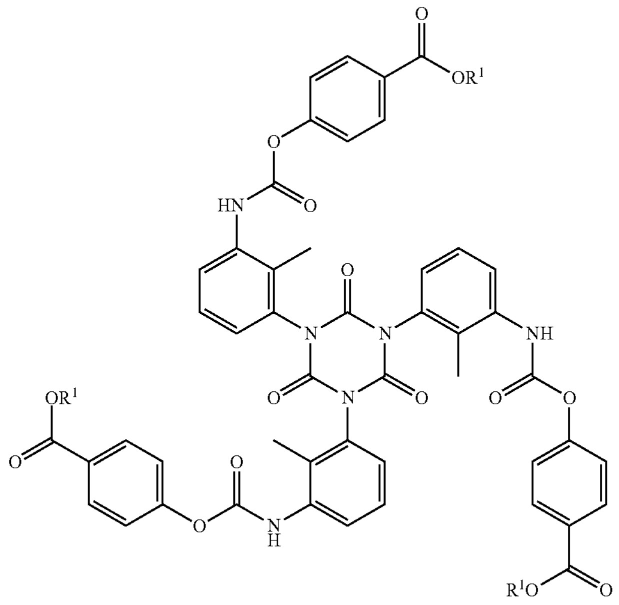
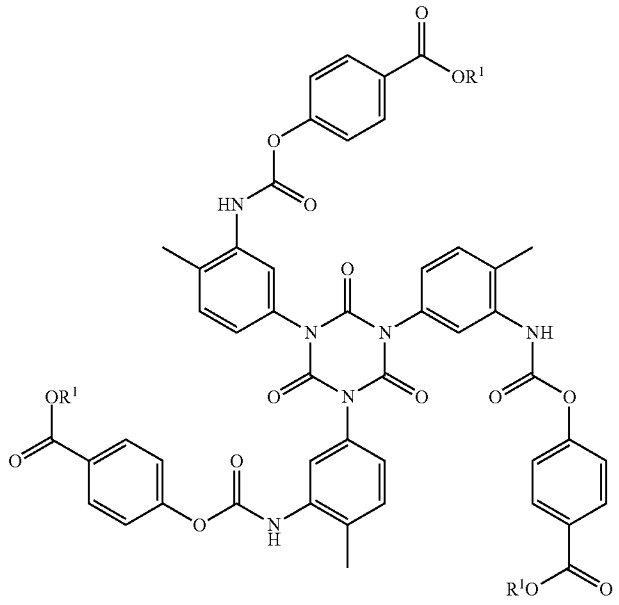

-continued
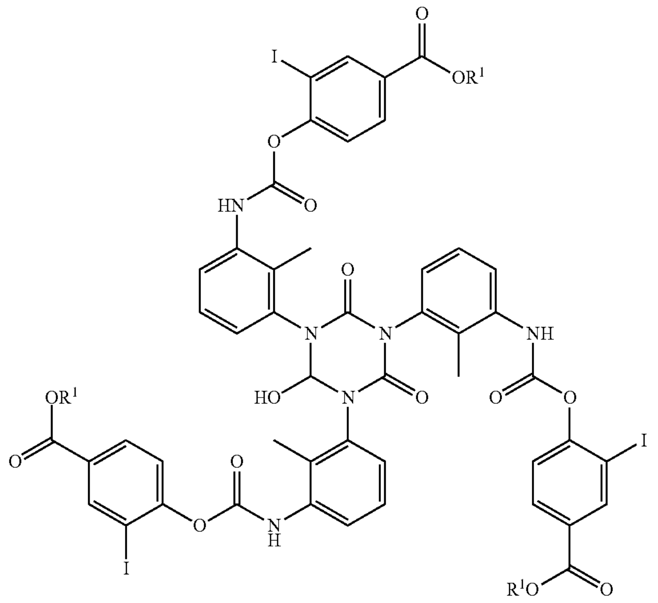
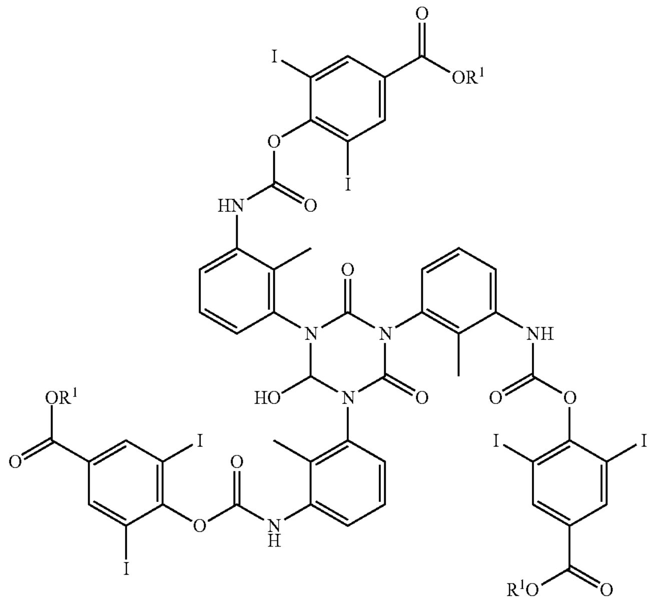

-continued
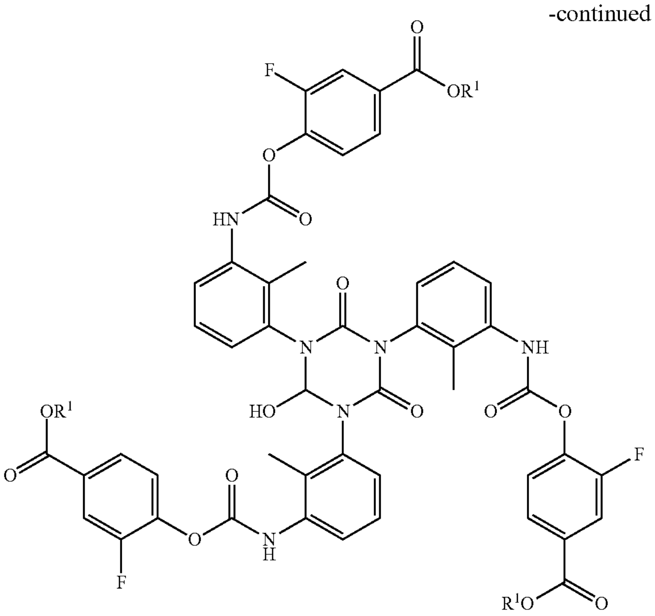
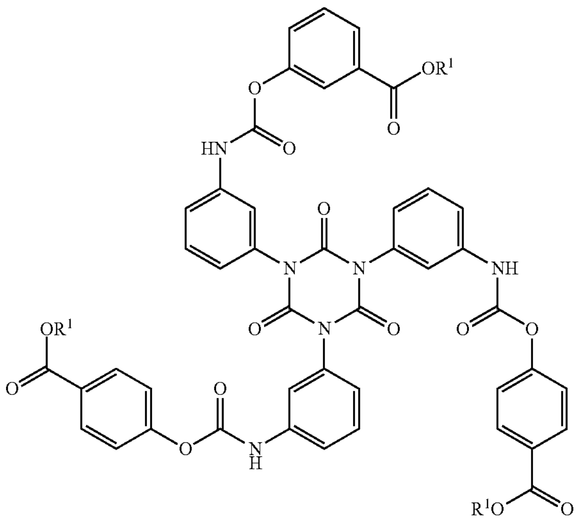
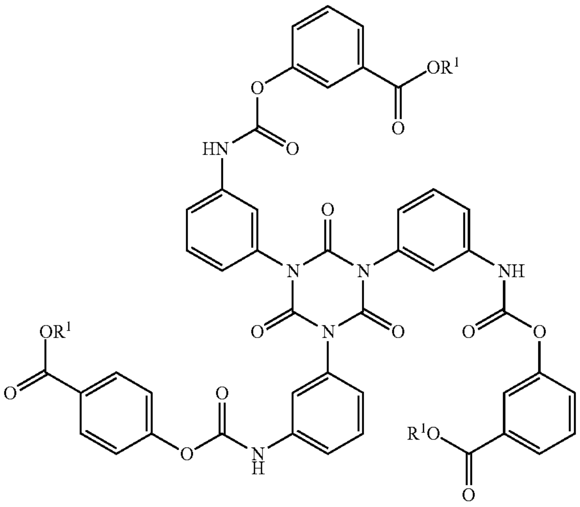
-continued
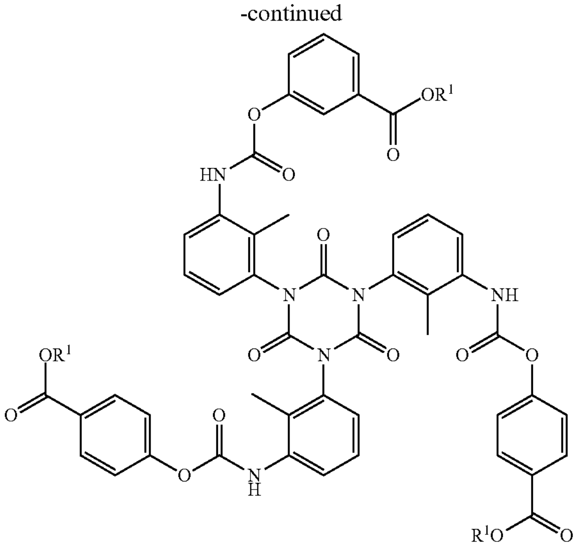
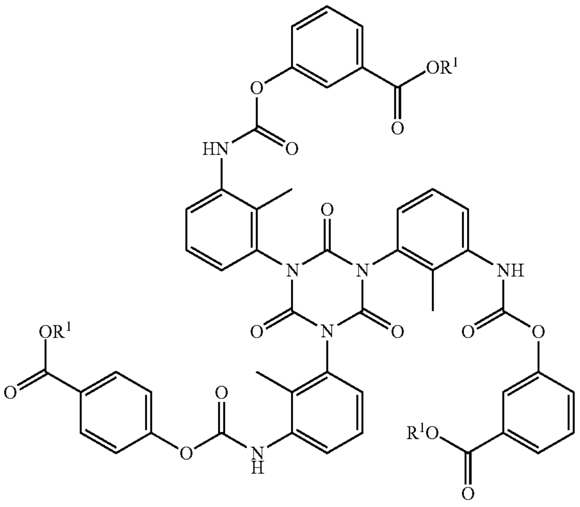

-continued
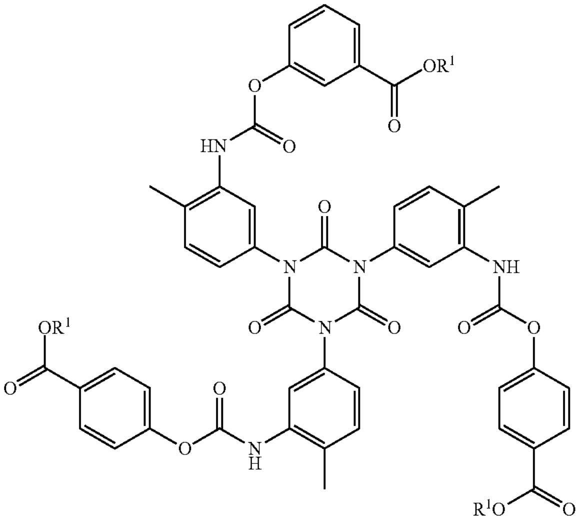
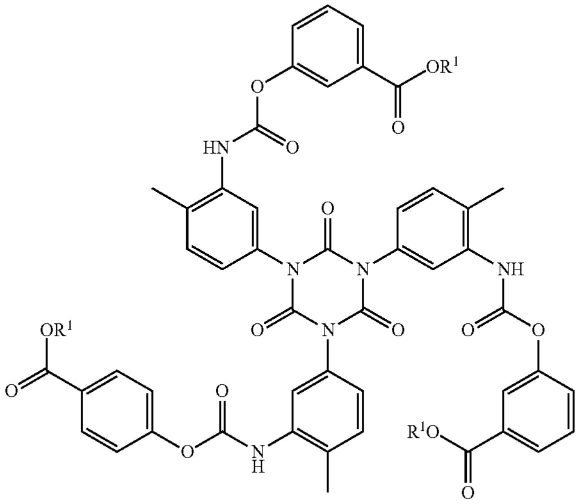
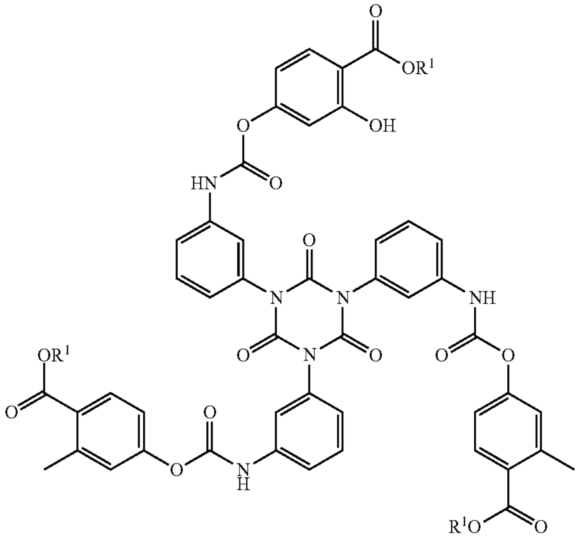
-continued
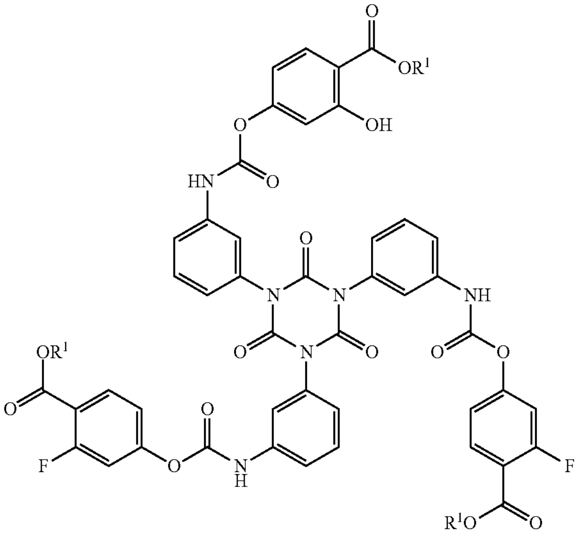
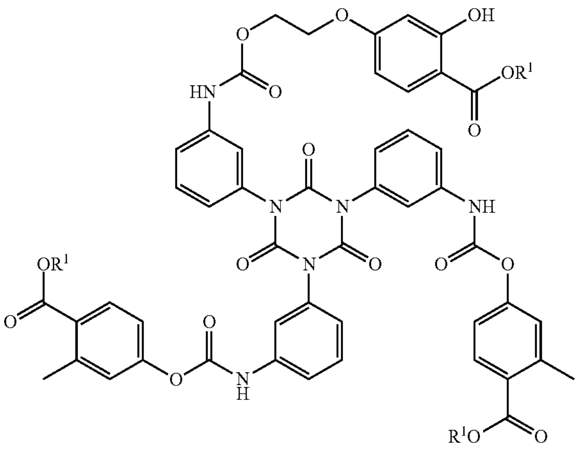
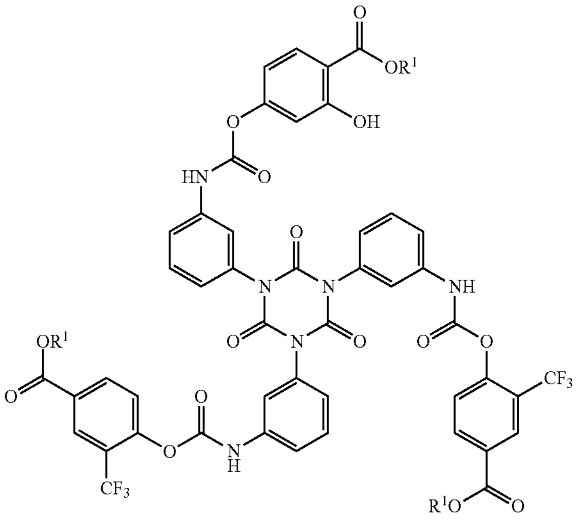

-continued
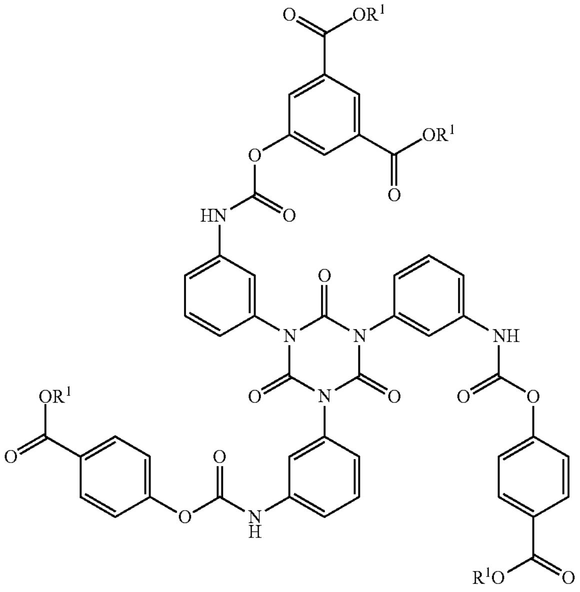
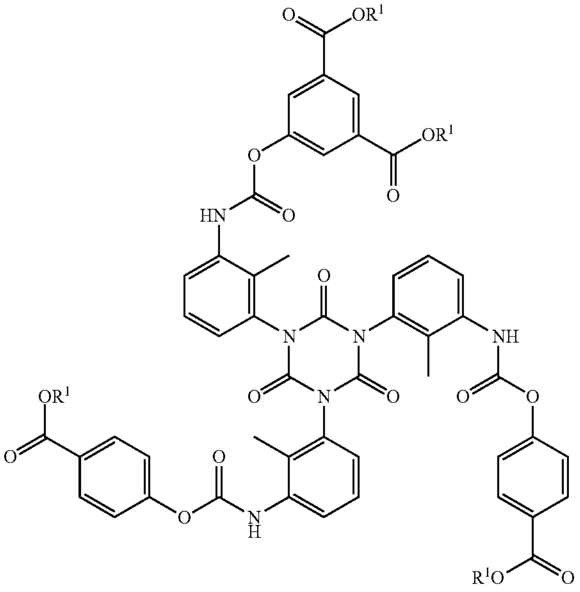
-continued
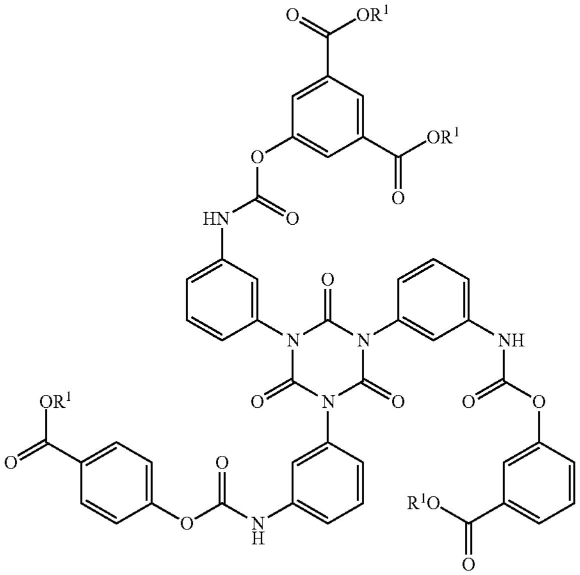
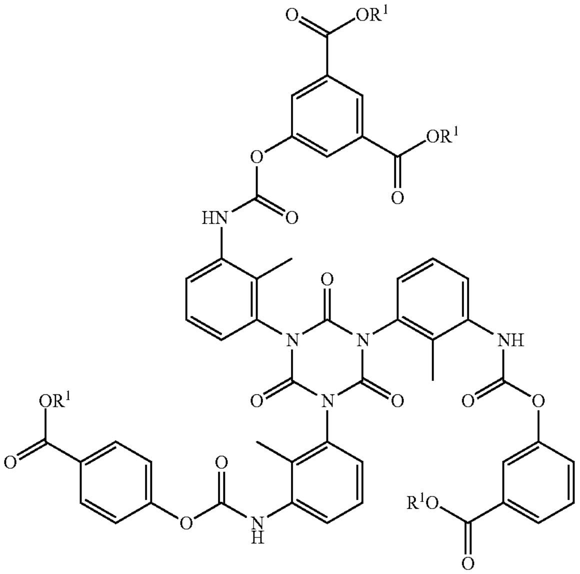

-continued
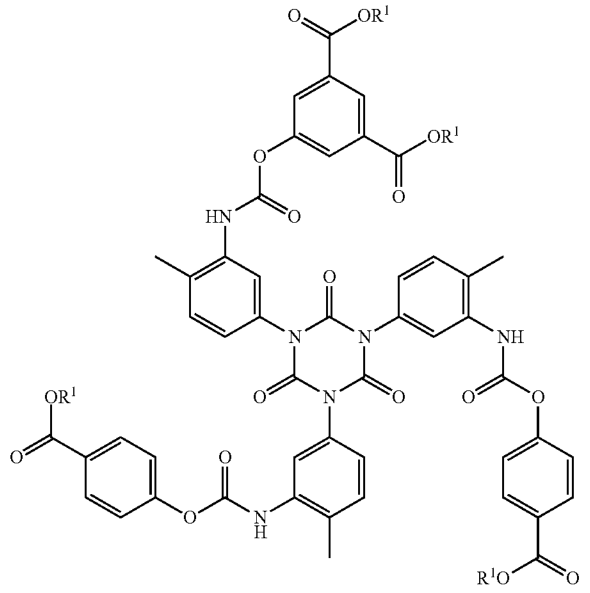
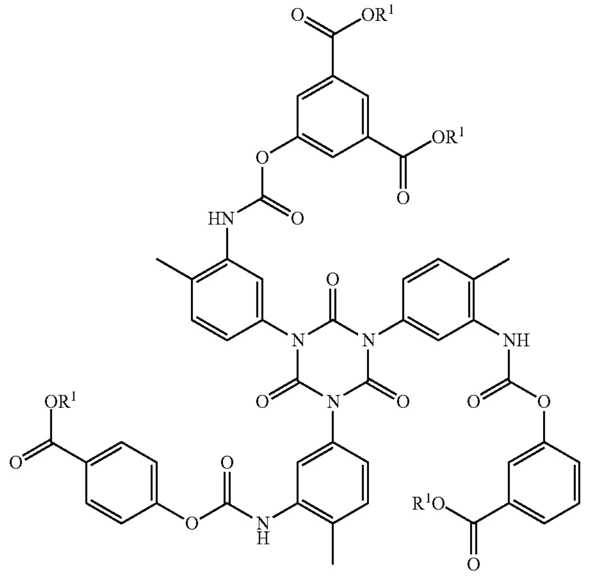
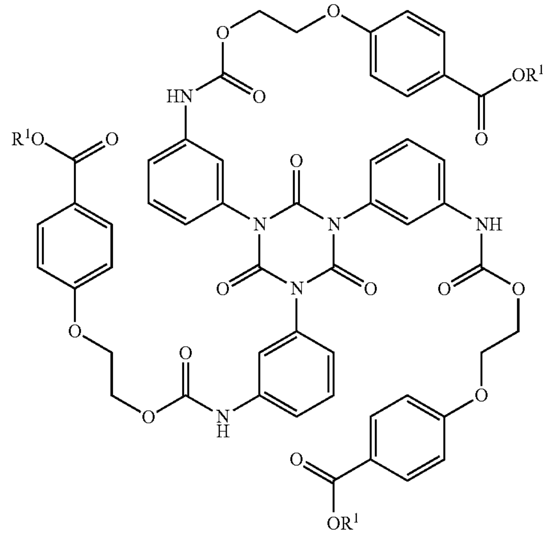
-continued
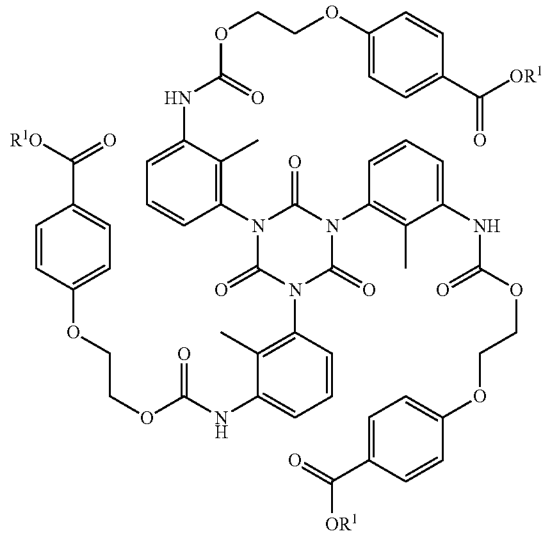
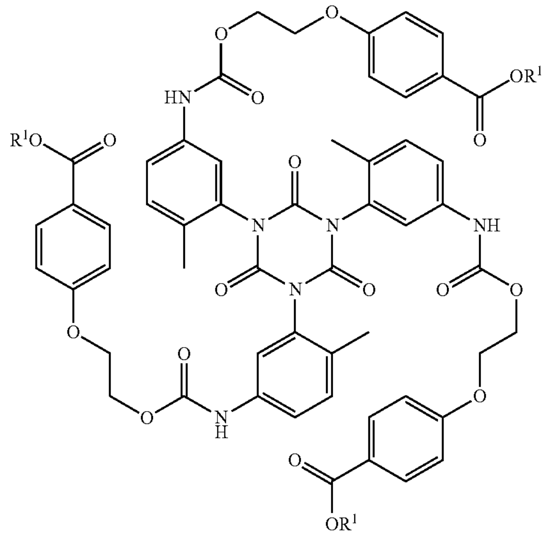
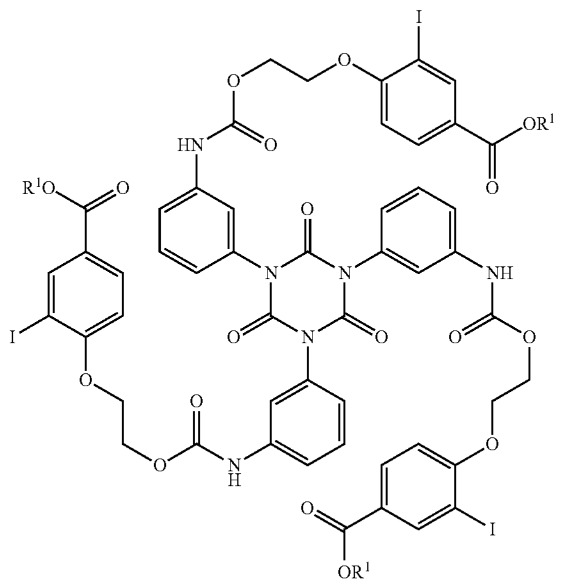

-continued
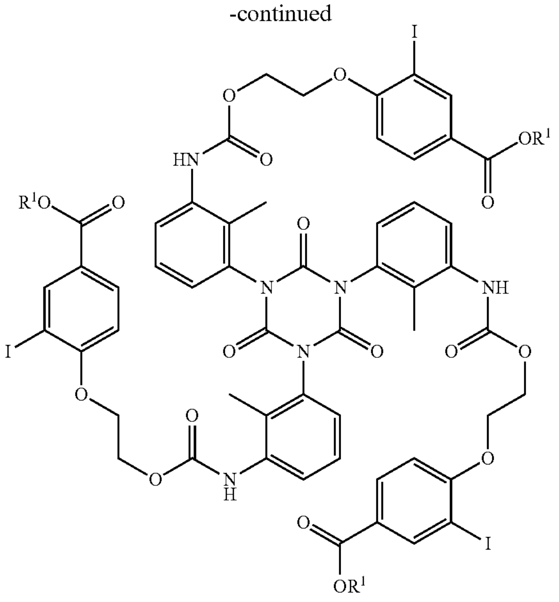
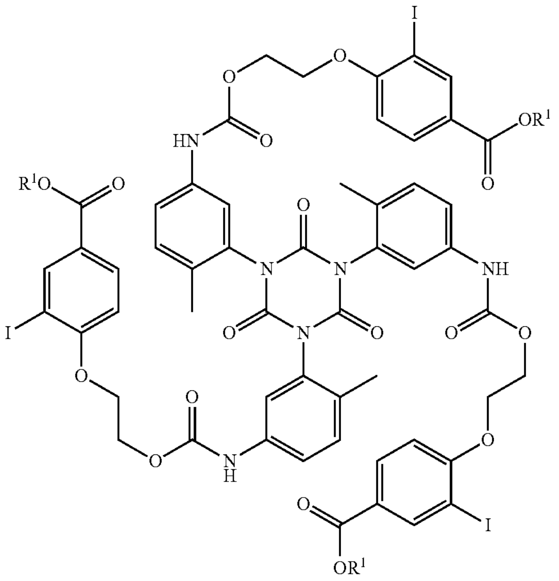
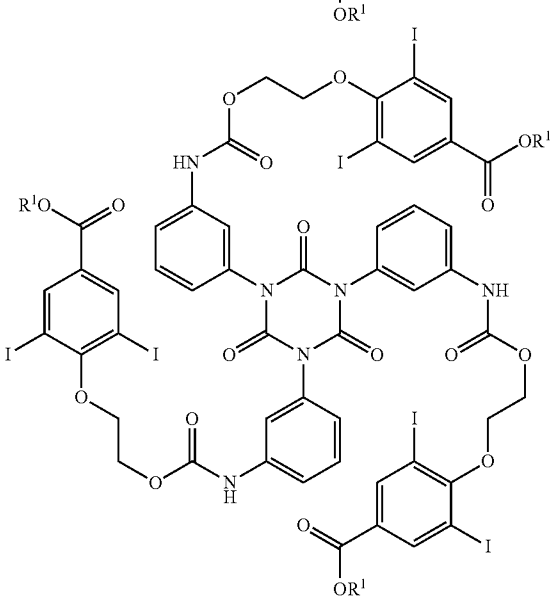
-continued
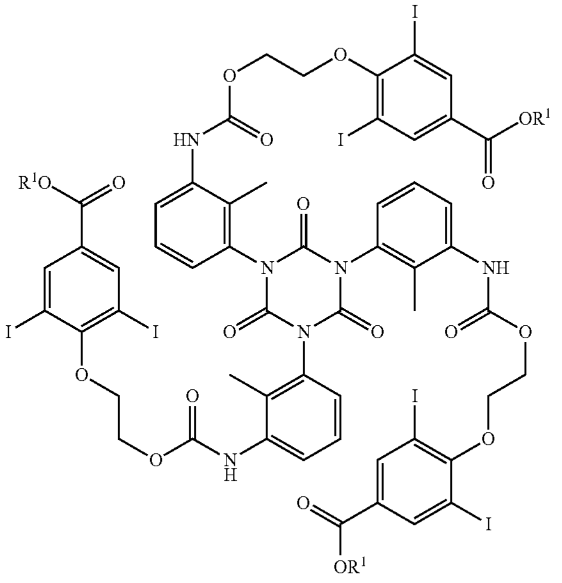
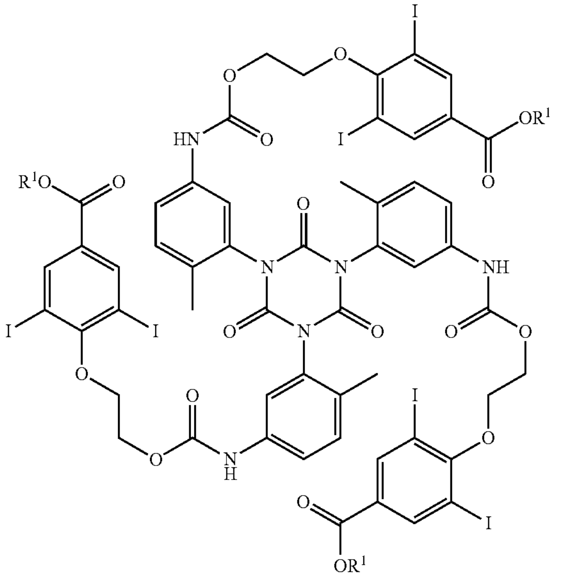

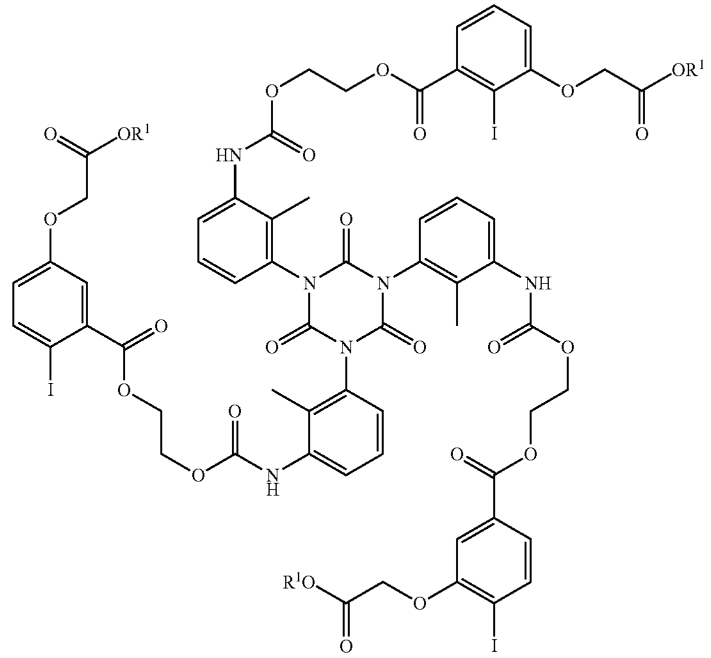
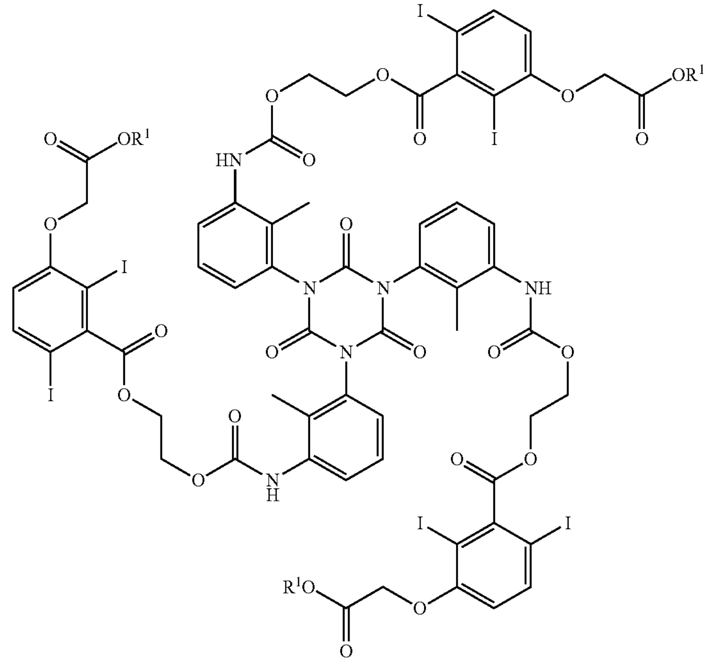

-continued
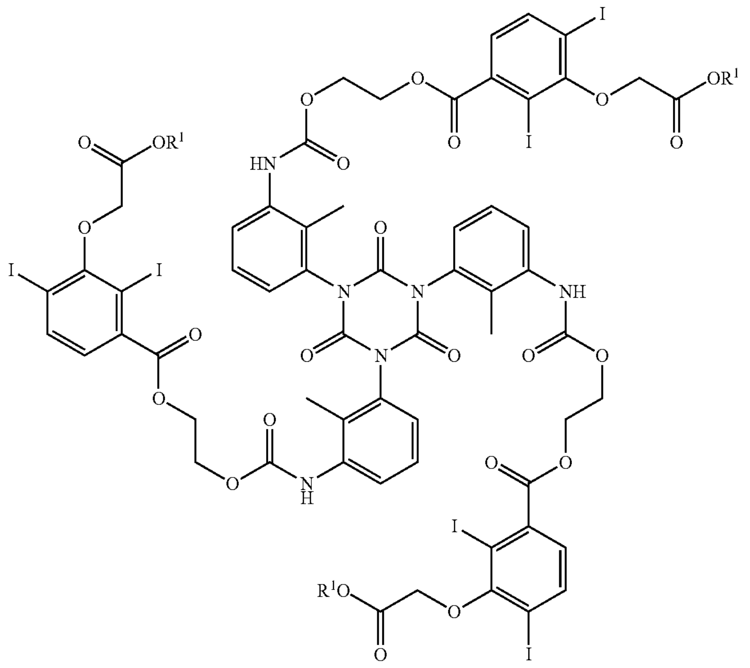
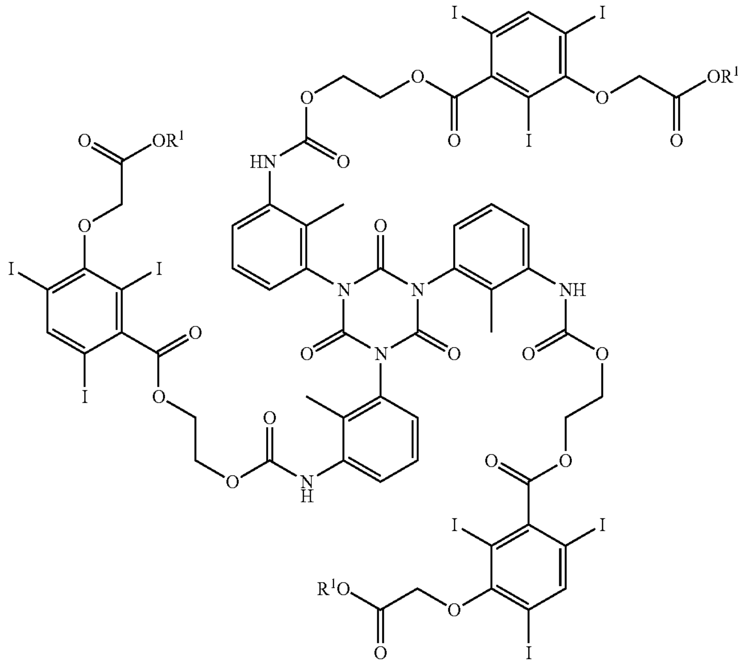

-continued
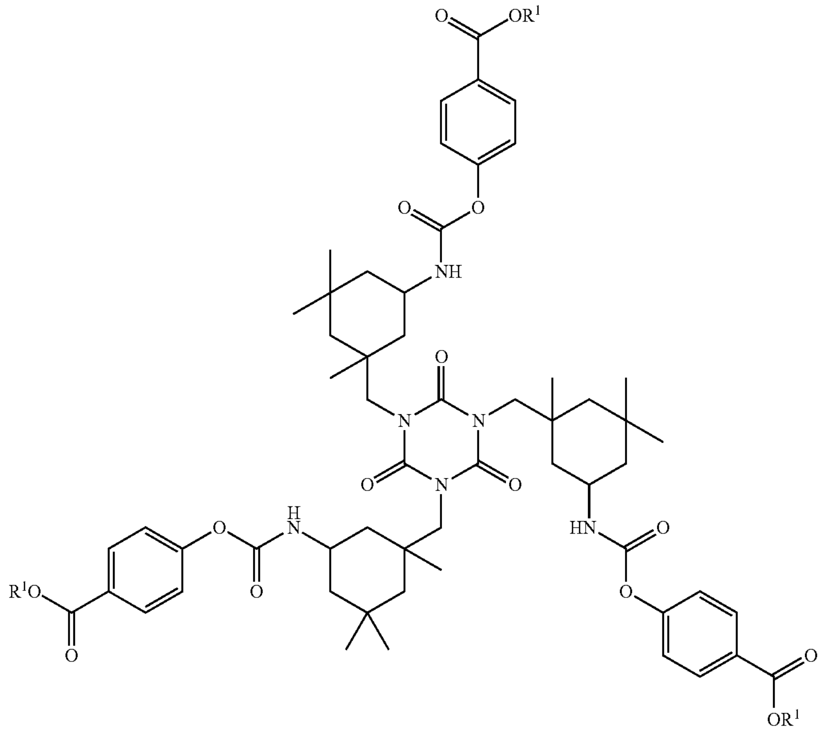
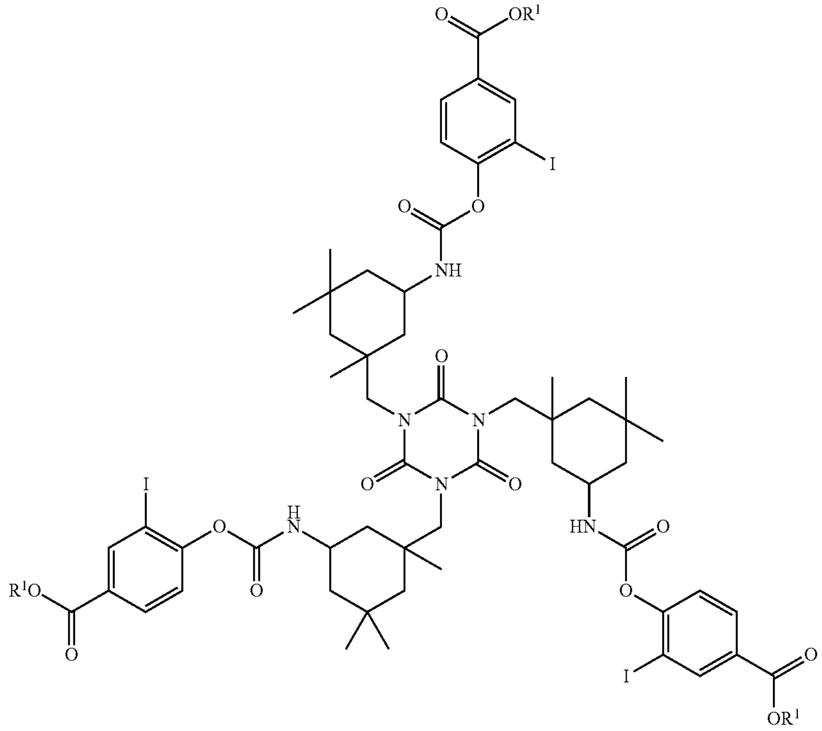

-continued
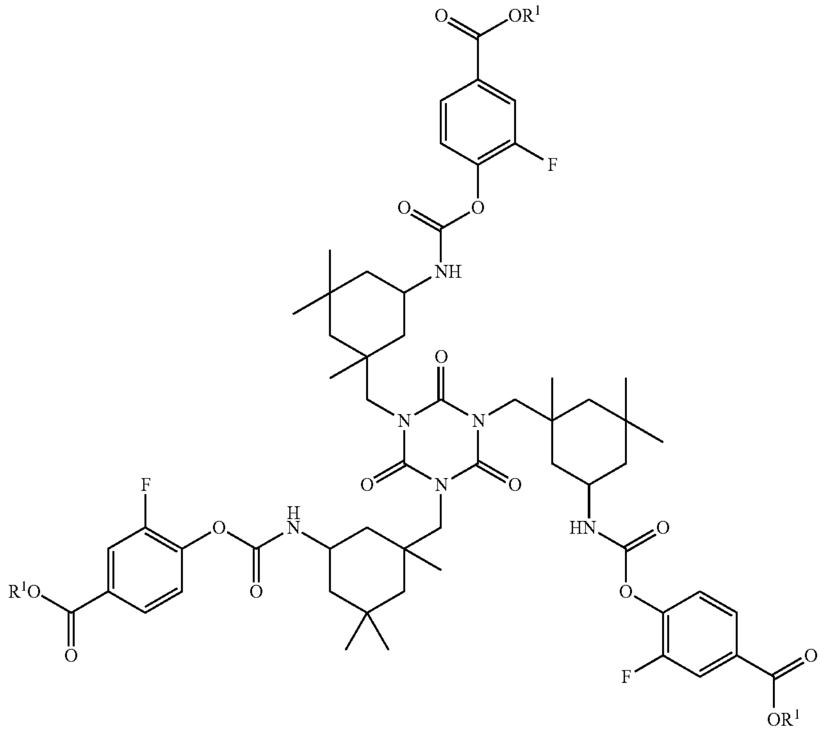
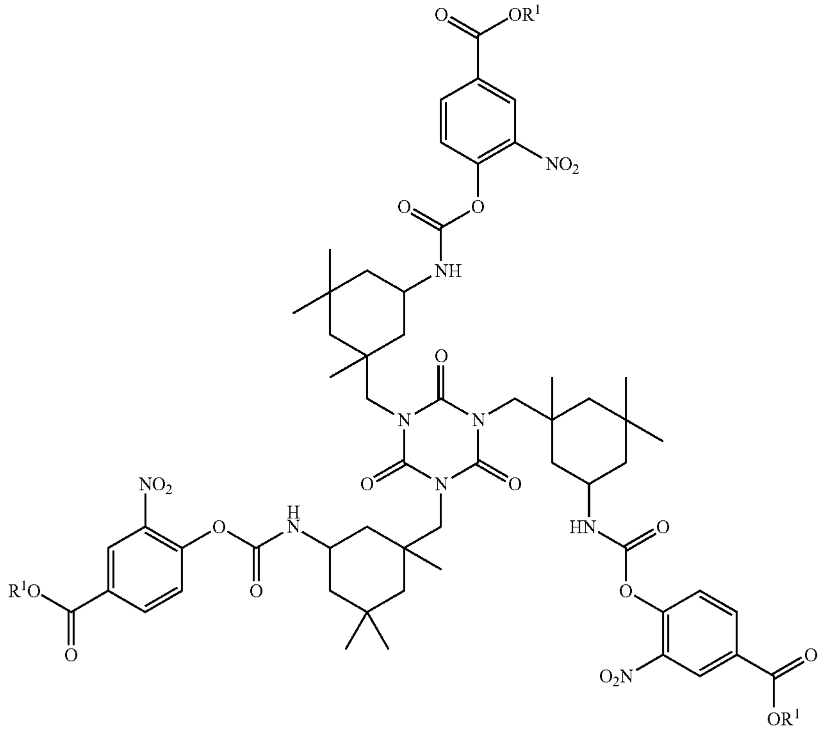

-continued
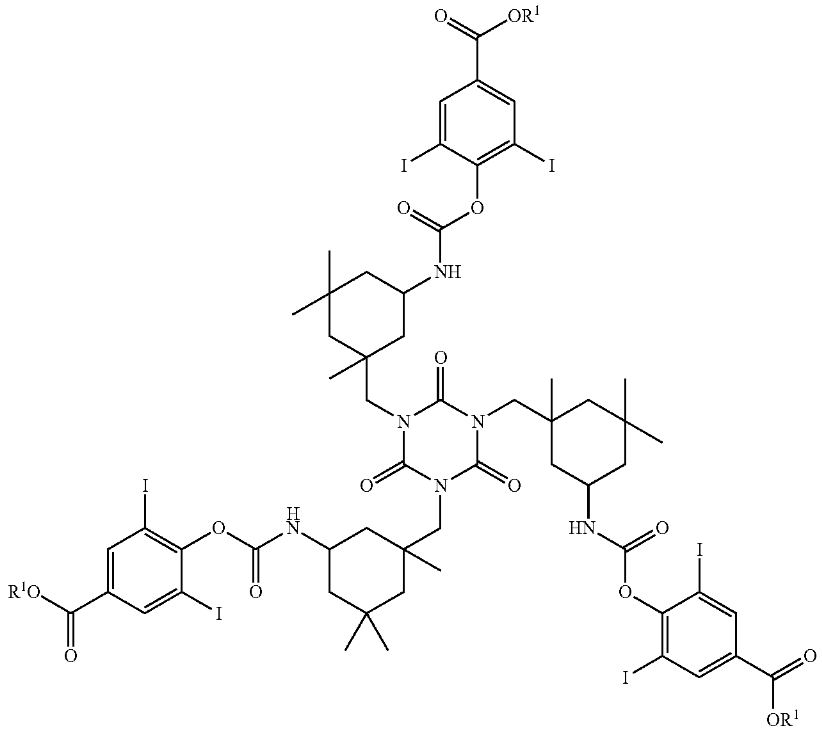
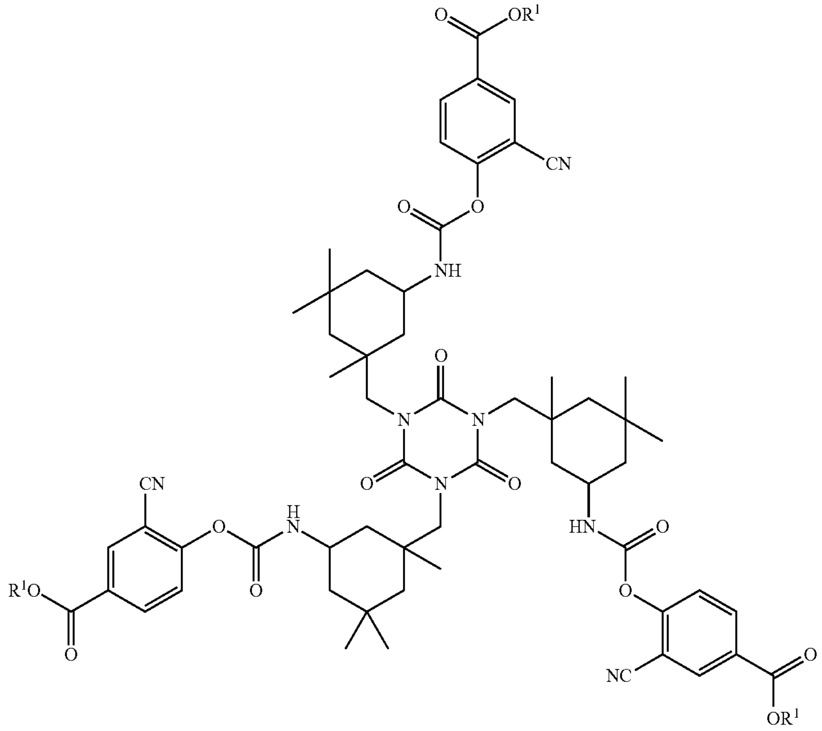

-continued
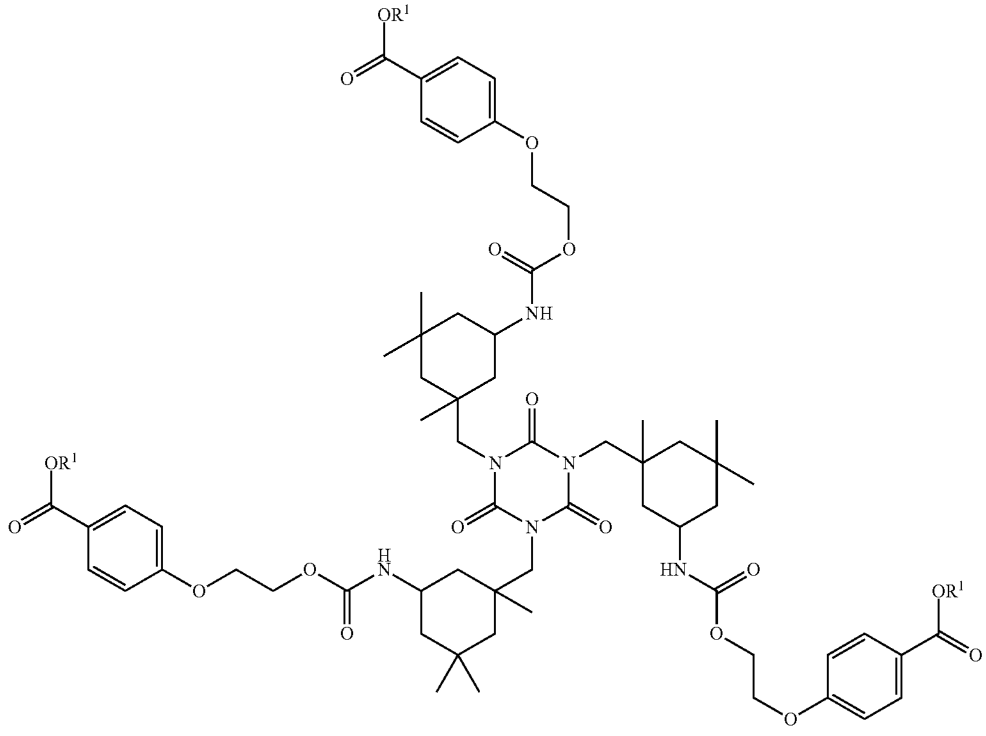
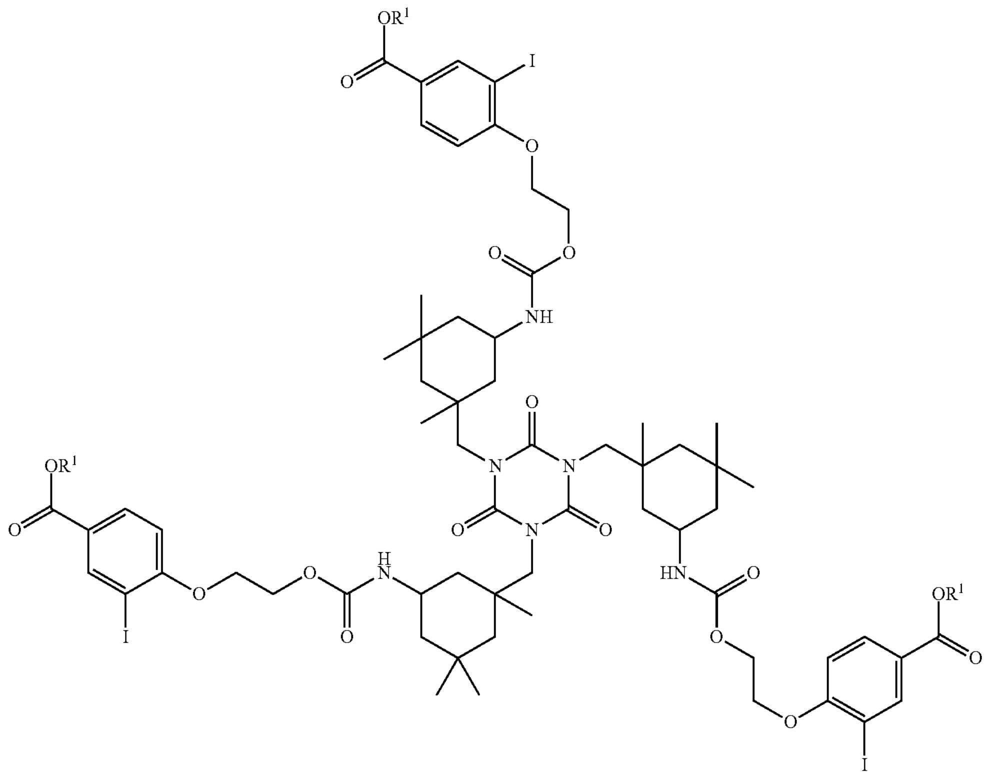

-continued
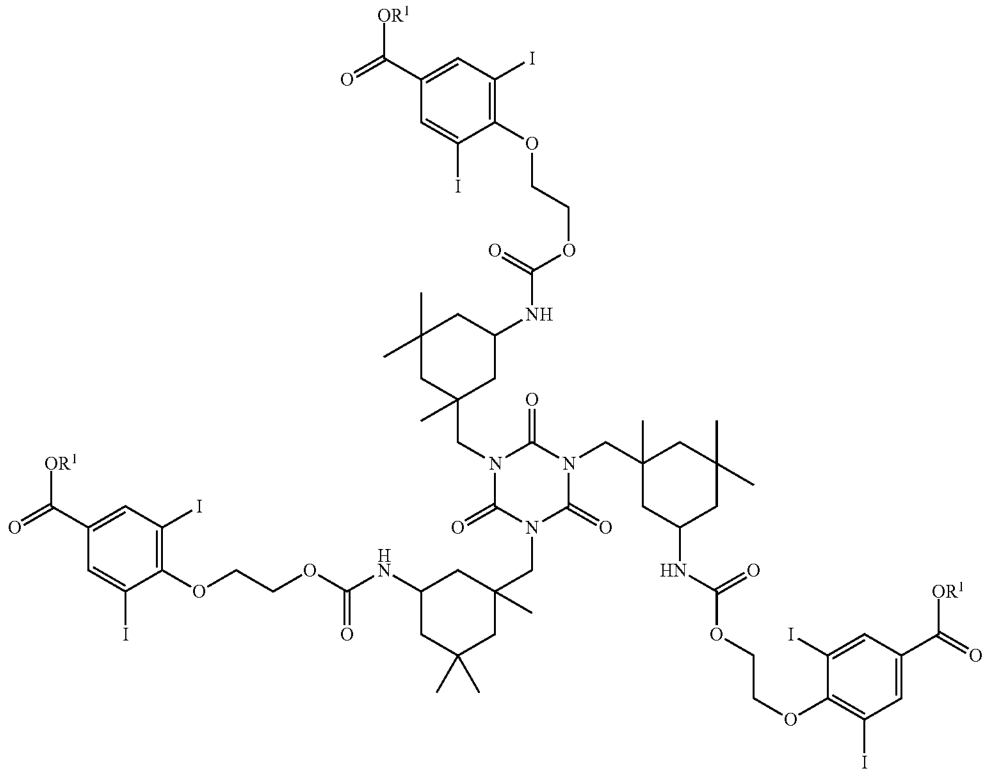
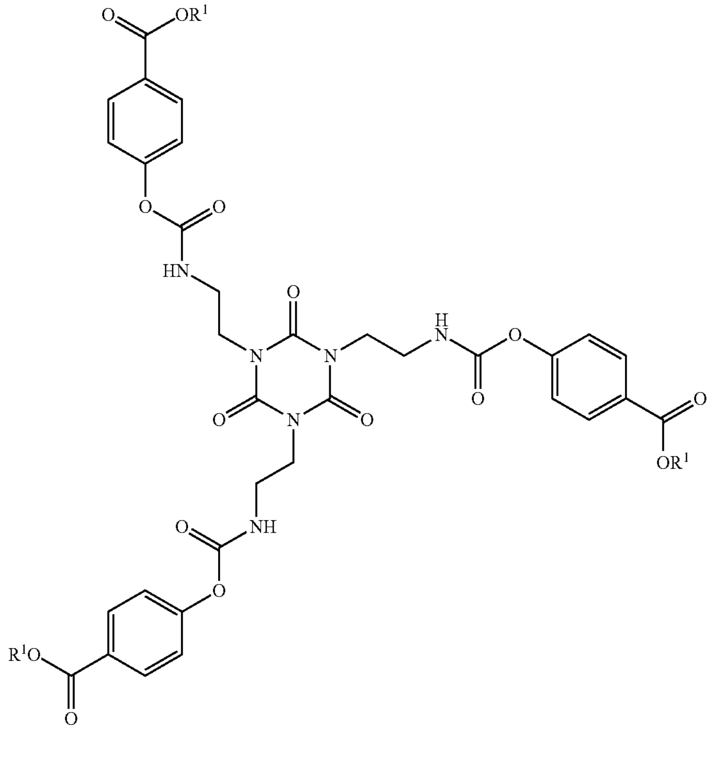

-continued
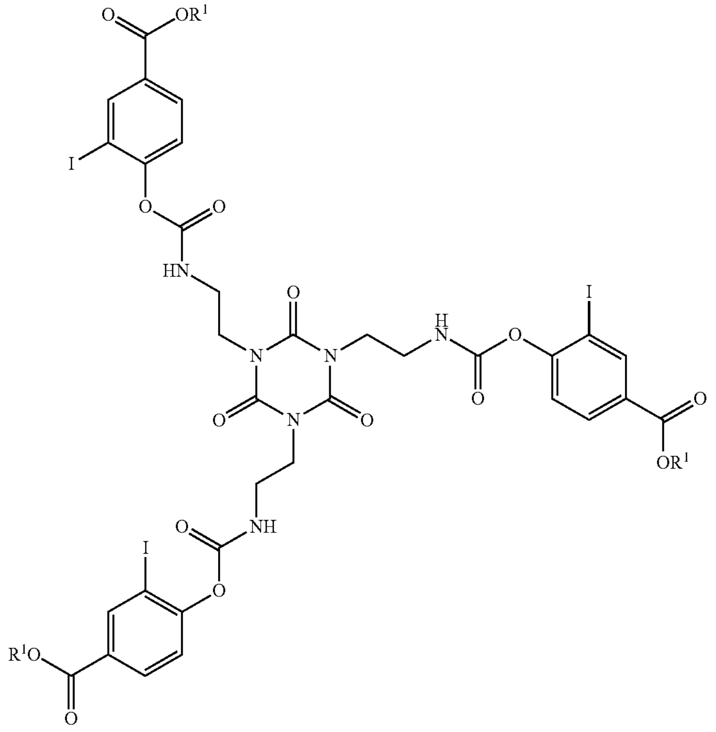
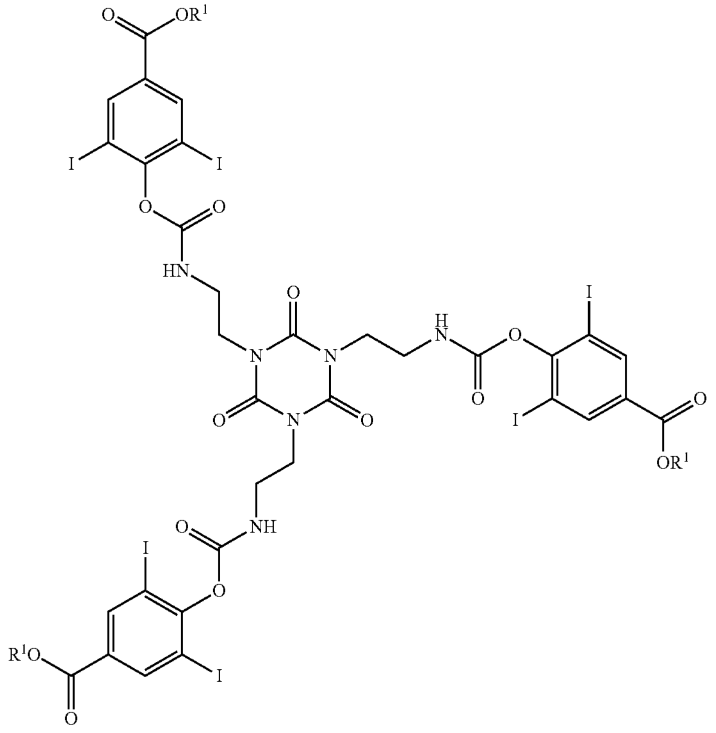

-continued
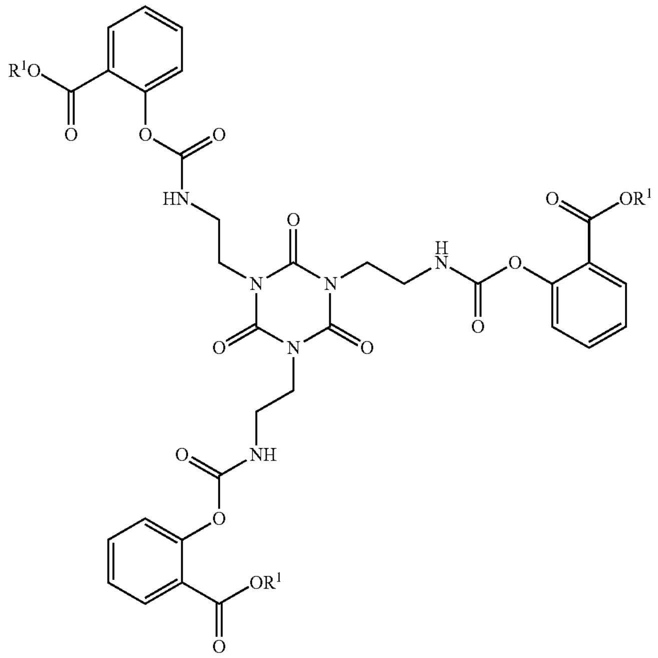
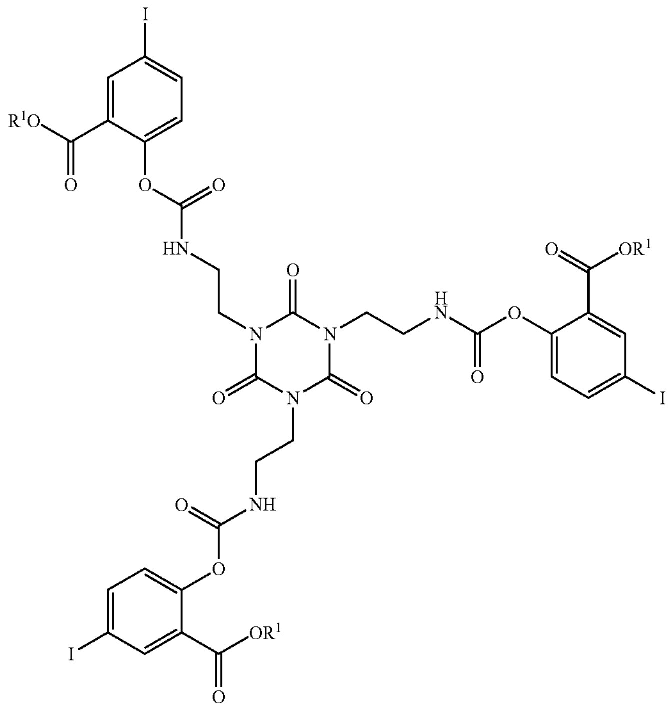

-continued
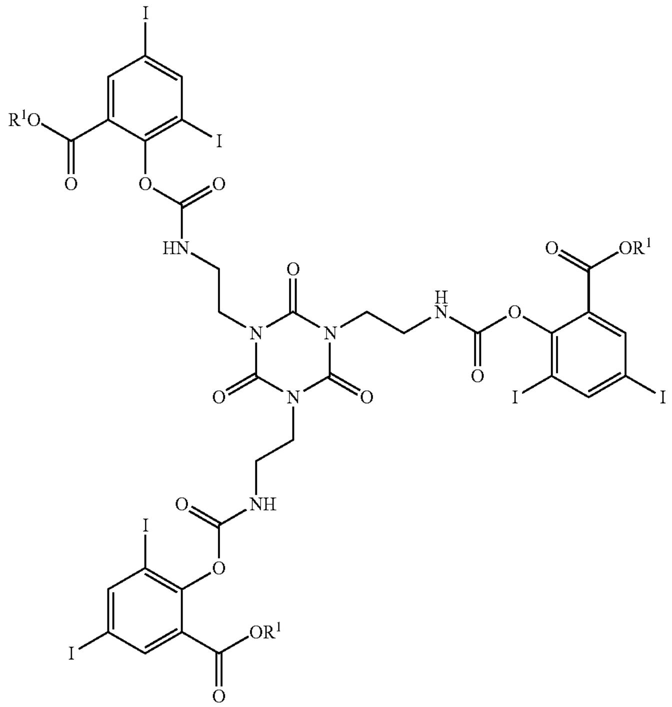
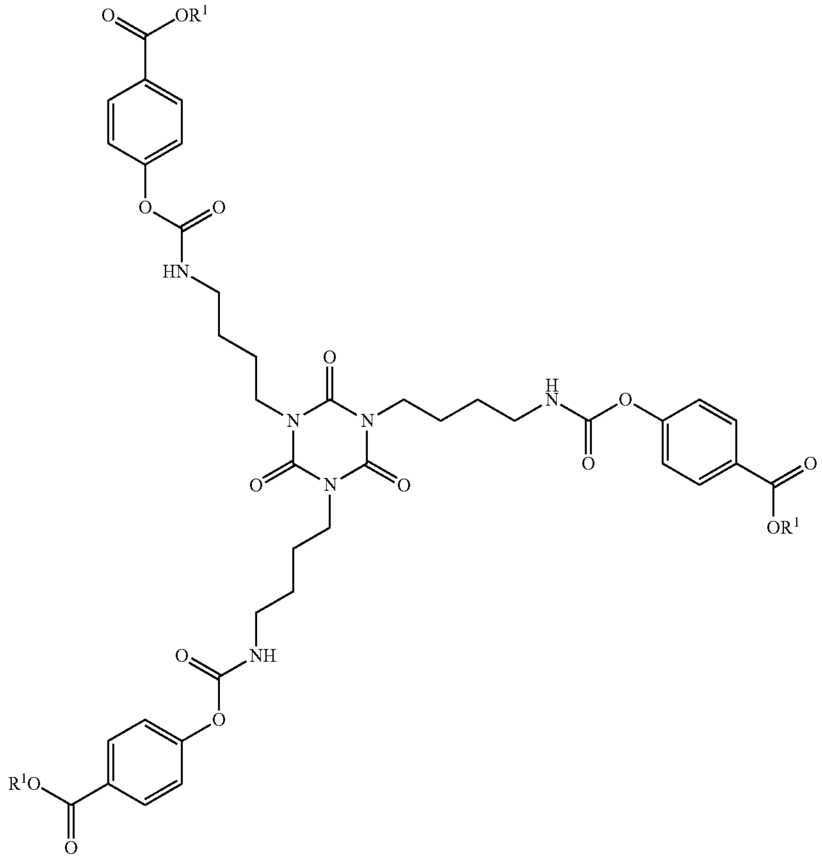

-continued
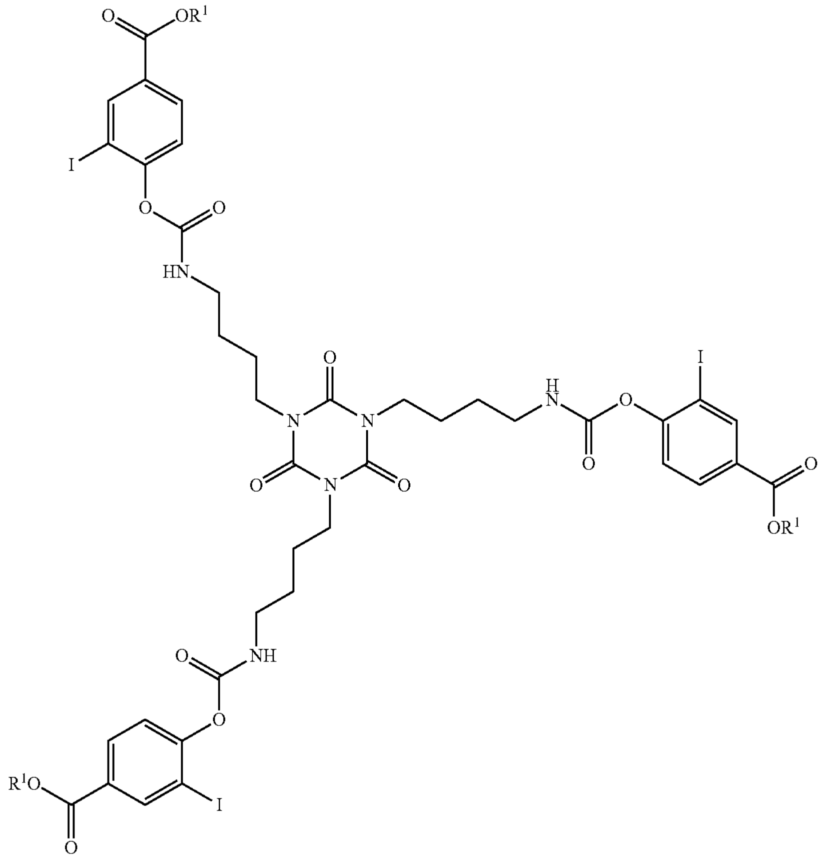
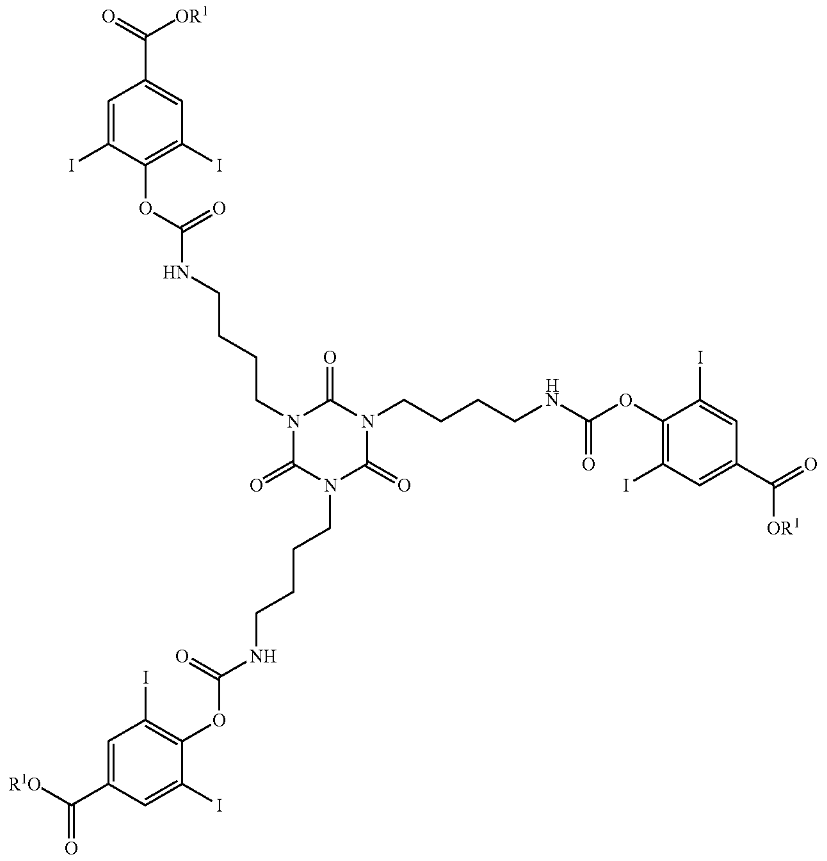

-continued
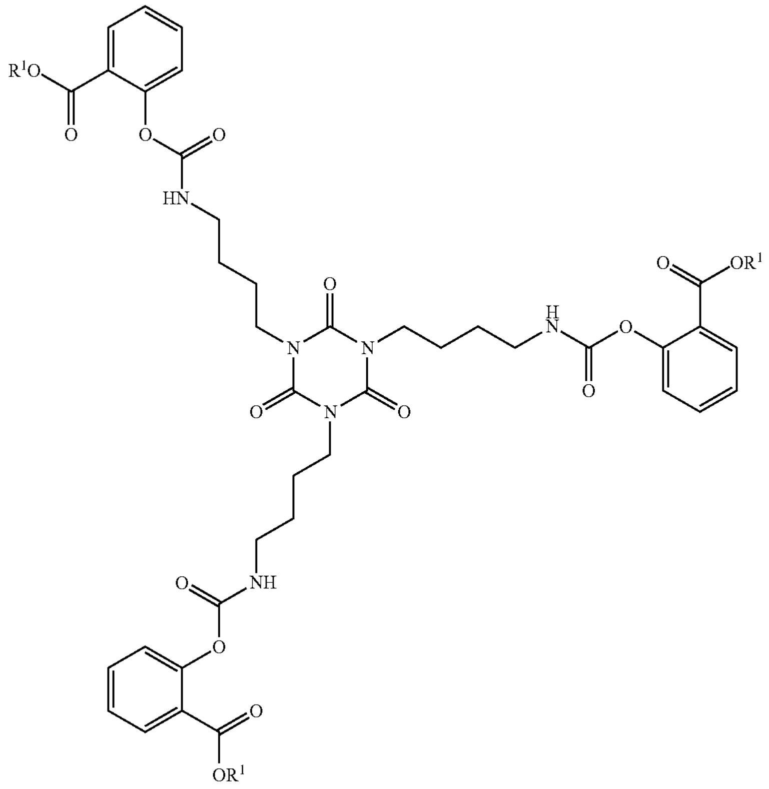
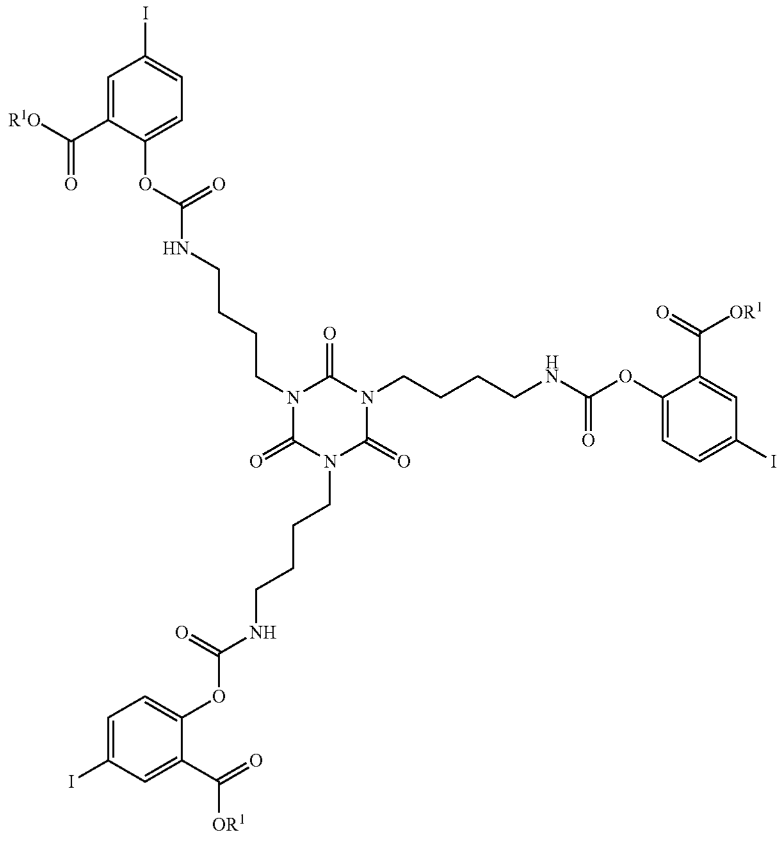

-continued
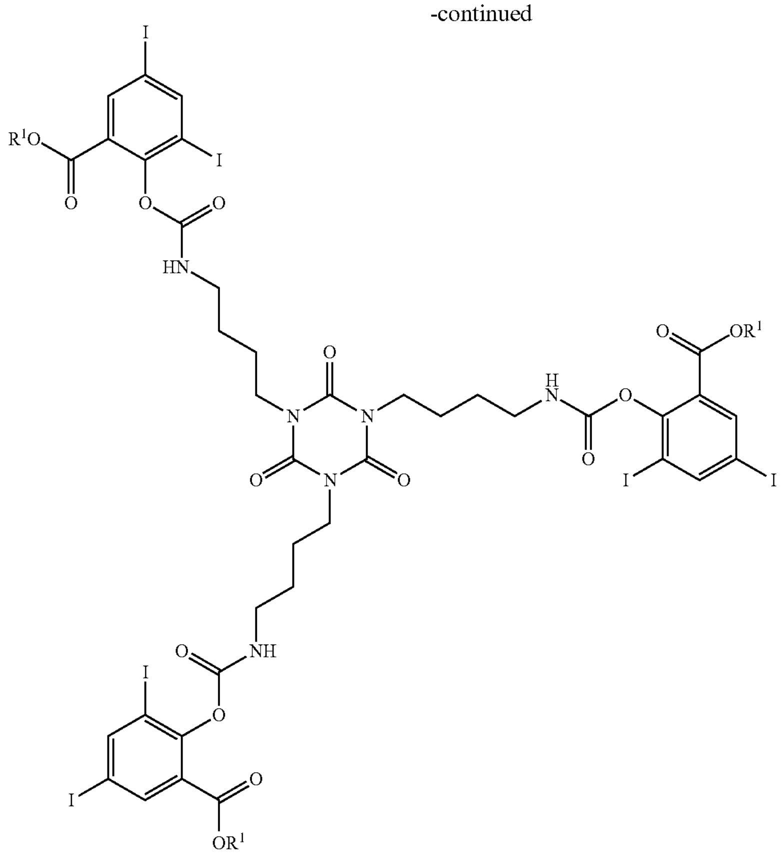
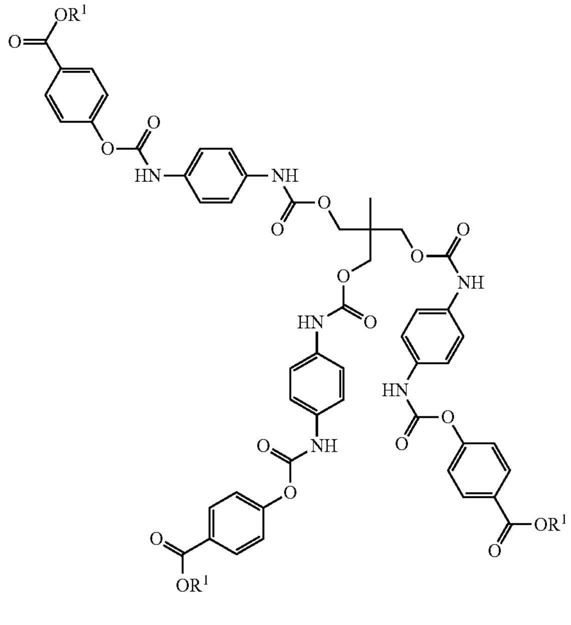
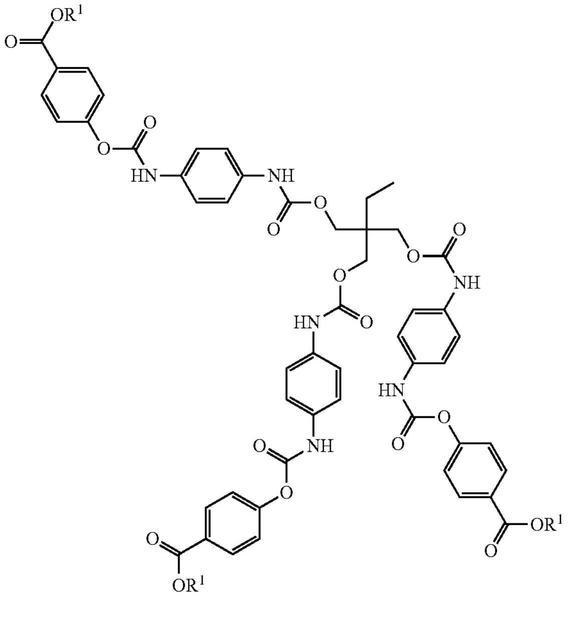

-continued
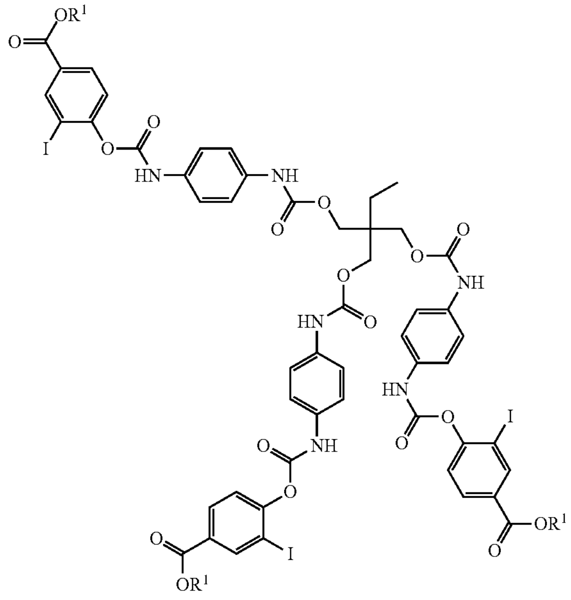
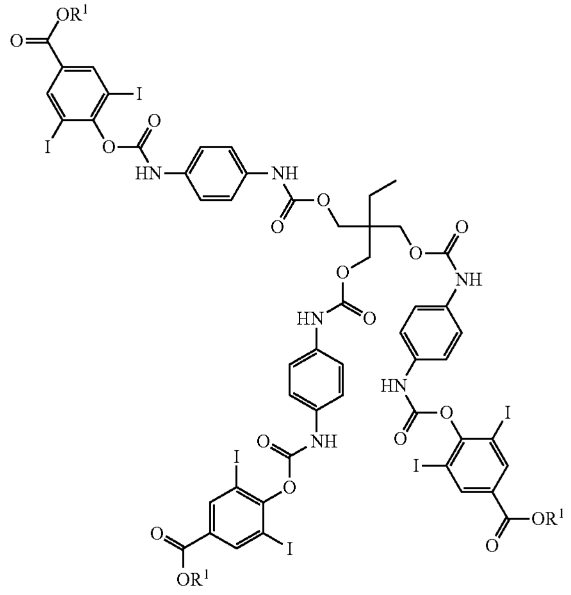
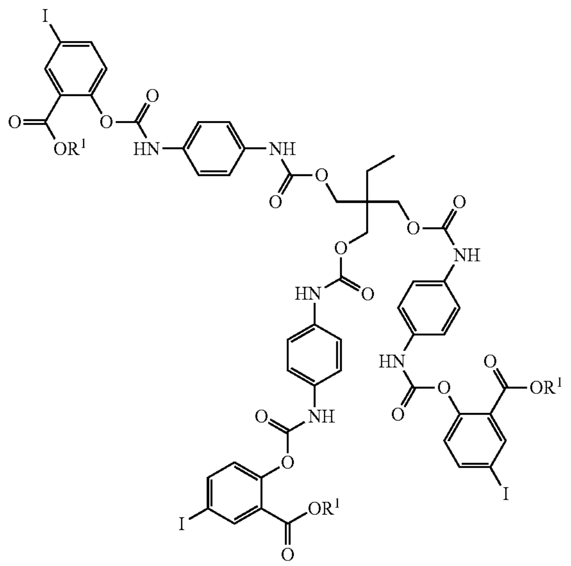
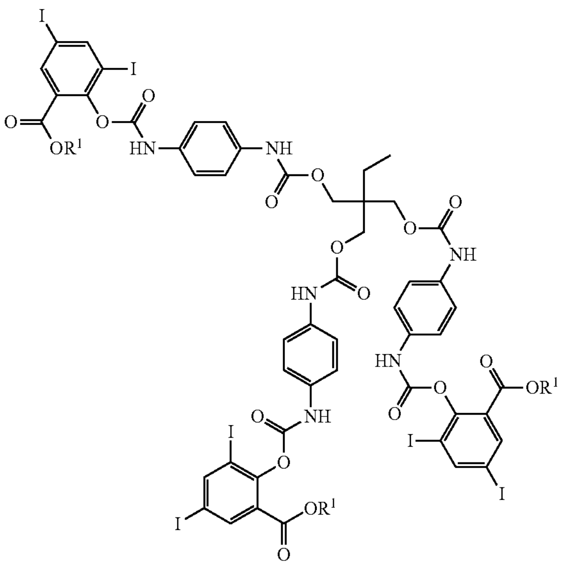

-continued
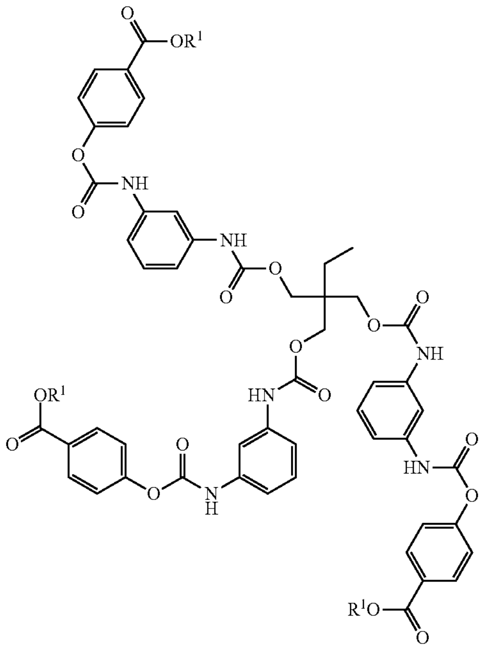
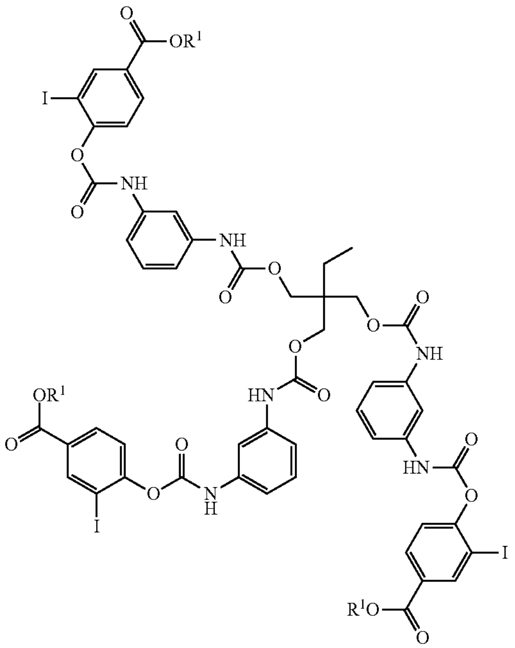
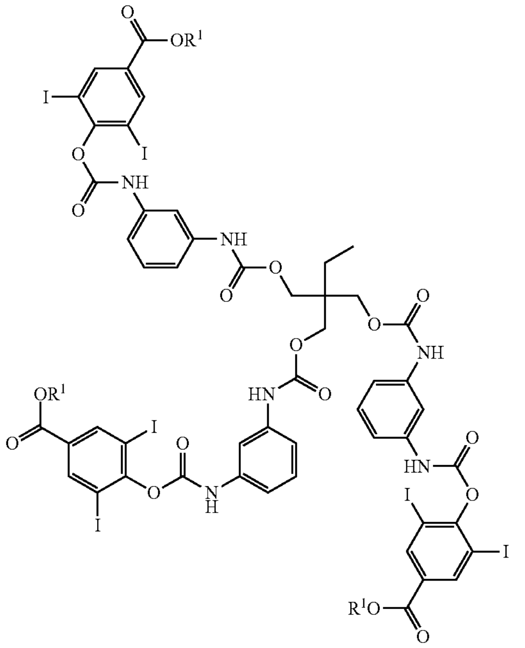
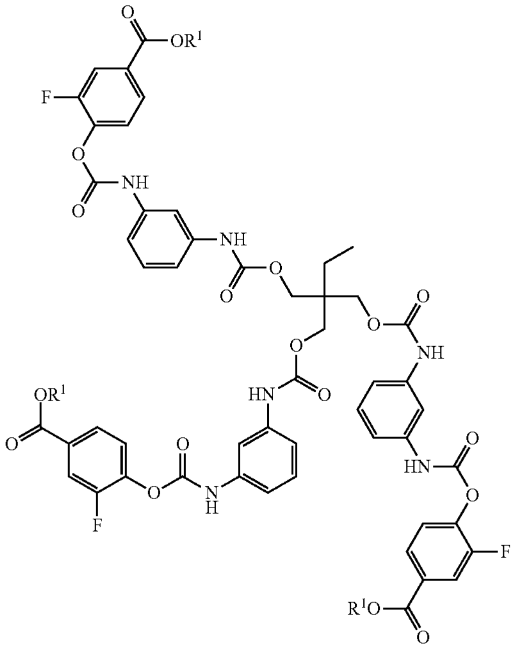

-continued
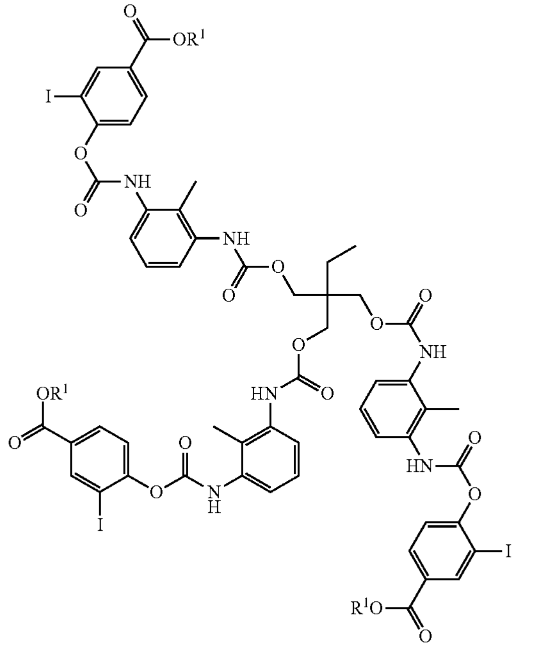
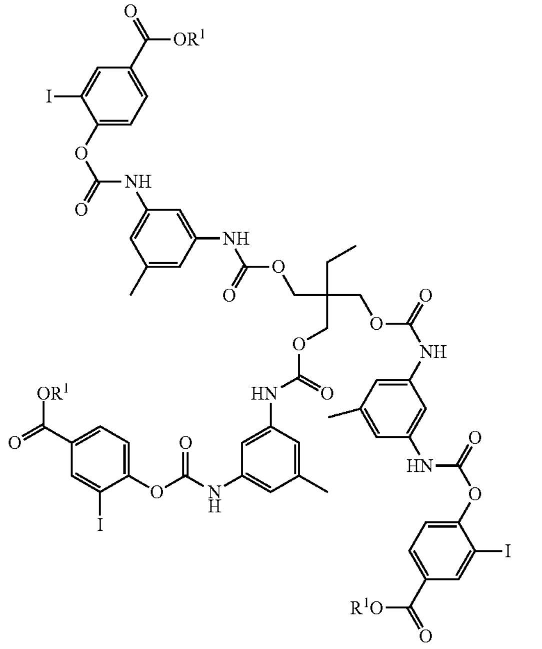
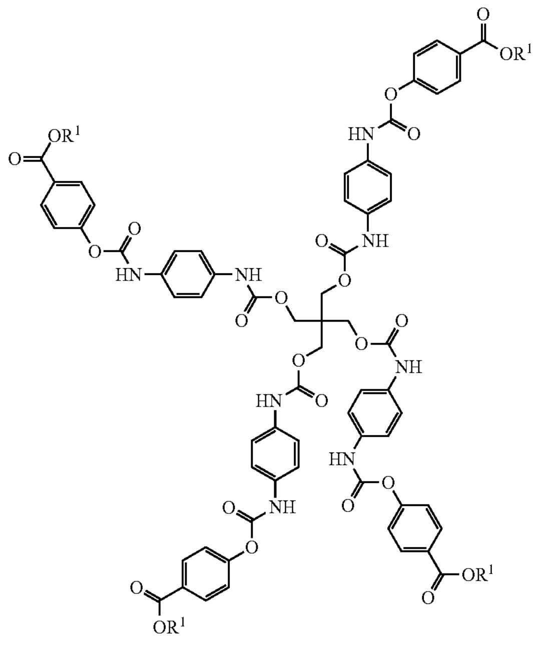
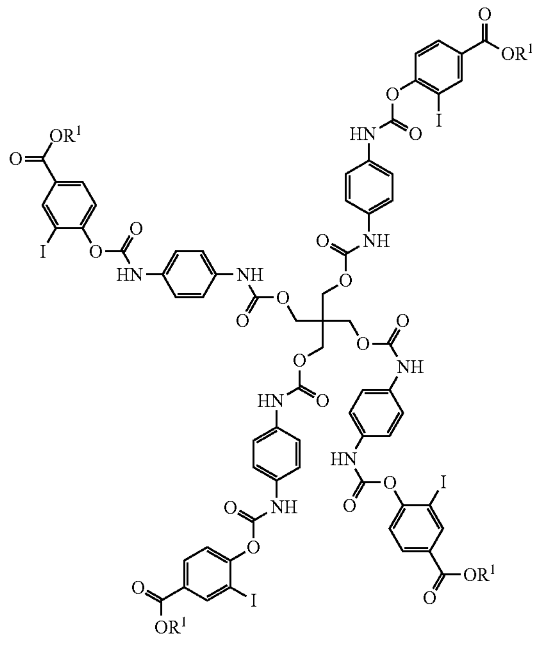

-continued
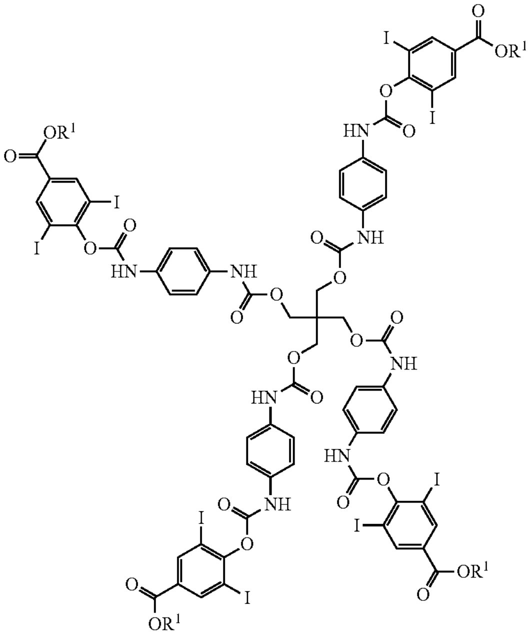
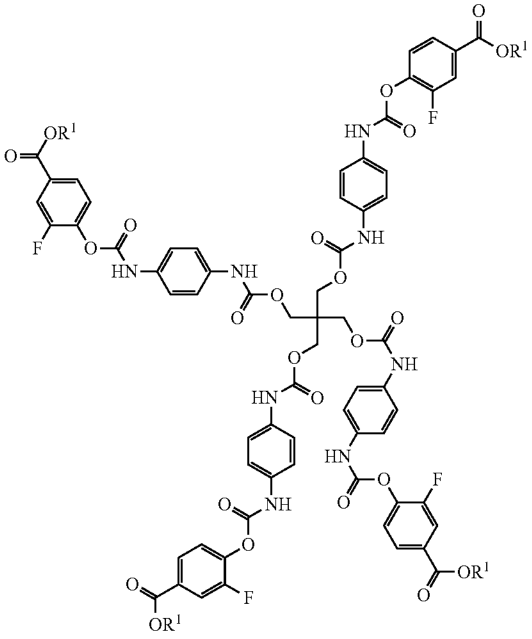
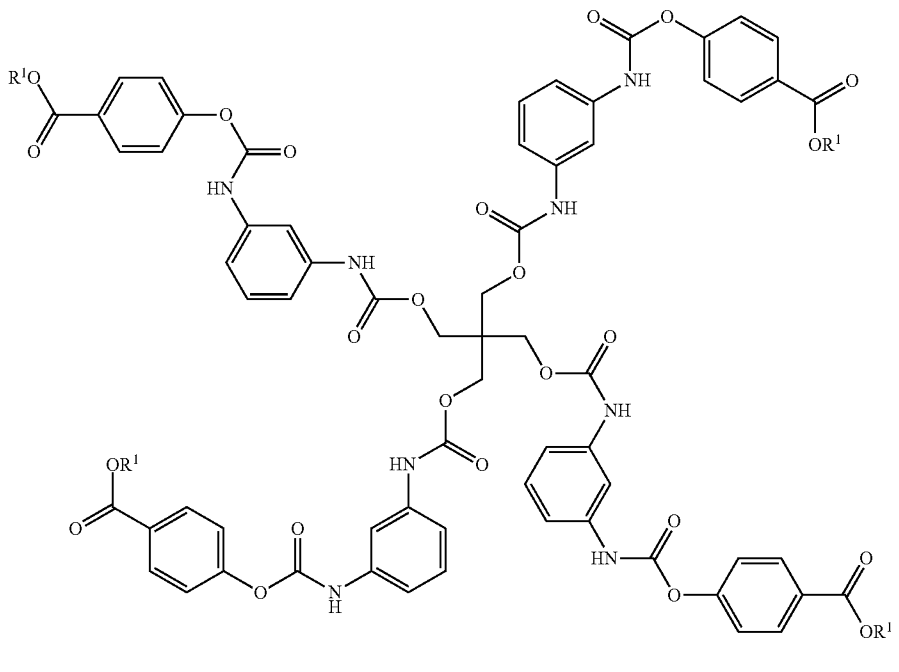

-continued
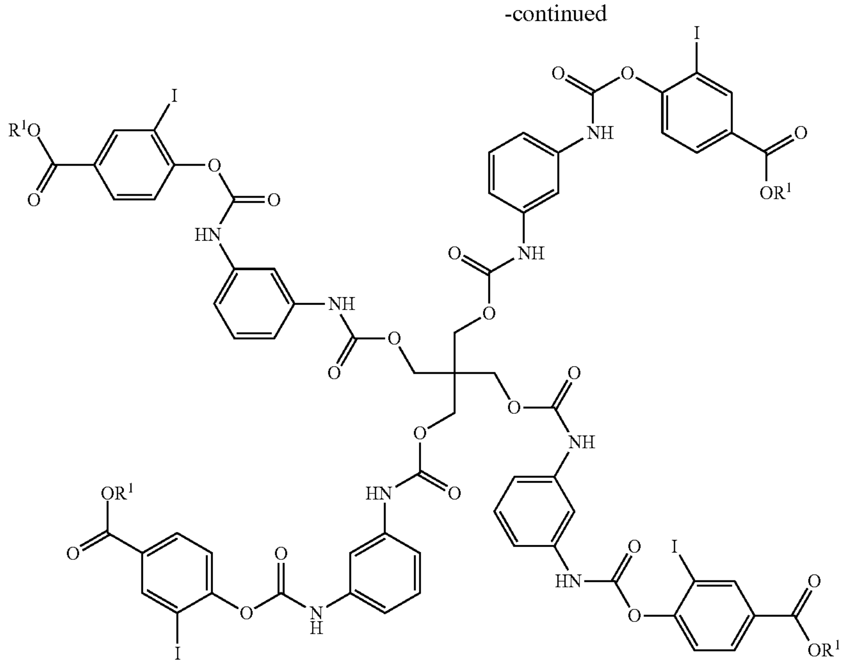
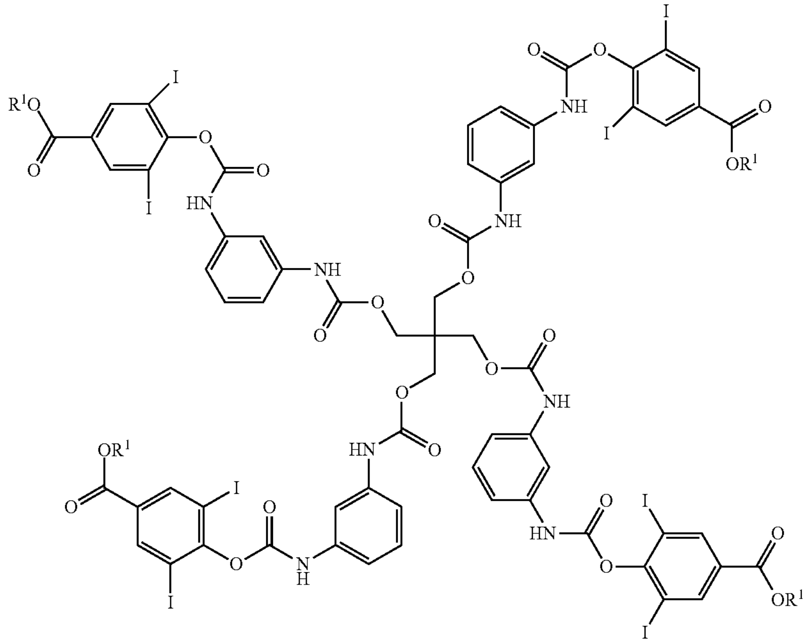

-continued
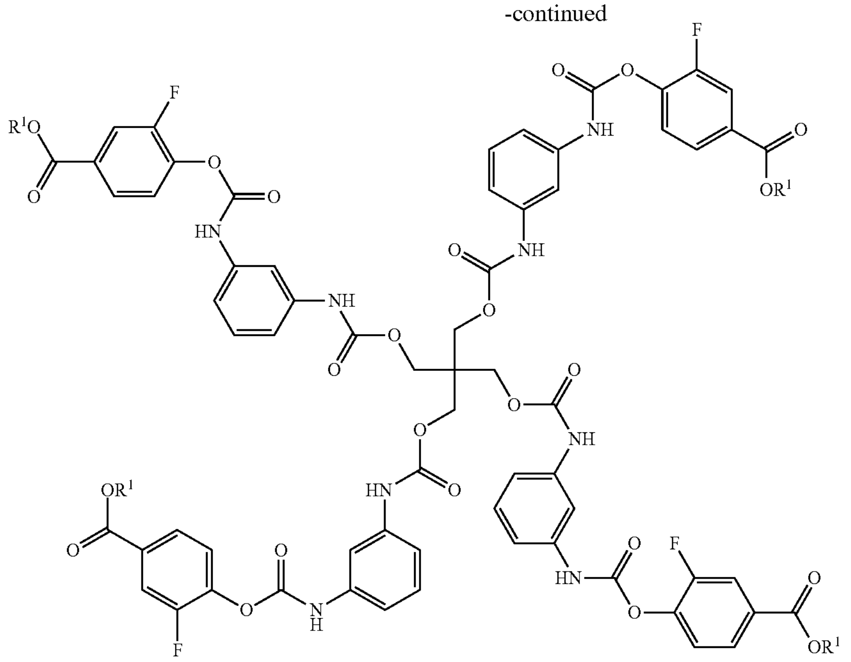
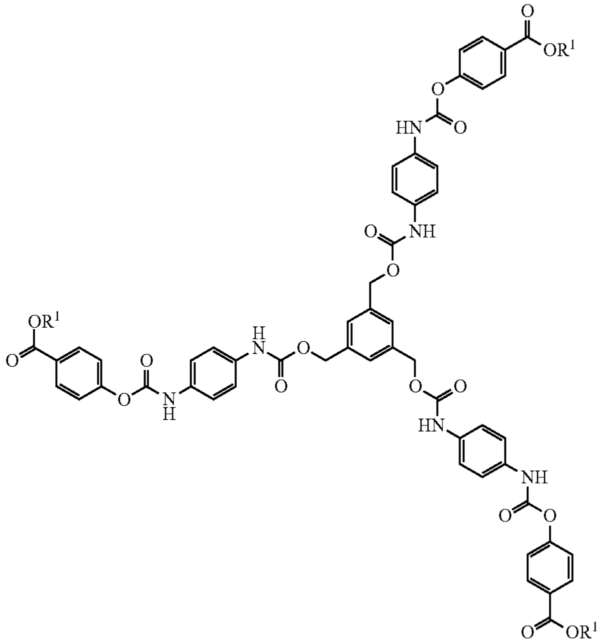

-continued
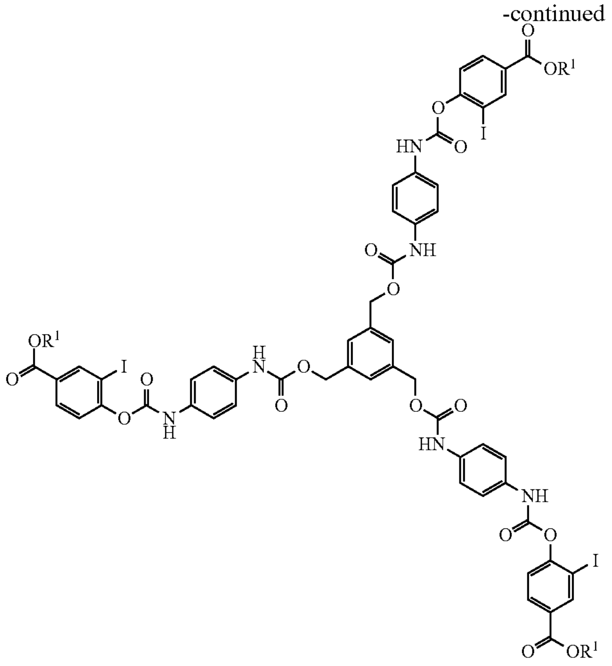
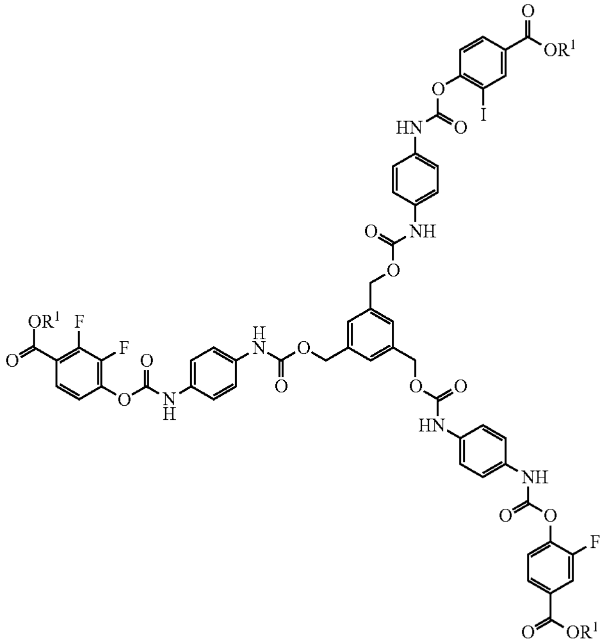

-continued
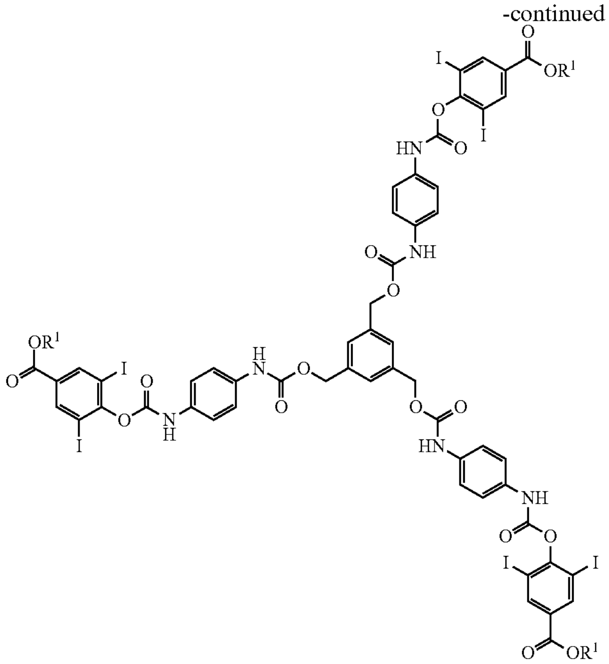
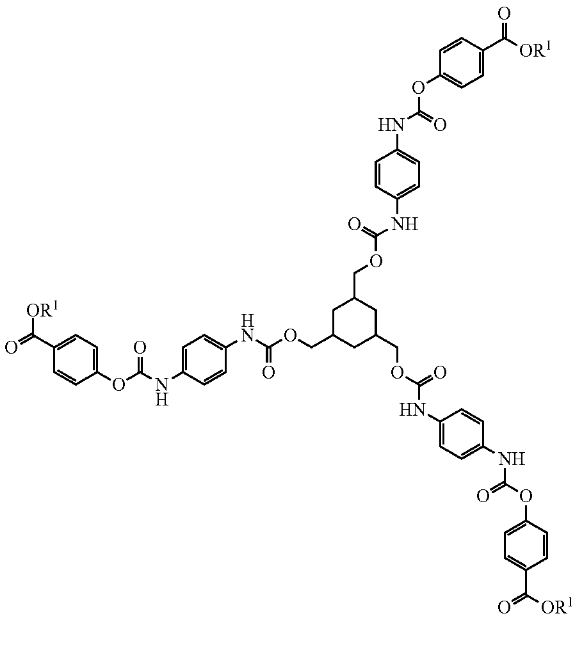
-continued
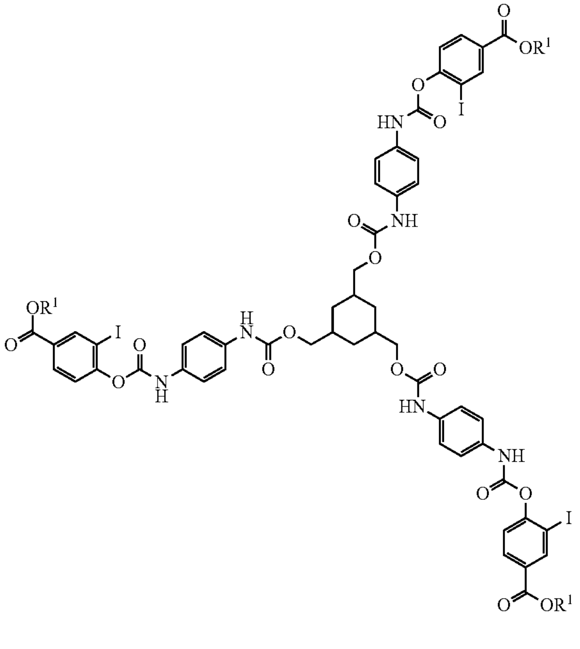

-continued
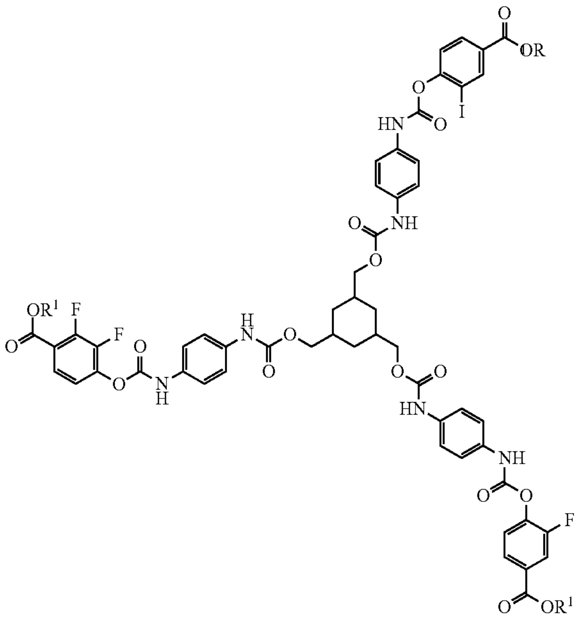
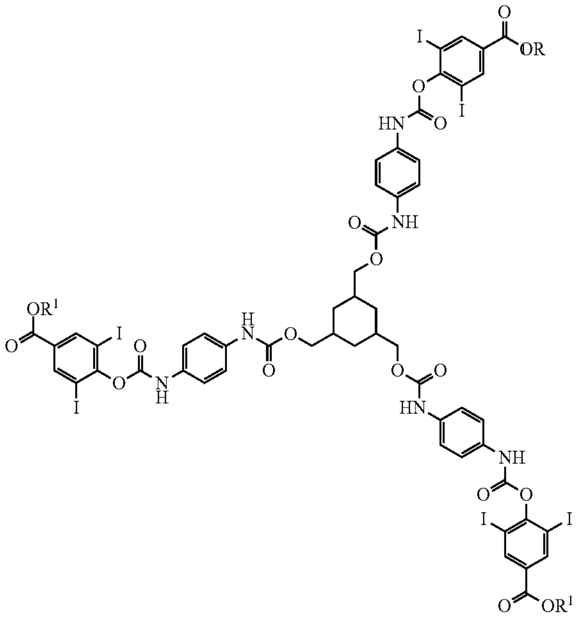
-continued
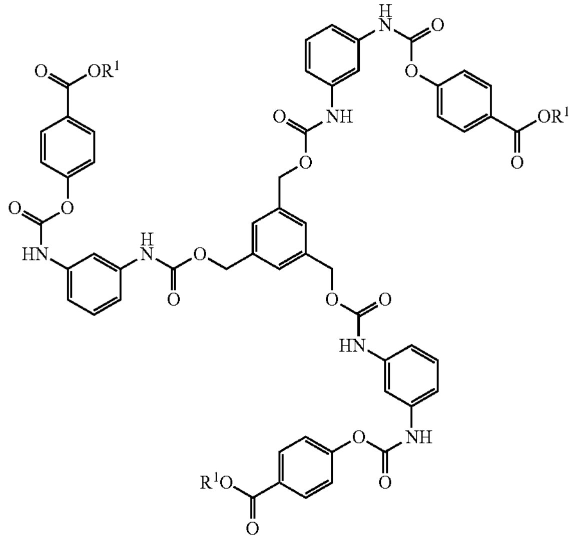
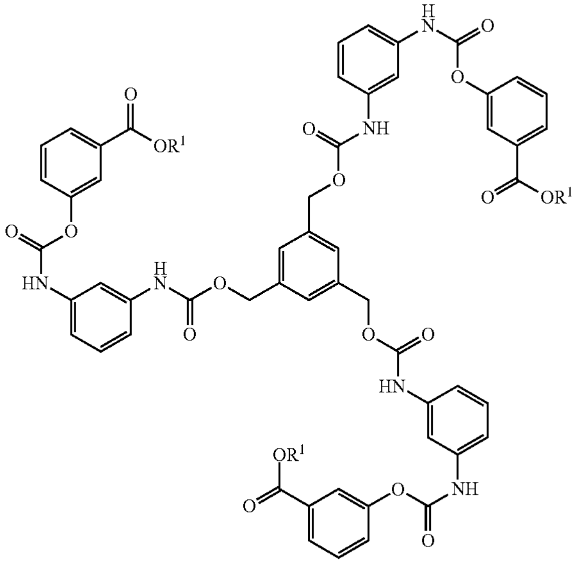
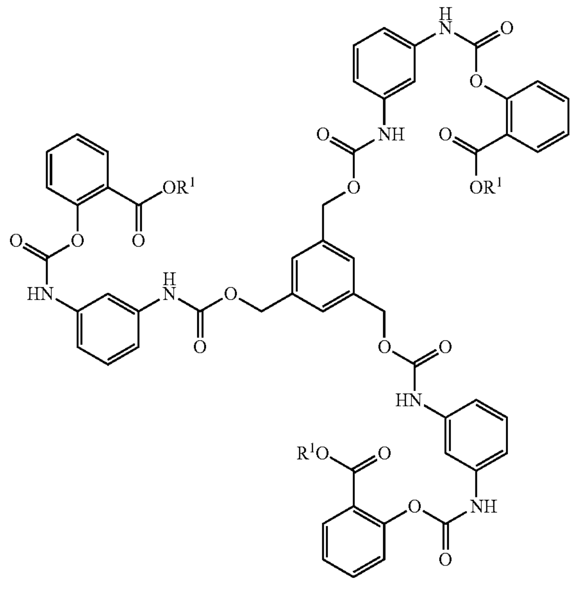

-continued

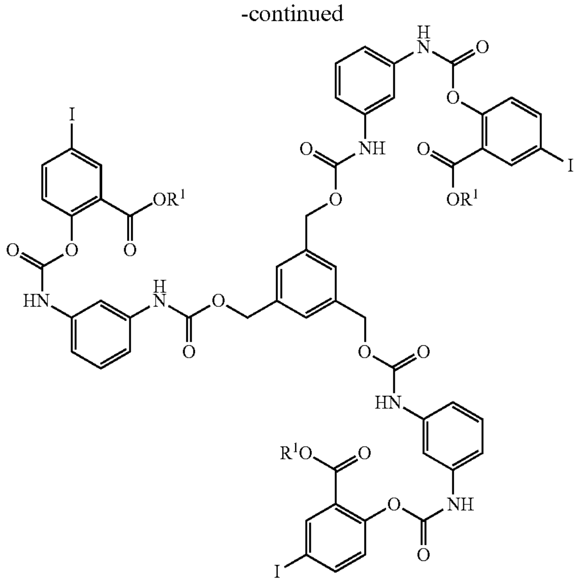

Here, $R^1$ represents an acid-labile group. The acid-labile groups $R^1$ may have the same structure or different structures within a molecule. Furthermore, the compound may also be a blend of compounds having different structures or compounds having different acid-labile groups.

The $R^1$ preferably satisfies one of the following 1) to 3):

1) a carbon atom bonded to an ester group is a tertiary carbon atom, and an alkyl group bonded to the tertiary carbon atom does not contain a halogen atom, a cyano group, or a nitro group;
2) a carbon atom bonded to an ester group is a secondary carbon atom and has a cyclic structure, does not contain a heteroatom, and has a double bond, a triple bond, or an aromatic group on a carbon atom other than the secondary carbon atom bonded to the ester group;
3) an acetal group having an ether group adjacent to a carbon atom bonded to an ester group.

As a method for synthesizing the compound, it is possible to obtain the compound by causing a reaction between a compound having two or more isocyanate groups and an acid compound having both a hydroxy group and a carboxy group substituted with an acid-labile group. This reaction may be performed without a catalyst, or may be performed with a catalyst. This catalyst is not particularly limited, but known catalysts include: organic tins, such as dibutyltin dilaurate; bismuth salts; zinc carboxylates, such as zinc 2-ethylhexanoate and zinc acetate; etc. Compounds having two or more isocyanate groups are disclosed in paragraphs [0082] and [0083] of JP 2020-023668 A.

In the reaction of the compound having two or more isocyanate groups, purity of the target compound is degraded by reaction with impurities also occurring if impurities, such as water, an amine compound, an alcohol compound, or a carboxy compound, are present. Therefore, it is necessary to remove impurities sufficiently before the reaction.

It is also possible to use a compound having two or more blocked isocyanate groups. A blocked isocyanate group gives an isocyanate group by a blocking group being removed by heating or a catalyst mentioned above. Specific examples of the blocked isocyanate groups include isocyanate groups substituted with alcohol, phenol, thioalcohol, imine, ketimine, amine, lactam, pyrazole, oxime, β-diketone, etc.

[Base Polymer]

The inventive positive resist material is a molecular resist material containing the above-described compound as a base, and can further contain a base polymer.

In order to improve dissolution contrast, the base polymer preferably contains: a repeating unit having an acid-labile group substituting a hydrogen atom of a carboxy group (hereinafter, also referred to as a repeating unit-a1); and/or a repeating unit having an acid-labile group substituting a hydrogen atom of a phenolic hydroxy group (hereinafter, also referred to as a repeating unit-a2).

Examples of the repeating units-a1 and -a2 respectively include repeating units represented by the following formulae (a1) and (a2).

(a1)

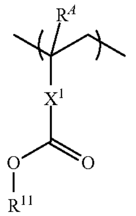

(a2)

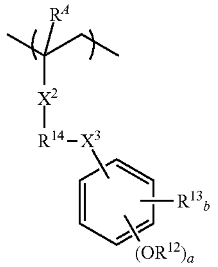

In the formulae (a1) and (a2), each $R^A$ independently represents a hydrogen atom or a methyl group. $X^1$ represents a single bond or a linking group having 1 to 14 carbon atoms and containing a phenylene group, a naphthylene group, an ester bond, an ether bond, or a lactone ring. $X^2$ represents a single bond, an ester bond, or an amide bond. $X^3$ represents a single bond, an ether bond, or an ester bond. $R^{11}$ and $R^{12}$ represent an acid-labile group. $R^{13}$ represents a fluorine atom, a trifluoromethyl group, a cyano group, or a saturated hydrocarbyl group having 1 to 6 carbon atoms. $R^{14}$ represents a single bond or a saturated hydrocarbylene group having 1 to 6 carbon atoms, part of the carbon atoms optionally being substituted with an ether bond or an ester bond. "a" represents 1 or 2 and "b" represents an integer of 0 to 4, provided that $1 \leq a+b \leq 5$.

Examples of a monomer to give the repeating unit-a1 include ones shown below, but are not limited thereto. Note that, in the following formulae, $R^A$ and $R^{11}$ are as defined above.

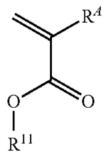

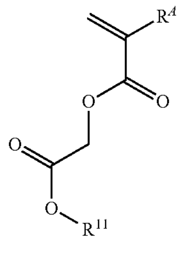

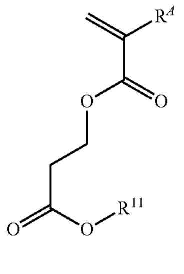

-continued
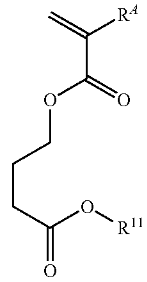
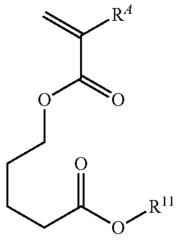
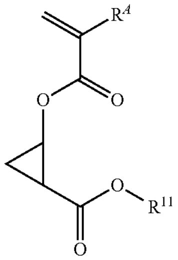
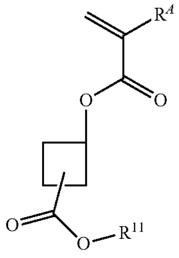
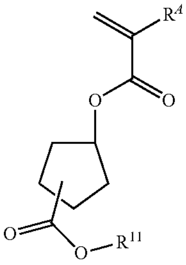
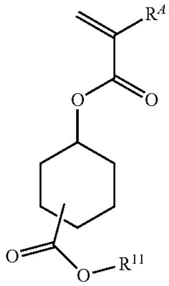
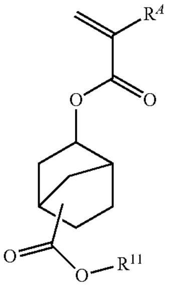
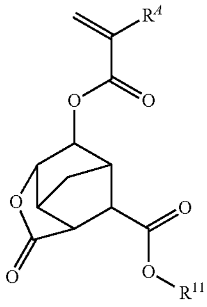
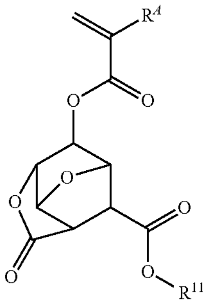
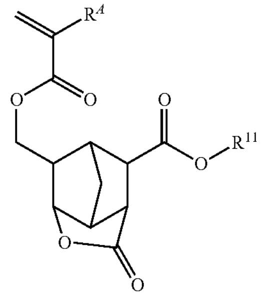
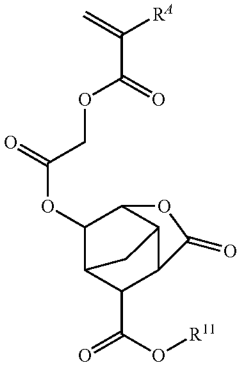
-continued
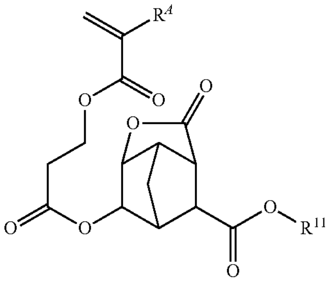
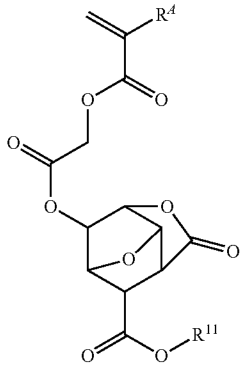
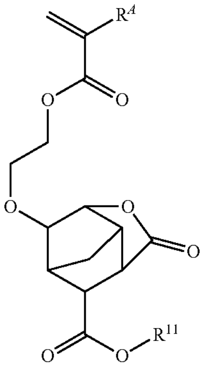
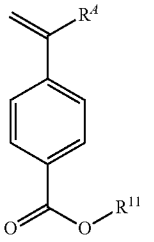
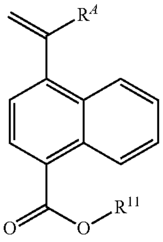
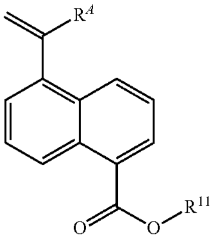
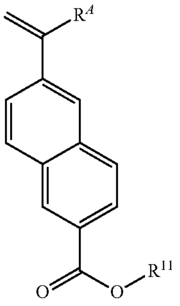
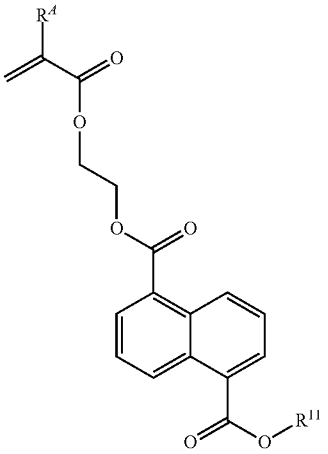

-continued
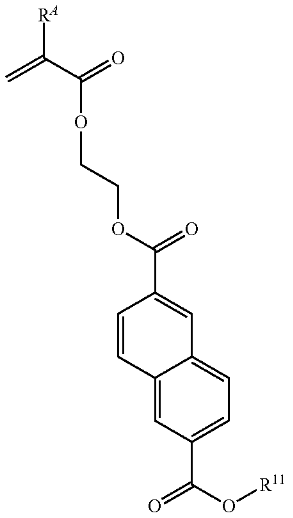
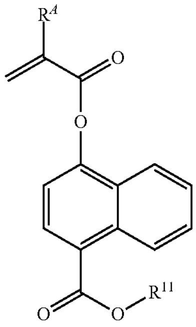
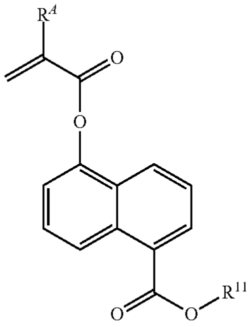
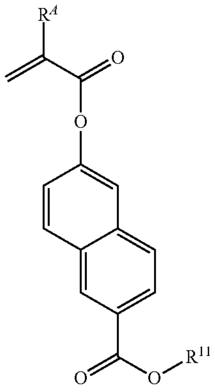
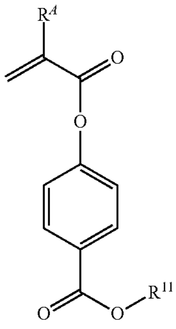
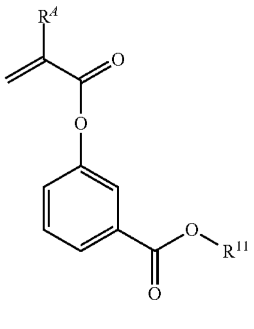
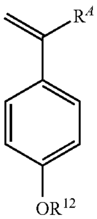
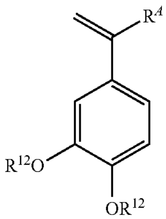
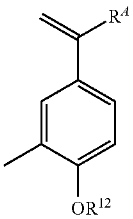
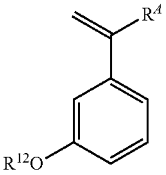
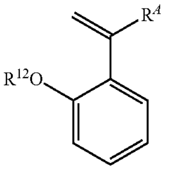
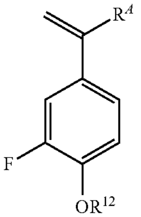
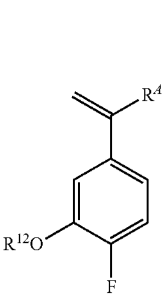
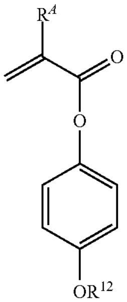
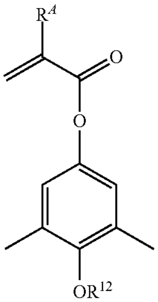
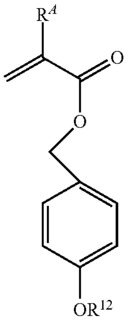
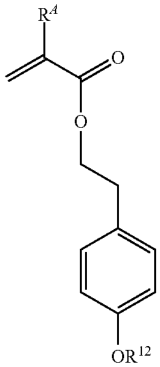
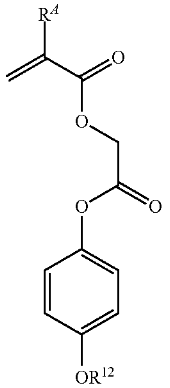
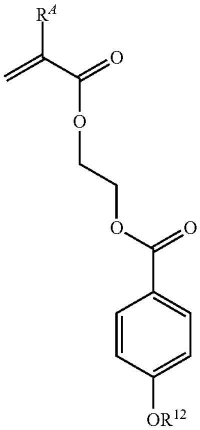
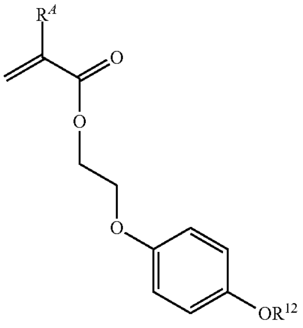
Examples of a monomer to give the repeating unit-a2 include ones shown below, but are not limited thereto. Note that, in the following formulae, $R^A$ and $R^{12}$ are as defined above.
Various acid-labile groups shown by $R^1$, $R^{11}$, or $R^{12}$ can be selected. Examples thereof include ones shown by the following formulae (AL-1) to (AL-3).

(AL-1)

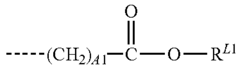

(AL-2)

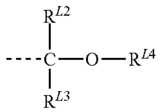

(AL-3)

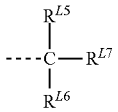

In the formulae, a broken line represents an attachment point.

In the formula (AL-1), $R^{L1}$ represents: a tertiary hydrocarbyl group having 4 to 61 carbon atoms, preferably 4 to 15 carbon atoms; a trihydrocarbylsilyl group in which hydrocarbyl groups are each a saturated hydrocarbyl group having 1 to 6 carbon atoms; a saturated hydrocarbyl group having 4 to 20 carbon atoms containing a carbonyl group, an ether bond, or an ester bond; or a group shown by the formula (AL-3). A1 represents an integer of 0 to 6. Note that a tertiary hydrocarbyl group means a group in which a hydrogen atom is removed from a tertiary carbon atom of a hydrocarbon.

The tertiary hydrocarbyl group shown by $R^{L1}$ may be saturated or unsaturated, and may be branched or cyclic. Specific examples thereof include a tert-butyl group, a tert-pentyl group, a 1,1-diethylpropyl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, a 2-methyl-2-adamantyl group, etc. Examples of the trihydrocarbylsilyl group include a trimethylsilyl group, a triethylsilyl group, a dimethyl-tert-butylsilyl group, etc. The saturated hydrocarbyl group containing a carbonyl group, an ether bond, or an ester bond may be linear, branched, or cyclic, and is preferably cyclic. Specific examples thereof include a 3-oxocyclohexyl group, a 4-methyl-2-oxooxan-4-yl group, a 5-methyl-2-oxooxolan-5-yl group, a 2-tetrahydropyranyl group, a 2-tetrahydrofuranyl group, etc.

Examples of the acid-labile group shown by the formula (AL-1) include a tert-butoxycarbonyl group, a tert-butoxycarbonylmethyl group, a tert-pentyloxycarbonyl group, a tert-pentyloxycarbonylmethyl group, a 1,1-diethylpropyloxycarbonyl group, a 1,1-diethylpropyloxycarbonylmethyl group, a 1-ethylcyclopentyloxycarbonyl group, a 1-ethylcyclopentyloxycarbonylmethyl group, a 1-ethyl-2-cyclopentenyloxycarbonyl group, a 1-ethyl-2-cyclopentenyloxycarbonylmethyl group, a 1-ethoxyethoxycarbonylmethyl group, a 2-tetrahydropyranyloxycarbonylmethyl group, a 2-tetrahydrofuranyloxycarbonylmethyl group, etc.

Other examples of the acid-labile group shown by the formula (AL-1) include groups shown by the following formulae (AL-1)-1 to (AL-1)-16.

(AL-1)-1

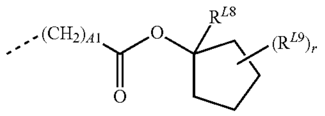

-continued (AL-1)-2

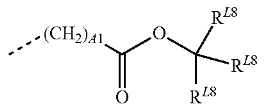

(AL-1)-3

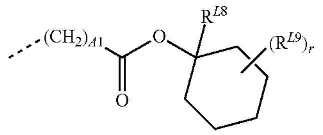

(AL-1)-4

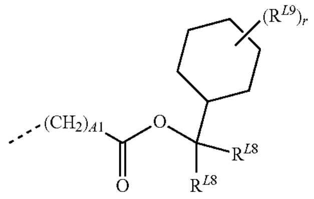

(AL-1)-5

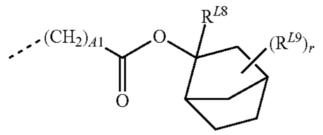

(AL-1)-6

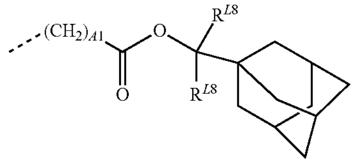

(AL-1)-7

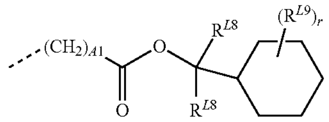

(AL-1)-8

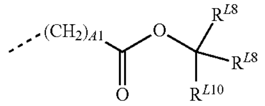

(AL-1)-9

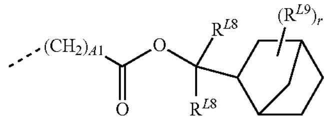

(AL-1)-10

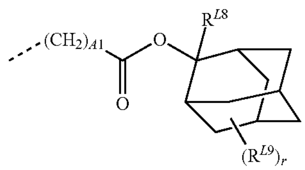

(AL-1)-11

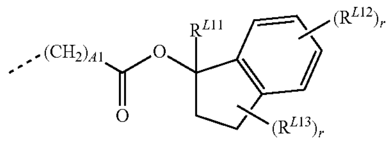

-continued (AL-1)-12

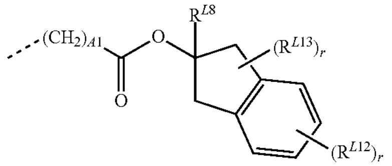

(AL-1)-13

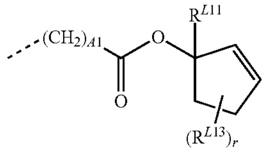

(AL-1)-14

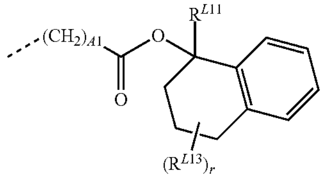

(AL-1)-15

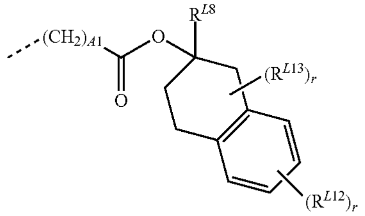

(AL-1)-16

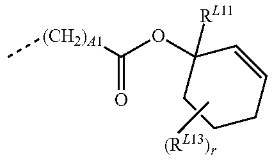

In the formulae, a broken line represents an attachment point.

In the formulae (AL-1)-1 to (AL-1)-16, A1 is as defined above. Each $R^{L8}$ independently represents a saturated or unsaturated hydrocarbyl group having 1 to 10 carbon atoms or an aryl group having 6 to 20 carbon atoms. $R^{L9}$ represents a hydrogen atom or a saturated or unsaturated hydrocarbyl group having 1 to 10 carbon atoms. $R^{L10}$ represents a saturated or unsaturated hydrocarbyl group having 1 to 10 carbon atoms or an aryl group having 6 to 20 carbon atoms. $R^{L11}$ represents a hydrogen atom, a saturated or unsaturated hydrocarbyl group having 1 to 10 carbon atoms, or an aryl group having 6 to 20 carbon atoms. $R^{L12}$ represents a hydrogen atom, a halogen atom, a difluoromethyl group, a trifluoromethyl group, a difluoromethoxy group, a trifluoromethoxy group, a cyano group, a nitro group, or a saturated or unsaturated hydrocarbyl group having 1 to 6 carbon atoms and optionally having an ether group or a sulfide group. A plurality of $R^{L12}$'s may be bonded to each other to form a ring. $R^{L13}$ represents a hydrogen atom or a saturated or unsaturated hydrocarbyl group having 1 to 6 carbon atoms. The saturated or unsaturated hydrocarbyl groups may be linear, branched, or cyclic. "r" represents an integer of 1 to 6.

In the formula (AL-2), $R^{L2}$ and $R^{L3}$ each independently represent a hydrogen atom or a saturated hydrocarbyl group having 1 to 18 carbon atoms, preferably 1 to 10 carbon atoms. The saturated hydrocarbyl group may be linear, branched, or cyclic. Specific examples thereof include a methyl group, an ethyl group, a propyl group, an isopropyl group, an n-butyl group, a sec-butyl group, a tert-butyl group, a cyclopentyl group, a cyclohexyl group, a 2-ethylhexyl group, an n-octyl group, etc.

In the formula (AL-2), $R^{L4}$ represents a hydrocarbyl group having 1 to 18 carbon atoms, preferably 1 to 10 carbon atoms, and optionally contains a heteroatom. The hydrocarbyl group may be saturated or unsaturated, and may be linear, branched, or cyclic. Examples of the hydrocarbyl group include saturated hydrocarbyl groups each having 1 to 18 carbon atoms, etc., and some of hydrogen atoms thereof may be substituted with a hydroxy group, an alkoxy group, an oxo group, an amino group, an alkylamino group, or the like. Examples of such substituted saturated hydrocarbyl groups include ones shown below, etc.

--(-$CH_2)_4OH$ --(-$CH_2)_2O(CH_2)_3CH_3$

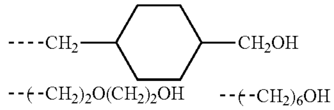

--(-$CH_2)_2O(CH_2)_2OH$ --(-$CH_2)_6OH$

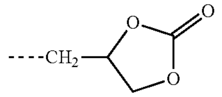

In the formulae, a broken line represents an attachment point.

$R^{L2}$ and $R^{L3}$, $R^{L2}$ and $R^{L4}$, or $R^{L3}$ and $R^{L4}$ optionally bond with each other to form a ring together with a carbon atom bonded therewith, or together with the carbon atom and an oxygen atom. In this case, $R^{L2}$ and $R^{L3}$, $R^{L2}$ and $R^{L4}$, or $R^{L3}$ and $R^{L4}$, involved in the ring formation, each independently represent an alkanediyl group having 1 to 18 carbon atoms, preferably 1 to 10 carbon atoms. The number of carbon atoms in the ring obtained by bonding these is preferably 3 to 10, more preferably 4 to 10.

Examples of the linear and branched acid-labile groups shown by the formula (AL-2) include ones shown by the following formulae (AL-2)-1 to (AL-2)-69, but are not limited thereto. Note that, in the following formulae, each broken line represents an attachment point.

(AL-2)-1

----$CH_2$—O—$CH_3$ (AL-2)-2

----$CH_2$—O—$CH_2$—$CH_3$ (AL-2)-3

----$CH_2$—O—$(CH_2)_2$—$CH_3$ (AL-2)-4

----$CH_2$—O—$(CH_2)_3$—$CH_3$ (AL-2)-5

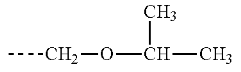

(AL-2)-6

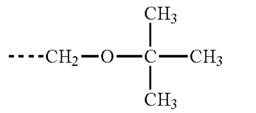

(AL-2)-7

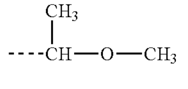

-continued
(AL-2)-8
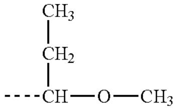
(AL-2)-9
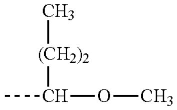
(AL-2)-10
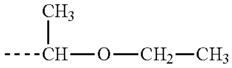
(AL-2)-11
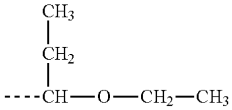
(AL-2)-12
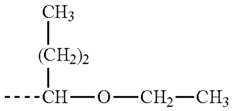
(AL-2)-13
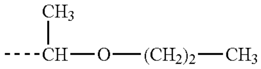
(AL-2)-14
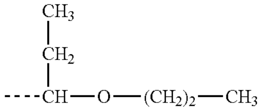
(AL-2)-15
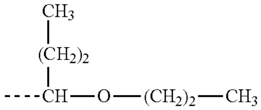
(AL-2)-16
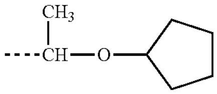
(AL-2)-17
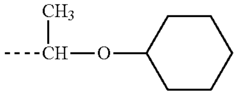
(AL-2)-18
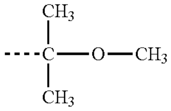
(AL-2)-19
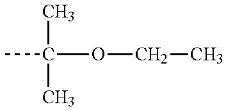
(AL-2)-20
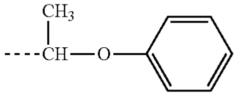
(AL-2)-21
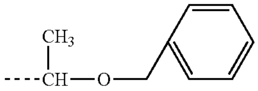
-continued
(AL-2)-22
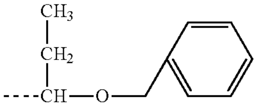
(AL-2)-23
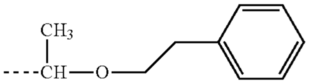
(AL-2)-24
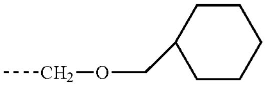
(AL-2)-25
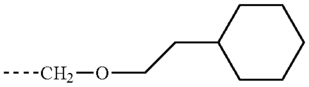
(AL-2)-26
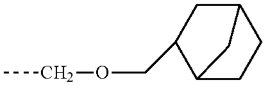
(AL-2)-27
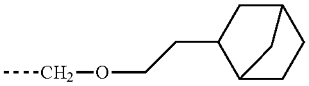
(AL-2)-28
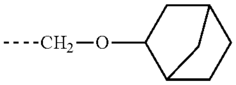
(AL-2)-29
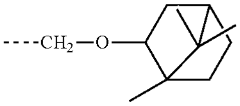
(AL-2)-30
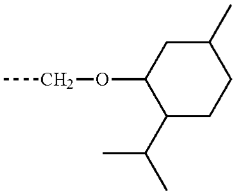
(AL-2)-31
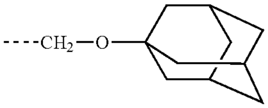
(AL-2)-32
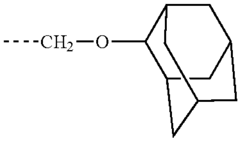
(AL-2)-33
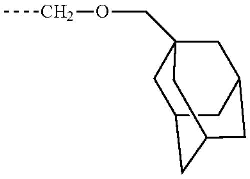

-continued
(AL-2)-34
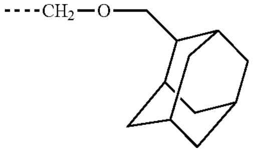
(AL-2)-35
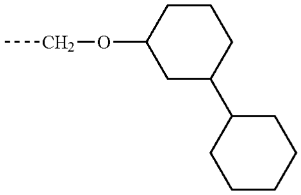
(AL-2)-36
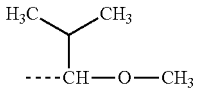
(AL-2)-37
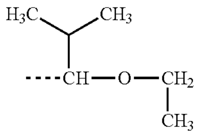
(AL-2)-38
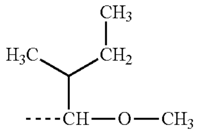
(AL-2)-39
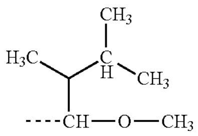
(AL-2)-40
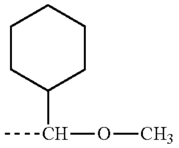
(AL-2)-41
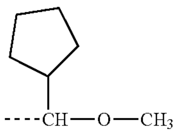
(AL-2)-42
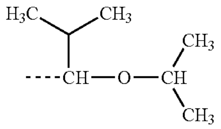
(AL-2)-43
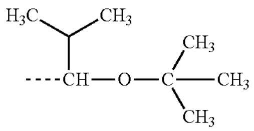
-continued
(AL-2)-44
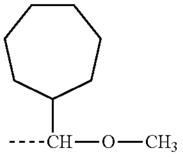
(AL-2)-45
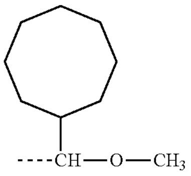
(AL-2)-46
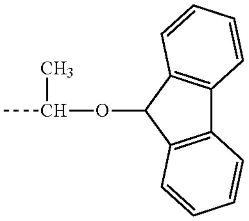
(AL-2)-47
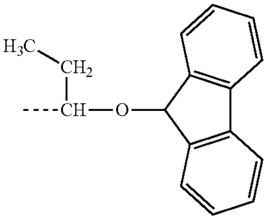
(AL-2)-48
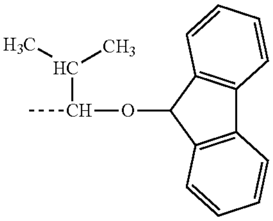
(AL-2)-49
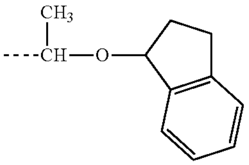
(AL-2)-50
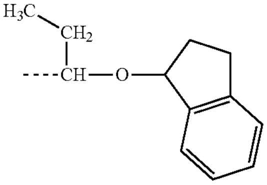
(AL-2)-51
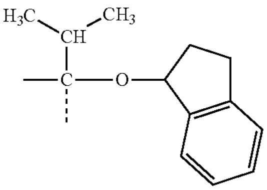

-continued
(AL-2)-52
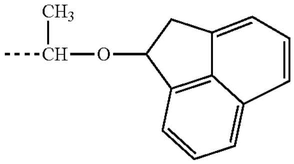
(AL-2)-53
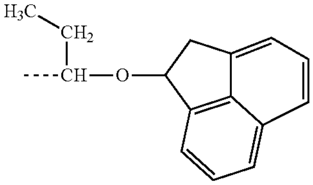
(AL-2)-54
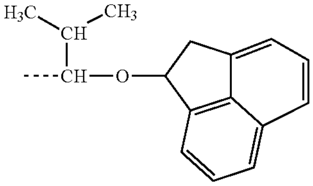
(AL-2)-55
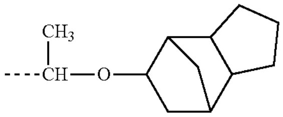
(AL-2)-56
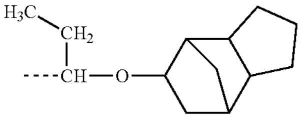
(AL-2)-57
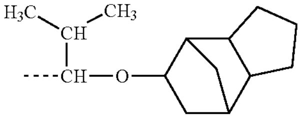
(AL-2)-58
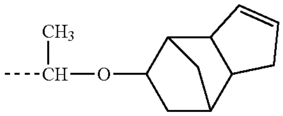
(AL-2)-59
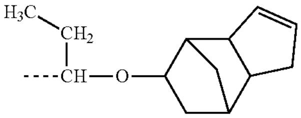
(AL-2)-60
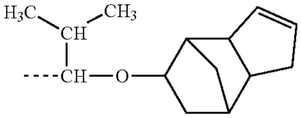
(AL-2)-61
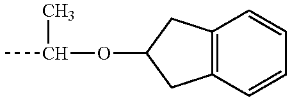
(AL-2)-62
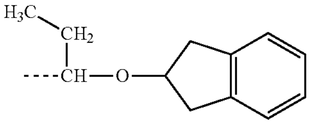
-continued
(AL-2)-63
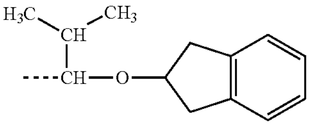
(AL-2)-64
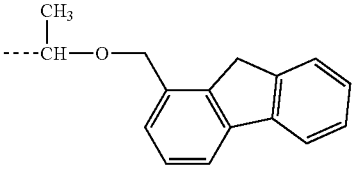
(AL-2)-65
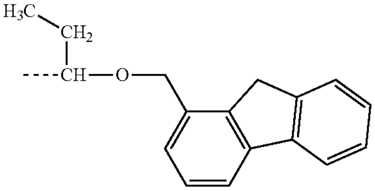
(AL-2)-66
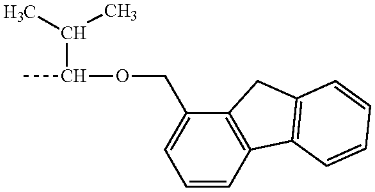
(AL-2)-67
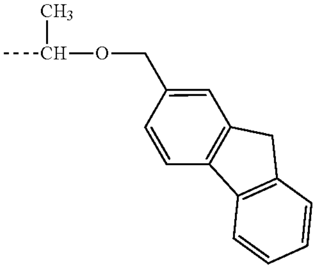
(AL-2)-68
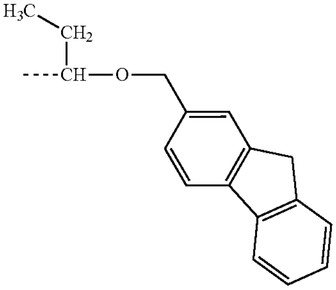
(AL-2)-69
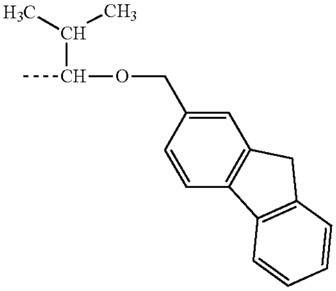
Examples of the cyclic acid-labile group shown by the formula (AL-2) include a tetrahydrofuran-2-yl group, a 2-methyltetrahydrofuran-2-yl group, a tetrahydropyran-2-yl group, a 2-methyltetrahydropyran-2-yl group, etc.

In addition, the examples of the acid-labile groups include groups shown by the following formula (AL-2a) or (AL-2b). The acid-labile group may crosslink the base polymer intermolecularly or intramolecularly.

(AL-2a)

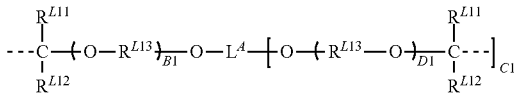

(AL-2b)

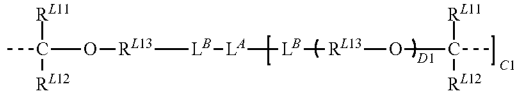

In the formulae, a broken line represents an attachment point.

In the formulae (AL-2a) and (AL-2b), $R^{L11}$ and $R^{L12}$ each independently represent a hydrogen atom or a saturated hydrocarbyl group having 1 to 8 carbon atoms. The saturated hydrocarbyl group may be linear, branched, or cyclic. Alternatively, $R^{L11}$ and $R^{L12}$ may bond with each other to form a ring together with a carbon atom bonded therewith. In this case, $R^{L11}$ and $R^{L12}$ each independently represent an alkanediyl group having 1 to 8 carbon atoms. Each $R^{L13}$ independently represents a saturated hydrocarbylene group having 1 to 10 carbon atoms. The saturated hydrocarbylene group may be linear, branched, or cyclic. B1 and D1 each independently represent an integer of 0 to 10, preferably an integer of 0 to 5. C1 represents an integer of 1 to 7, preferably an integer of 1 to 3.

In the formula (AL-2a) or (AL-2b), $L^A$ represents an aliphatic saturated hydrocarbon group having a valency of (C1+1) with 1 to 50 carbon atoms, an alicyclic saturated hydrocarbon group having a valency of (C1+1) with 3 to 50 carbon atoms, an aromatic hydrocarbon group having a valency of (C1+1) with 6 to 50 carbon atoms, or a heterocyclic group having a valency of (C1+1) with 3 to 50 carbon atoms. Some of the carbon atoms of these groups may be substituted with a heteroatom-containing group, and some hydrogen atoms bonded to the carbon atoms of these groups may be substituted with a hydroxy group, a carboxy group, an acyl group, or a fluorine atom. $L^A$ is preferably an arylene group having 6 to 30 carbon atoms, a saturated hydrocarbon group, such as a saturated hydrocarbylene group, a trivalent saturated hydrocarbon group, and a tetravalent saturated hydrocarbon group each of which have 1 to 20 carbon atoms, or the like. The saturated hydrocarbon groups may be linear, branched, or cyclic. $L^B$ represents —C(═O)—O—, —NH—C(═O)—O—, or —NH—C(═O)—NH—.

Examples of the crosslinking acetal groups shown by the formulae (AL-2a) and (AL-2b) include groups shown by the following formulae (AL-2)-70 to (AL-2)-77, etc.

(AL-2)-70

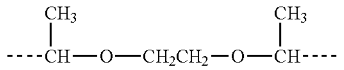

(AL-2)-71

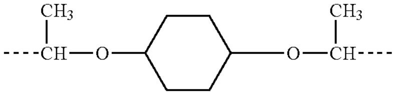

(AL-2)-72

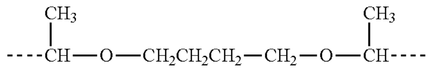

(AL-2)-73

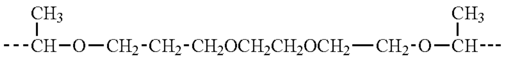

(AL-2)-74

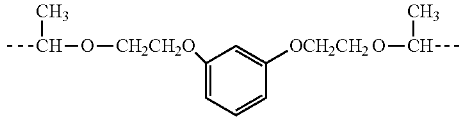

(AL-2)-75

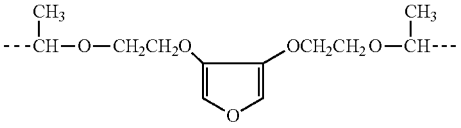

(AL-2)-76

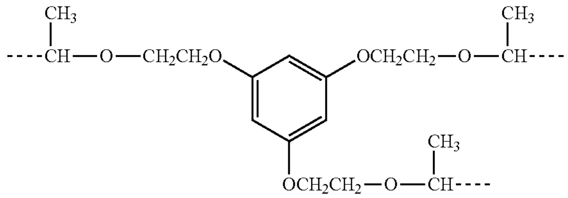

(AL-2)-77

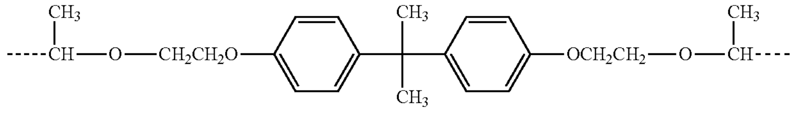

In the formulae, a broken line represents an attachment point.

In the formula (AL-3), $R^{L5}$, $R^{L6}$, and $R^{L7}$ each independently represent a hydrocarbyl group having 1 to 20 carbon atoms, and optionally contain a heteroatom, such as an oxygen atom, a sulfur atom, a nitrogen atom, and a fluorine atom. The hydrocarbyl group may be saturated or unsaturated, and may be linear, branched, or cyclic. Specific examples thereof include alkyl groups having 1 to 20 carbon atoms, cyclic saturated hydrocarbyl groups having 3 to 20 carbon atoms, alkenyl groups having 2 to 20 carbon atoms, cyclic unsaturated hydrocarbyl groups having 3 to 20 carbon atoms, aryl groups having 6 to 10 carbon atoms, etc. Alternatively, $R^{L5}$ and $R^{L6}$, $R^{L5}$ and $R^{L7}$, or $R^{L6}$ and $R^{L7}$, may bond with each other to form an alicyclic group having 3 to 20 carbon atoms, together with a carbon atom bonded therewith.

Examples of the group shown by the formula (AL-3) include a tert-butyl group, a 1,1-diethylpropyl group, a 1-ethylnorbornyl group, a 1-methylcyclohexyl group, a 1-ethylcyclopentyl group, a 2-(2-methyl)adamantyl group, a 2-(2-ethyl)adamantyl group, a tert-pentyl group, etc.

The examples of the group shown by the formula (AL-3) also include groups shown by the following formulae (AL-3)-1 to (AL-3)-19.

(AL-3)-1

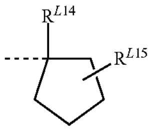

(AL-3)-2

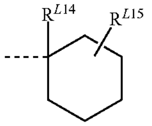

(AL-3)-3

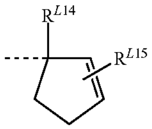

(AL-3)-4

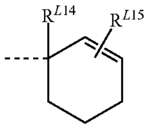

(AL-3)-5

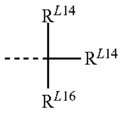

(AL-3)-6

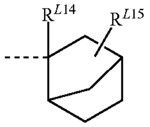

(AL-3)-7

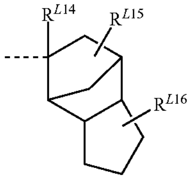

(AL-3)-8

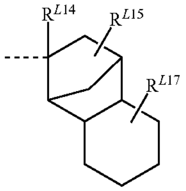

-continued (AL-3)-9

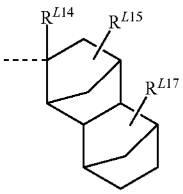

(AL-3)-10

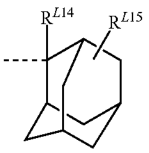

(AL-3)-11

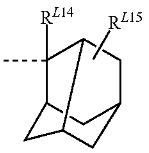

(AL-3)-12

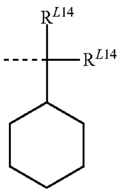

(AL-3)-13

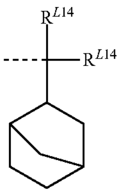

(AL-3)-14

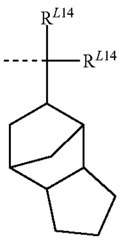

(AL-3)-15

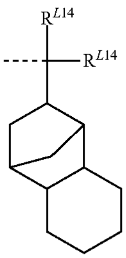

-continued (AL-3)-16

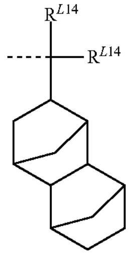

(AL-3)-17

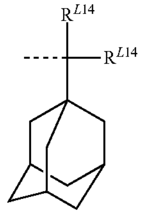

(AL-3)-18

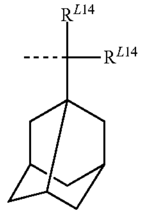

(AL-3)-19

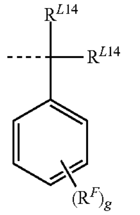

In the formulae, a broken line represents an attachment point.

In the formulae (AL-3)-1 to (AL-3)-19, each $R^{L14}$ independently represents a saturated hydrocarbyl group having 1 to 8 carbon atoms or an aryl group having 6 to 20 carbon atoms. $R^{L15}$ and $R^{L17}$ each independently represent a hydrogen atom or a saturated hydrocarbyl group having 1 to 20 carbon atoms. $R^{L16}$ represents an aryl group having 6 to 20 carbon atoms. The saturated hydrocarbyl groups may be linear, branched, or cyclic. The aryl groups are preferably a phenyl group or the like. $R^F$ represents a fluorine atom, an iodine atom, a difluoromethyl group, a trifluoromethyl group, a cyano group, or a nitro group. "g" represents an integer of 0 to 5.

Examples of the acid-labile group further include groups shown by the following formula (AL-3)-20 or (AL-3)-21. The acid-labile group may crosslink the polymer intramolecularly or intermolecularly.

(AL-3)-20

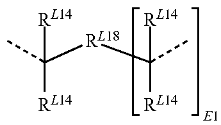

-continued (AL-3)-21

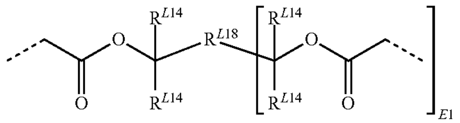

In the formulae, a broken line represents an attachment point.

In the formulae (AL-3)-20 and (AL-3)-21, $R^{L14}$ is as defined above. $R^{L18}$ represents a saturated or unsaturated hydrocarbylene group having a valency of (E1+1) and having 1 to 20 carbon atoms or represents an arylene group having a valency of (E1+1) and having 6 to 20 carbon atoms, and optionally contains a heteroatom such as an oxygen atom, a sulfur atom, or a nitrogen atom. The saturated hydrocarbylene group may be linear, branched, or cyclic. E1 represents an integer of 1 to 3.

Examples of a monomer to give the repeating unit containing the acid-labile group shown by the formula (AL-3) include (meth)acrylate having an exo-form structure shown by the following formula (AL-3)-22.

(AL-3)-22

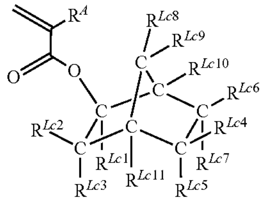

In the formula (AL-3)-22, $R^A$ is as defined above. $R^{Lc1}$ represents a saturated hydrocarbyl group having 1 to 8 carbon atoms or an aryl group having 6 to 20 carbon atoms and optionally containing a substituent. The saturated hydrocarbyl group may be linear, branched, or cyclic. $R^{Lc2}$ to $R^{Lc11}$ each independently represent a hydrogen atom or a hydrocarbyl group having 1 to 15 carbon atoms and optionally containing a heteroatom. Examples of the heteroatom include an oxygen atom, etc. Examples of the hydrocarbyl group include alkyl groups having 1 to 15 carbon atoms, aryl groups having 6 to 15 carbon atoms, etc. $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$ may bond with each other to form a ring together with a carbon atom bonded therewith. In this case, a group involved in the bonding is a hydrocarbylene group having 1 to 15 carbon atoms and optionally containing a heteroatom. Alternatively, $R^{Lc2}$ and $R^{Lc11}$, $R^{Lc8}$ and $R^{Lc11}$, or $R^{Lc4}$ and $R^{Lc6}$, all pairs of which are bonded to carbon atoms next to each other, may directly bond with each other to form a double bond. Note that the formula also represents an enantiomer.

Examples of the monomer shown by the formula (AL-3)-22 to give the repeating unit include ones disclosed in JP 2000-327633 A, etc. Specific examples thereof include ones shown below, but are not limited thereto. Note that, in the following formulae, $R^A$ is as defined above.

-continued
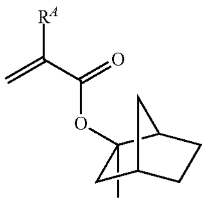
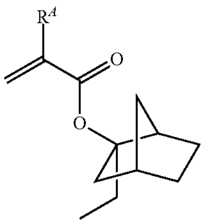
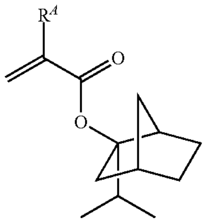
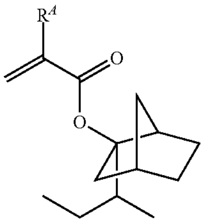
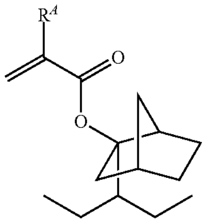
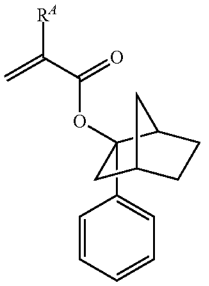
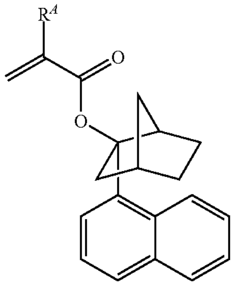
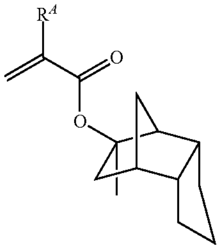
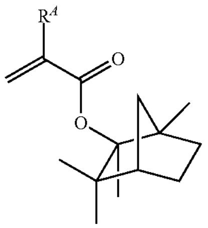
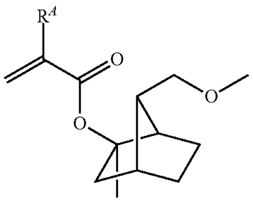
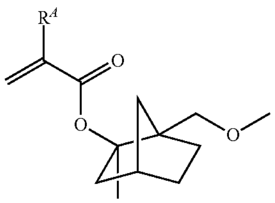
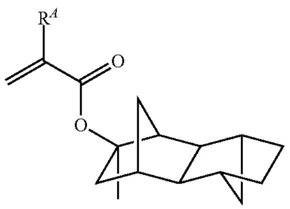
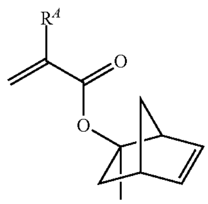
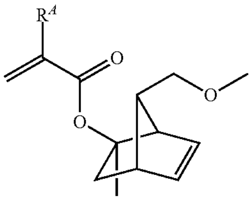
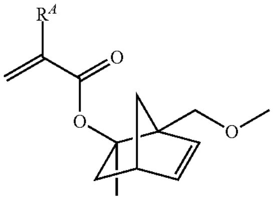
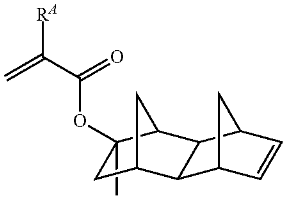
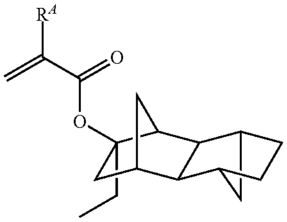
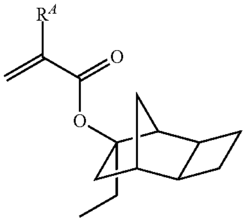
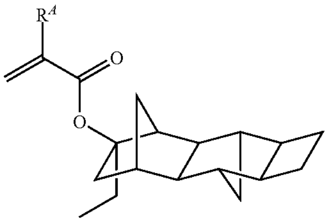
Other examples of the monomer to give the repeating unit containing the acid-labile group shown by the formula (AL-3) include (meth)acrylate containing a furandiyl group, a tetrahydrofurandiyl group, or an oxanorbornanediyl group as shown by the following formula (AL-3)-23.
(AL-3)-23
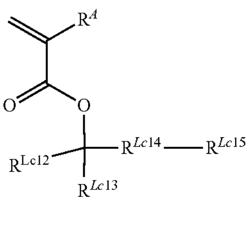

In the formula (AL-3)-23, $R^A$ is as defined above. $R^{Lc12}$ and $R^{Lc13}$ each independently represent a hydrocarbyl group having 1 to 10 carbon atoms. $R^{Lc12}$ and $R^{Lc13}$ may bond with each other to form an alicyclic group together with a carbon atom bonded therewith. $R^{Lc14}$ represents a furandiyl group, a tetrahydrofurandiyl group, or an oxanorbornanediyl group. $R^{Lc15}$ represents a hydrogen atom, or a hydrocarbyl group having 1 to 10 carbon atoms and optionally containing a heteroatom. The hydrocarbyl groups may be linear, branched, or cyclic. Specific examples thereof include a saturated hydrocarbyl group having 1 to 10 carbon atoms, etc.

Examples of the monomer shown by the formula (AL-3)-23 to give the repeating unit include ones shown below, but are not limited thereto. Note that, in the following formulae, $R^A$ is as defined above, Ac represents an acetyl group, and Me represents a methyl group.

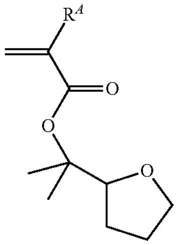
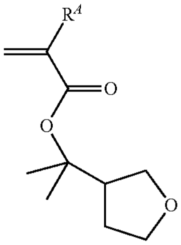
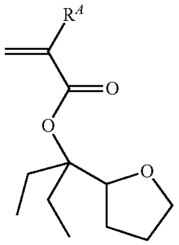
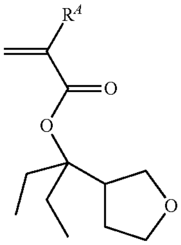
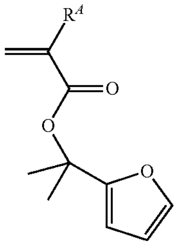
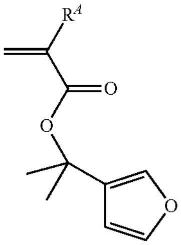
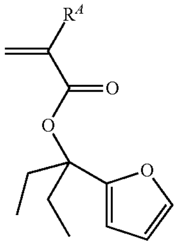
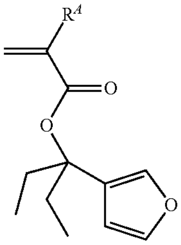
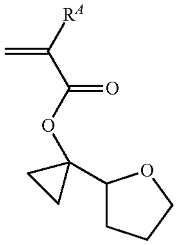
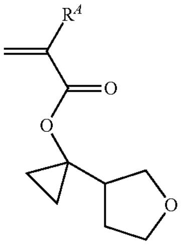

-continued

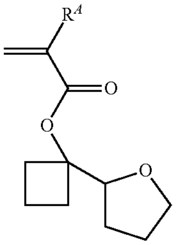
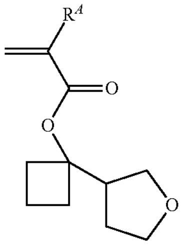
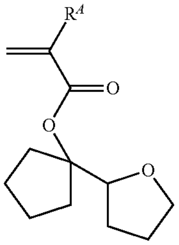
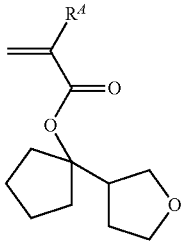
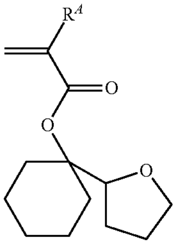
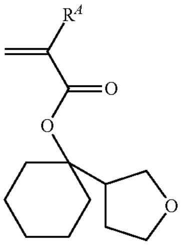
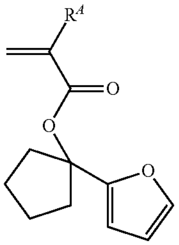
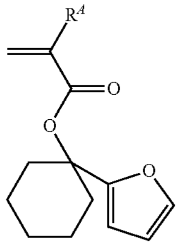
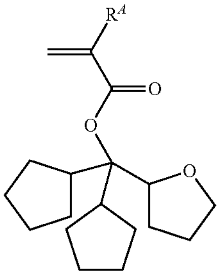
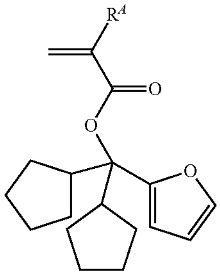
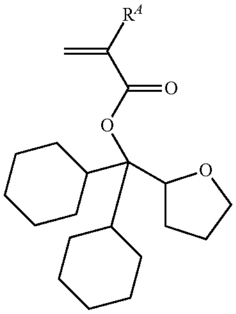
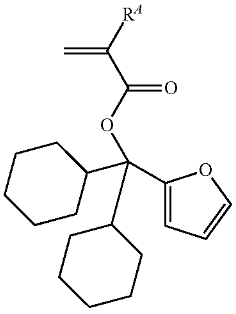

-continued
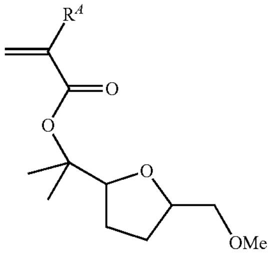
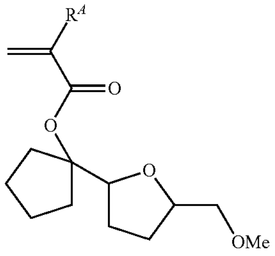
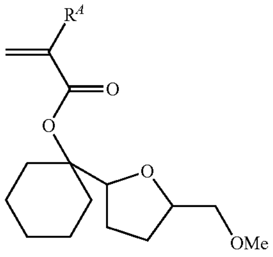
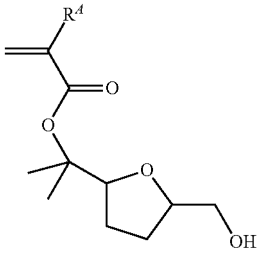
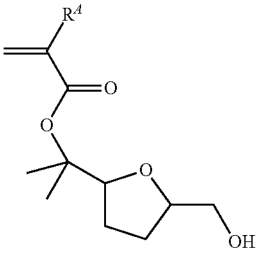
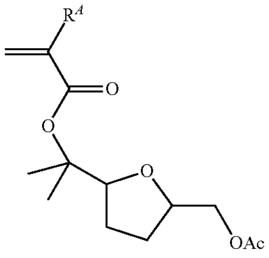
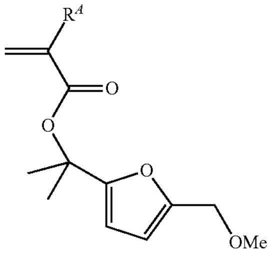
-continued
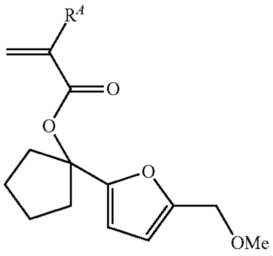
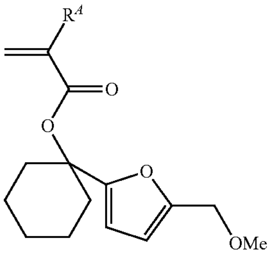
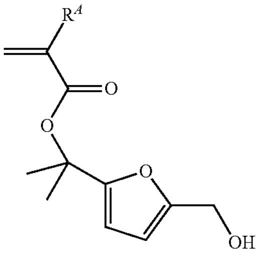
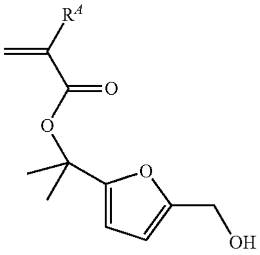
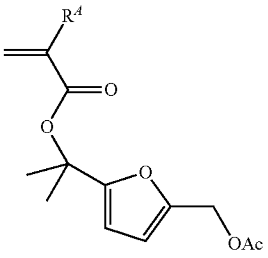
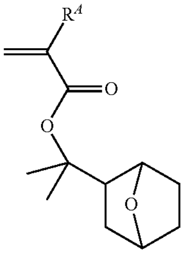
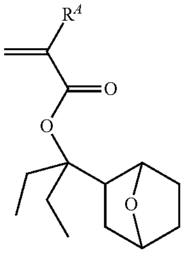
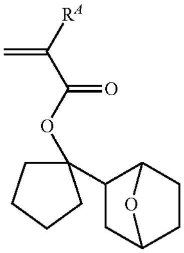
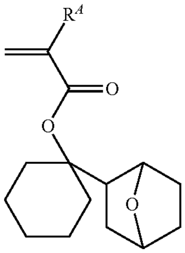

-continued

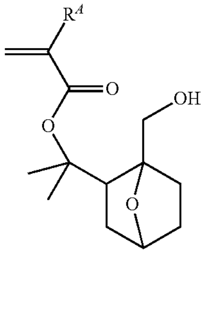
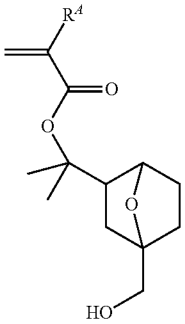
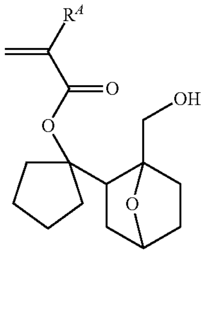
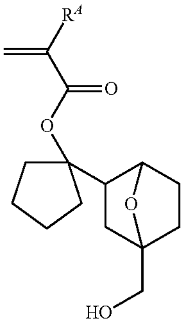
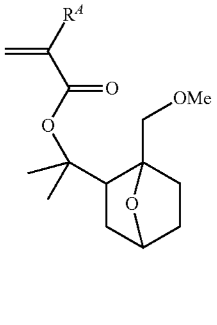
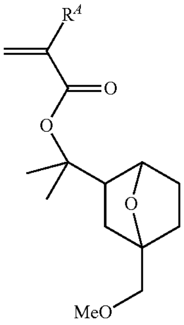
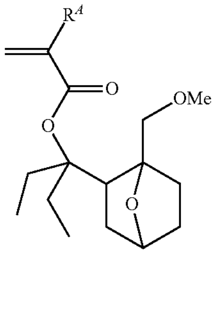
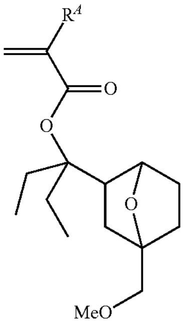
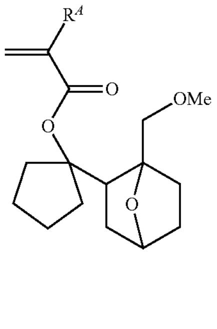
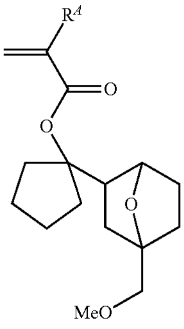

-continued

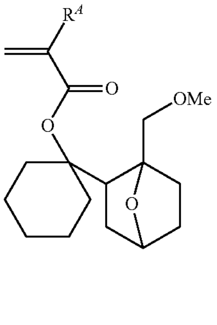
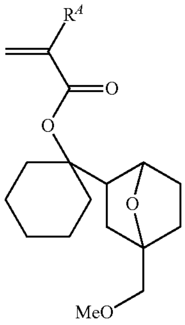
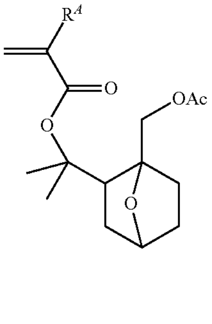
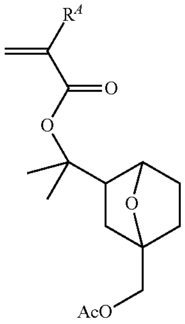
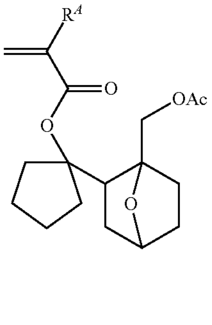
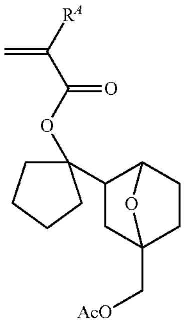

The base polymer may further contain a repeating unit-b containing an adhesive group selected from the group consisting of a hydroxy group, a carboxy group, a lactone ring, a carbonate group, a thiocarbonate group, a carbonyl group, a cyclic acetal group, an ether bond, an ester bond, a sulfonic acid ester bond, a cyano group, an amide bond, —O—C(═O)—S—, and —O—C(═O)—NH—.

Examples of a monomer to give the repeating unit-b include ones shown below, but are not limited thereto. Note that, in the following formulae, $R^A$ is as defined above.

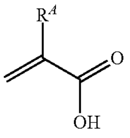
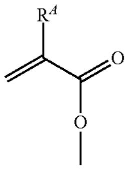
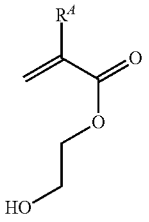

-continued
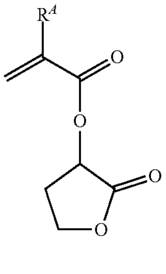
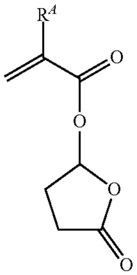
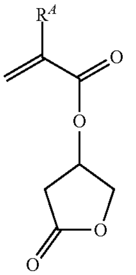
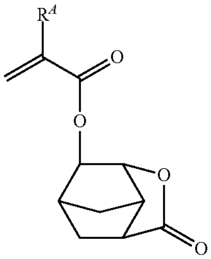
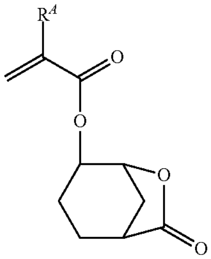
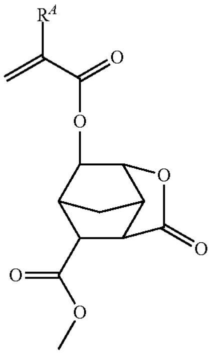
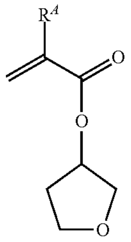
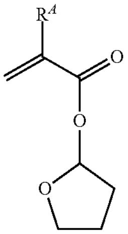
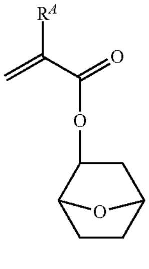
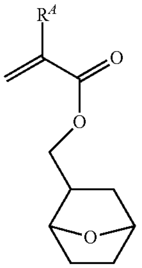
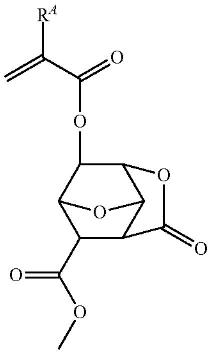
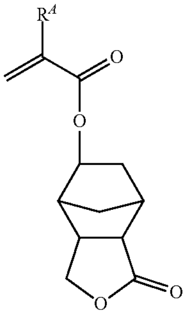
-continued
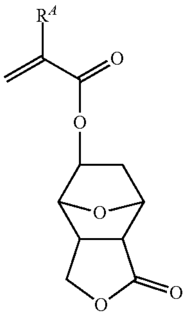
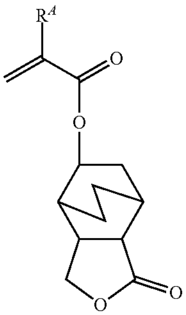
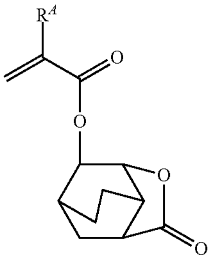
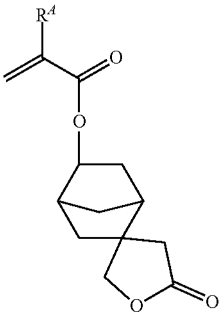
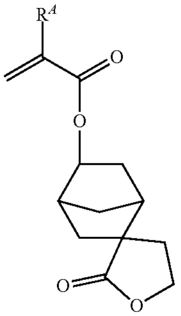
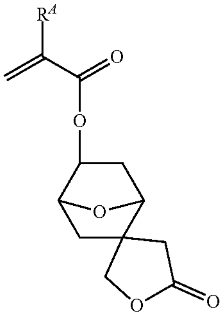
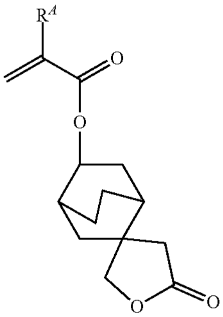
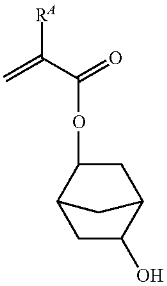
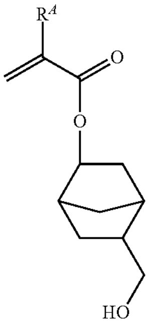
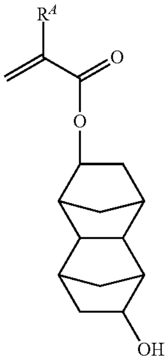
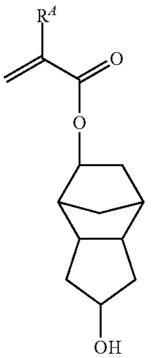

-continued
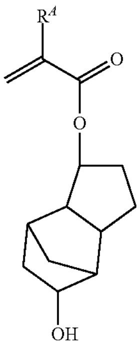
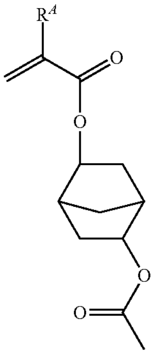
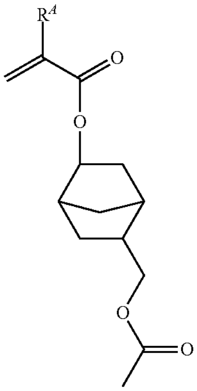
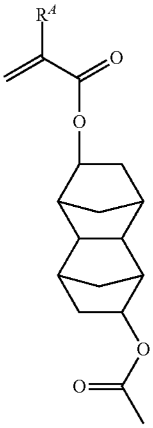
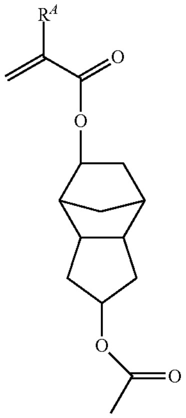
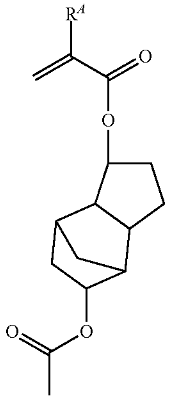
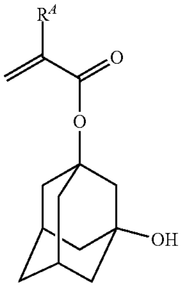
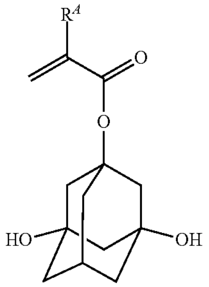
-continued
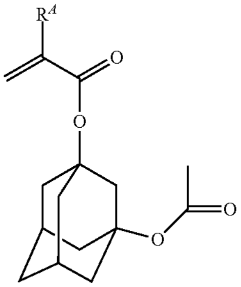
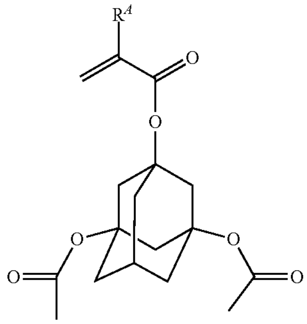
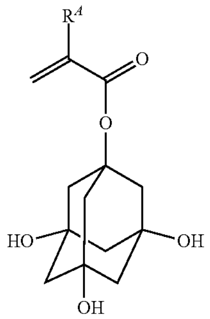
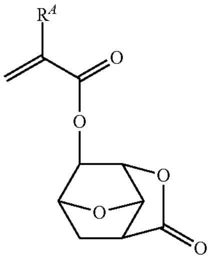
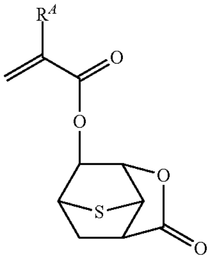
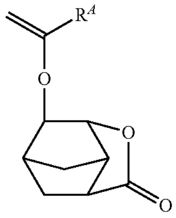
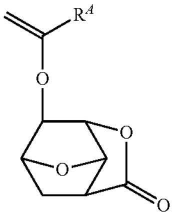
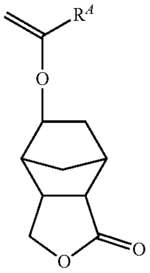
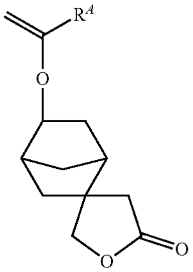
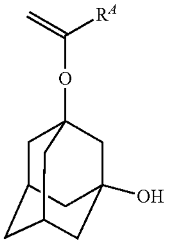

-continued
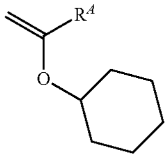
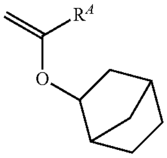
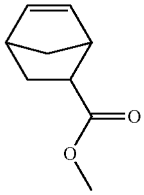
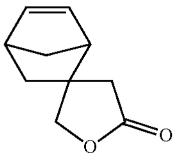
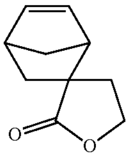
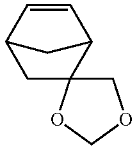
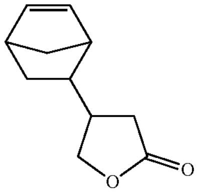
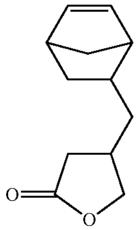
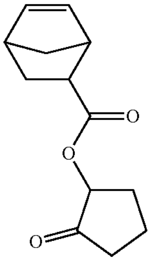
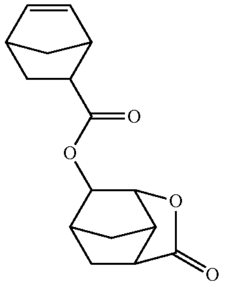
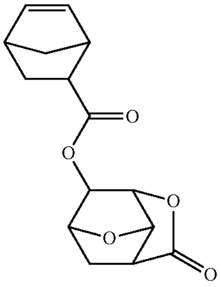
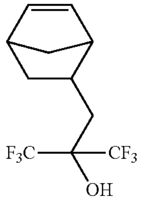
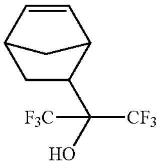
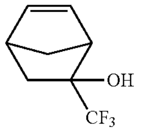
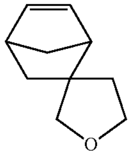
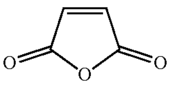
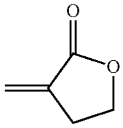
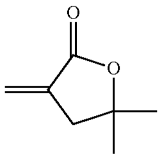
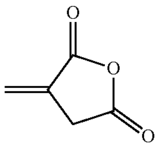
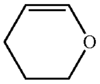
-continued
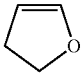
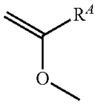
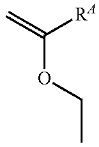
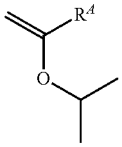
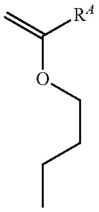
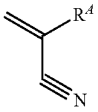
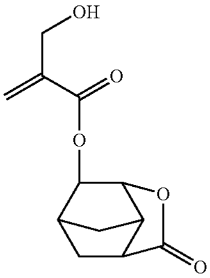
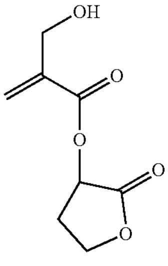
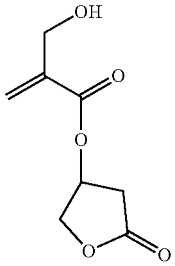
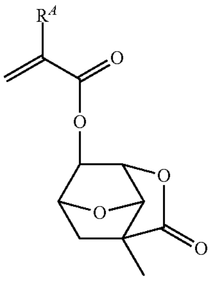
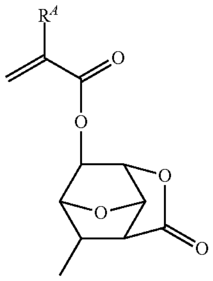
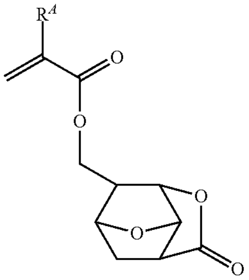
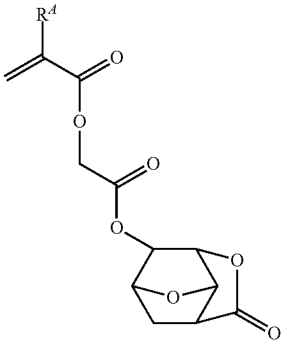

-continued
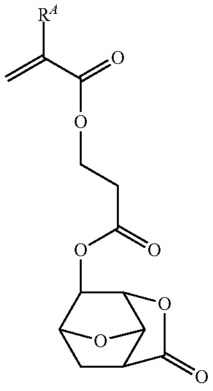
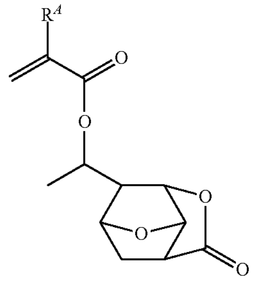
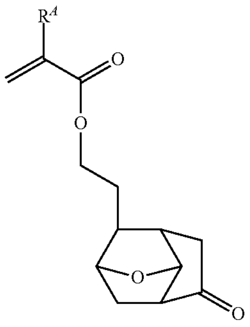
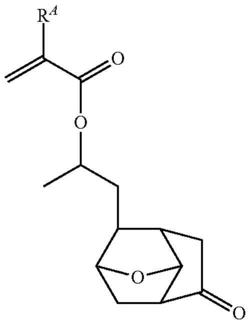
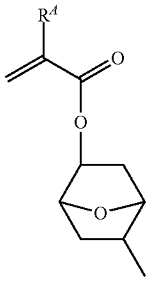
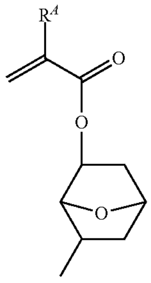
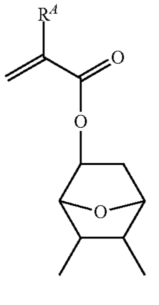
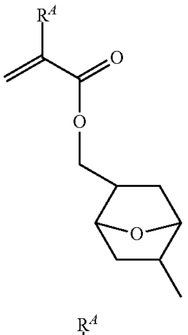
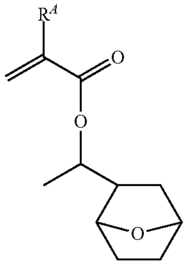
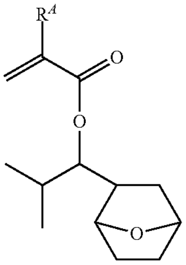
-continued
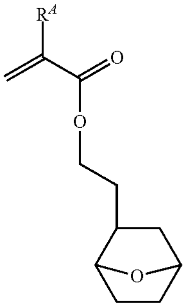
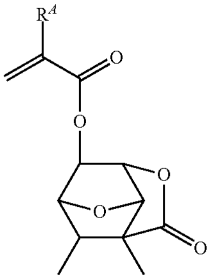
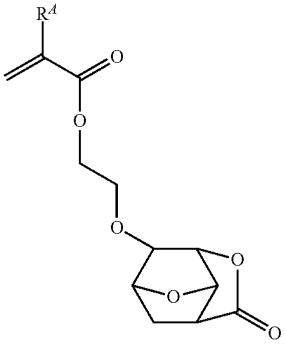
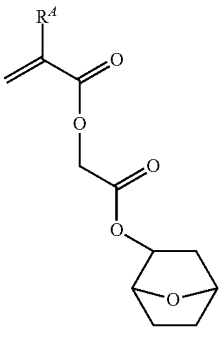
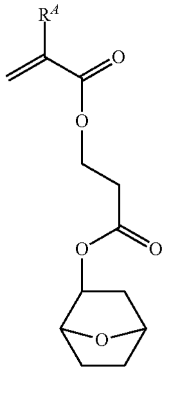
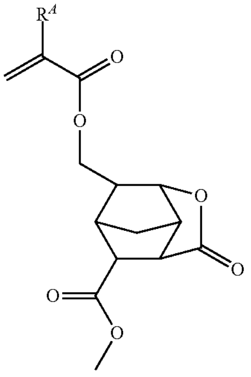

-continued
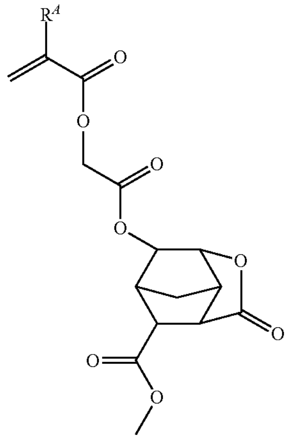
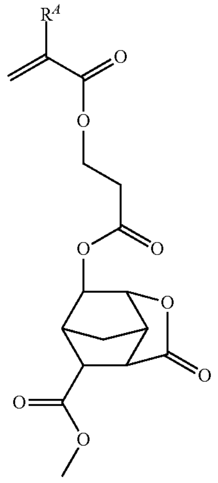
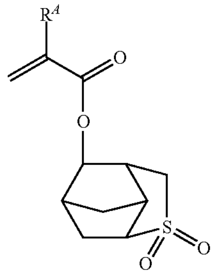
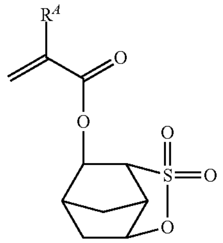
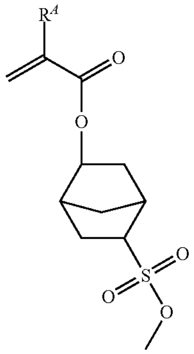
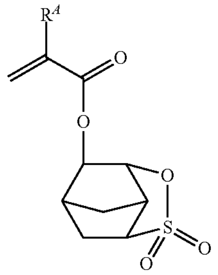
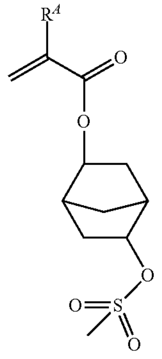
-continued
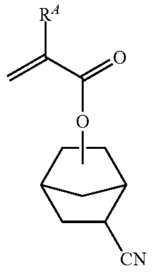
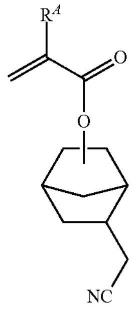
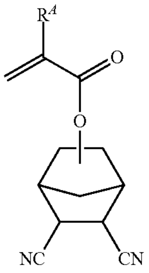
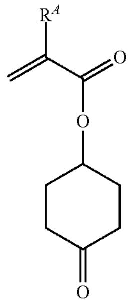
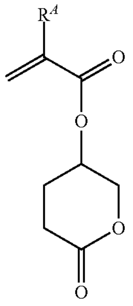
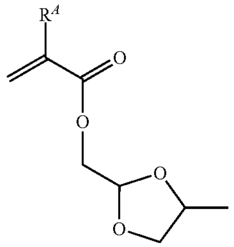
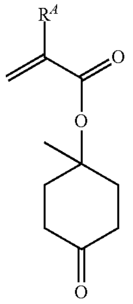
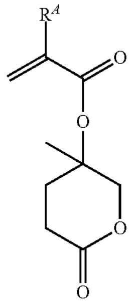
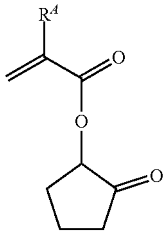
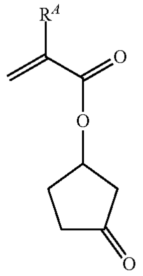
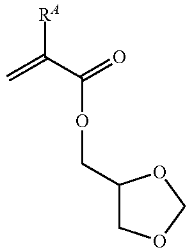

-continued
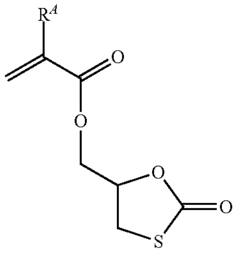
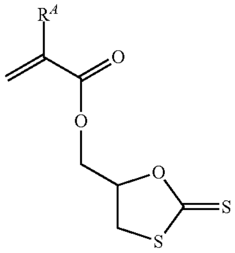
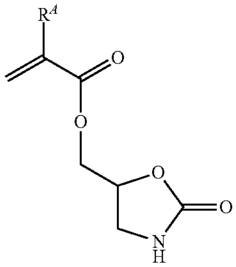
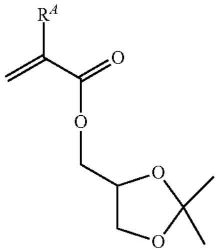
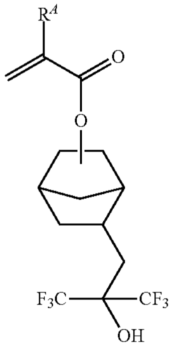
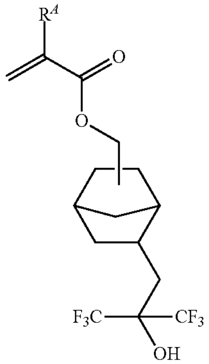
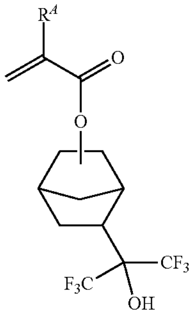
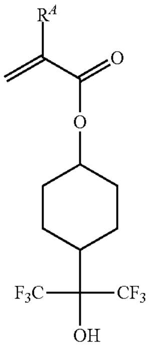
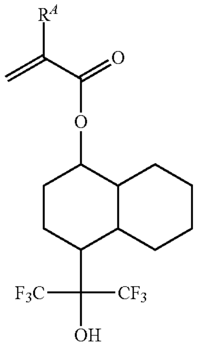
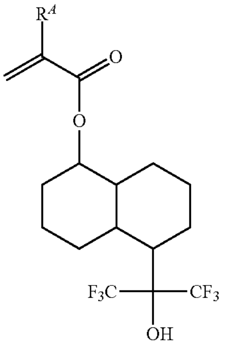
-continued
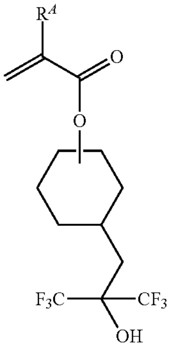
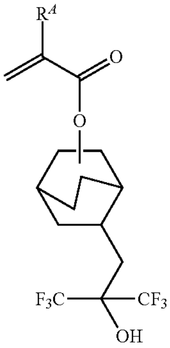
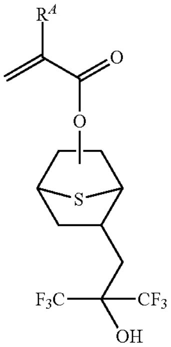
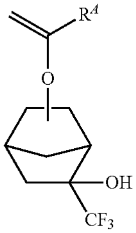
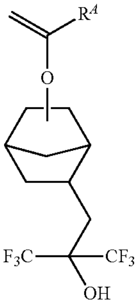
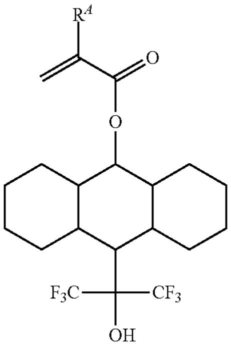
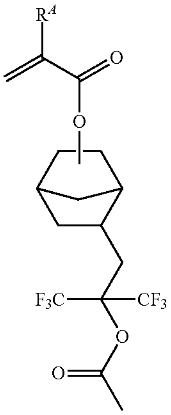
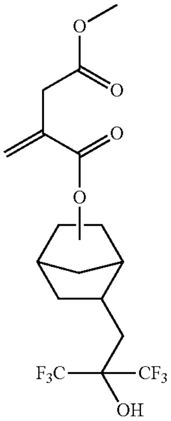

-continued
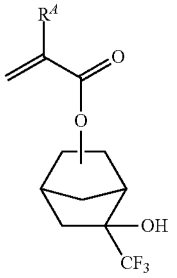
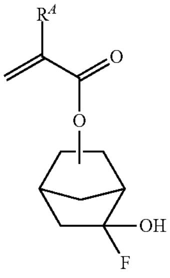
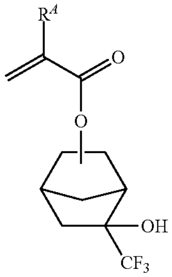
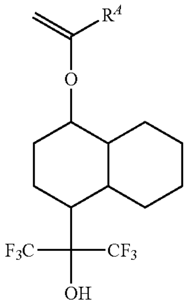
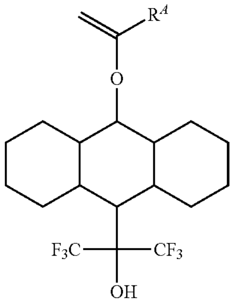
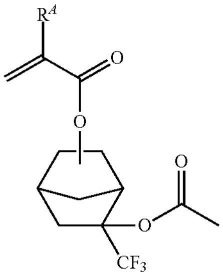
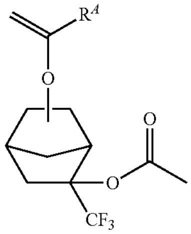
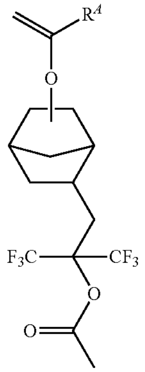
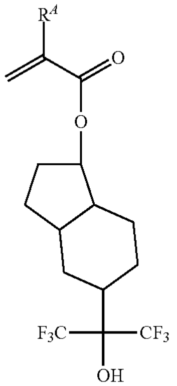
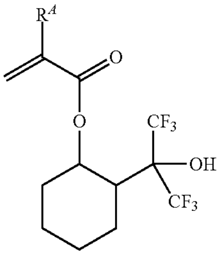
-continued
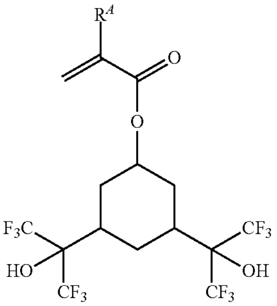
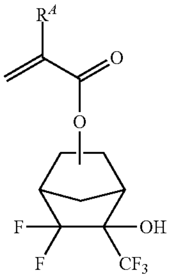
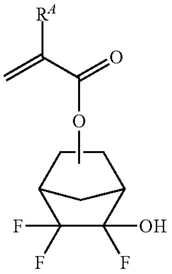
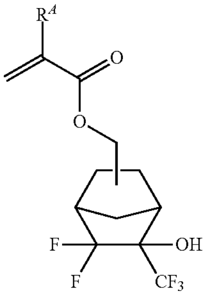
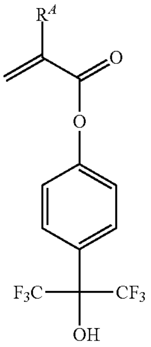
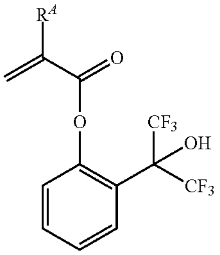
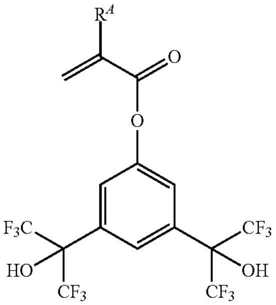
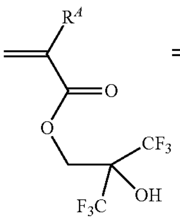
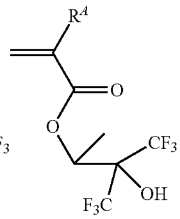
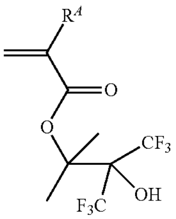
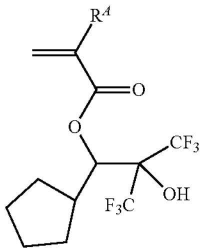

-continued
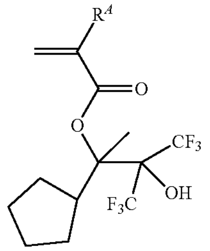
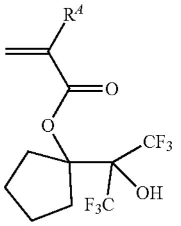
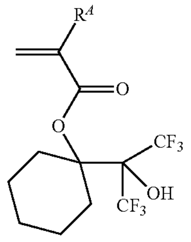
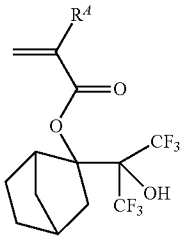
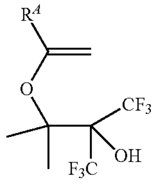
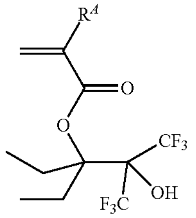
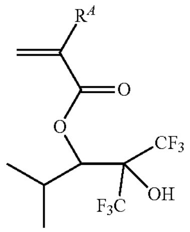
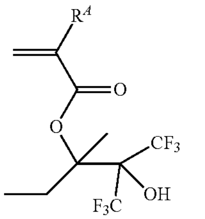
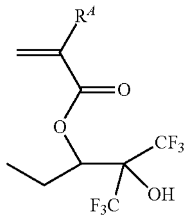
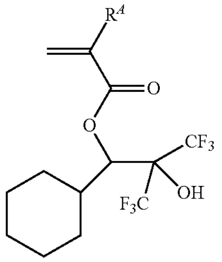
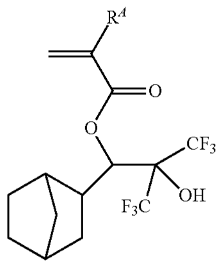
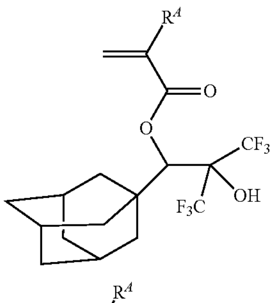
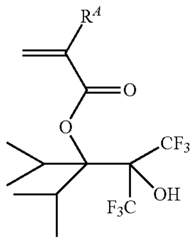
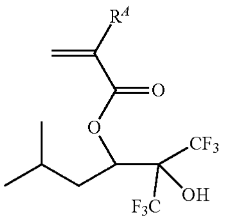
-continued
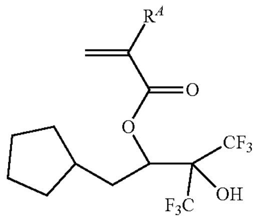
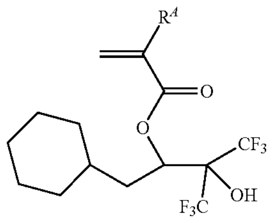
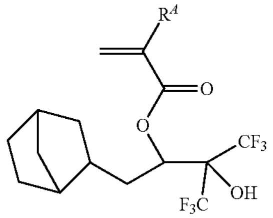
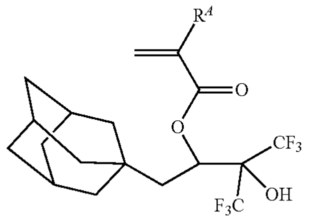
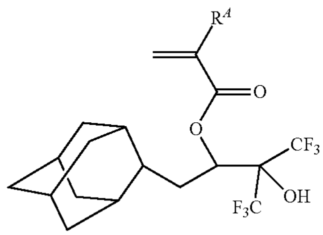
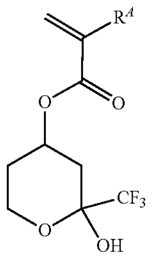
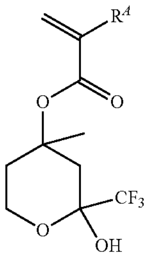
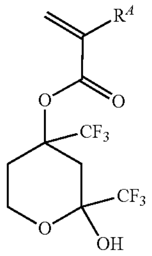
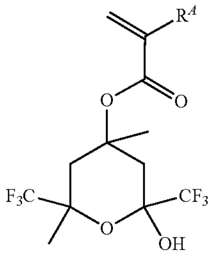

-continued
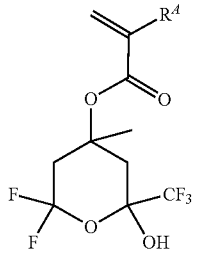
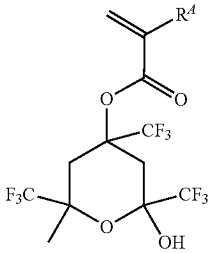
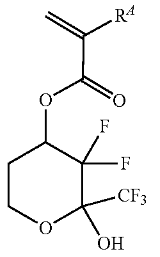
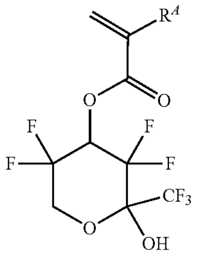
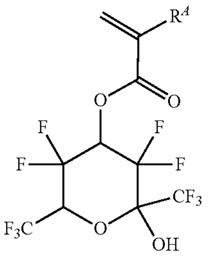
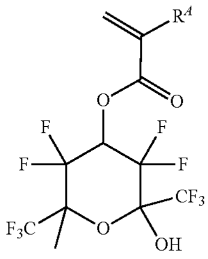
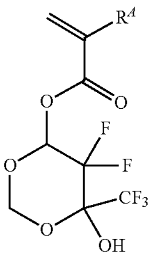
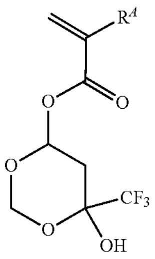
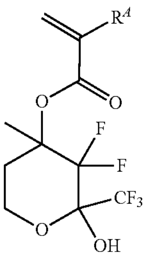
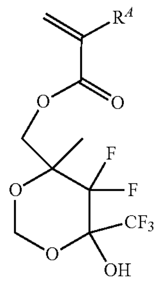
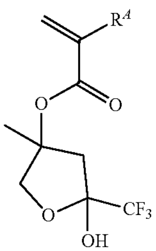
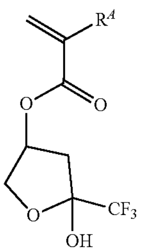
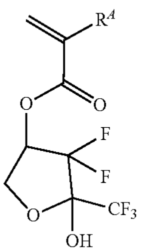
-continued
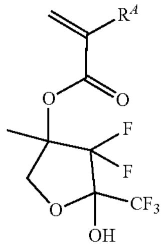
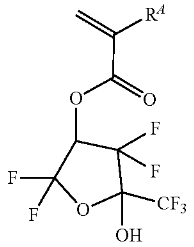
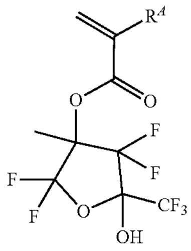
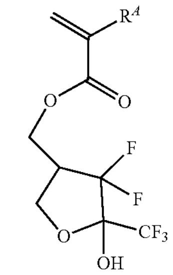
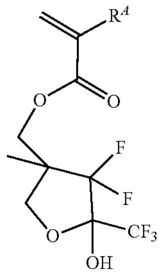
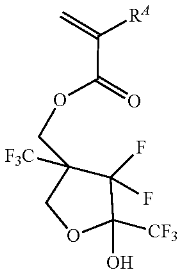
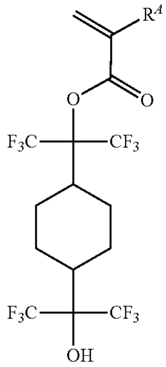
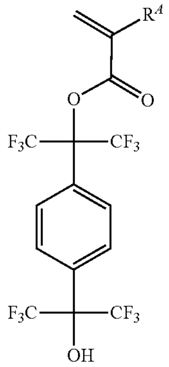
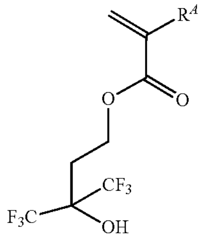
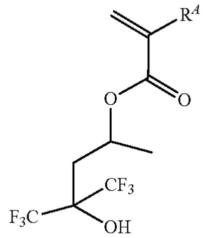
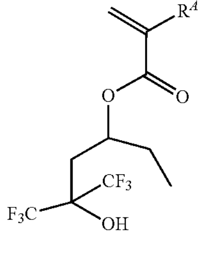
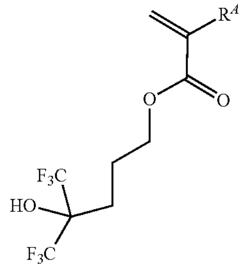

-continued
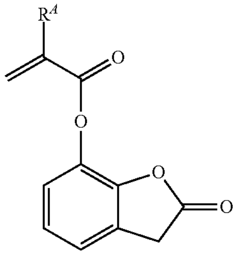
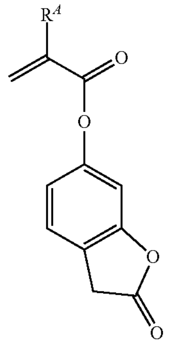
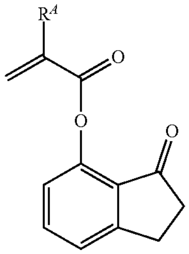
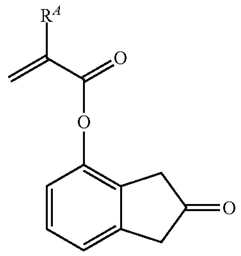
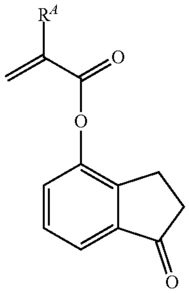
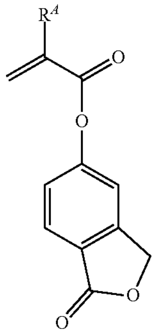
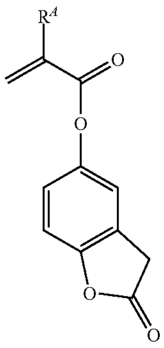
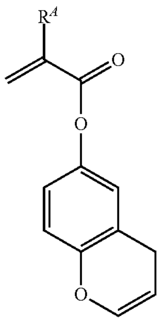
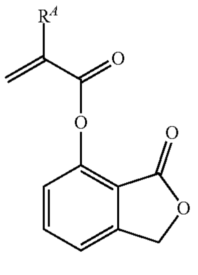
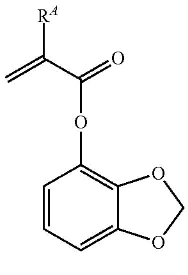
-continued
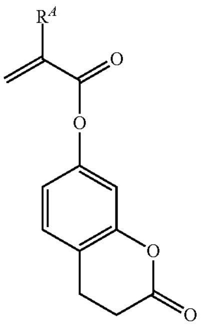
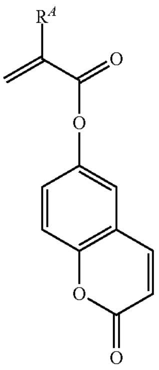
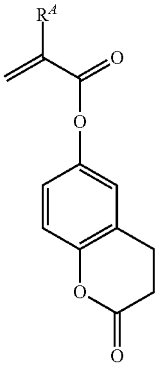
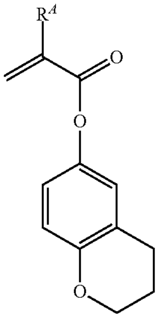
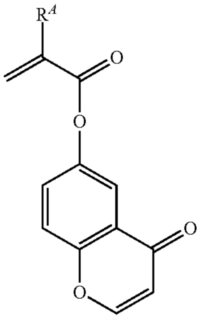
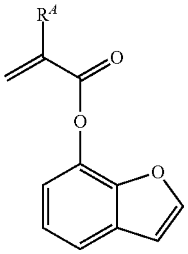
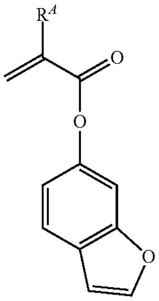
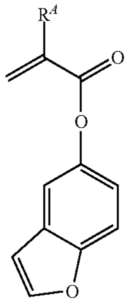
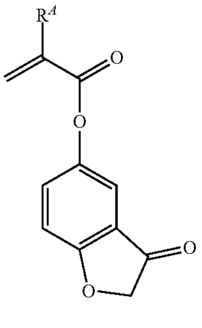
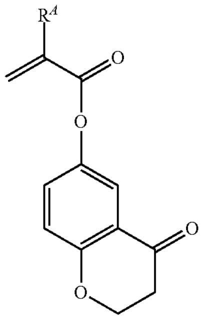

-continued
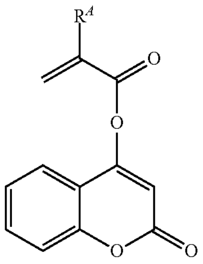
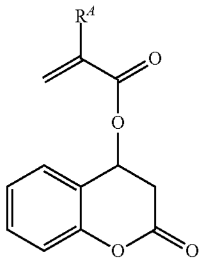
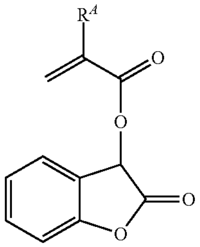
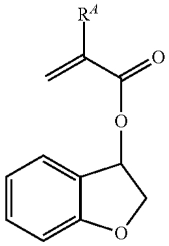
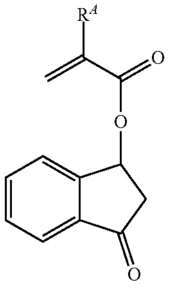
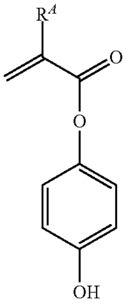
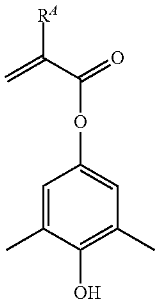
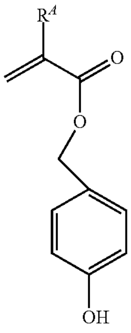
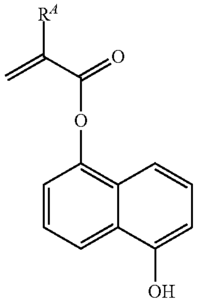
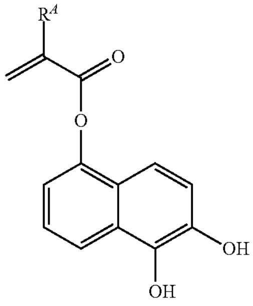
-continued
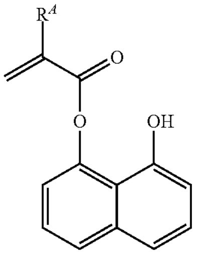
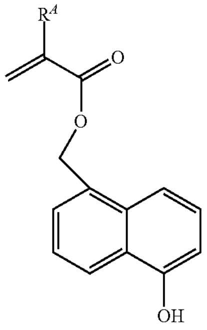
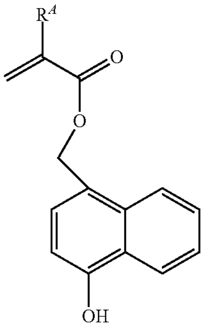
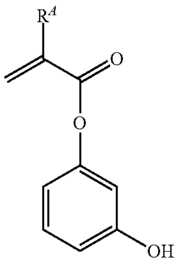
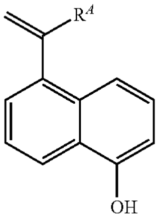
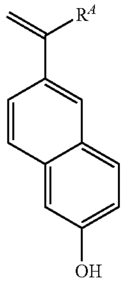
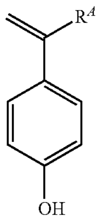
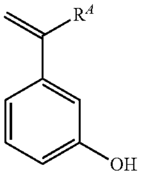
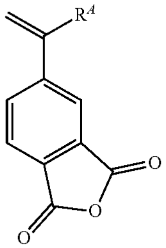
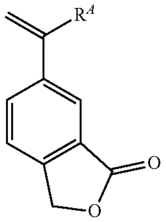
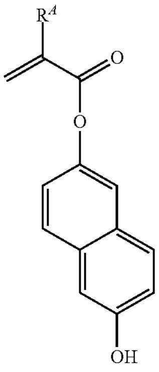
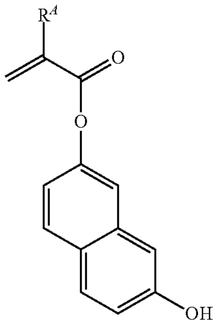

-continued
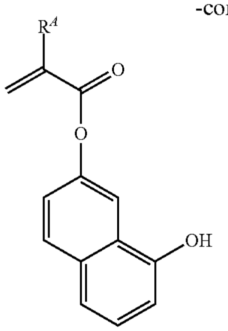
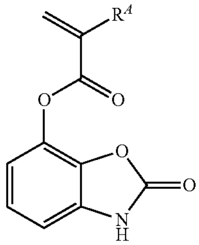
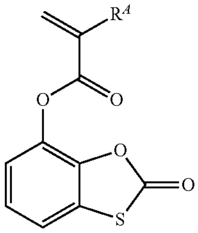
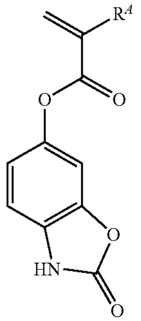
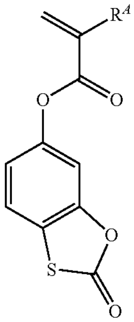
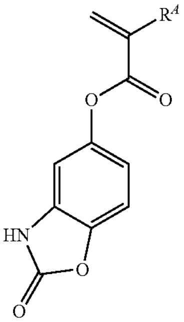
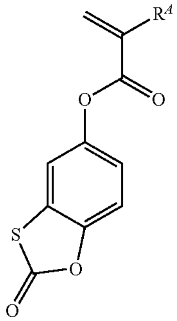
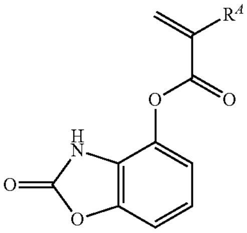
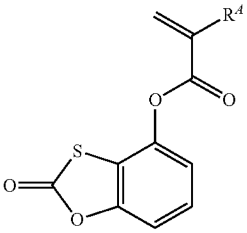
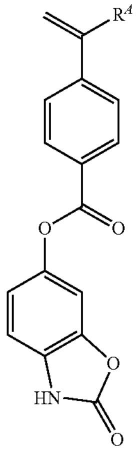
-continued
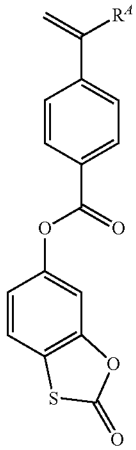
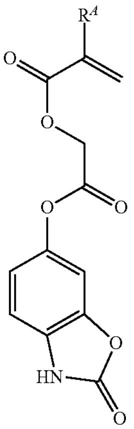
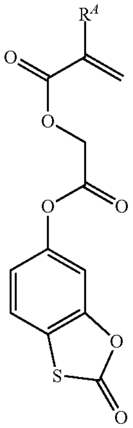
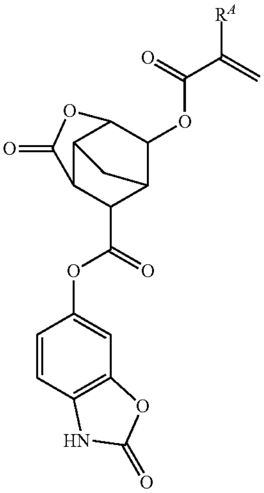
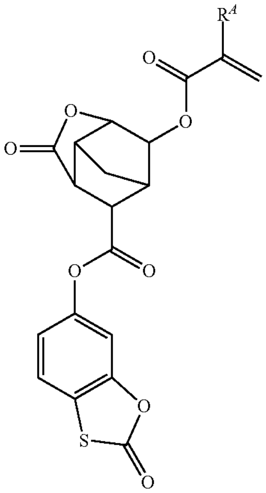
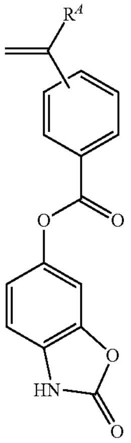

-continued

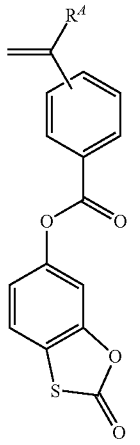

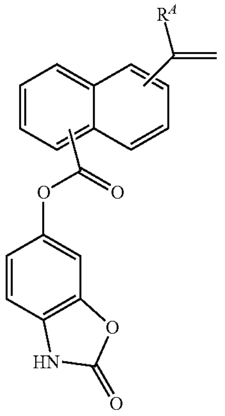

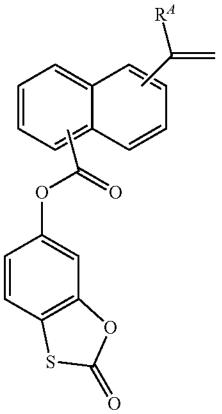

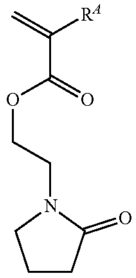

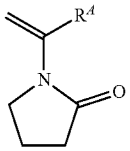

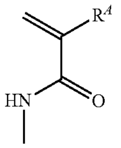

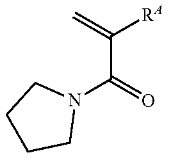

The base polymer may further contain a repeating unit-c derived from an onium salt having a polymerizable unsaturated bond. Examples of a preferable repeating unit-c include repeating units represented by the following formula (c1) (hereinafter, also referred to as repeating unit-c1), repeating units represented by the following formula (c2) (hereinafter, also referred to as repeating unit-c2), and repeating units represented by the following formula (c3) (hereinafter, also referred to as repeating unit-c3). Note that one kind of the repeating units-c1 to -c3 can be used, or two or more kinds thereof can be used in combination. That is, the base polymer preferably further contains a repeating unit-c represented by any one or more of the following formulae (c1) to (c3).

(c1)

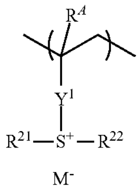

-continued (c2)

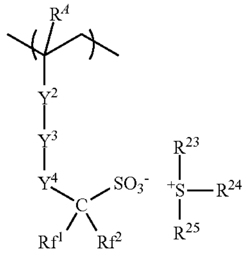

(c3)

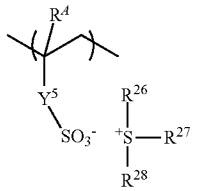

In the formulae, each $R^A$ independently represents a hydrogen atom or a methyl group. $Y^1$ represents a single bond, a phenylene group, a naphthylene group, $-O-Y^{11}-$, $-C(=O)-O-Y^{11}-$, or $-C(=O)-NH-Y^{11}-$. $Y^{11}$ represents an aliphatic hydrocarbylene group having 1 to 6 carbon atoms, a phenylene group, a naphthylene group, or a group having 7 to 18 carbon atoms derived from a combination of these groups, $Y^{11}$ optionally containing a carbonyl group, an ester bond, an ether bond, or a hydroxy group. $Y^2$ represents a single bond or an ester bond. $Y^3$ represents a single bond, $-Y^{31}-C(=O)-O-$, $-Y^{31}-O-$, or $-Y^{31}-O-C(=O)-$. $Y^{31}$ represents a hydrocarbylene group having 1 to 12 carbon atoms, a phenylene group, or a group having 7 to 18 carbon atoms derived from a combination of these groups, $Y^{31}$ optionally containing a carbonyl group, an ester bond, an ether bond, an iodine atom, or a bromine atom. $Y^4$ represents a single bond, a methylene group, or a 2,2,2-trifluoro-1,1-ethanediyl group. $Y^5$ represents a single bond, a methylene group, an ethylene group, a phenylene group, a fluorinated phenylene group, $-O-Y^{51}-$, $-C(=O)-O-Y^{51}-$, or $-C(=O)-NH-Y^{51}-$. $Y^{51}$ represents an aliphatic hydrocarbylene group having 1 to 6 carbon atoms, a phenylene group, or a group having 7 to 18 carbon atoms derived from a combination of these groups, $Y^{51}$ optionally containing a carbonyl group, an ester bond, an ether bond, or a hydroxy group. $Rf^1$ and $Rf^2$ each independently represent a hydrogen atom, a fluorine atom, or a trifluoromethyl group, provided that at least one of $Rf^1$ and $Rf^2$ is a fluorine atom. $R^{21}$ to $R^{28}$ each independently represent a hydrocarbyl group having 1 to 20 carbon atoms and optionally containing a fluorine atom, a chlorine atom, a bromine atom, an iodine atom, or a heteroatom. $R^{23}$ and $R^{24}$ or $R^{26}$ and $R^{27}$ are optionally bonded with each other to form a ring together with a sulfur atom bonded to $R^{23}$ and $R^{24}$ or $R^{26}$ and $R^{27}$. $M^-$ represents a non-nucleophilic counter ion.

In the formulae (c1) to (c3), each $R^A$ independently represents a hydrogen atom or a methyl group. $Y^1$ represents a single bond, a phenylene group, a naphthylene group, $-O-Y^{11}-$, $-C(=O)-O-Y^{11}-$, or $-C(=O)-NH-Y^{11}-$. $Y^{11}$ represents an aliphatic hydrocarbylene group having 1 to 6 carbon atoms, a phenylene group, a naphthylene group, or a group having 7 to 18 carbon atoms derived from a combination of these groups, $Y^{11}$ optionally containing a carbonyl group, an ester bond, an ether bond, or a hydroxy group. $Y^2$ represents a single bond or an ester bond.

$Y^3$ represents a single bond, —$Y^{31}$—C(═O)—O—, —$Y^{31}$—O—, or —$Y^{31}$—O—C(═O)—. $Y^{31}$ represents a hydrocarbylene group having 1 to 12 carbon atoms, a phenylene group, or a group having 7 to 18 carbon atoms derived from a combination of these groups, $Y^{31}$ optionally containing a carbonyl group, an ester bond, an ether bond, an iodine atom, or a bromine atom. $Y^4$ represents a single bond, a methylene group, or a 2,2,2-trifluoro-1,1-ethanediyl group. $Y^5$ represents a single bond, a methylene group, an ethylene group, a phenylene group, a fluorinated phenylene group, —O—$Y^{51}$—, —C(═O)—O—$Y^{51}$—, or —C(═O)—NH—$Y^{51}$—. $Y^{51}$ represents an aliphatic hydrocarbylene group having 1 to 6 carbon atoms, a phenylene group, or a group having 7 to 18 carbon atoms derived from a combination of these groups, $Y^{51}$ optionally containing a carbonyl group, an ester bond, an ether bond, or a hydroxy group.

In the formula (c2), $Rf^1$ and $Rf^2$ each independently represent a hydrogen atom, a fluorine atom, or a trifluoromethyl group, provided that at least one of $Rf^1$ and $Rf^2$ is a fluorine atom. In particular, $Rf^1$ and $Rf^2$ are preferably both a fluorine atom.

In the formulae (c1) to (c3), $R^{21}$ to $R^{28}$ each independently represent a hydrocarbyl group having 1 to 20 carbon atoms and optionally containing a fluorine atom, a chlorine atom, a bromine atom, an iodine atom, or a heteroatom. The hydrocarbyl group may be linear, branched, or cyclic, and specific examples thereof include those given as examples in the description of $R^{101}$ to $R^{105}$ in formulae (2-1) and (2-2) described below.

$R^{23}$ and $R^{24}$ or $R^{26}$ and $R^{27}$ are optionally bonded with each other to form a ring together with a sulfur atom bonded to $R^{23}$ and $R^{24}$ or $R^{26}$ and $R^{27}$. In this event, examples of the ring include those given as rings that may be formed by $R^{101}$ and $R^{102}$ being bonded to each other together with a sulfur atom bonded to $R^{101}$ and $R^{102}$ in the description of the formula (2-1) below.

In the formula (c1), $M^-$ represents a non-nucleophilic counter ion. Examples of the non-nucleophilic counter ion include halide ions, such as chloride and bromide ions; fluoroalkylsulfonate ions, such as triflate, 1,1,1-trifluoroethanesulfonate, and nonafluorobutanesulfonate ions; arylsulfonate ions, such as tosylate, benzenesulfonate, 4-fluorobenzenesulfonate, and 1,2,3,4,5-pentafluorobenzenesulfonate ions; alkylsulfonate ions, such as mesylate and butanesulfonate ions; imide ions, such as bis(trifluoromethylsulfonyl)imide, bis(perfluoroethylsulfonyl)imide and bis(perfluorobutylsulfonyl)imide ions; and methide ions such as tris(trifluoromethylsulfonyl)methide and tris(perfluoroethylsulfonyl)methide ions.

Examples of the non-nucleophilic counter ion further include: sulfonate ions represented by the following formula (c1-1), having a substituting fluorine atom at α position; sulfonate ions represented by the following formula (c1-2), having a substituting fluorine atom at α position and having a substituting trifluoromethyl group at β position; etc.

$$R^{31}—CF_2—SO_3^- \quad (c1\text{-}1)$$

(c1-2)

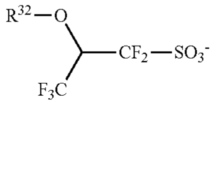

In the formula (c1-1), $R^{31}$ represents a hydrogen atom or a hydrocarbyl group having 1 to 20 carbon atoms and optionally containing an ether bond, an ester bond, a carbonyl group, a lactone ring, or a fluorine atom. The hydrocarbyl group may be linear, branched, or cyclic. Specific examples thereof include those given as examples of a hydrocarbyl group represented by $R^{107}$ in a formula (2A') described below.

In the formula (c1-2), $R^{32}$ represents a hydrogen atom, a hydrocarbyl group having 1 to 30 carbon atoms, or a hydrocarbylcarbonyl group having 2 to 30 carbon atoms, and optionally contains an ether bond, an ester bond, a carbonyl group, or a lactone ring. The hydrocarbyl group and the hydrocarbyl moiety of the hydrocarbylcarbonyl group may be saturated or unsaturated, and may be linear, branched, or cyclic. Specific examples of the hydrocarbyl group include the groups given below as examples of the hydrocarbyl group represented by $R^{107}$ in the formula (2A').

Examples of a cation of a monomer to give the repeating unit-c1 include those shown below, but are not limited thereto. Note that, in the following formulae, $R^A$ is as defined above.

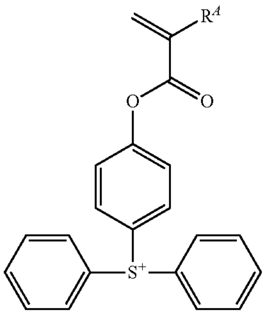

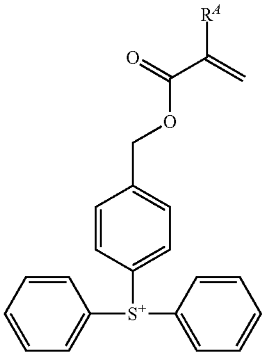

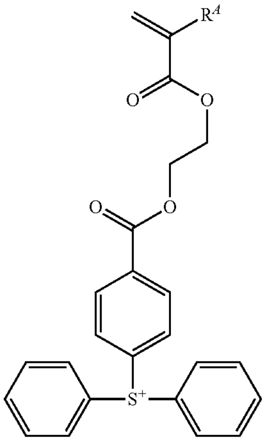

-continued
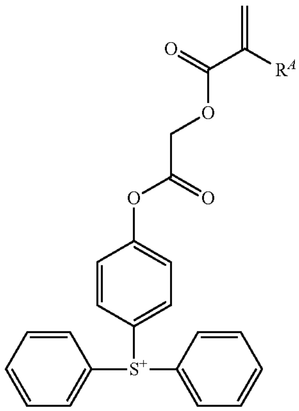
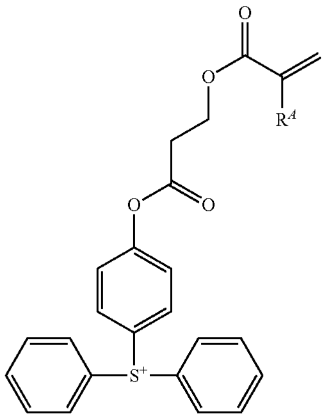
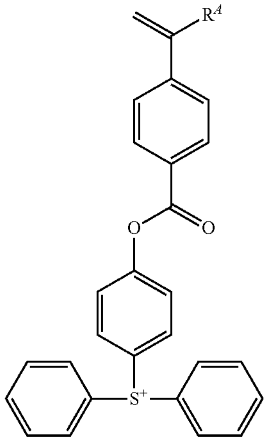
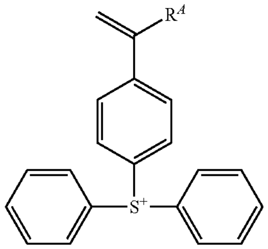
-continued
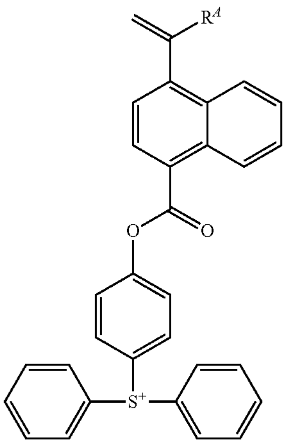
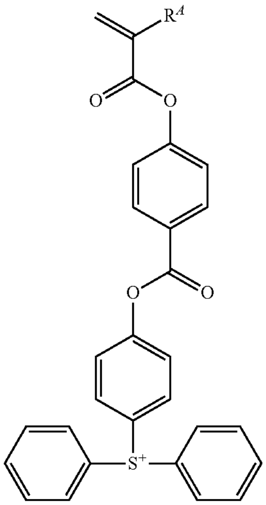
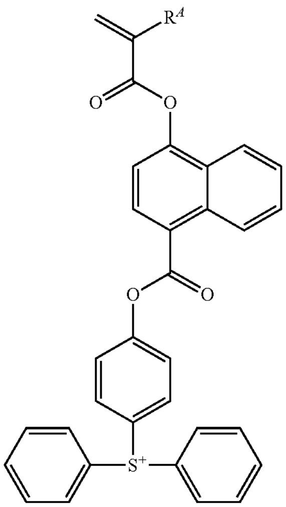

-continued

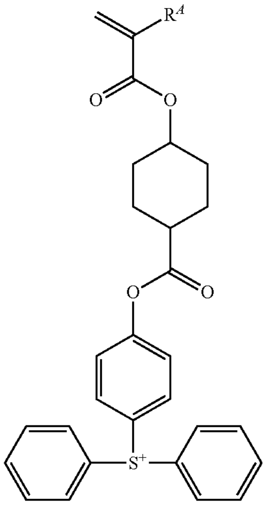

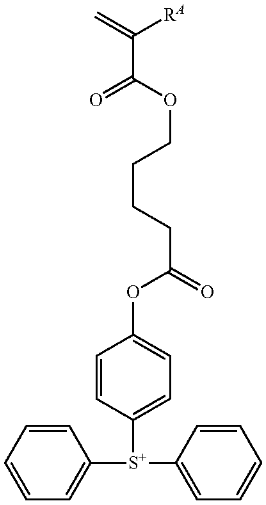

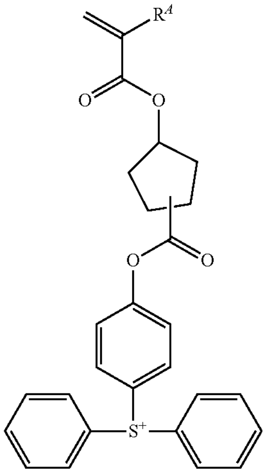

-continued

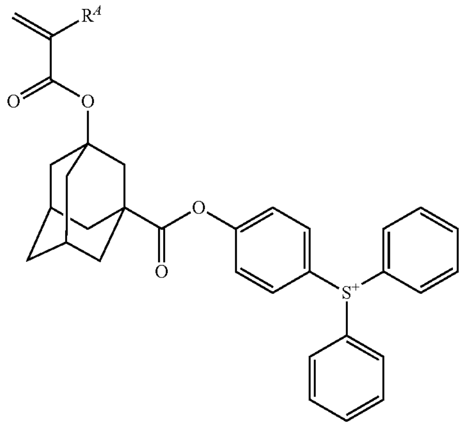

Specific examples of a cation of a monomer to give the repeating unit-c2 or -c3 include those given below as examples of a cation of a sulfonium salt represented by the formula (2-1).

Examples of an anion of a monomer to give the repeating unit-c2 include those shown below, but are not limited thereto. Note that, in the following formulae, $R^A$ is as defined above.

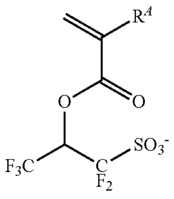

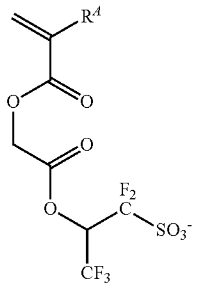

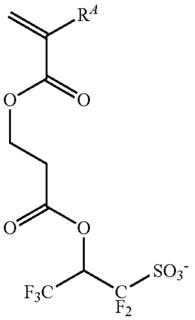

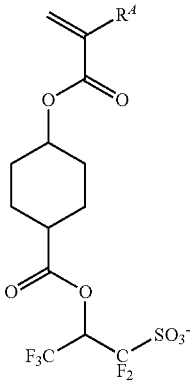

-continued
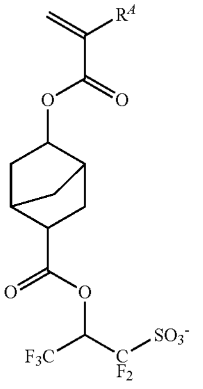
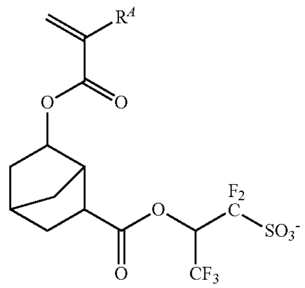
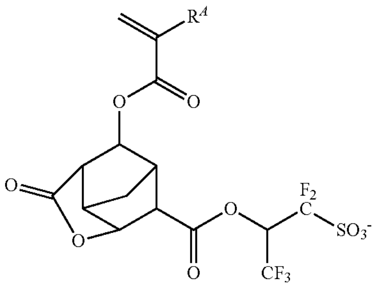
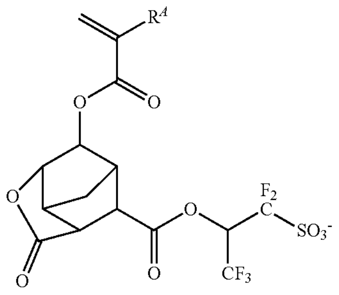
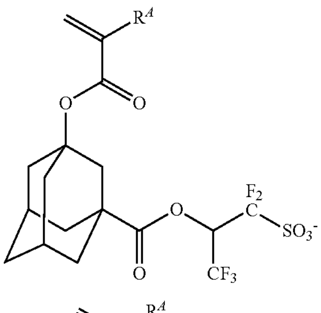
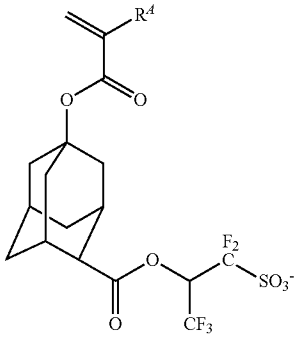
-continued
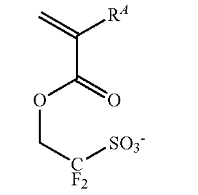
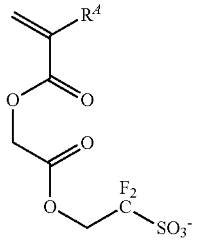
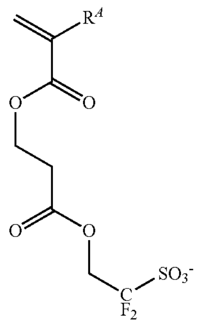
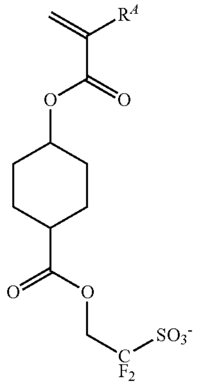
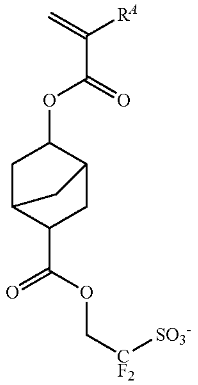
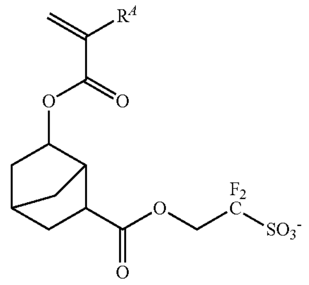
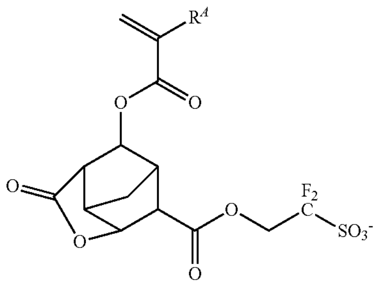
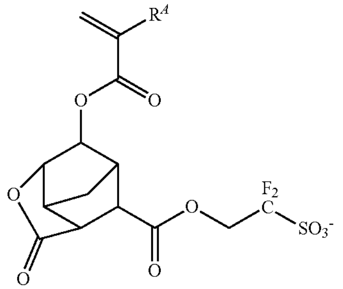

-continued
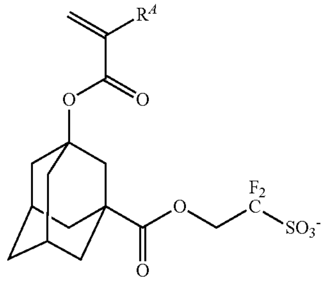
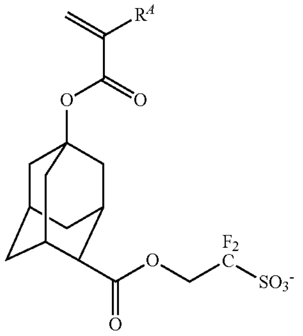
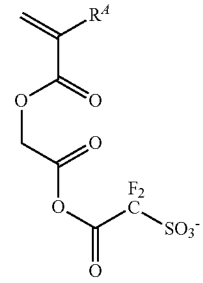
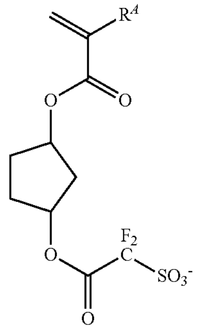
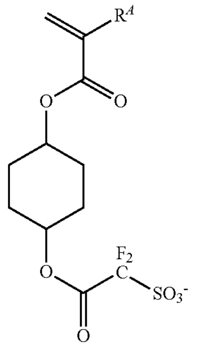
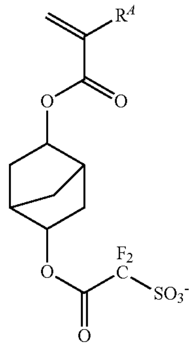
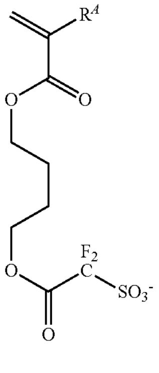
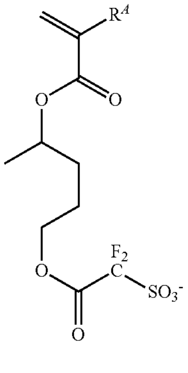
-continued
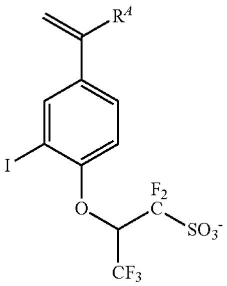
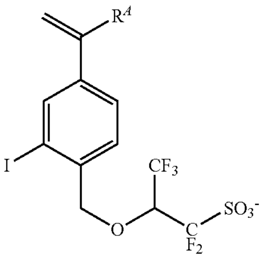
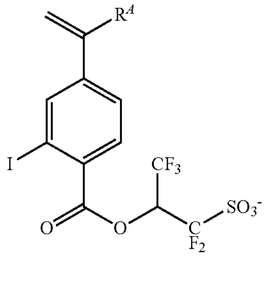
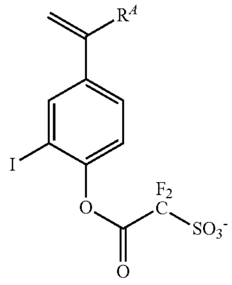
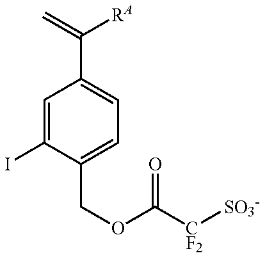
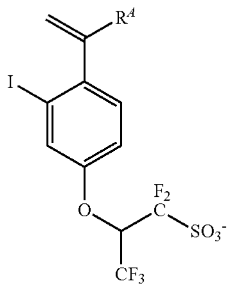
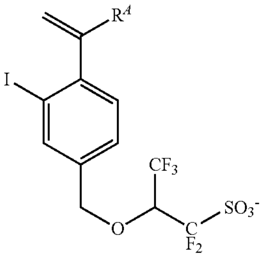
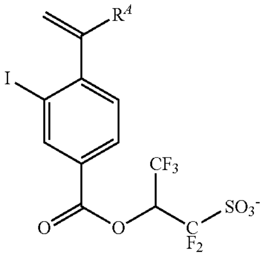
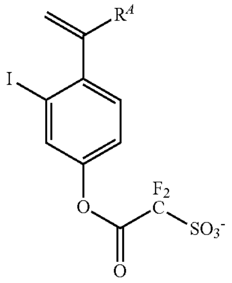
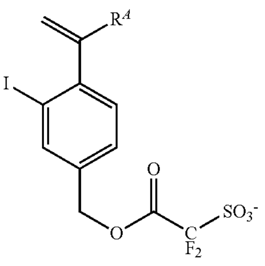
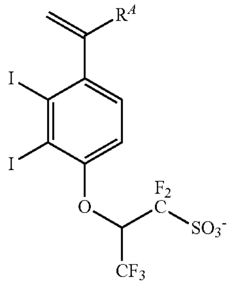

-continued
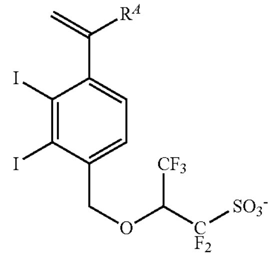
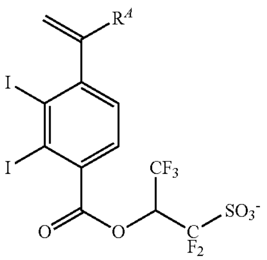
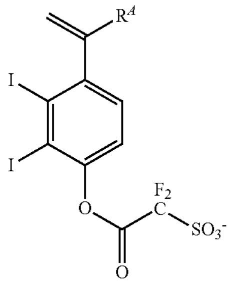
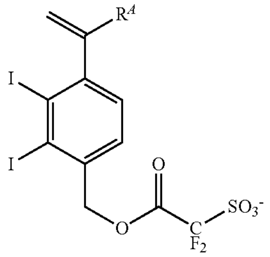
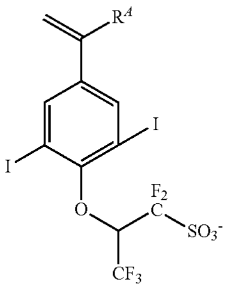
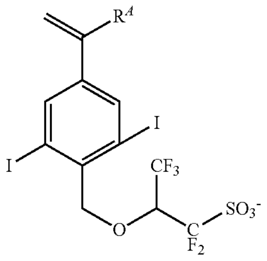
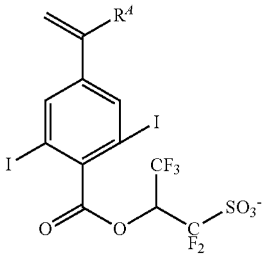
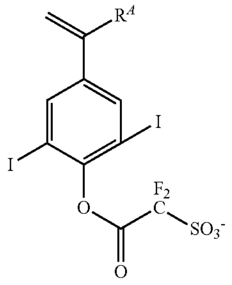
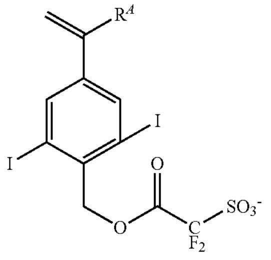
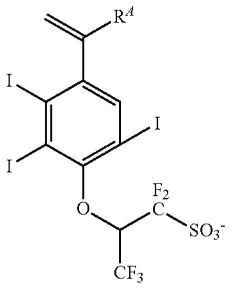
-continued
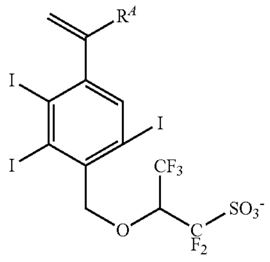
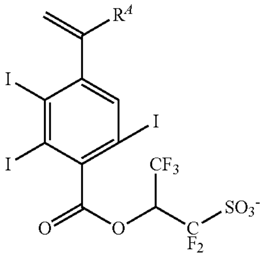
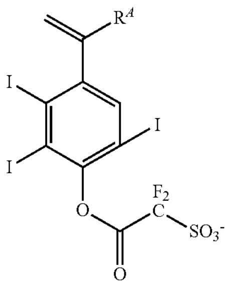
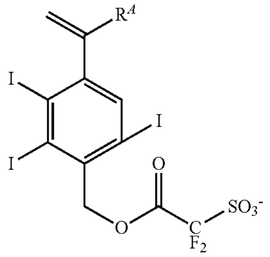
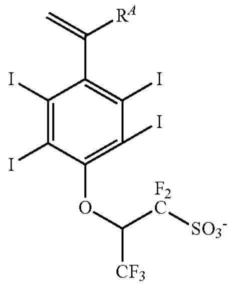
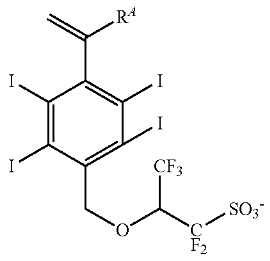
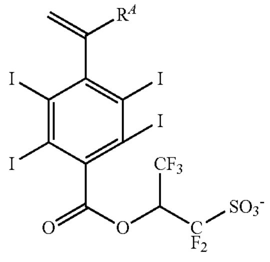
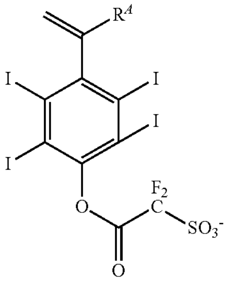
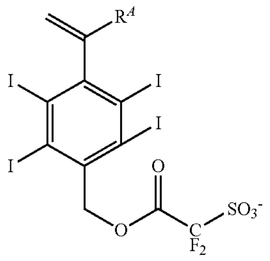

-continued
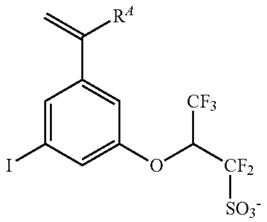
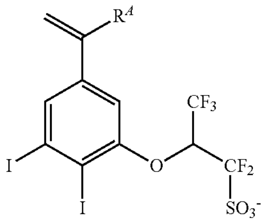
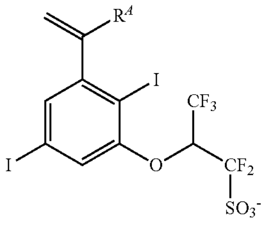
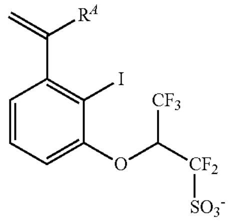
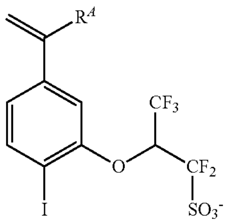
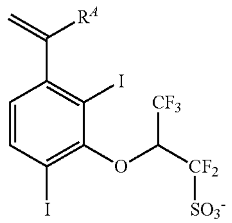
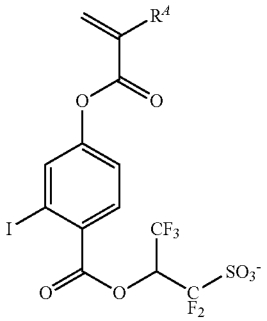
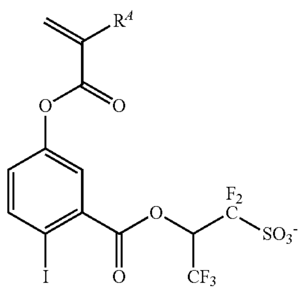
-continued
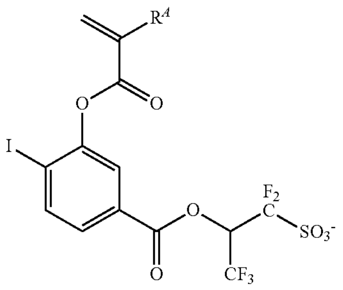
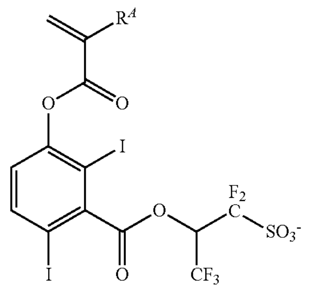
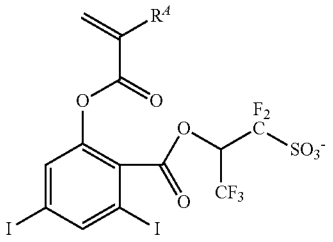
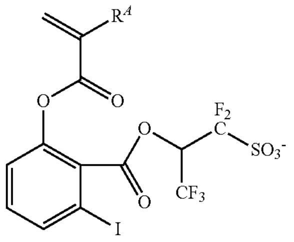
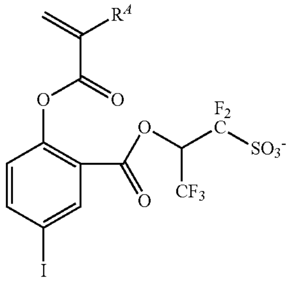
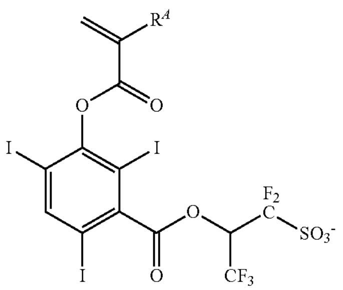

-continued
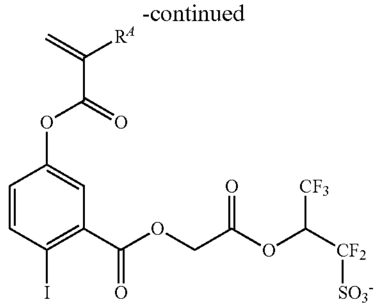
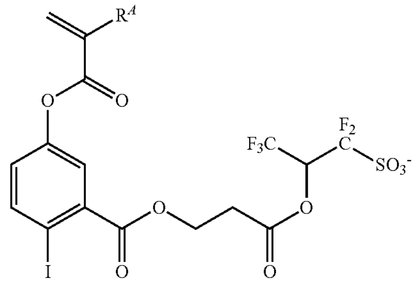
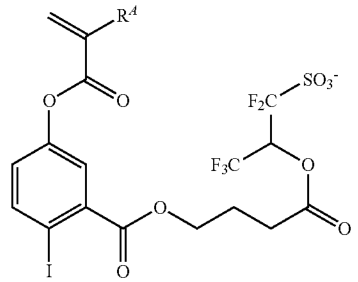
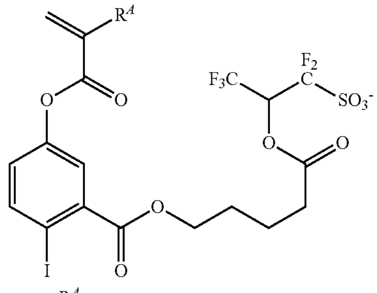
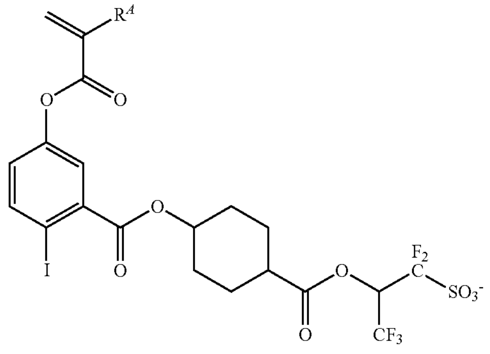
-continued
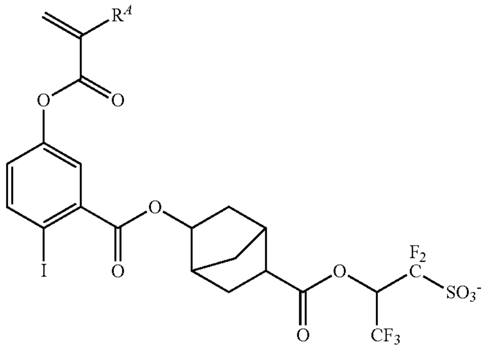
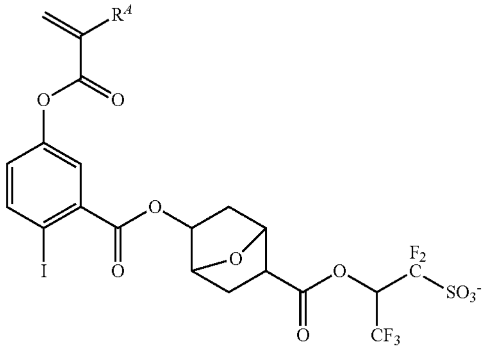
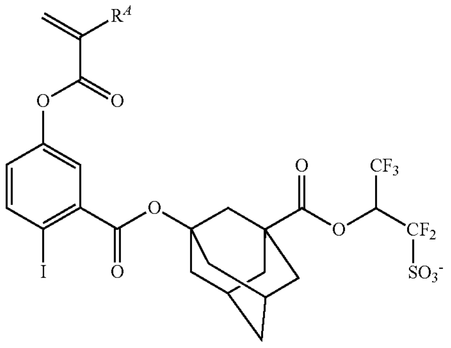
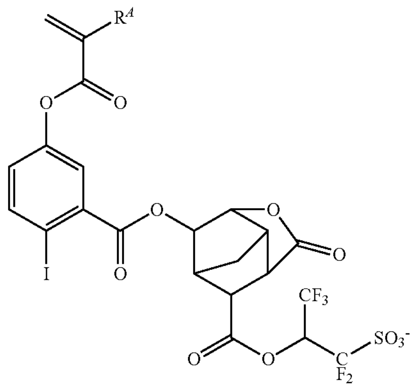

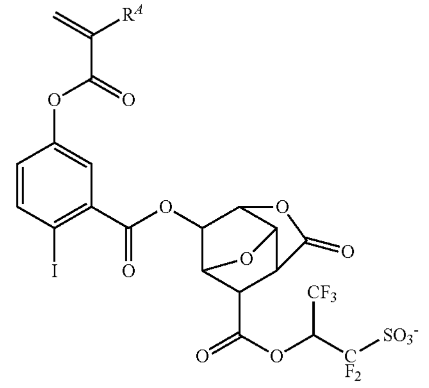
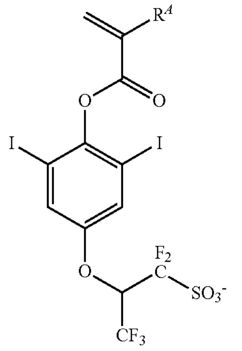
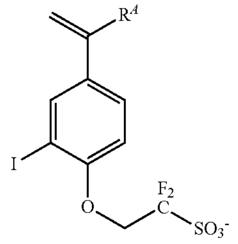
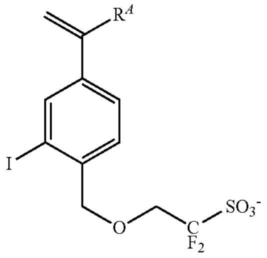
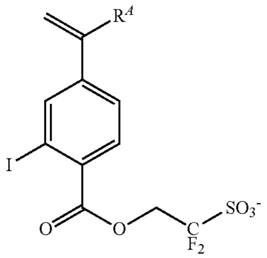
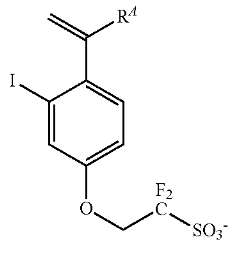
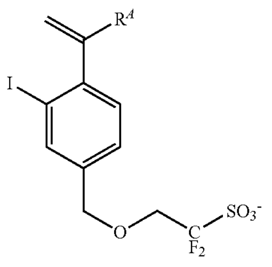
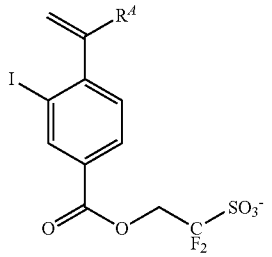
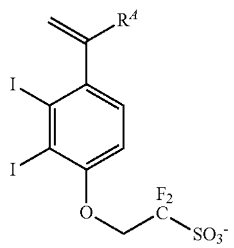
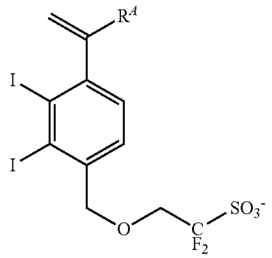
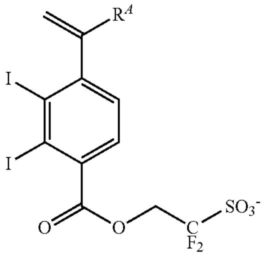
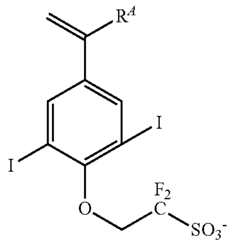
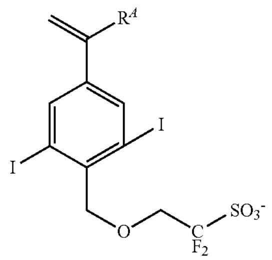
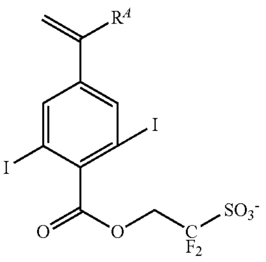
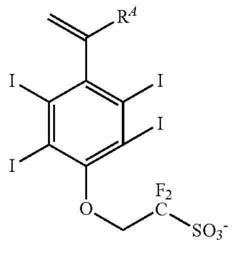
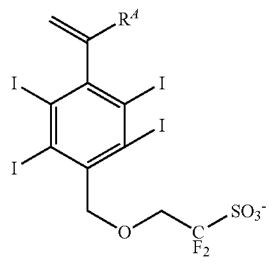

-continued
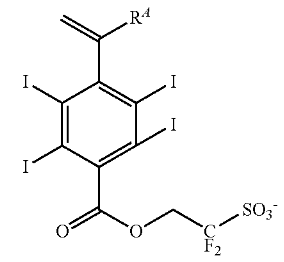
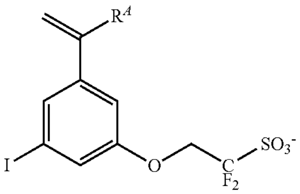
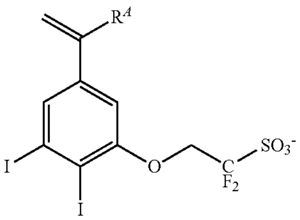
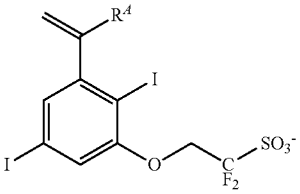
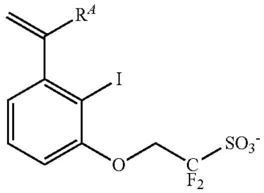
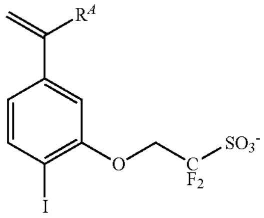
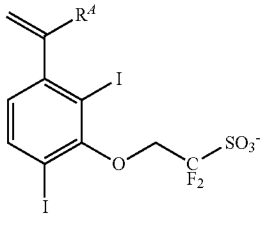
-continued
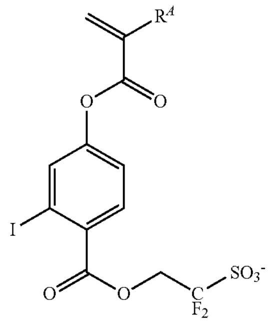
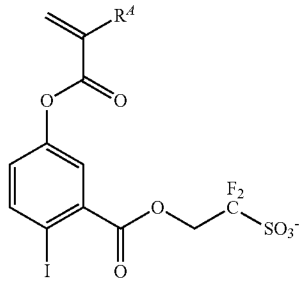
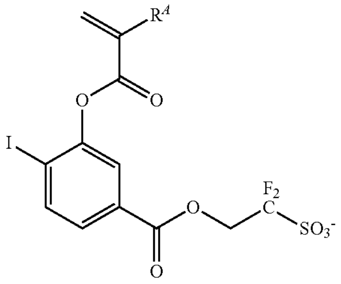
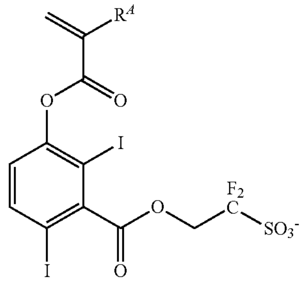
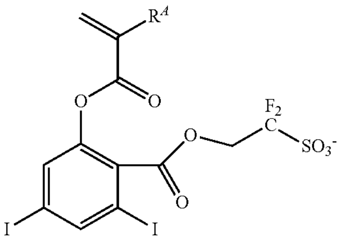
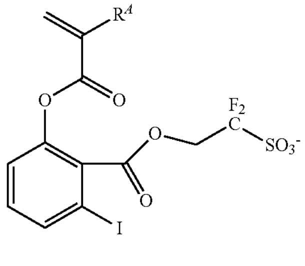

-continued
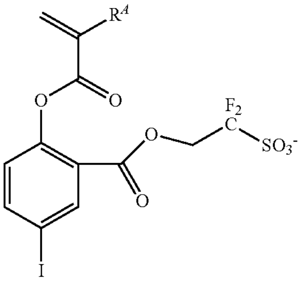
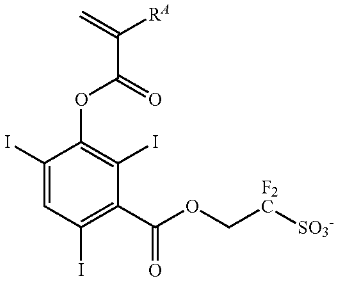
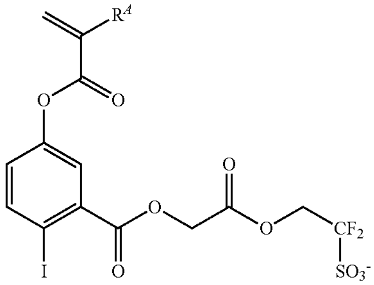
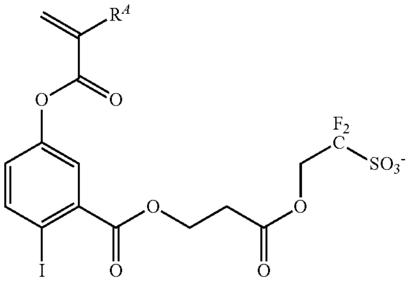
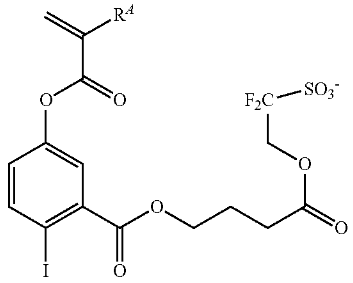
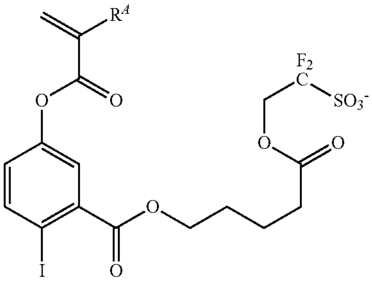
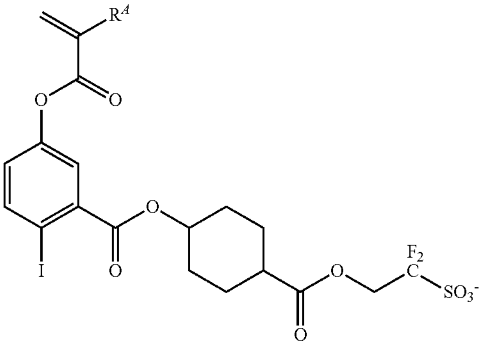
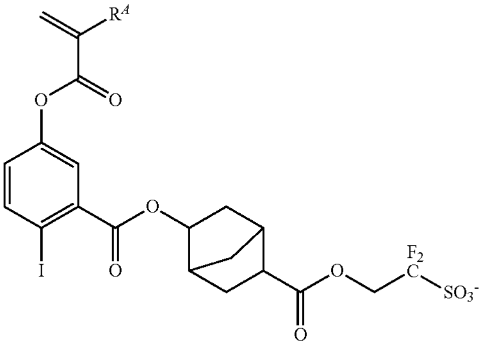
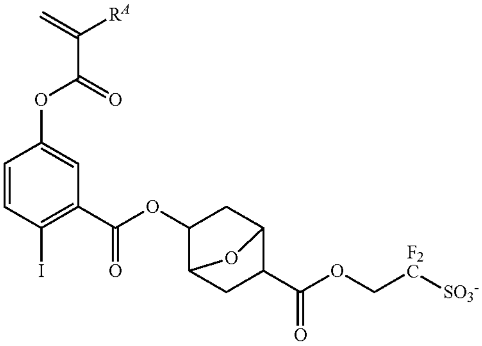
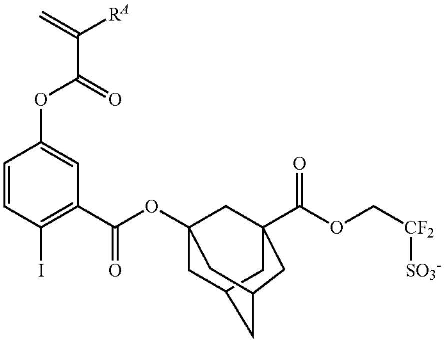

-continued
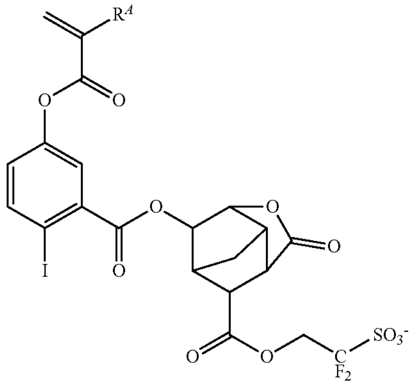
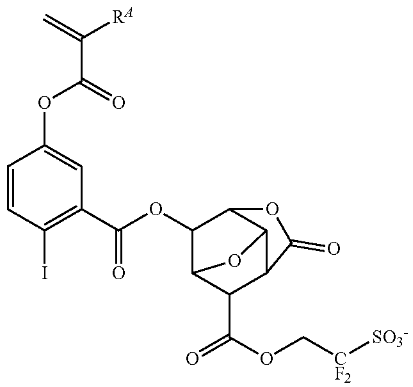
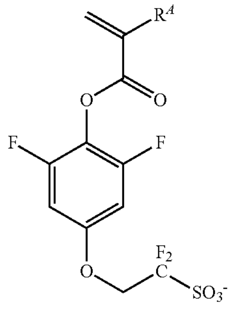
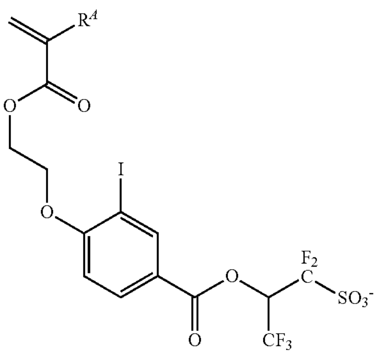
-continued
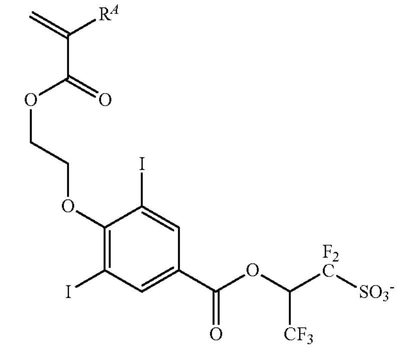
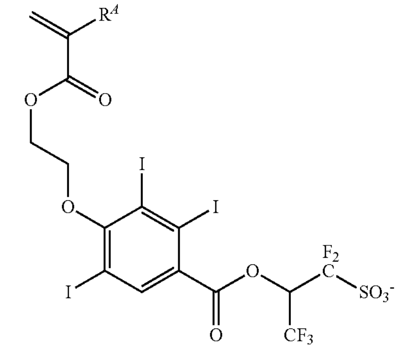
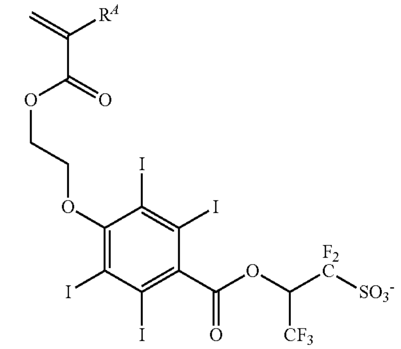
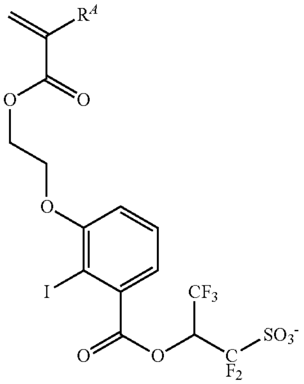

-continued

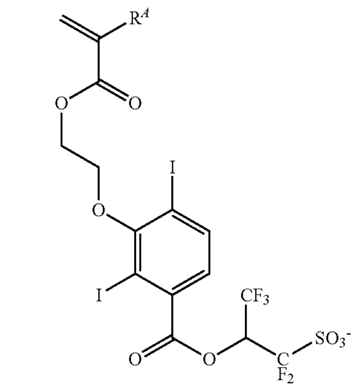

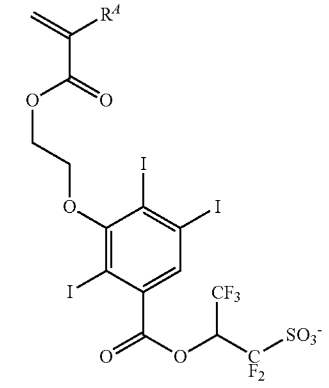

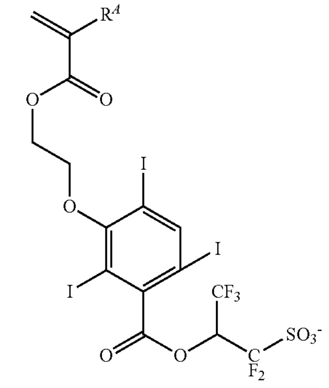

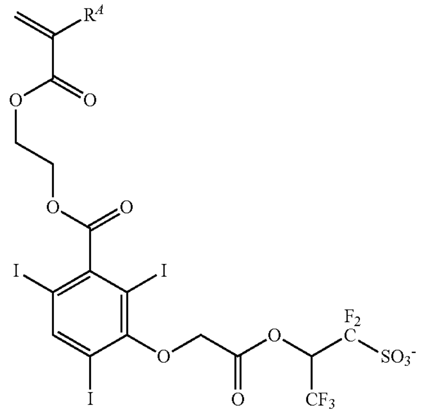

Examples of an anion of a monomer to give the repeating unit-c3 include those shown below, but are not limited thereto. Note that, in the following formulae, $R^A$ is as defined above.

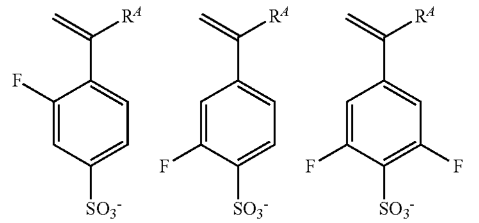

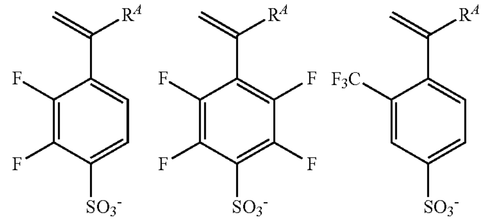

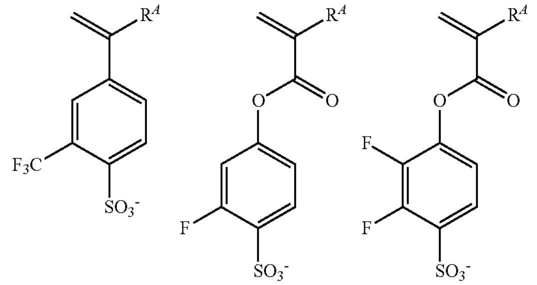

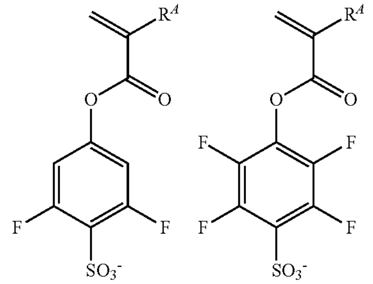

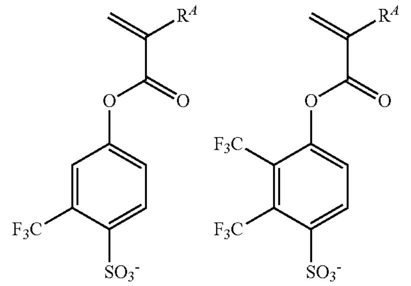

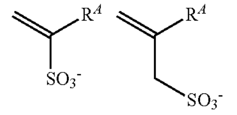

The repeating units-c1 to -c3 have the function of an acid generator. Acid diffusion can be reduced when an acid generator is bonded to a polymer main chain. Thus, it is possible to prevent the degradation of resolution due to blurring caused by acid diffusion. Furthermore, LWR can be improved when the acid generator is dispersed uniformly. Note that, when a base polymer having the repeating unit-c is contained, blending of an additive-type acid generator described below may be omitted.

Furthermore, it is possible for the base polymer to contain no amino group and contain a repeating unit-d having an iodine atom. Examples of a monomer to give the repeating unit-d include those shown below, but are not limited thereto. Note that, in the following formulae, $R^A$ represents a hydrogen atom or a methyl group.
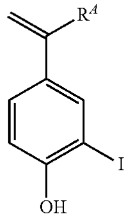
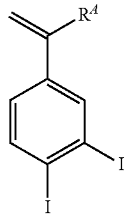
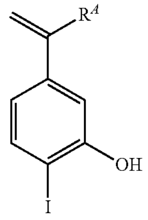
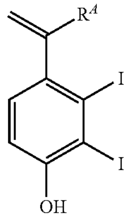
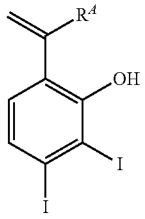
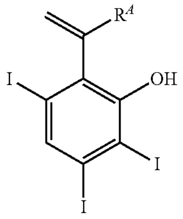
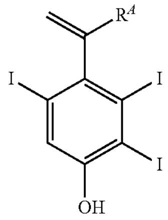
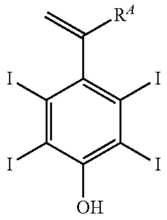
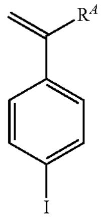
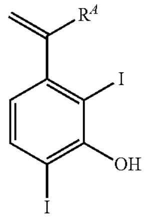
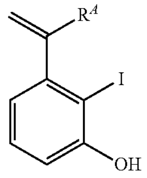
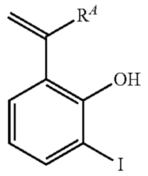
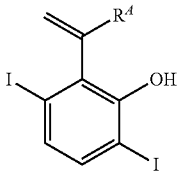
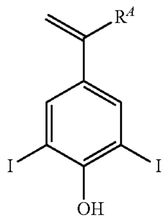
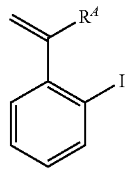
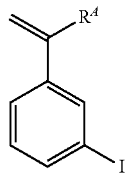
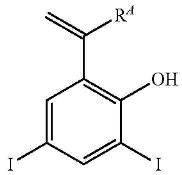
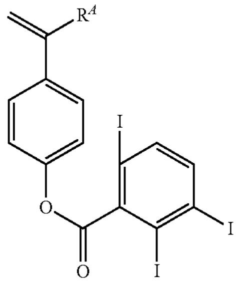
-continued
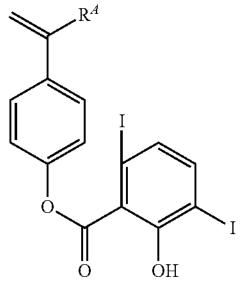
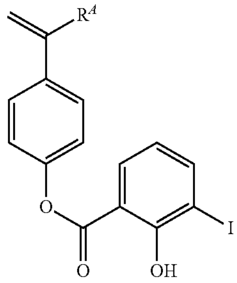
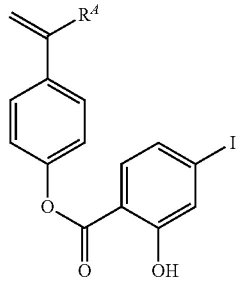
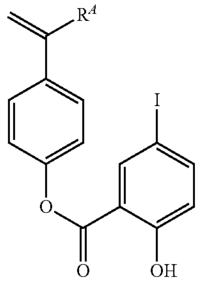
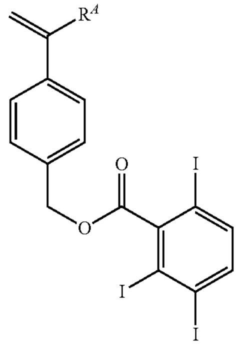
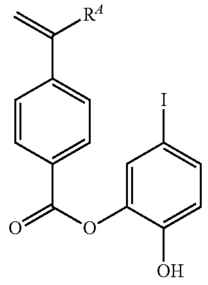
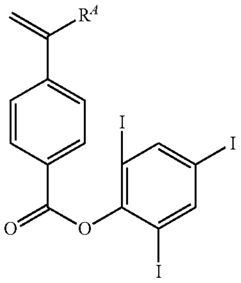
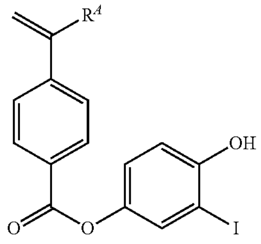
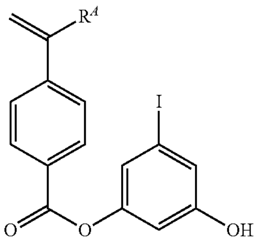
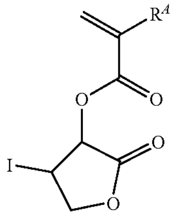
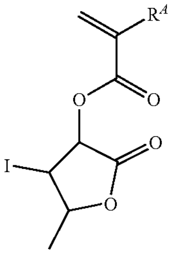
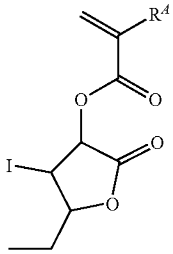

-continued

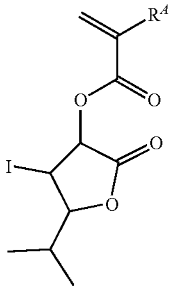
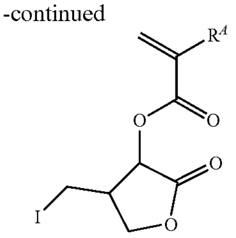
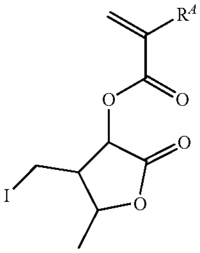
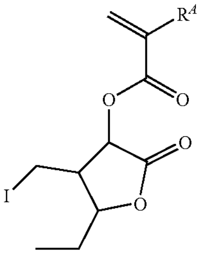
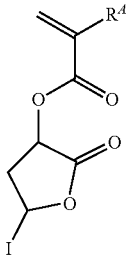
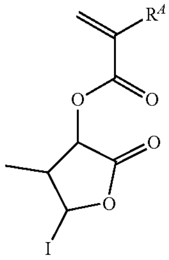
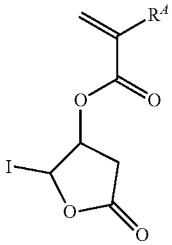
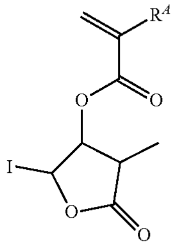
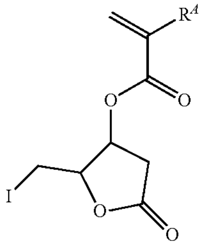
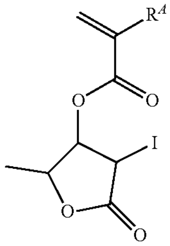
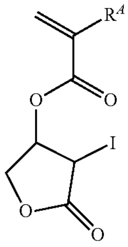

The base polymer may contain a repeating unit-e different from the above-described repeating units. Examples of the repeating unit-e include ones derived from styrene, acenaphthylene, indene, coumarin, coumarone, etc.

In the base polymer, the content ratios of the repeating units-a1, -a2, -b, -c1, -c2, -c3, -d, and -e are preferably $0 \le a1 \le 0.9$, $0 \le a2 \le 0.9$, $0 < a1+a2 \le 0.9$, $0 \le b \le 0.9$, $0 \le c1 \le 0.5$, $0 \le c2 \le 0.5$, $0 \le c3 \le 0.5$, $0 \le c1+c2+c3 \le 0.5$, $0 \le d \le 0.5$, and $0 \le e \le 0.5$; more preferably $0 \le a1 \le 0.8$, $0 \le a2 \le 0.8$, $0 < a1+a2 \le 0.8$, $0 \le b \le 0.8$, $0 \le c1 \le 0.4$, $0 \le c2 \le 0.4$, $0 \le c3 \le 0.4$, $0 \le c1+c2+c3 \le 0.4$, $0 \le d \le 0.4$, and $0 \le e \le 0.4$; and further preferably $0 \le a1 \le 0.7$, $0 \le a2 \le 0.7$, $0 < a1+a2 \le 0.7$, $0 \le b \le 0.7$, $0 \le c1 \le 0.3$, $0 \le c2 \le 0.3$, $0 \le c3 \le 0.3$, $0 \le c1+c2+c3 \le 0.3$, $0 \le d \le 0.3$, and $0 \le e \le 0.3$, provided that $a1+a2+b+c1+c2+c3+d+e=1.0$.

The base polymer may be synthesized, for example, by subjecting the monomers to give the repeating units described above to heat polymerization in an organic solvent to which a radical polymerization initiator has been added.

Examples of the organic solvent used in the polymerization include toluene, benzene, tetrahydrofuran (THF), diethyl ether, dioxane, etc. Examples of the polymerization initiator include 2,2'-azobisisobutyronitrile (AIBN), 2,2'-azobis(2,4-dimethylvaleronitrile), dimethyl-2,2-azobis(2-methylpropionate), benzoyl peroxide, lauroyl peroxide, etc. The temperature during the polymerization is preferably 50 to 80° C. The reaction time is preferably 2 to 100 hours, more preferably 5 to 20 hours.

In the case where the monomer containing a hydroxy group is copolymerized, the process may include: substituting the hydroxy group with an acetal group susceptible to deprotection with acid, such as an ethoxyethoxy group, prior to the polymerization; and the deprotection with weak acid and water after the polymerization. Alternatively, the process may include: substituting the hydroxy group with an acetyl group, a formyl group, a pivaloyl group, or the like; and performing alkaline hydrolysis after the polymerization.

In a case where hydroxystyrene or hydroxyvinylnaphthalene is copolymerized, at first, acetoxystyrene or acetoxyvinylnaphthalene may be used in place of hydroxystyrene or hydroxyvinylnaphthalene; after the polymerization, the acetoxy group may be deprotected by the alkaline hydrolysis as described above to convert the acetoxystyrene or acetoxyvinylnaphthalene to hydroxystyrene or hydroxyvinylnaphthalene.

In the alkaline hydrolysis, a base is usable, such as ammonia water or triethylamine. The reaction temperature is preferably −20 to 100° C., more preferably 0 to 60° C. The reaction time is preferably 0.2 to 100 hours, more preferably 0.5 to 20 hours.

The base polymer has a polystyrene-based weight-average molecular weight (Mw) of preferably 1,000 to 500,000, more preferably 2,000 to 30,000, determined by gel permeation chromatography (GPC) using THF as an eluent. When the Mw is 1,000 or more, the resist material has excellent heat resistance. When the Mw is 500,000 or less, the alkali solubility is sufficient, and a footing phenomenon after pattern formation is prevented.

Furthermore, when the base polymer has a broad molecular weight distribution (Mw/Mn), there are risks that foreign matters may be found on the pattern after the exposure or pattern profile may be degraded due to the presence of low-molecular-weight or high-molecular-weight polymers. The finer the pattern rule, the stronger the influences of Mw and Mw/Mn. Hence, in order to obtain a resist material suitably used for finer pattern dimensions, the base polymer preferably has a narrow dispersity Mw/Mn of 1.0 to 2.0, particularly preferably 1.0 to 1.5.

When the inventive positive resist material contains a base polymer, the base polymer is preferably contained in an amount of 10 to 1,000 parts by mass, more preferably 20 to 500 parts by mass, and further preferably 50 to 200 parts by mass based on 100 parts by mass of the above-described compound. The base polymer may include two or more polymers having different composition ratios, Mw, and Mw/Mn.

[Acid Generator]

The inventive positive resist material may further contain an acid generator that generates a strong acid (hereinafter also referred to as additive-type acid generator). Here, the term strong acid means a compound that has sufficient acidity to cause a deprotection reaction of the acid-labile groups of the compound or the base polymer. Examples of the acid generator include compounds that generate acids in response to actinic light or radiation (photo-acid generator). The photo-acid generator is not particularly limited, as long as the compound generates an acid upon high-energy beam irradiation. Preferably, the photo-acid generator generates a sulfonic acid, imide acid, or methide acid. Suitable photo-acid generators are sulfonium salt, iodonium salt, sulfonyl-diazomethane, N-sulfonyloxyimide, oxime-O-sulfonate type acid generators, etc. Specific examples of the photo-acid generator include ones disclosed in paragraphs [0122] to [0142] of JP 2008-111103 A.

Moreover, a sulfonium salt shown by the following formula (2-1) and an iodonium salt shown by the following formula (2-2) can also be used suitably as photo-acid generators.

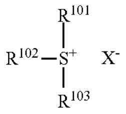

(2-1)

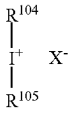

(2-2)

In the formulae (2-1) and (2-2), $R^{101}$ to $R^{105}$ each independently represent a hydrocarbyl group having 1 to 25 carbon atoms and optionally containing a fluorine atom, a chlorine atom, a bromine atom, an iodine atom, or a heteroatom.

The hydrocarbyl group represented by $R^{101}$ to $R^{105}$ may be saturated or unsaturated, and may be linear, branched, or cyclic. Specific examples thereof include: alkyl groups having 1 to 25 carbon atoms, such as a methyl group, an ethyl group, an n-propyl group, an isopropyl group, an n-butyl group, an isobutyl group, a sec-butyl group, a tert-butyl group, an n-pentyl group, an n-hexyl group, an n-octyl group, an n-nonyl group, an n-decyl group, an undecyl group, a dodecyl group, a tridecyl group, a tetradecyl group, a pentadecyl group, a heptadecyl group, an octadecyl group, a nonadecyl group, and an icosyl group; cyclic saturated hydrocarbyl groups having 3 to 25 carbon atoms, such as a cyclopropyl group, a cyclopentyl group, a cyclohexyl group, a cyclopropylmethyl group, a 4-methylcyclohexyl group, a cyclohexylmethyl group, a norbornyl group, and an adamantyl group; alkenyl groups having 2 to 25 carbon atoms, such as a vinyl group, a propenyl group, a butenyl group, and a hexenyl group; cyclic unsaturated aliphatic hydrocarbyl groups having 6 to 25 carbon atoms, such as a cyclohexenyl group and a norbornenyl group; alkynyl groups having 2 to 25 carbon atoms, such as an ethynyl group, a propynyl group, and a butynyl group; aryl groups having 6 to 25 carbon atoms, such as a phenyl group, a methylphenyl group, an ethylphenyl group, an n-propylphenyl group, an isopropylphenyl group, an n-butylphenyl group, an isobutylphenyl group, a sec-butylphenyl group, a tert-butylphenyl group, a naphthyl group, a methylnaphthyl group, an ethylnaphthyl group, an n-propylnaphthyl group, an isopropylnaphthyl group, an n-butylnaphthyl group, an isobutylnaphthyl group, a sec-butylnaphthyl group, and a tert-butylnaphthyl group; aralkyl groups having 7 to 25 carbon atoms, such as a benzyl group and a phenethyl group; etc. Additionally, these groups may have some of hydrogen atoms substituted with a group containing a heteroatom, such as an oxygen atom, a sulfur atom, a nitrogen atom, or a halogen atom, while these groups may have some of carbon atoms substituted with a group containing a heteroatom, such as an oxygen atom, a sulfur atom, or a nitrogen atom. Thus, the resulting hydrocarbyl group may contain a hydroxy group, a cyano group, a carbonyl group, an ether bond, an ester bond, a sulfonic acid ester bond, a carbonate group, a lactone ring, a sultone ring, a carboxylic anhydride, a haloalkyl group, etc.

Alternatively, $R^{101}$ and $R^{102}$ may bond with each other to form a ring together with a sulfur atom bonded therewith. In this event, the ring preferably has any of structures shown below.

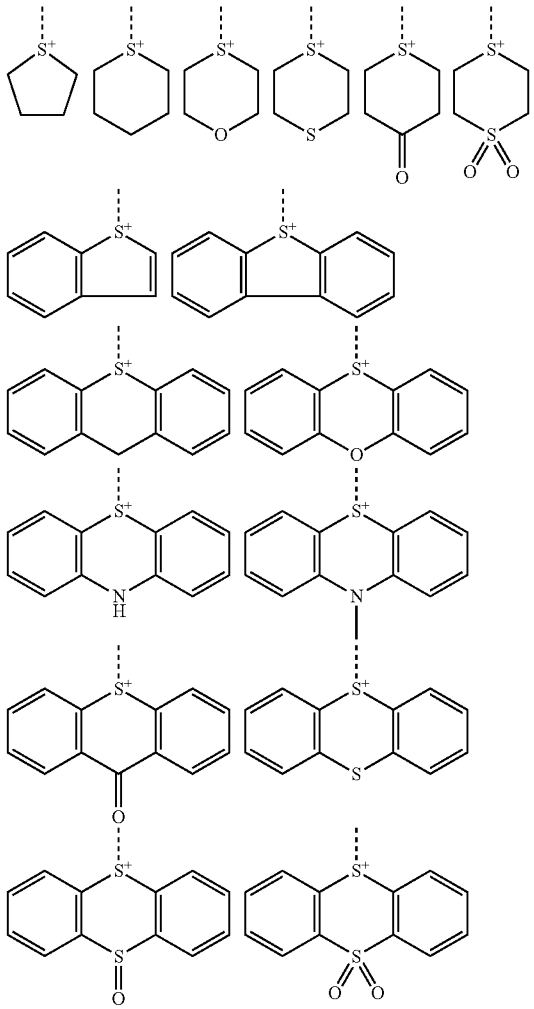

In the formulae, a broken line represents an attachment point to $R^{103}$.

Examples of a cation of the sulfonium salt shown by the formula (2-1) include ones shown below, but are not limited thereto.
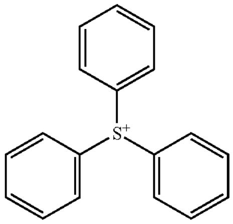
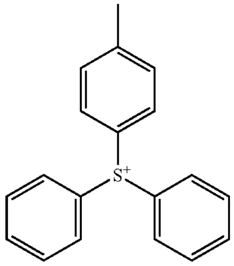
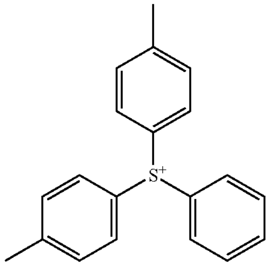
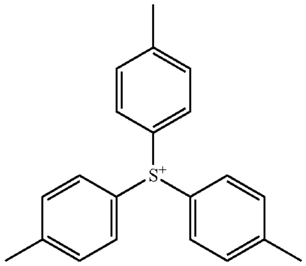
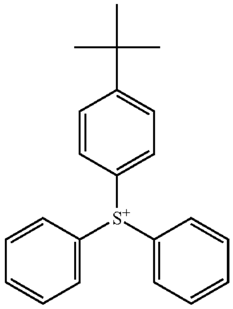
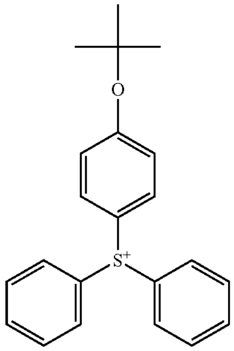
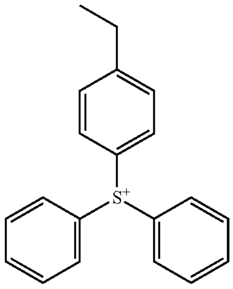
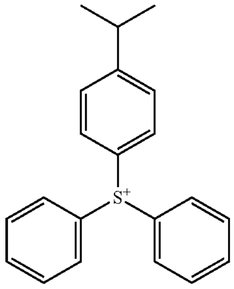
-continued
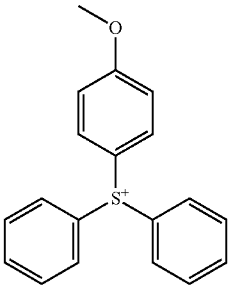
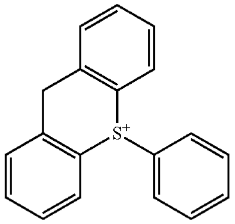
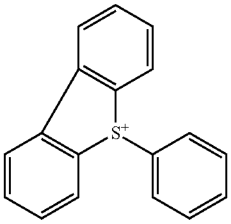
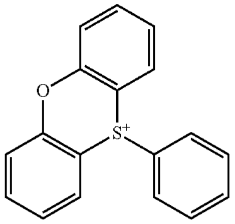
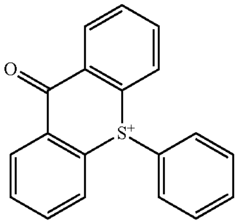
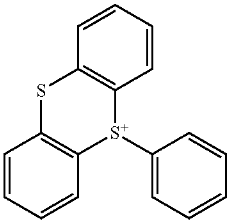
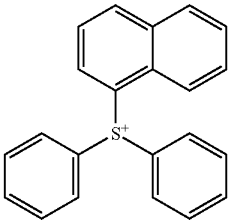
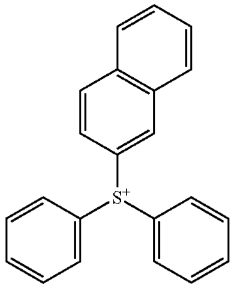
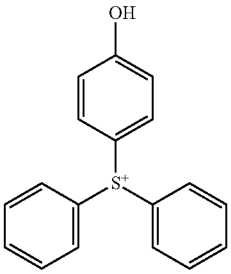
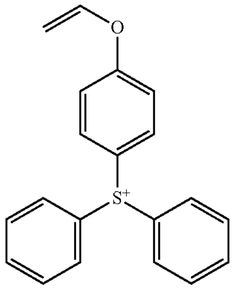
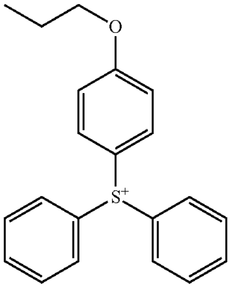
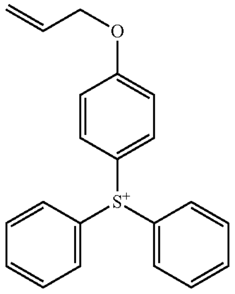

-continued
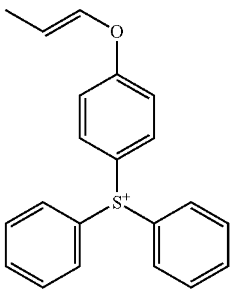
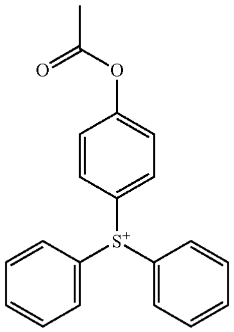
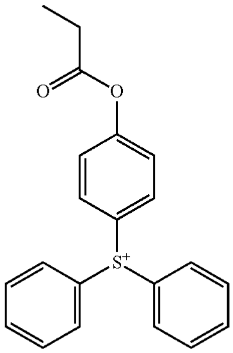
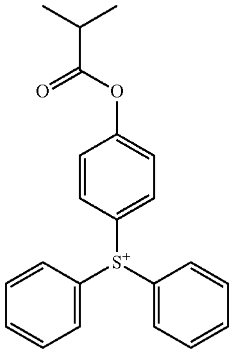
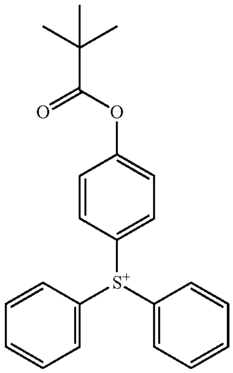
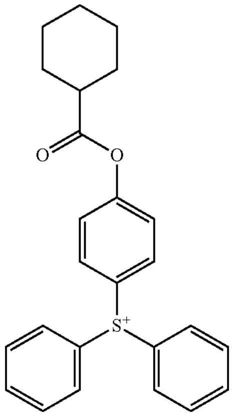
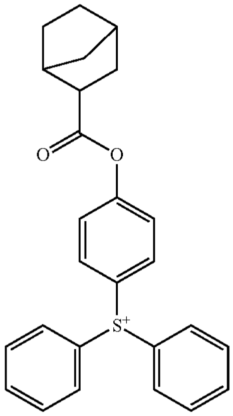
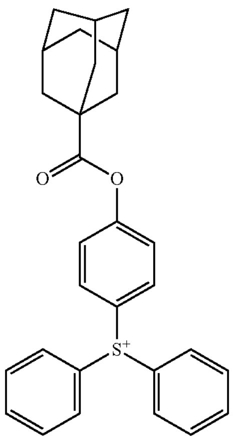
-continued
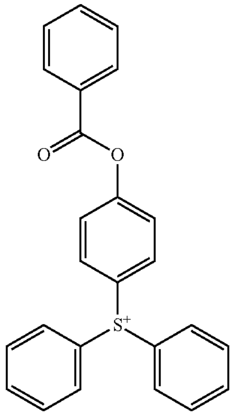
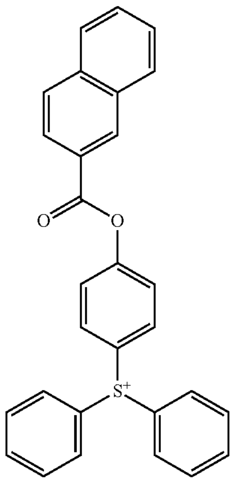
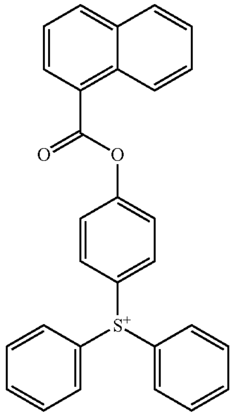
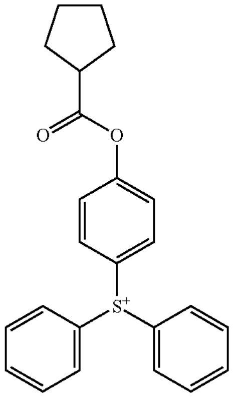
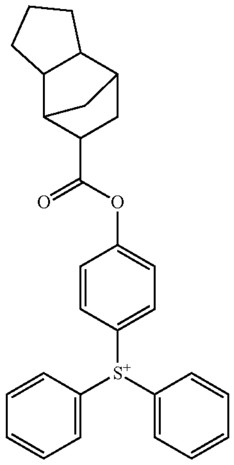
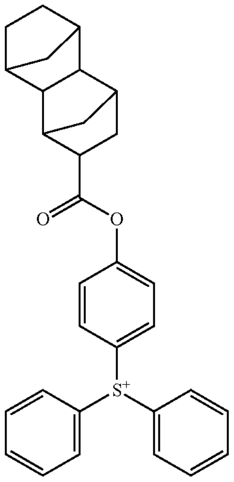
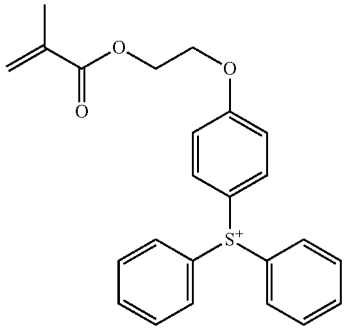

-continued
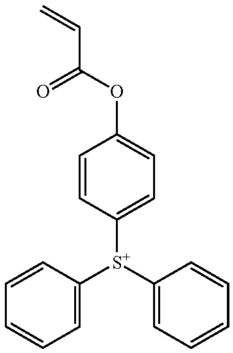
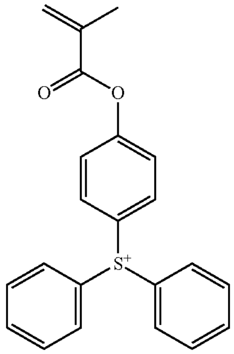
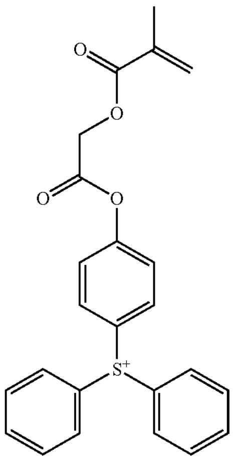
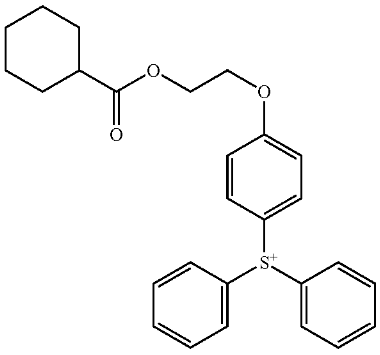
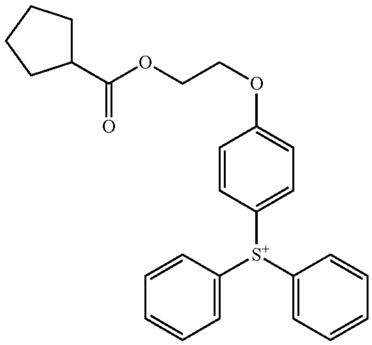
-continued
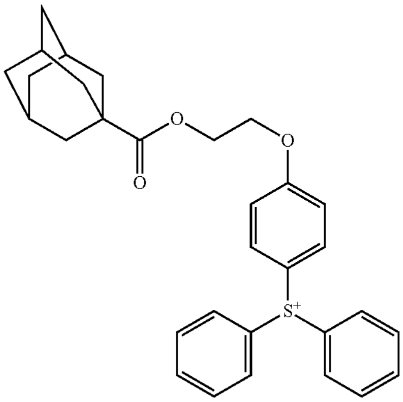
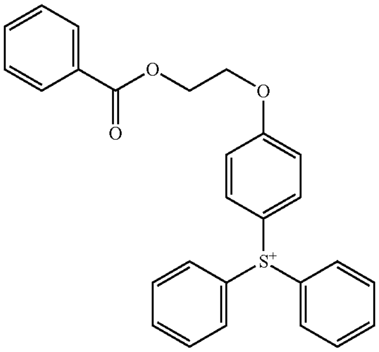
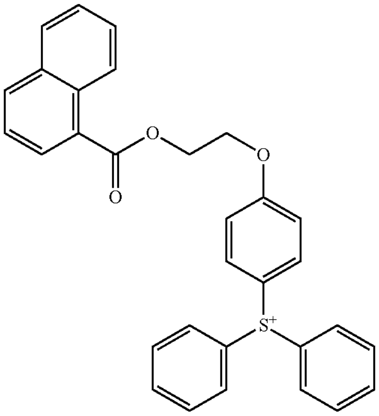
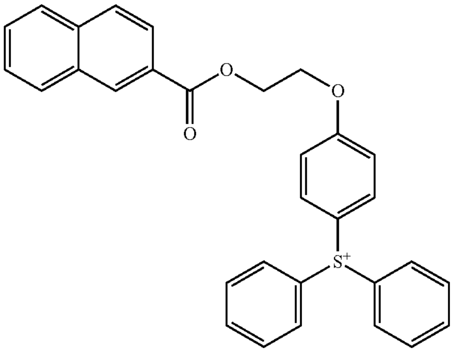

-continued
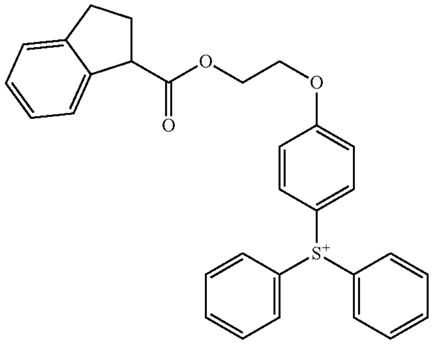
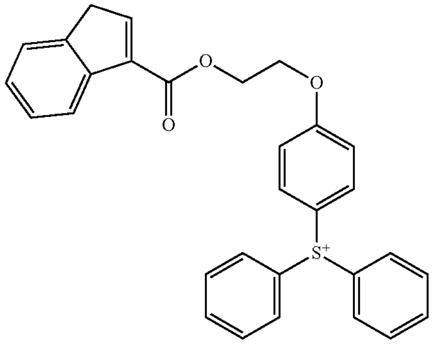
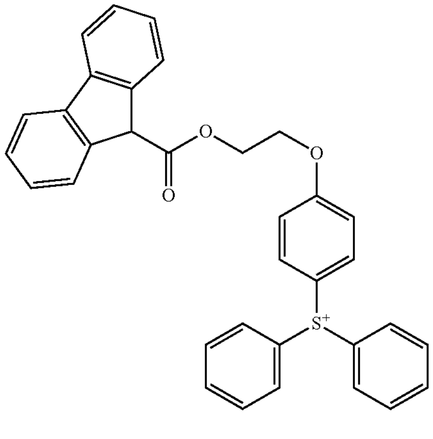
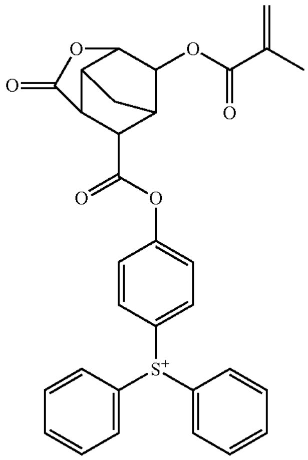
-continued
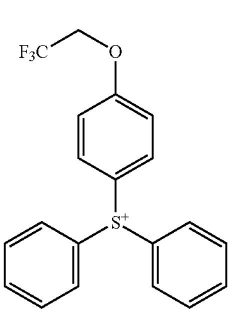
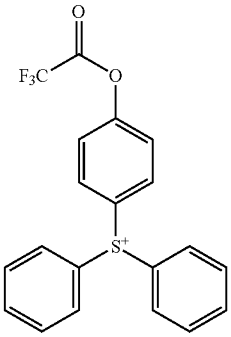
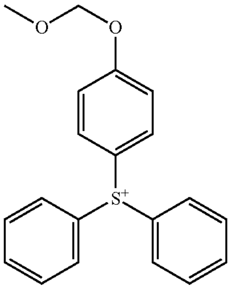
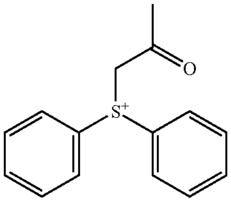
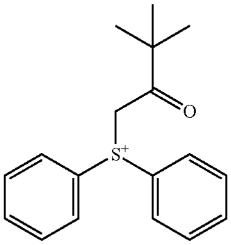
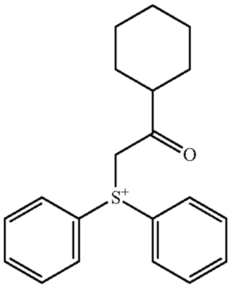
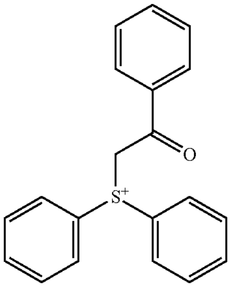
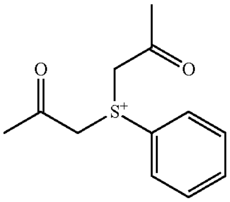
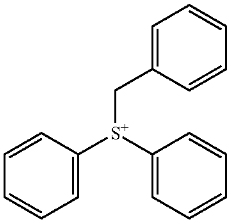
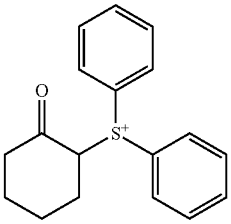
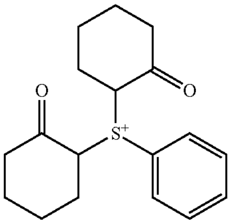
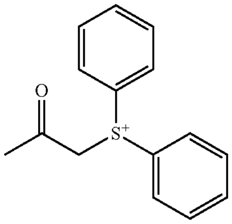

-continued
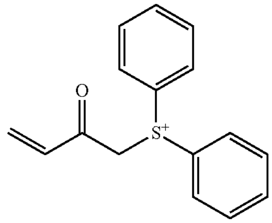
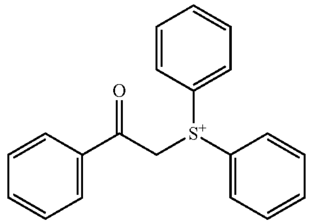
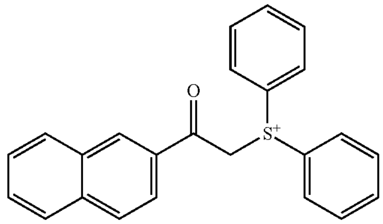
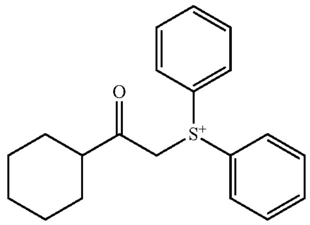
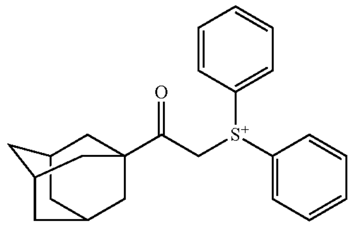
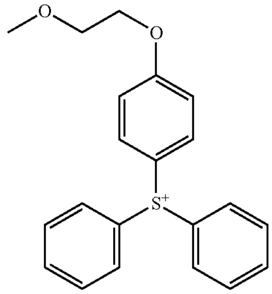
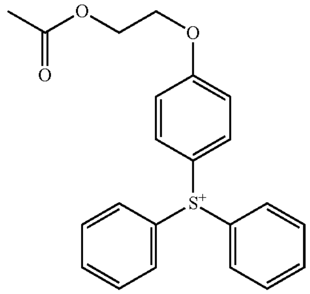
-continued
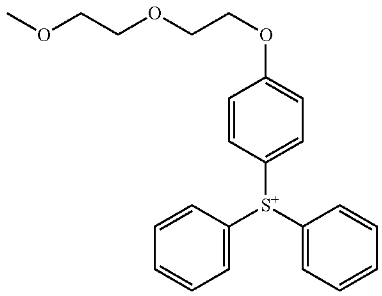
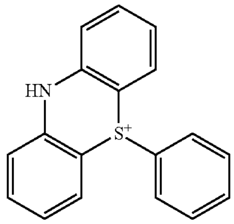
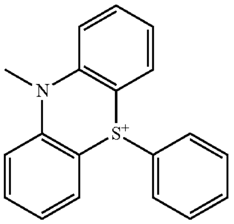
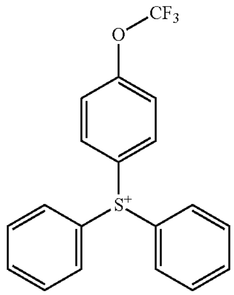
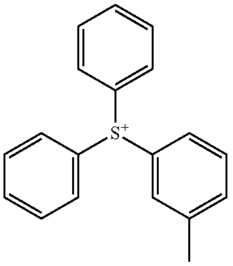
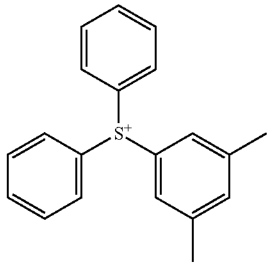
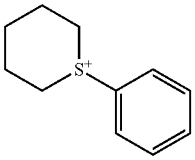
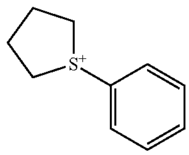
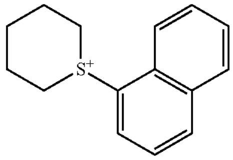
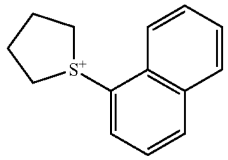
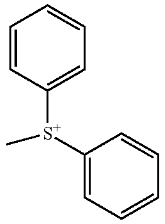
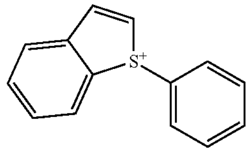
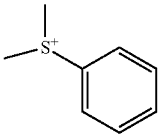

-continued
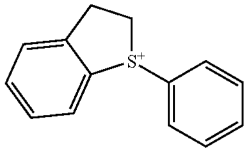
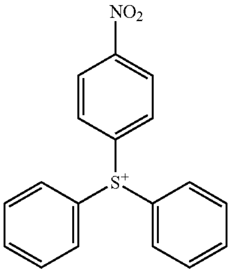
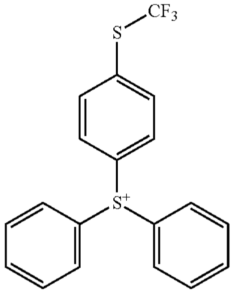
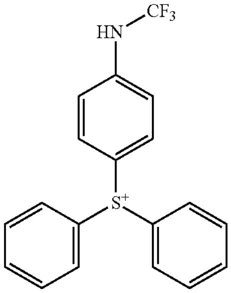
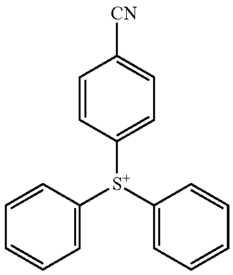
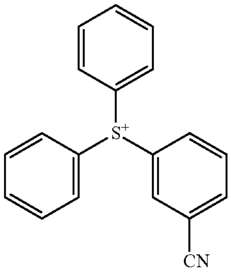
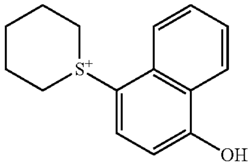
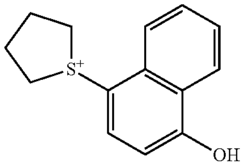
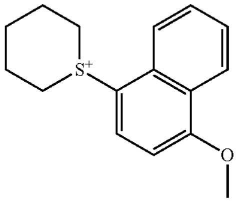
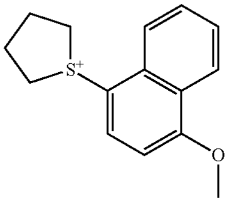
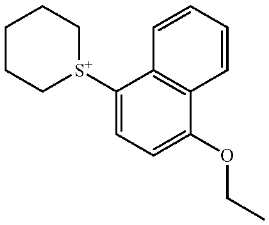
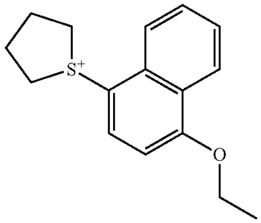
-continued
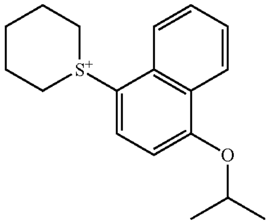
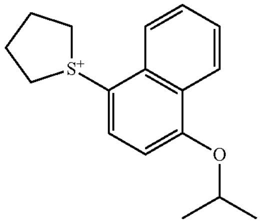
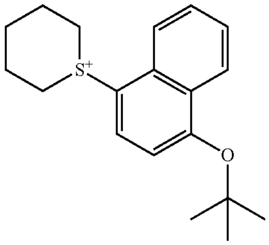
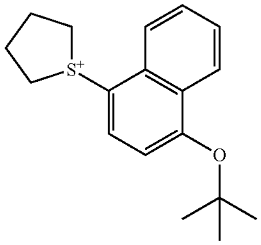
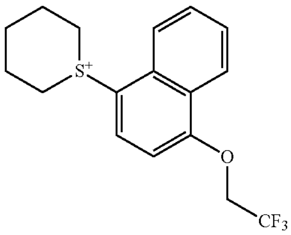
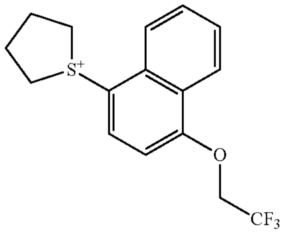
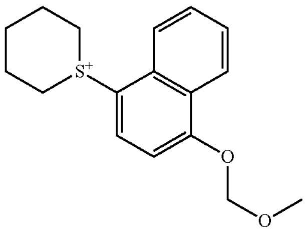

-continued
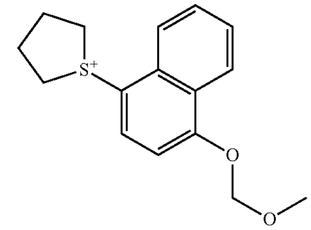
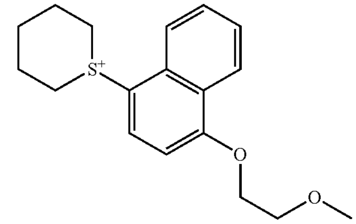
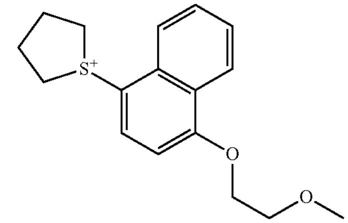
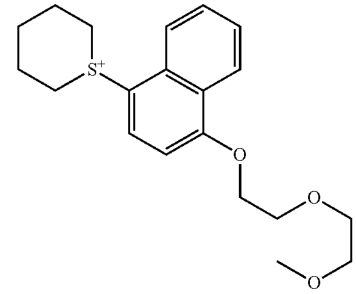
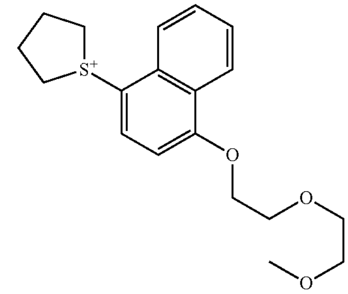
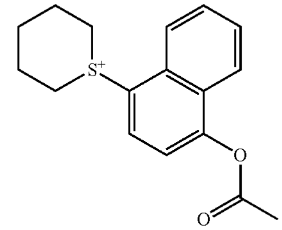
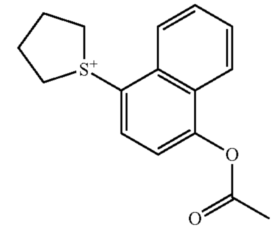
-continued
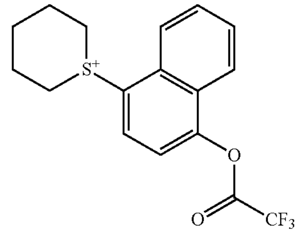
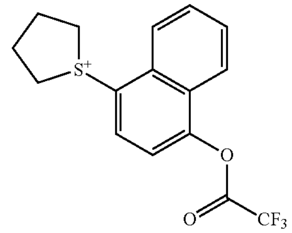
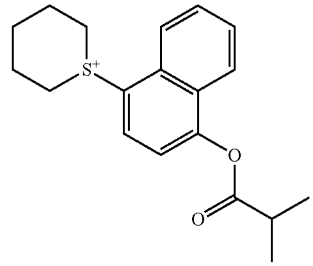
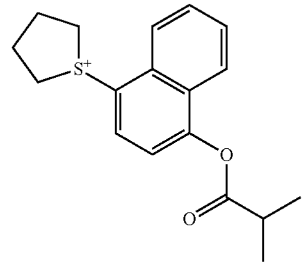
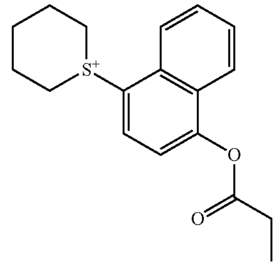
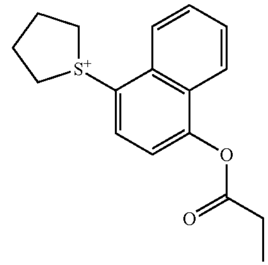

-continued
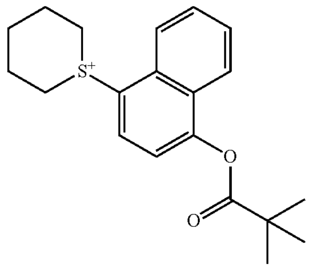
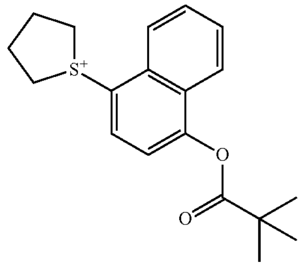
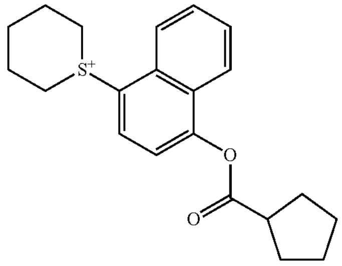
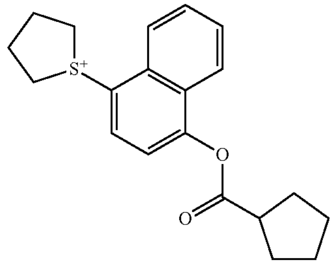
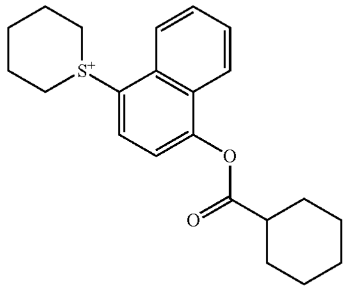
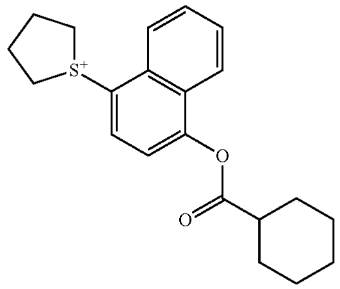
-continued
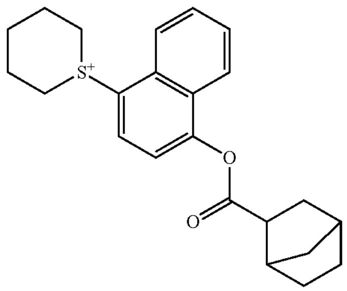
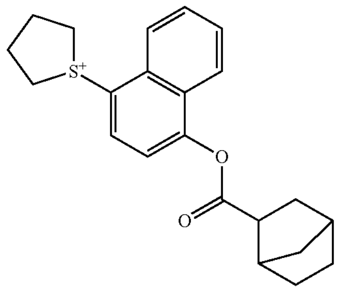
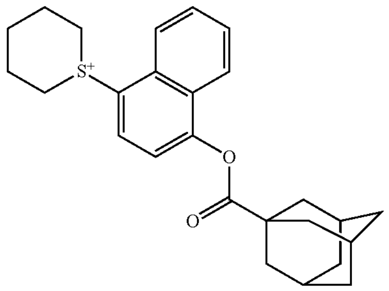
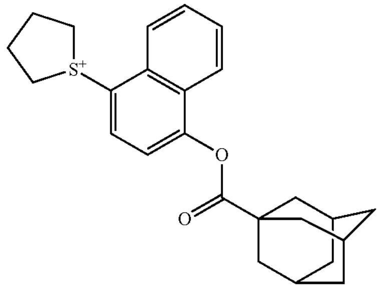
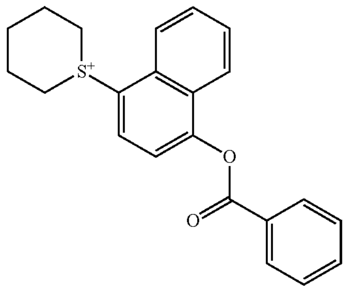

-continued
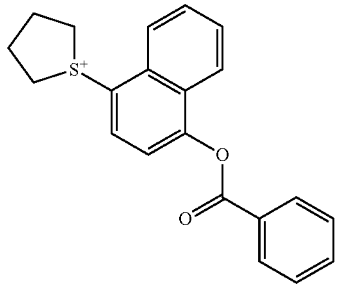
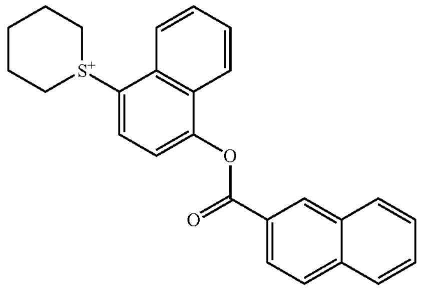
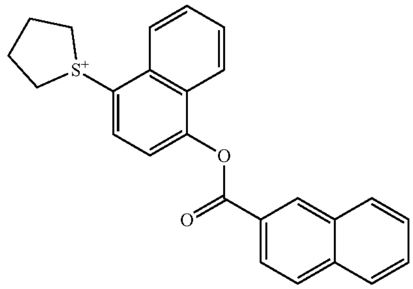
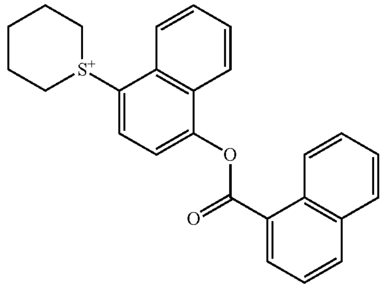
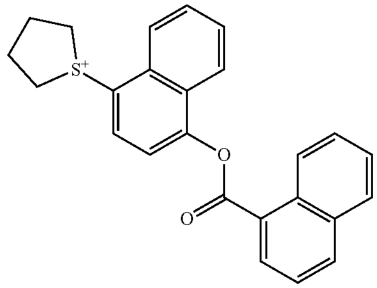
-continued
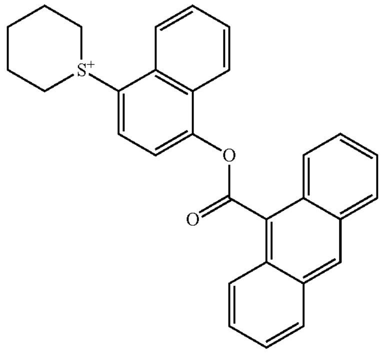
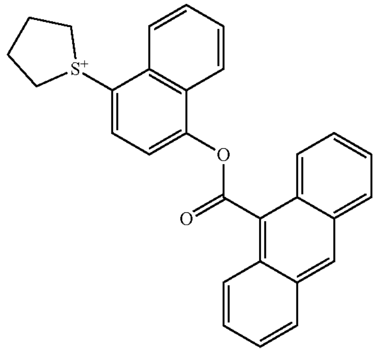
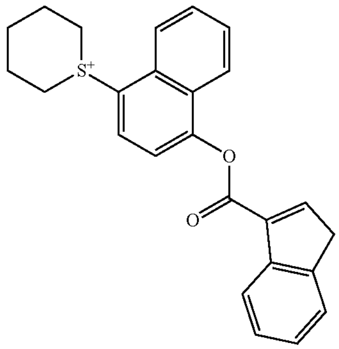
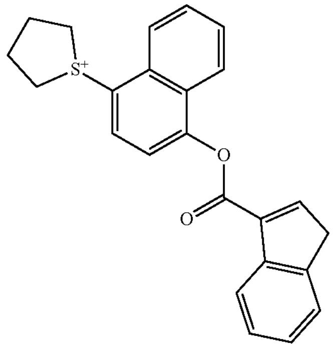

-continued
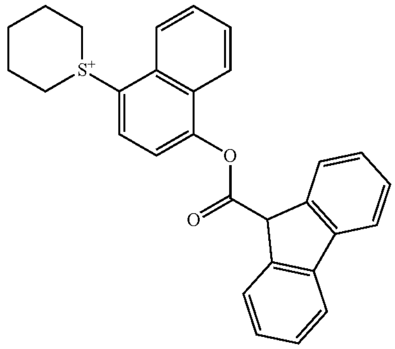
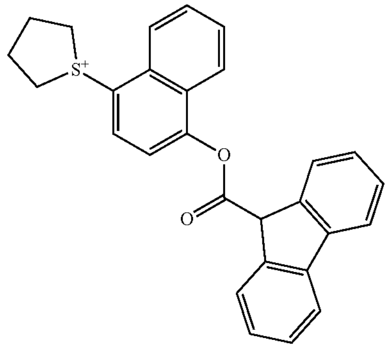
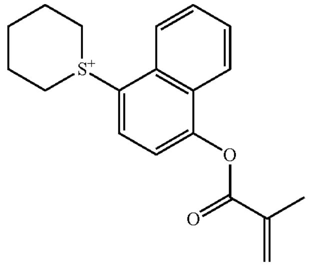
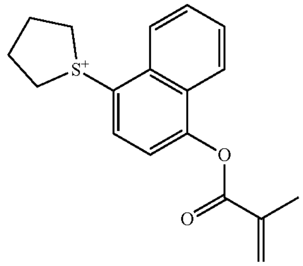
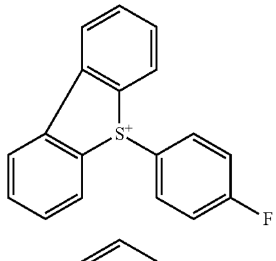
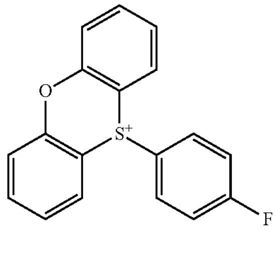
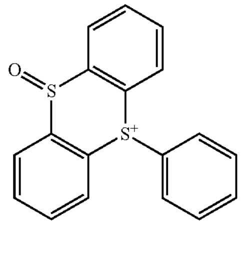
-continued
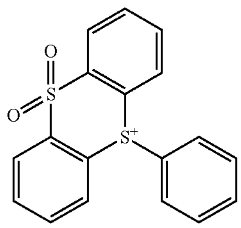
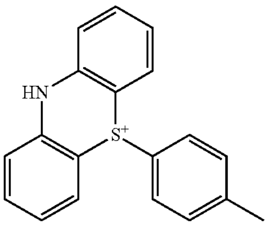
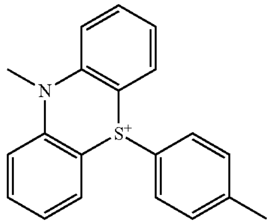
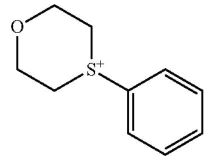
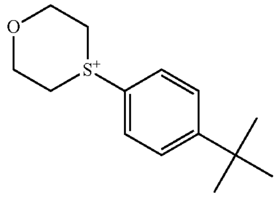
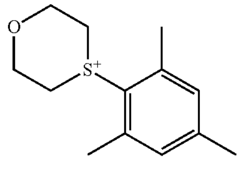
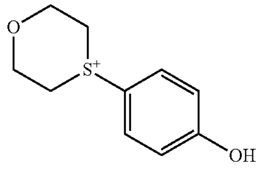
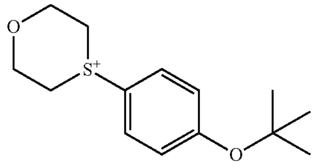
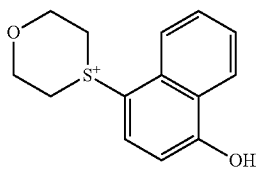
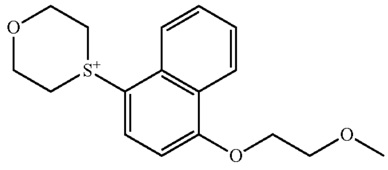
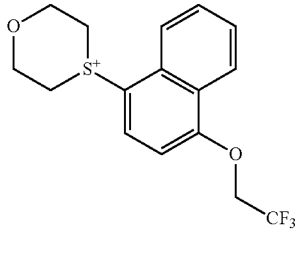

-continued
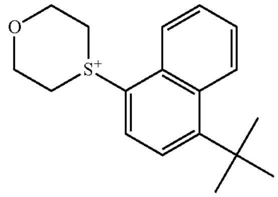
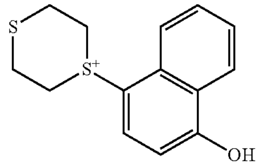
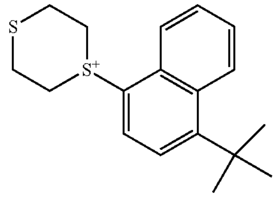
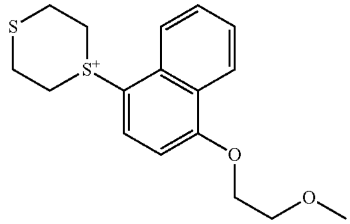
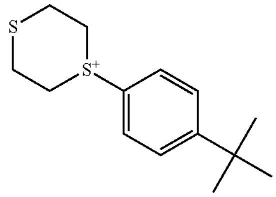
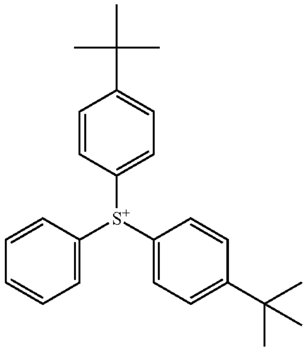
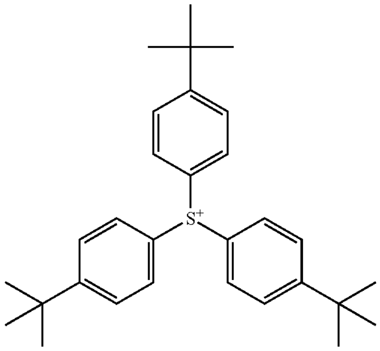
-continued
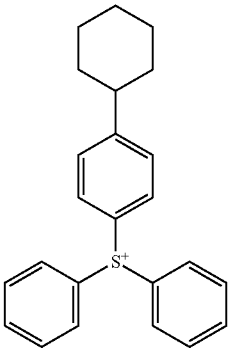
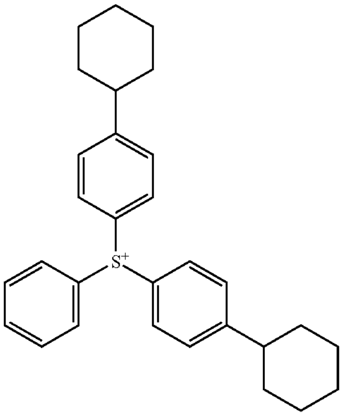
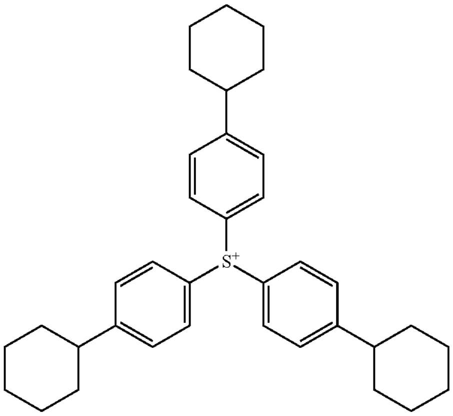
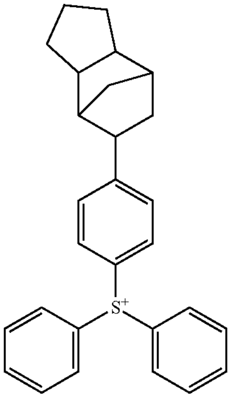

-continued
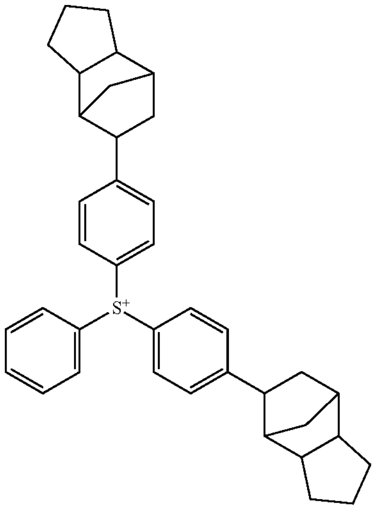
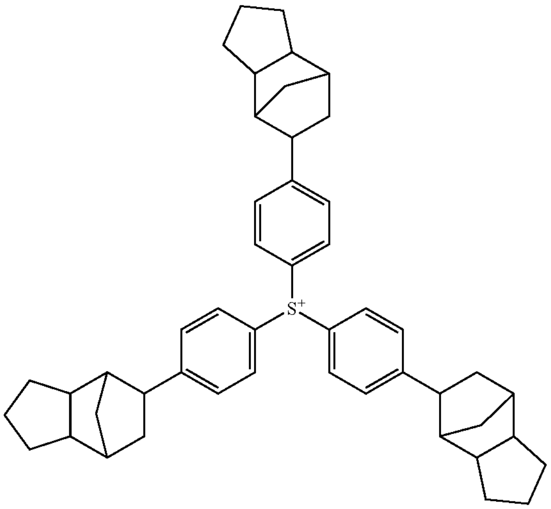
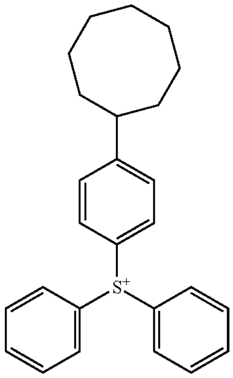
-continued
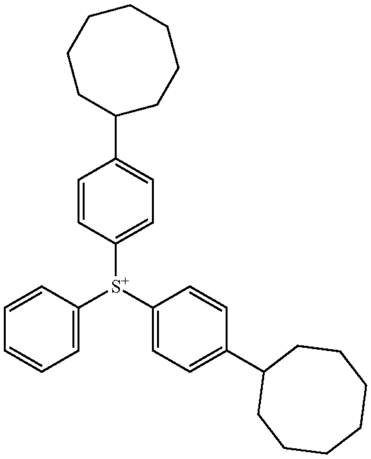
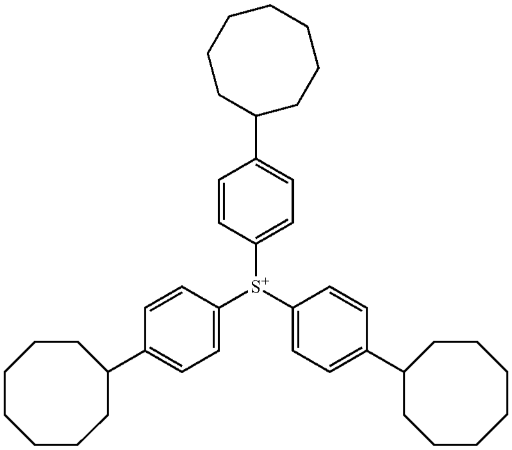
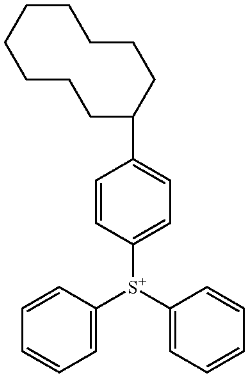

-continued
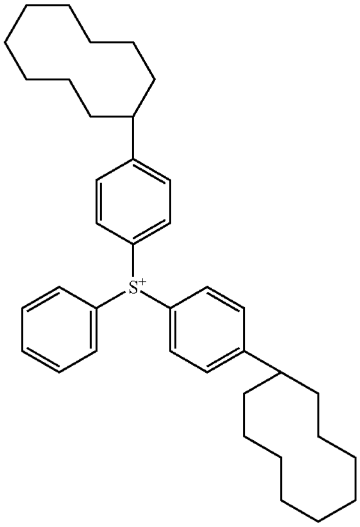
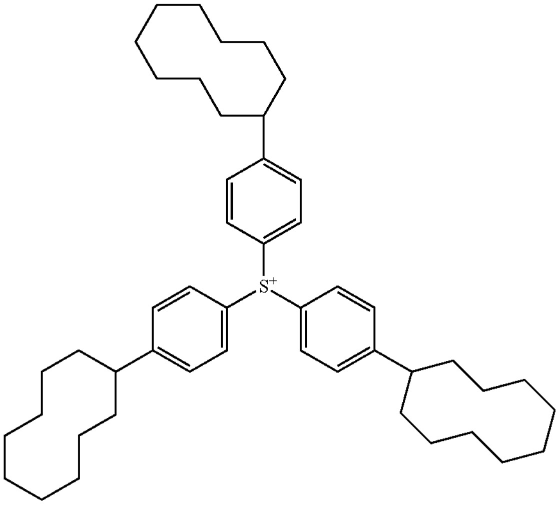
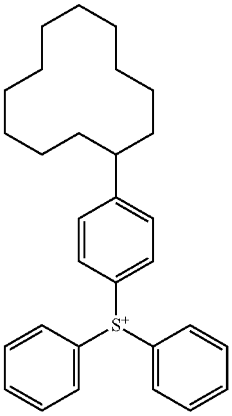
-continued
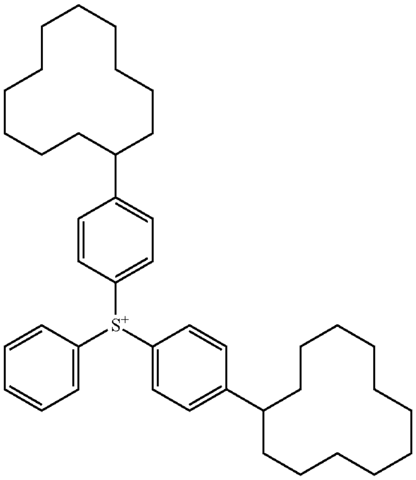
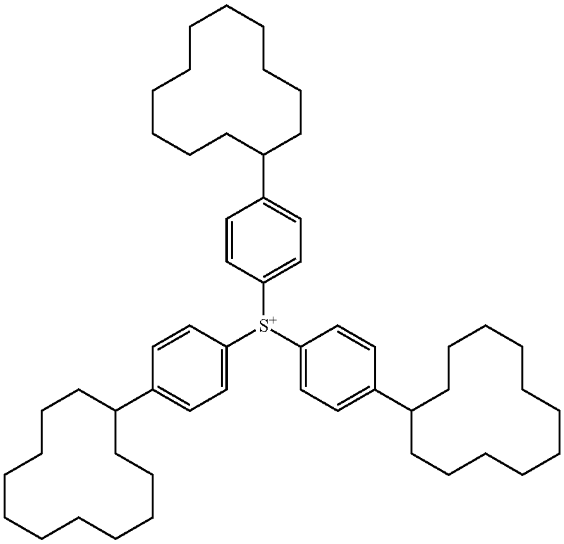
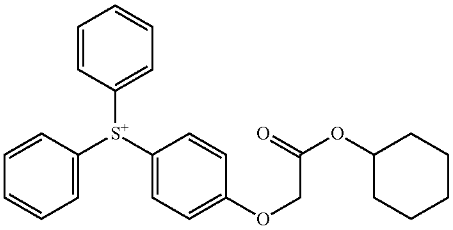
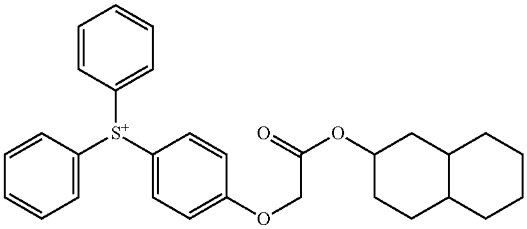
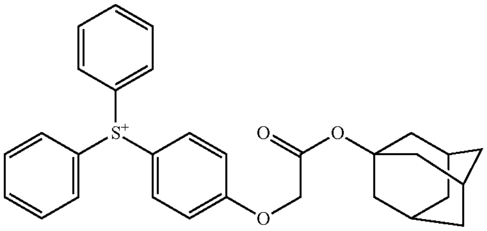

-continued
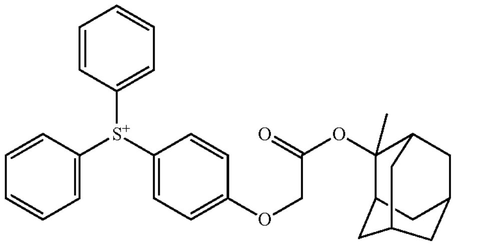
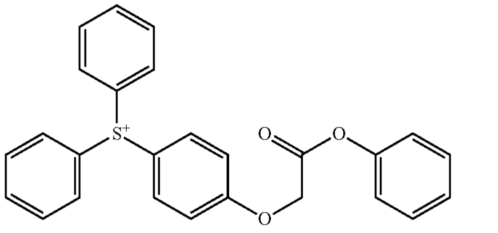
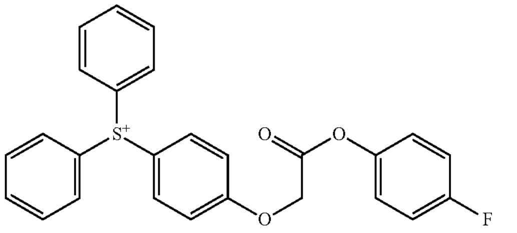
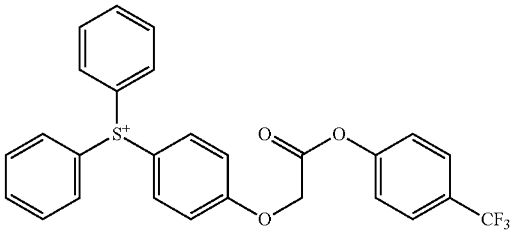
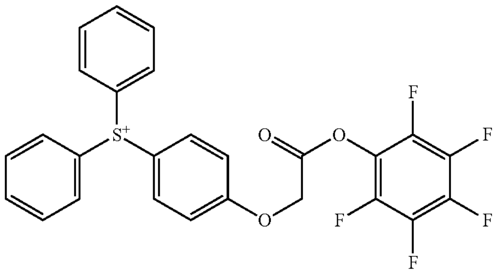
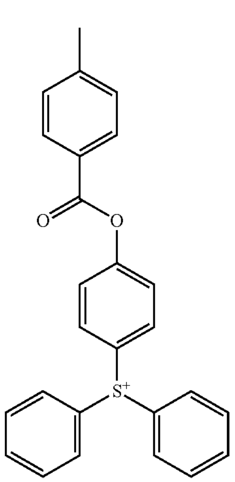
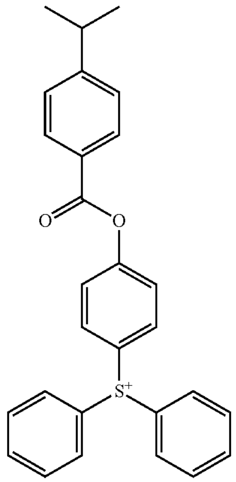
-continued
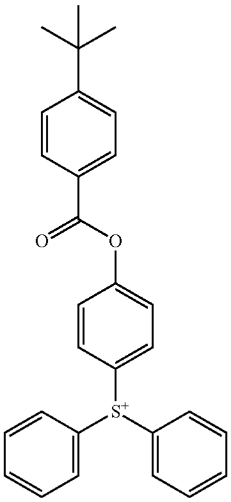
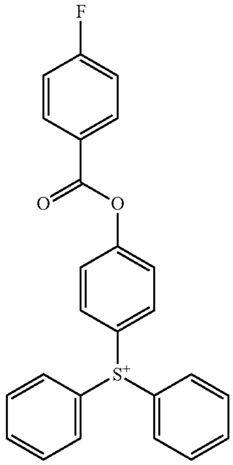
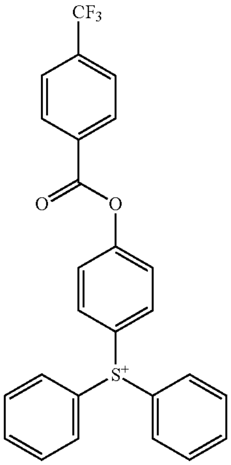
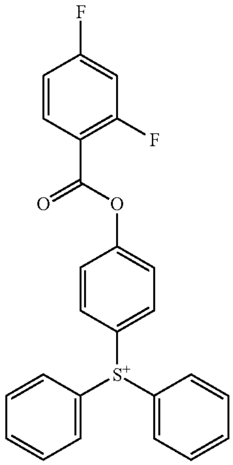
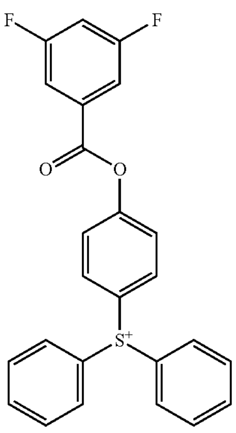
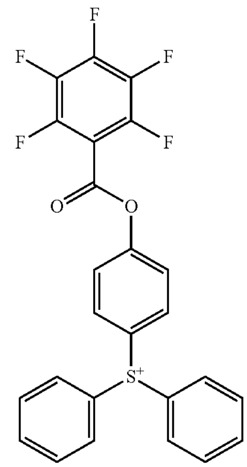
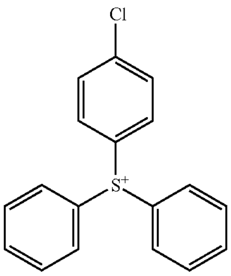
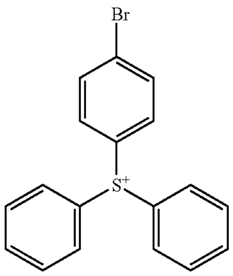

-continued
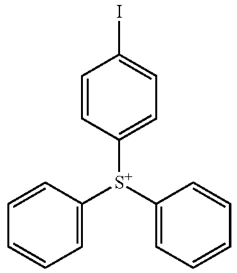
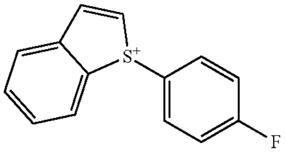
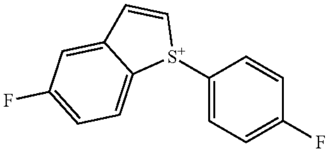
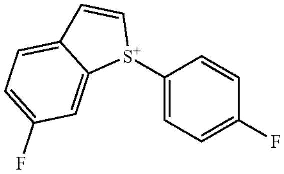
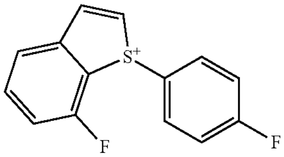
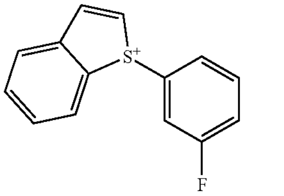
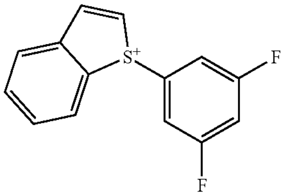
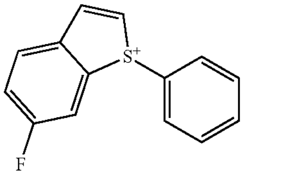
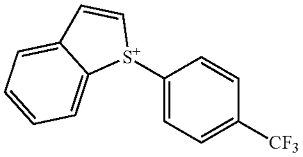
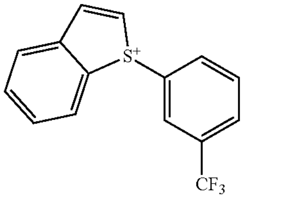
-continued
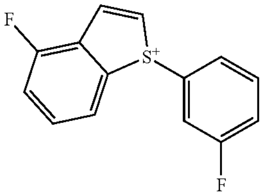
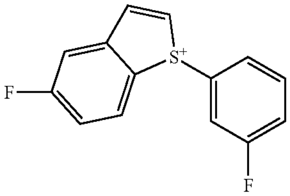
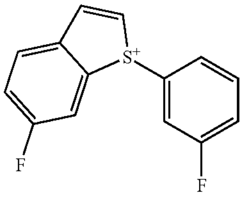
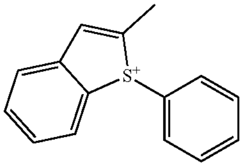
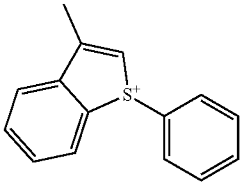
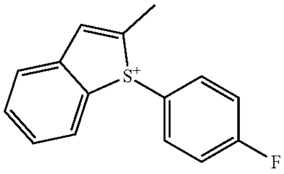
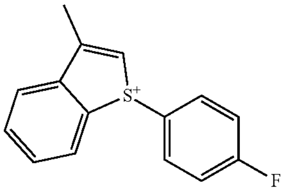
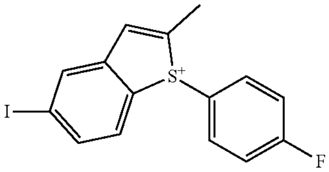
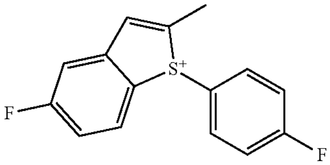
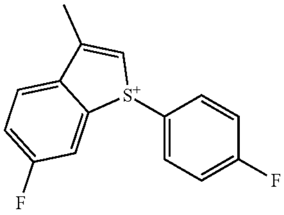

-continued
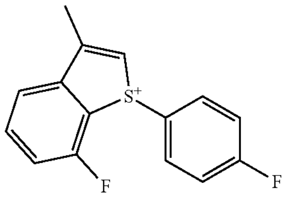
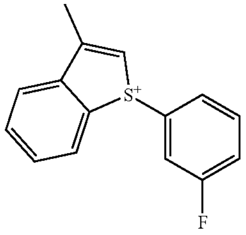
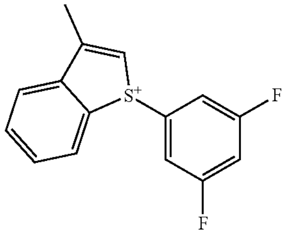
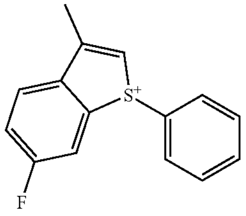
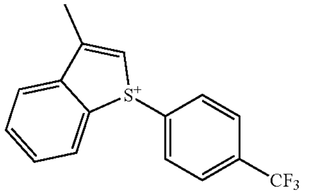
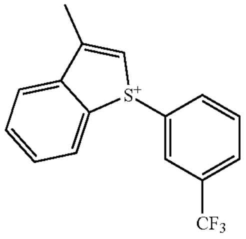
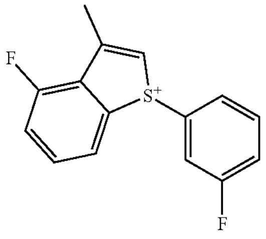
-continued
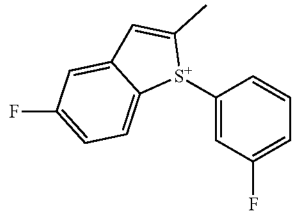
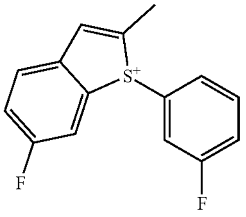
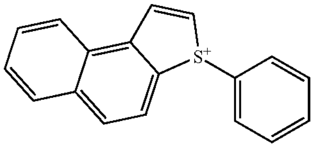
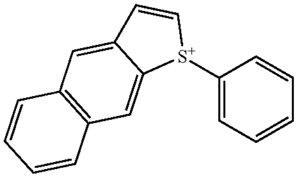
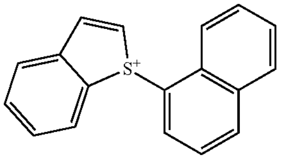
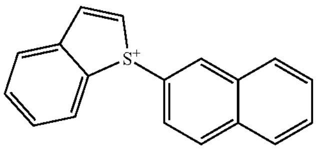
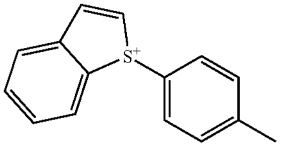
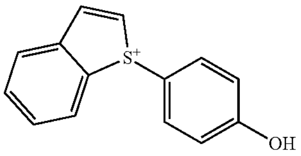
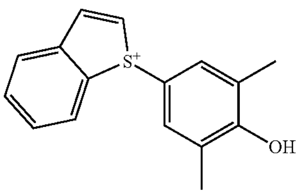

-continued
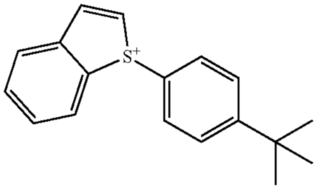
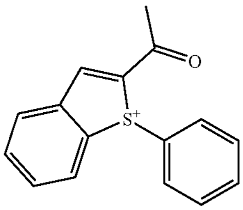
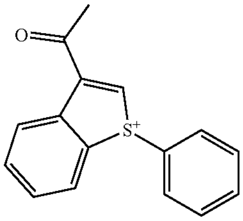
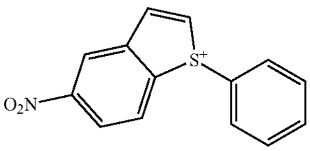
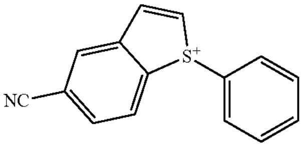
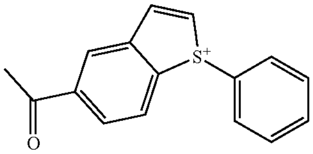
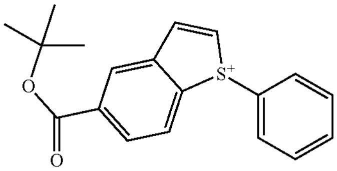
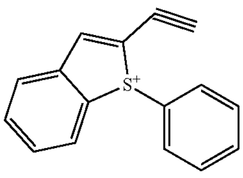
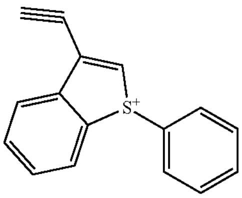
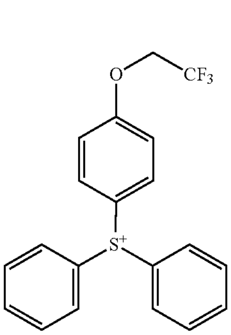
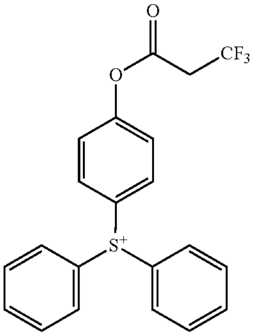
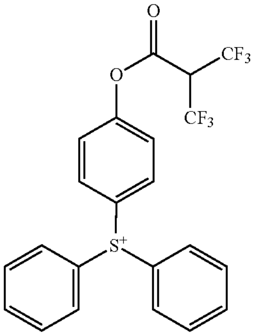
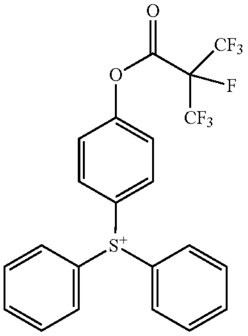
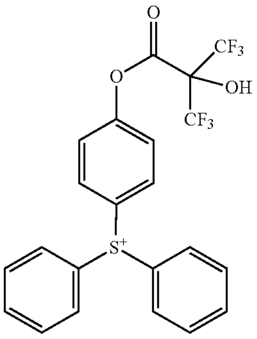
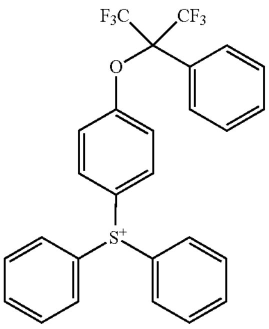
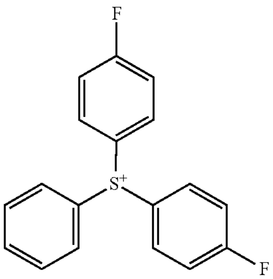
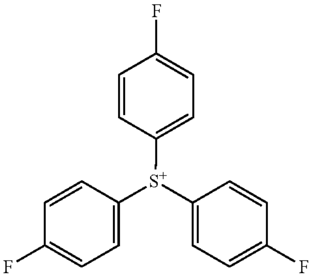

-continued
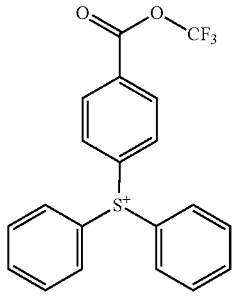
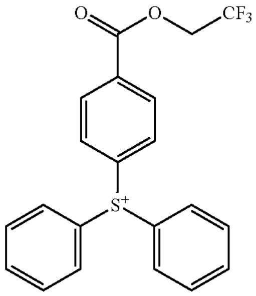
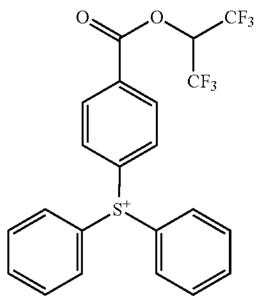
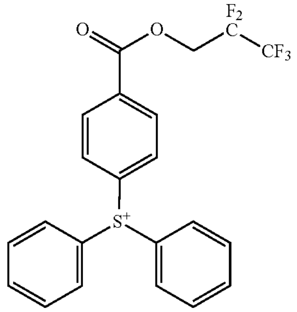
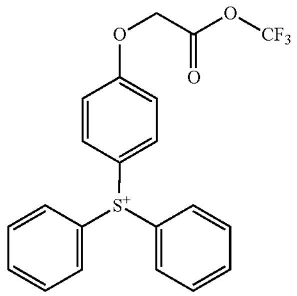
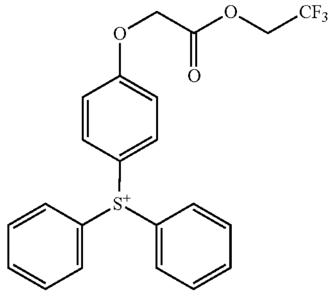
-continued
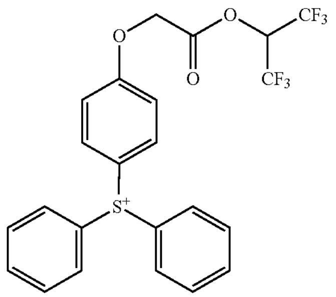
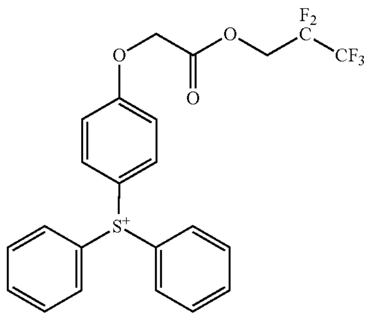
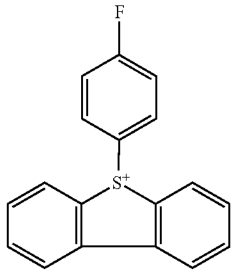
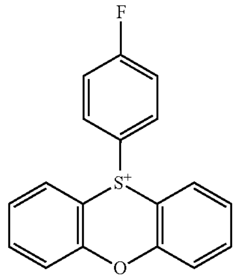
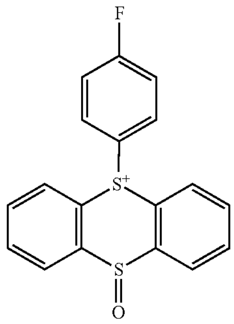
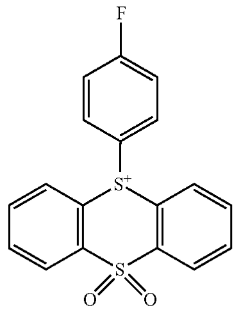
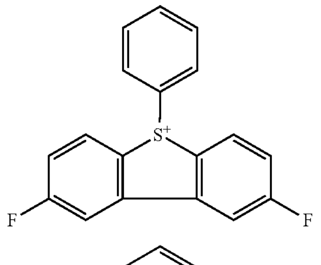
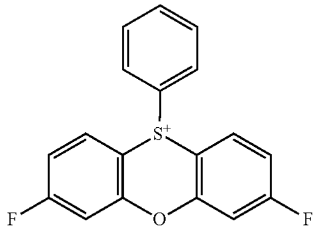

-continued
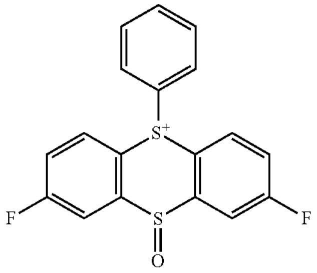
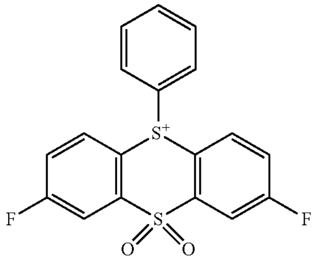
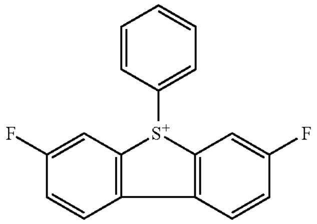
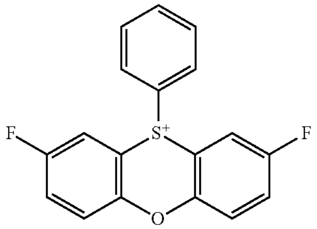
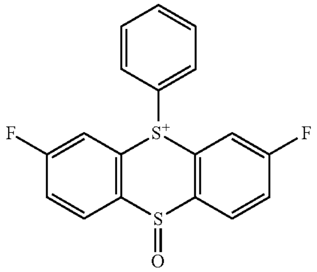
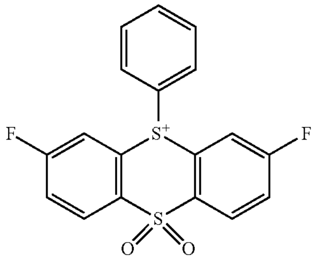
-continued
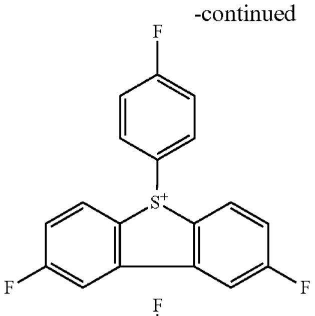
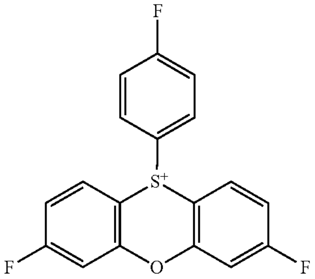
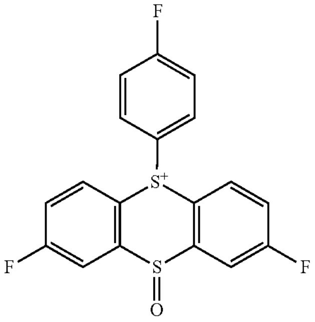
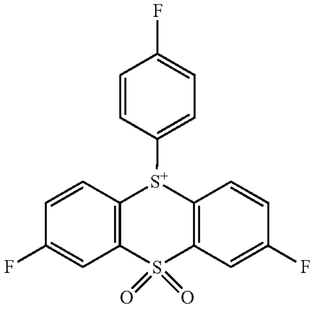
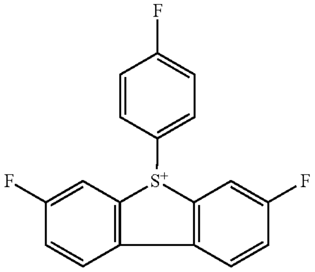
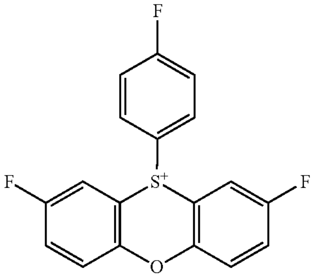

-continued
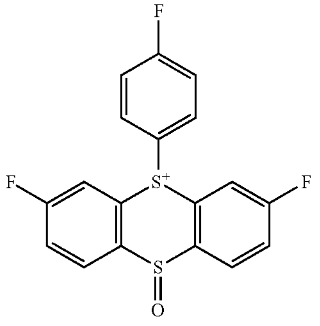
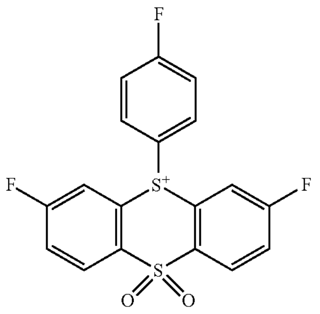
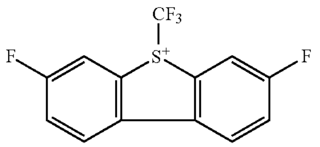
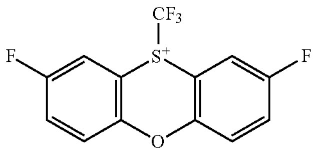
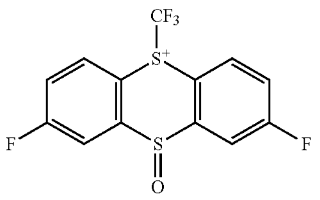
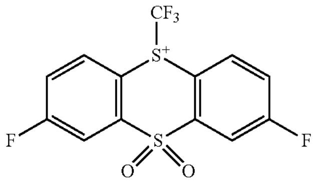
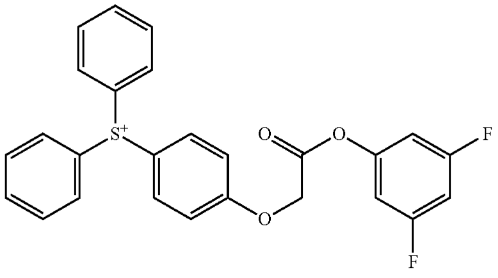
-continued
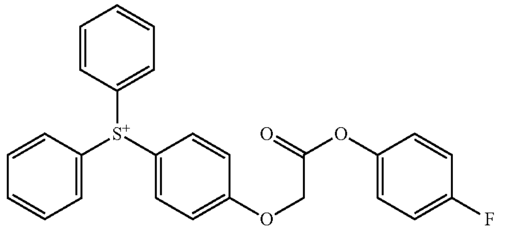
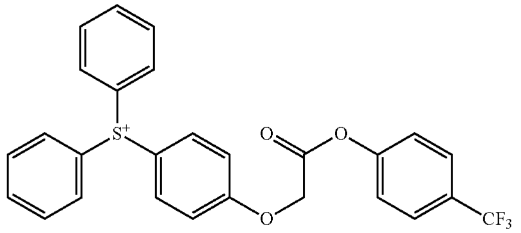
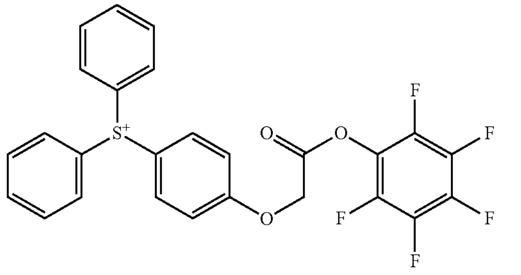
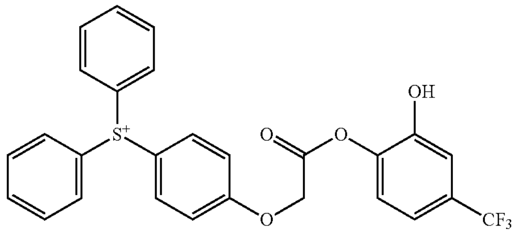
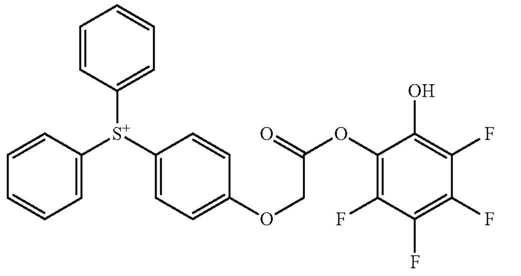
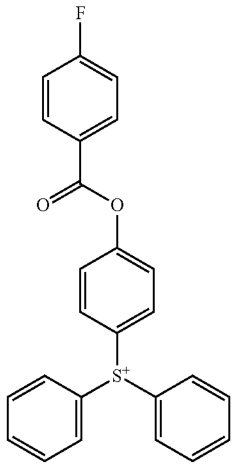
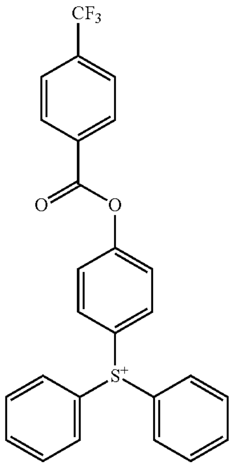

-continued
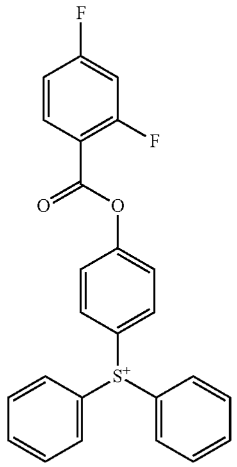
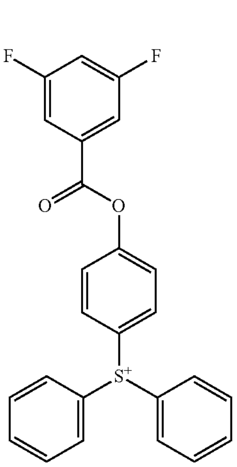
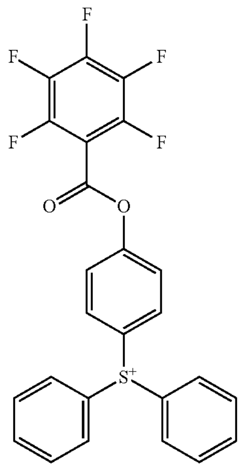
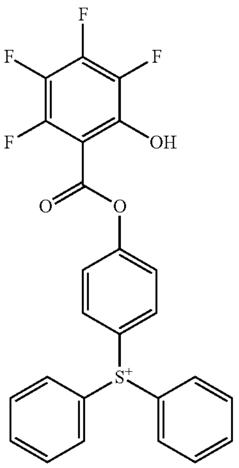
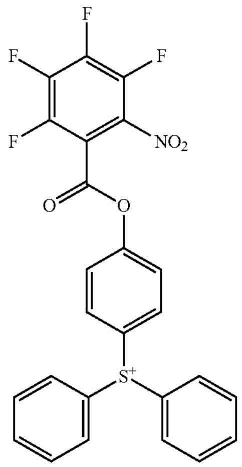
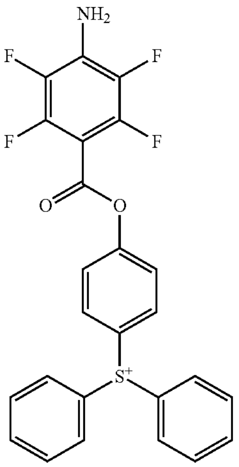
-continued
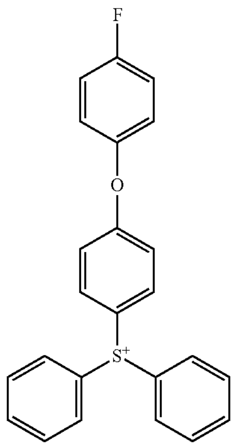
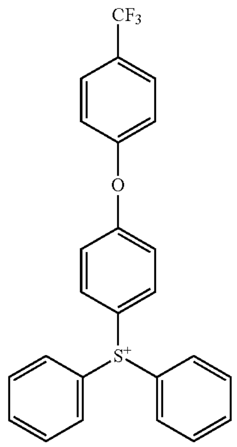
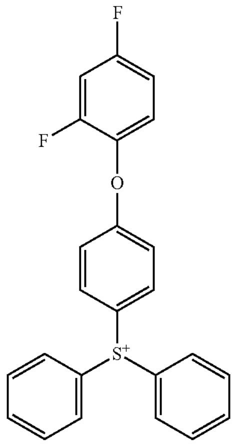
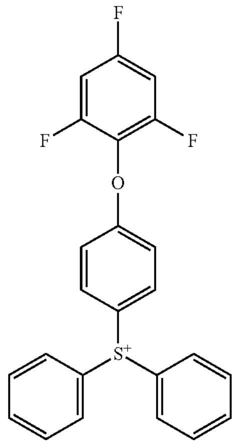
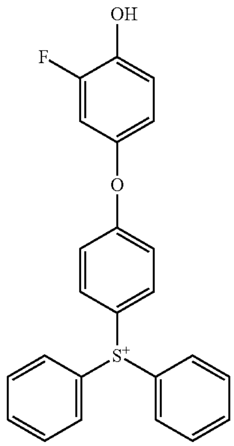
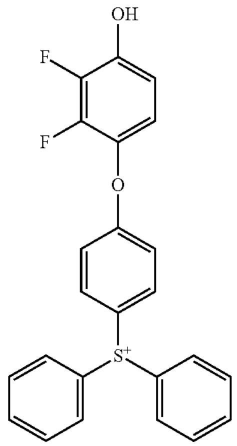

-continued
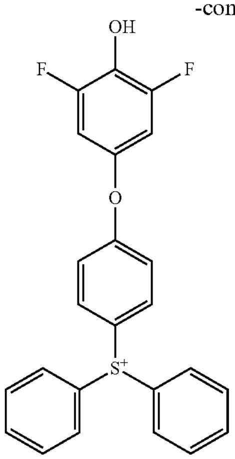
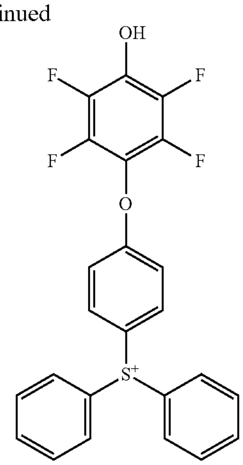
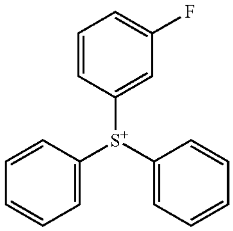
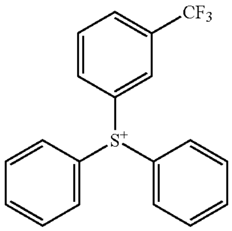
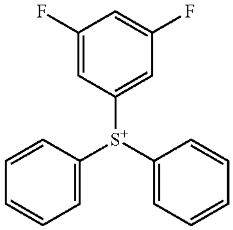
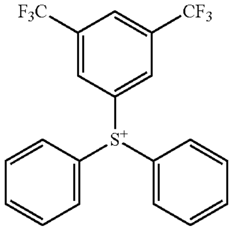
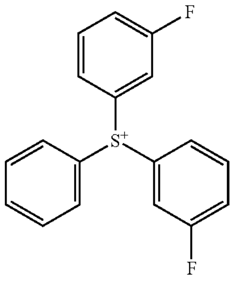
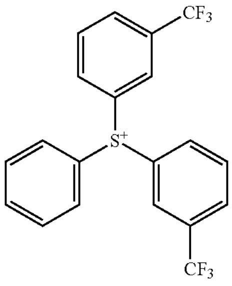
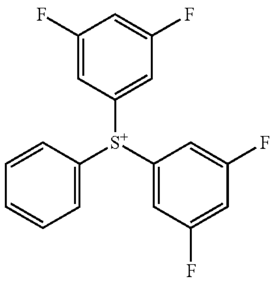
-continued
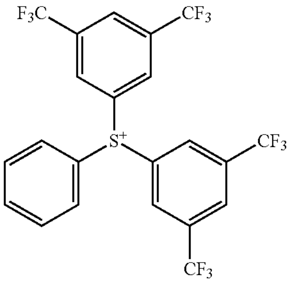
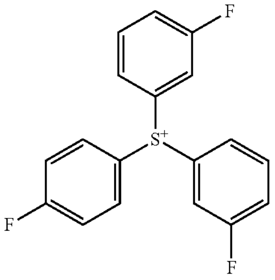
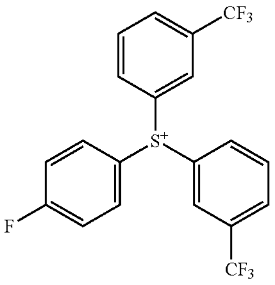
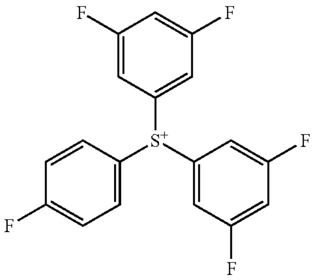
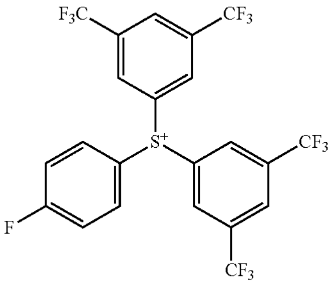
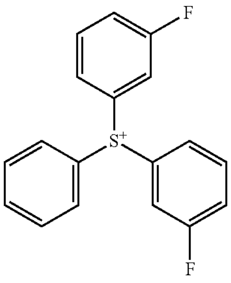
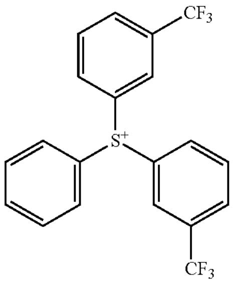

-continued
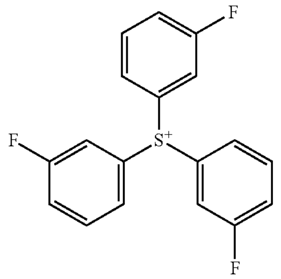
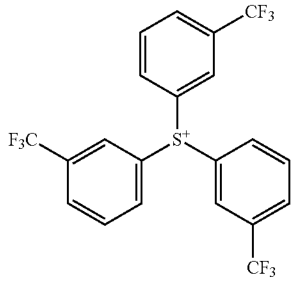
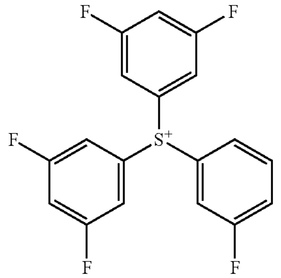
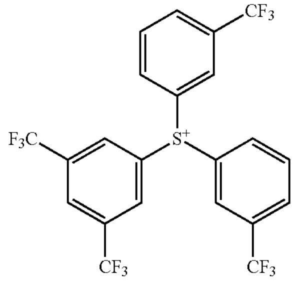
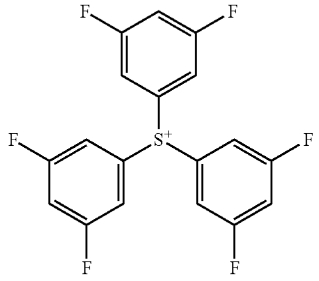
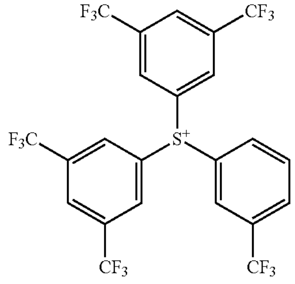
-continued
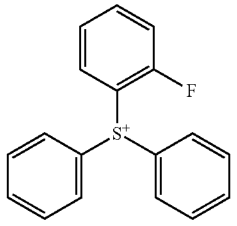
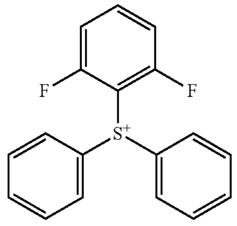
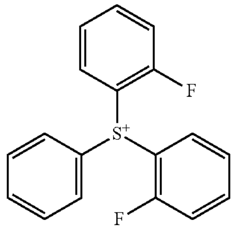
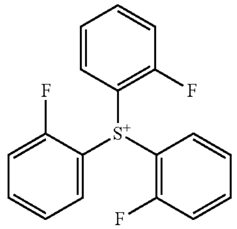
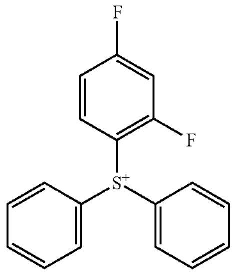
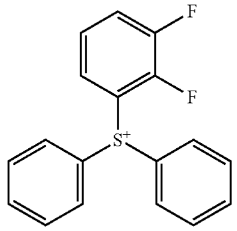
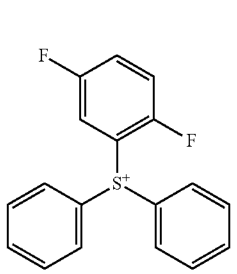
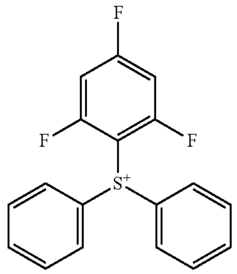
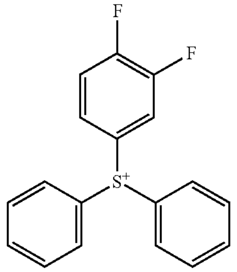
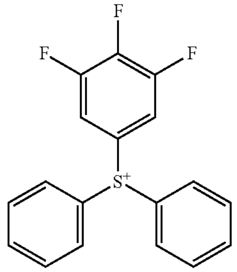
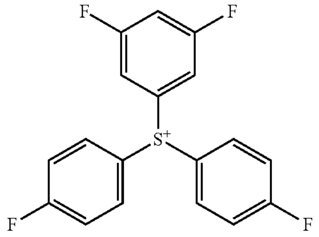

-continued
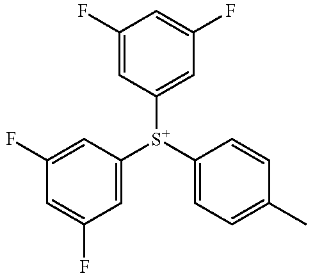
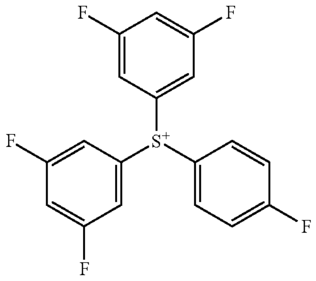
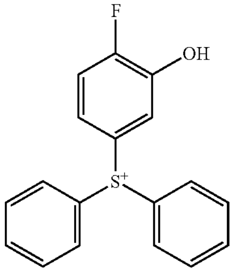
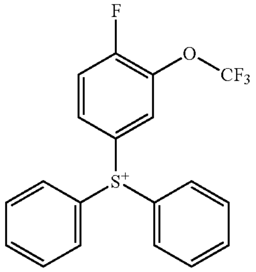
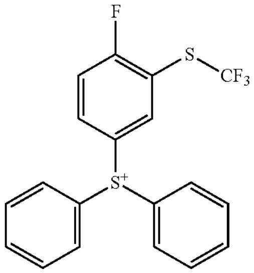
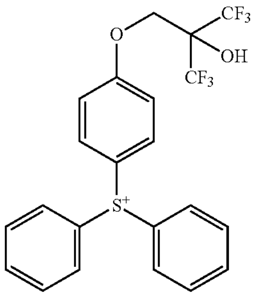
-continued
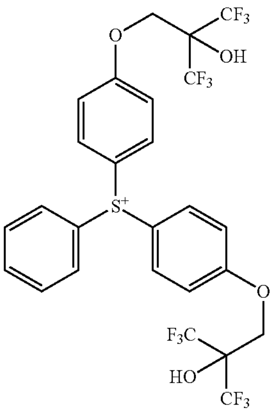
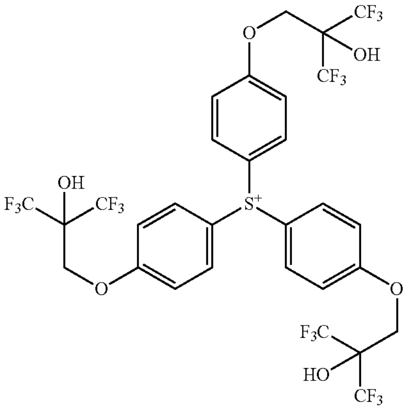
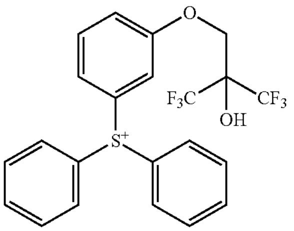
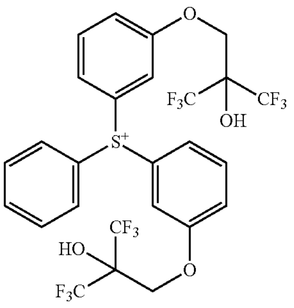
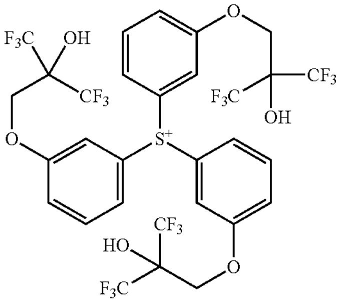

-continued
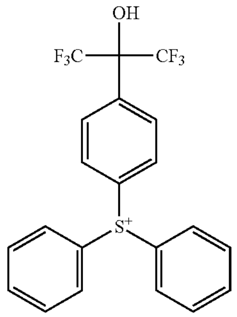
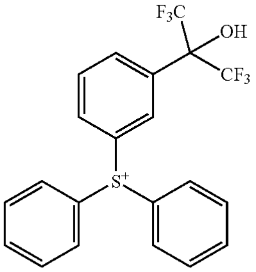
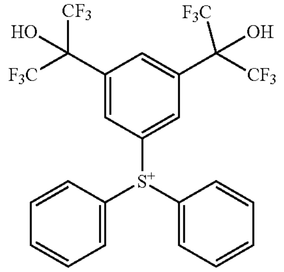
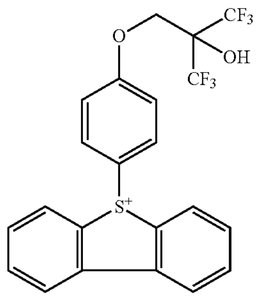
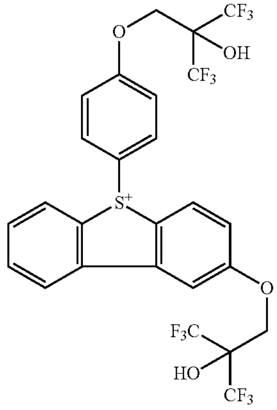
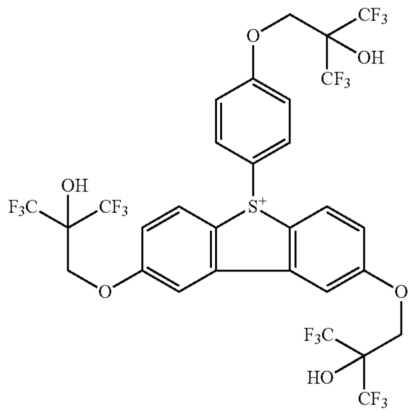
-continued
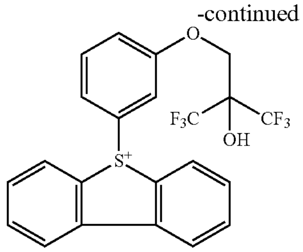
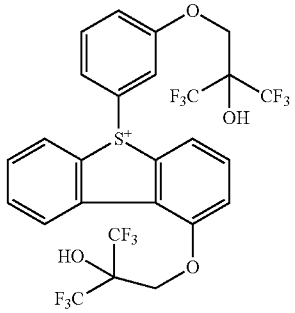
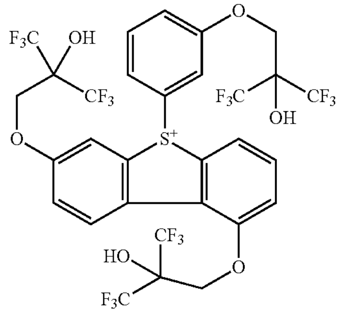
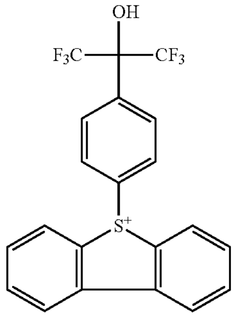
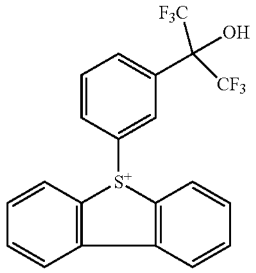
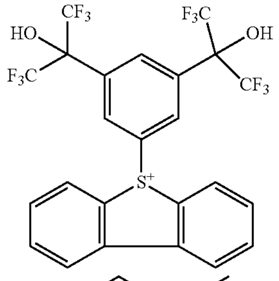
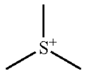
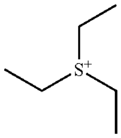
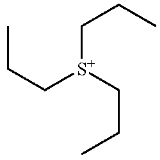
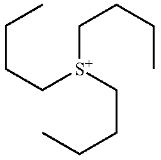
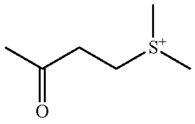
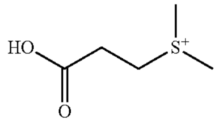
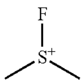

-continued
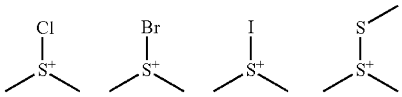
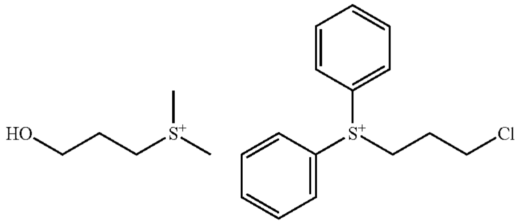
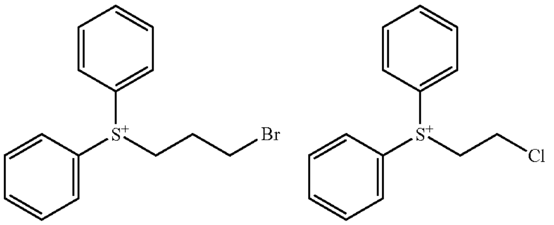
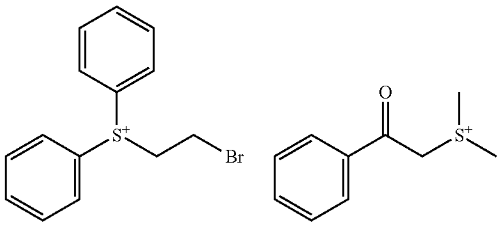
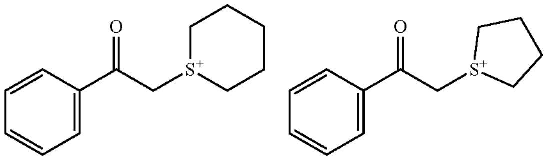
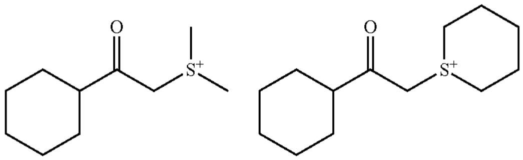
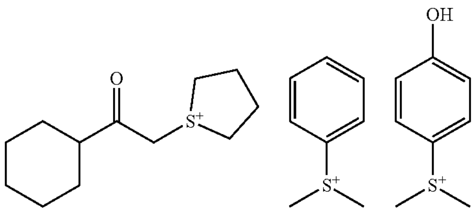
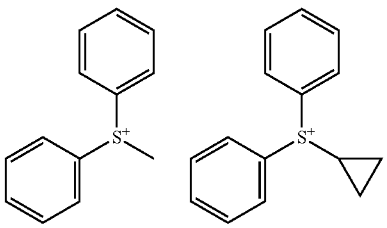
-continued
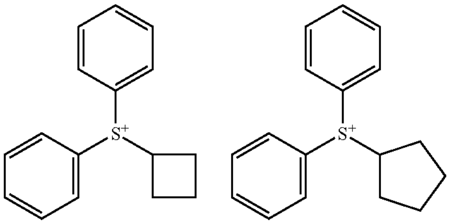
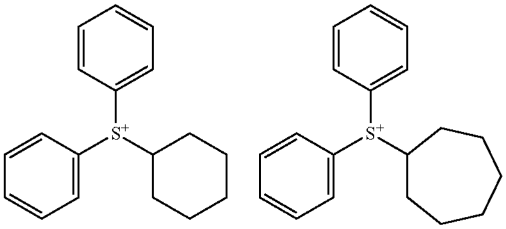
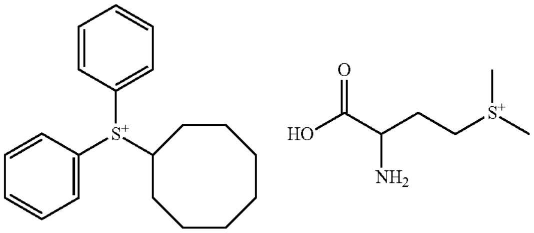
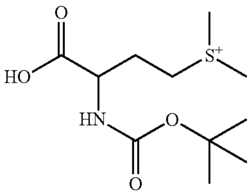
Examples of a cation of the iodonium salt shown by the formula (2-2) include ones shown below, but are not limited thereto.
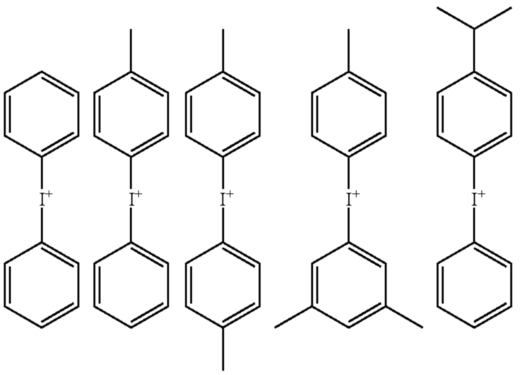

-continued
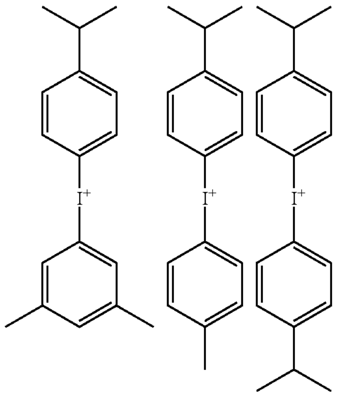
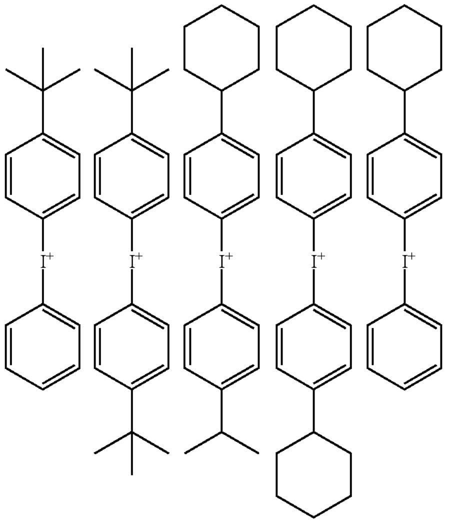
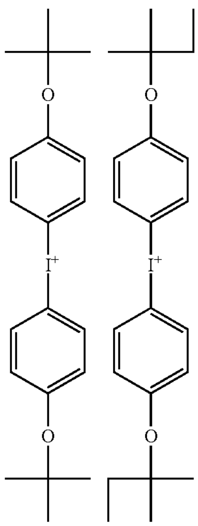
-continued
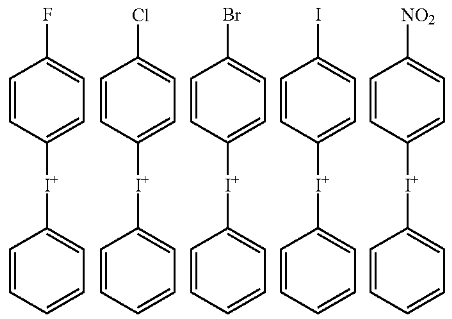
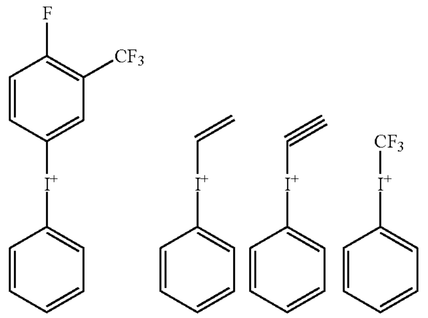
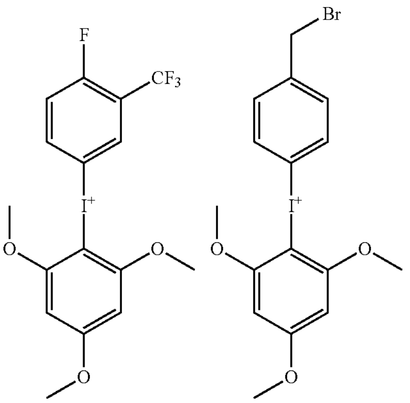
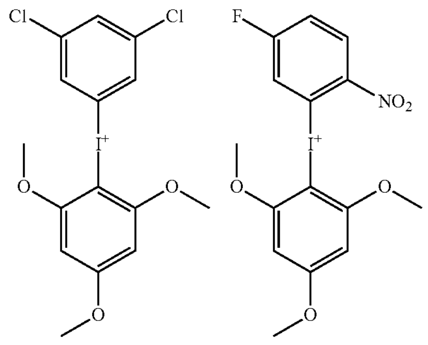
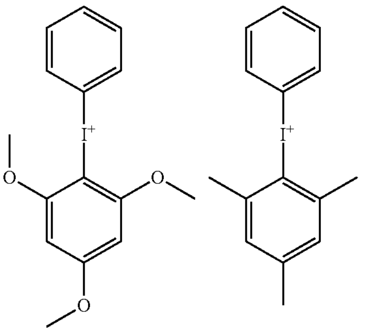

-continued

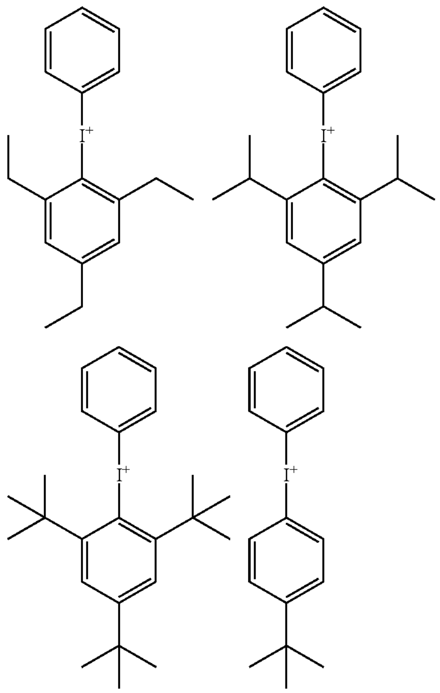

In the formulae (2-1) and (2-2), $X^-$ represents an anion selected from the following formulae (2A) to (2D).

(2A)

$R^{fa}—CF_2—SO_3^-$ (2B)

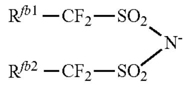

(2C)

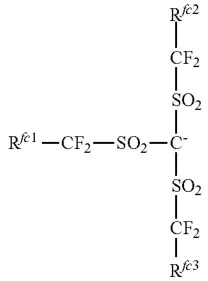

(2D)

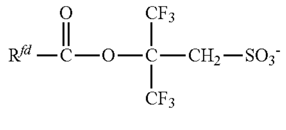

In the formula (2A), $R^{fa}$ represents a fluorine atom or a hydrocarbyl group having 1 to 40 carbon atoms and optionally containing a heteroatom. The hydrocarbyl group may be saturated or unsaturated, and may be linear, branched, or cyclic. Specific examples thereof include ones described below in a description of $R^{107}$.

The anion shown by the formula (2A) is preferably shown by the following formula (2A').

(2A')

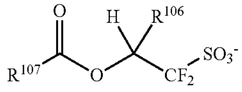

In the formula (2A'), $R^{106}$ represents a hydrogen atom or a trifluoromethyl group, preferably a trifluoromethyl group. $R^{107}$ represents a hydrocarbyl group having 1 to 38 carbon atoms and optionally containing a heteroatom. The heteroatom is preferably an oxygen atom, a nitrogen atom, a sulfur atom, a halogen atom, or the like, more preferably an oxygen atom. The hydrocarbyl group particularly preferably has 6 to 30 carbon atoms from the viewpoint of obtaining high resolution in fine pattern formation.

The hydrocarbyl group represented by $R^{107}$ may be saturated or unsaturated, and may be linear, branched, or cyclic. Specific examples thereof include alkyl groups, such as a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, a nonyl group, an undecyl group, a tridecyl group, a pentadecyl group, a heptadecyl group, and an icosanyl group; cyclic saturated hydrocarbyl groups, such as a cyclopentyl group, a cyclohexyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, and a dicyclohexylmethyl group; unsaturated hydrocarbyl groups, such as an allyl group and a 3-cyclohexenyl group; aryl groups, such as a phenyl group, a 1-naphthyl group, and a 2-naphthyl group; aralkyl groups, such as a benzyl group and a diphenylmethyl group; etc.

In addition, these groups may have some or all of hydrogen atoms substituted with a group containing a heteroatom, such as an oxygen atom, a sulfur atom, a nitrogen atom, or a halogen atom, while these groups may have some of carbon atoms substituted with a group containing a heteroatom, such as an oxygen atom, a sulfur atom, or a nitrogen atom. Thus, the resulting hydrocarbyl group may contain a hydroxy group, a cyano group, a carbonyl group, an ether bond, an ester bond, a sulfonic acid ester bond, a carbonate group, a lactone ring, a sultone ring, a carboxylic anhydride, a haloalkyl group, etc. Examples of the hydrocarbyl group containing a heteroatom include a tetrahydrofuryl group, a methoxymethyl group, an ethoxymethyl group, a methylthiomethyl group, an acetamidomethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group, a 3-oxocyclohexyl group, etc.

The synthesis of the sulfonium salt containing the anion shown by the formula (2A') is described in detail in JP 2007-145797 A, JP 2008-106045 A, JP 2009-007327 A, JP 2009-258695 A, etc. In addition, sulfonium salts disclosed in JP 2010-215608 A, JP 2012-041320 A, JP 2012-106986 A, JP 2012-153644 A, etc. are also suitably used.

Examples of the anion shown by the formula (2A) include ones exemplified as an anion shown by formula (1A) in JP 2018-197853 A.

In the formula (2B), $R^{fb1}$ and $R^{fb2}$ each independently represent a fluorine atom or a hydrocarbyl group having 1 to 40 carbon atoms and optionally containing a heteroatom. The hydrocarbyl group may be saturated or unsaturated, and may be linear, branched, or cyclic. Specific examples thereof include those exemplified in the description of $R^{107}$ in the formula (2A'). $R^{fb1}$ and $R^{fb2}$ are preferably a fluorine atom or a linear fluorinated alkyl group having 1 to 4 carbon atoms. Alternatively, $R^{fb1}$ and $R^{fb2}$ may bond with each other to form a ring together with a group ($—CF_2—SO_2—N^-—SO_2—CF_2—$) bonded therewith. In this event, the group obtained by bonding $R^{fb1}$ and $R^{fb2}$ with each other is preferably a fluorinated ethylene group or a fluorinated propylene group.

In the formula (2C), $R^{fc1}$, $R^{fc2}$, and $R^{fc3}$ each independently represent a fluorine atom or a hydrocarbyl group having 1 to 40 carbon atoms and optionally containing a heteroatom. The hydrocarbyl group may be saturated or unsaturated, and may be linear, branched, or cyclic. Specific examples thereof include those exemplified in the description of $R^{107}$ in the formula (2A'). $R^{fc1}$, $R^{fc2}$, and $R^{fc3}$ are preferably a fluorine atom or a linear fluorinated alkyl group having 1 to 4 carbon atoms. Alternatively, $R^{fc1}$ and $R^{fc2}$ may bond with each other to form a ring together with a group ($—CF_2—SO_2—C^-—SO_2—CF_2—$) bonded therewith. In this event, the group obtained by bonding $R^{fc1}$ and $R^{fc2}$ with each other is preferably a fluorinated ethylene group or a fluorinated propylene group.

In the formula (2D), $R^{fd}$ represents a hydrocarbyl group having 1 to 40 carbon atoms and optionally containing a heteroatom. The hydrocarbyl group may be saturated or unsaturated, and may be linear, branched, or cyclic. Specific examples thereof include those exemplified in the description of $R^{107}$ in the formula (2A').

The synthesis of the sulfonium salt containing the anion shown by the formula (2D) is described in detail in JP 2010-215608 A and JP 2014-133723 A.

Examples of the anion shown by the formula (2D) include ones exemplified as an anion shown by formula (1D) in JP 2018-197853 A.

Note that the photo-acid generator containing the anion shown by the formula (2D) does not have fluorine at α position of the sulfo group, but has two trifluoromethyl groups at β position, thereby providing sufficient acidity to cut the acid-labile group in the compound or in the base polymer. Thus, this photo-acid generator is utilizable.

One shown by the following formula (3) can also be used suitably as a photo-acid generator.

(3)

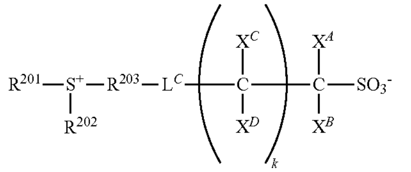

In the formula (3), $R^{201}$ and $R^{202}$ each independently represent a hydrocarbyl group having 1 to 30 carbon atoms and optionally containing a heteroatom. $R^{203}$ represents a hydrocarbylene group having 1 to 30 carbon atoms and optionally containing a heteroatom. Alternatively, $R^{201}$ and $R^{202}$, or $R^{201}$ and $R^{203}$, may bond with each other to form a ring together with a sulfur atom bonded therewith. In this event, examples of the ring include those exemplified as the ring which can be formed by bonding $R^{101}$ and $R^{102}$ together with the sulfur atom bonded thereto in the description of the formula (2-1).

The hydrocarbyl group represented by $R^{201}$ and $R^{202}$ may be saturated or unsaturated, and may be linear, branched, or cyclic. Specific examples thereof include: alkyl groups, such as a methyl group, an ethyl group, a propyl group, an isopropyl group, an n-butyl group, a sec-butyl group, a tert-butyl group, an n-pentyl group, a tert-pentyl group, an n-hexyl group, an n-octyl group, a 2-ethylhexyl group, an n-nonyl group, and an n-decyl group; cyclic saturated hydrocarbyl groups, such as a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.$0^{2,6}$]decanyl group, and an adamantyl group; aryl groups, such as a phenyl group, a methylphenyl group, an ethylphenyl group, an n-propylphenyl group, an isopropylphenyl group, an n-butylphenyl group, an isobutylphenyl group, a sec-butylphenyl group, a tert-butylphenyl group, a naphthyl group, a methylnaphthyl group, an ethylnaphthyl group, an n-propylnaphthyl group, an isopropylnaphthyl group, an n-butylnaphthyl group, an isobutylnaphthyl group, a sec-butylnaphthyl group, a tert-butylnaphthyl group, and an anthracenyl group; etc. Additionally, these groups may have some of hydrogen atoms substituted with a group containing a heteroatom, such as an oxygen atom, a sulfur atom, a nitrogen atom, or a halogen atom, while these groups may have some of carbon atoms substituted with a group containing a heteroatom, such as an oxygen atom, a sulfur atom, or a nitrogen atom. Thus, the resulting hydrocarbyl group may contain a hydroxy group, a cyano group, a carbonyl group, an ether bond, an ester bond, a sulfonic acid ester bond, a carbonate group, a lactone ring, a sultone ring, a carboxylic anhydride, a haloalkyl group, etc.

The hydrocarbylene group represented by $R^{203}$ may be saturated or unsaturated, and may be linear, branched, or cyclic. Specific examples thereof include alkanediyl groups, such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; cyclic saturated hydrocarbylene groups, such as a cyclopentanediyl group, a cyclohexanediyl group, a norbornanediyl group, and an adamantanediyl group; arylene groups, such as a phenylene group, a methylphenylene group, an ethylphenylene group, an n-propylphenylene group, an isopropylphenylene group, an n-butylphenylene group, an isobutylphenylene group, a sec-butylphenylene group, a tert-butylphenylene group, a naphthylene group, a methylnaphthylene group, an ethylnaphthylene group, an n-propylnaphthylene group, an isopropylnaphthylene group, an n-butylnaphthylene group, an isobutylnaphthylene group, a sec-butylnaphthylene group, and a tert-butylnaphthylene group; etc. Additionally, these groups may have some of hydrogen atoms substituted with an alkyl group, such as a methyl group, an ethyl group, a propyl group, an n-butyl group, or a tert-butyl group, and these groups may have some of hydrogen atoms substituted with a group containing a heteroatom, such as an oxygen atom, a sulfur atom, a nitrogen atom, or a halogen atom, or these groups may have some of carbon atoms substituted with a group containing a heteroatom, such as an oxygen atom, a sulfur atom, or a nitrogen atom. Thus, the resulting hydrocarbylene group may contain a hydroxy group, a cyano group, a carbonyl group, an ether bond, an ester bond, a sulfonic acid ester bond, a carbonate group, a lactone ring, a sultone ring, a carboxylic anhydride, a haloalkyl group, etc. The heteroatom is preferably an oxygen atom.

In the formula (3), $L^C$ represents a single bond, an ether bond, or a hydrocarbylene group having 1 to 20 carbon atoms and optionally containing a heteroatom. The hydrocarbylene group may be saturated or unsaturated, and may be linear, branched, or cyclic. Specific examples thereof include those exemplified as the hydrocarbylene group represented by $R^{203}$.

In the formula (3), $X^A$, $X^B$, $X^C$, and $X^D$ each independently represent a hydrogen atom, a fluorine atom, or a trifluoromethyl group. Nevertheless, at least one of $X^A$, $X^B$, $X^C$, and $X^D$ is a fluorine atom or a trifluoromethyl group.

In the formula (3), "k" represents an integer of 0 to 3.

The photo-acid generator shown by the formula (3) is preferably shown by the following formula (3').

(3')

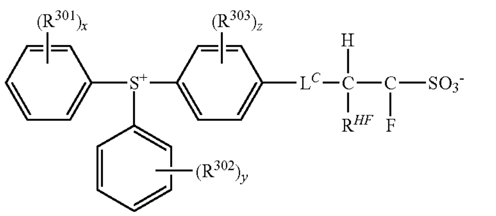

In the formula (3'), $L^C$ is as defined above. $R^{HF}$ represents a hydrogen atom or a trifluoromethyl group, preferably a trifluoromethyl group. $R^{301}$, $R^{302}$, and $R^{303}$ each independently represent a hydrogen atom or a hydrocarbyl group having 1 to 20 carbon atoms and optionally containing a heteroatom. The hydrocarbyl group may be saturated or unsaturated, and may be linear, branched, or cyclic. Specific examples thereof include those exemplified in the description of $R^{107}$ in the formula (2A'). "x" and "y" each independently represent an integer of 0 to 5. "z" represents an integer of 0 to 4.

Examples of the photo-acid generator shown by the formula (3) include ones exemplified as a photo-acid generator shown by formula (2) in JP 2017-026980 A.

The photo-acid generators containing the anion shown by the formula (2A') or (2D) are particularly preferable because of small acid diffusion and excellent solubility to a resist solvent. One shown by the formula (3') is also particularly preferable because the acid diffusion is quite small.

Furthermore, it is also possible to use, as the photo-acid generator, a sulfonium salt or an iodonium salt having an anion containing an aromatic ring substituted with an iodine atom or a bromine atom. Examples of such salts include those shown by the following formula (4-1) or (4-2).

(4-1)

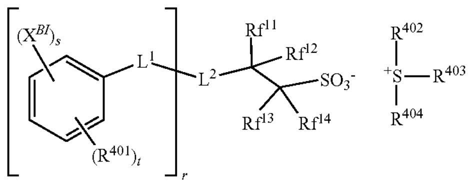

-continued (4-2)

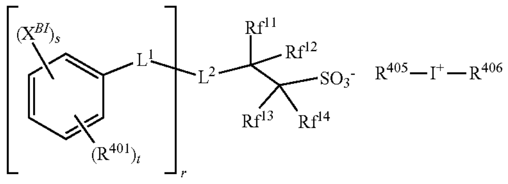

In the formulae (4-1) and (4-2), "r" represents an integer that satisfies 1≤r≤3. "s" and "t" represent integers that satisfy 1≤s≤5, 0≤t≤3, and 1≤s+t≤5. "s" is preferably an integer that satisfies 1≤s≤3, more preferably 2 or 3. "t" is preferably an integer that satisfies 0≤t≤2.

In the formulae (4-1) and (4-2), $X^{BI}$ represents an iodine atom or a bromine atom, and when "s" is 2 or more, the $X^{BI}$'s may be identical to or different from each other.

In the formulae (4-1) and (4-2), $L^1$ represents a single bond, an ether bond, an ester bond, or a saturated hydrocarbylene group having 1 to 6 carbon atoms and optionally containing an ether bond or an ester bond. The saturated hydrocarbylene group may be linear, branched, or cyclic.

In the formulae (4-1) and (4-2), $L^2$ represents a single bond or a divalent linking group having 1 to 20 carbon atoms when "r" is 1, and represents a trivalent or tetravalent linking group having 1 to 20 carbon atoms when "r" is 2 or 3, the linking groups optionally containing an oxygen atom, a sulfur atom, or a nitrogen atom.

In the formulae (4-1) and (4-2), $R^{401}$ represents a hydroxy group, a carboxy group, a fluorine atom, a chlorine atom, a bromine atom, an amino group, $—NR^{401A}—C(=O)—R^{401B}$, $—NR^{401A}—C(=O)—O—R^{401B}$, or a saturated hydrocarbyl group having 1 to 20 carbon atoms, a saturated hydrocarbyloxy group having 1 to 20 carbon atoms, a saturated hydrocarbyloxycarbonyl group having 2 to 10 carbon atoms, a saturated hydrocarbylcarbonyloxy group having 2 to 20 carbon atoms or a saturated hydrocarbylsulfonyloxy group having 1 to 20 carbon atoms, each of which optionally contains a fluorine atom, a chlorine atom, a bromine atom, a hydroxy group, an amino group, or an ether bond. $R^{401A}$ represents a hydrogen atom or a saturated hydrocarbyl group having 1 to 6 carbon atoms, and optionally contains a halogen atom, a hydroxy group, an alkoxy group having 1 to 6 carbon atoms, a saturated hydrocarbylcarbonyl group having 2 to 6 carbon atoms, or a saturated hydrocarbylcarbonyloxy group having 2 to 6 carbon atoms. $R^{401B}$ represents an aliphatic hydrocarbyl group having 1 to 16 carbon atoms or an aryl group having 6 to 12 carbon atoms, and optionally contains a halogen atom, a hydroxy group, a saturated hydrocarbyloxy group having 1 to 6 carbon atoms, a saturated hydrocarbylcarbonyl group having 2 to 6 carbon atoms, or a saturated hydrocarbylcarbonyloxy group having 2 to 6 carbon atoms. The aliphatic hydrocarbyl group may be saturated or unsaturated, and may be linear, branched, or cyclic. The saturated hydrocarbyl group, saturated hydrocarbyloxy group, saturated hydrocarbyloxycarbonyl group, saturated hydrocarbylcarbonyl group, and saturated hydrocarbylcarbonyloxy group may be linear, branched, or cyclic. When "r" is 2 or more, the $R^{401}$'s may be identical to or different from each other.

In particular, $R^{401}$ is preferably a hydroxy group, $—NR^{401A}—C(=O)—R^{401B}$, $—NR^{401A}—C(=O)—O—R^{401B}$, a fluorine atom, a chlorine atom, a bromine atom, a methyl group, a methoxy group, etc.

$Rf^{11}$ to $Rf^{14}$ are each independently a hydrogen atom, a fluorine atom, or a trifluoromethyl group, provided that at least one of $Rf^{11}$ to $Rf^{14}$ is a fluorine atom or a trifluoromethyl group. $Rf^{11}$ and $Rf^{12}$ may also bond with each other to form a carbonyl group. $Rf^{13}$ and $Rf^{14}$ particularly preferably both represent a fluorine atom.

In the formulae (4-1) and (4-2), $R^{402}$, $R^{403}$, $R^{404}$, $R^{405}$, and $R^{406}$ each independently represent a hydrocarbyl group having 1 to 20 carbon atoms and optionally containing a fluorine atom, a chlorine atom, a bromine atom, an iodine atom, or a heteroatom. The hydrocarbyl group may be saturated or unsaturated, and may be linear, branched, or cyclic. Specific examples thereof include alkyl groups having 1 to 20 carbon atoms, cyclic saturated hydrocarbyl groups having 3 to 20 carbon atoms, alkenyl groups having 2 to 20 carbon atoms, alkynyl groups having 2 to 20 carbon atoms, cyclic unsaturated aliphatic hydrocarbyl groups having 3 to 20 carbon atoms, aryl groups having 6 to 20 carbon atoms, aralkyl groups having 7 to 20 carbon atoms, etc. The groups as $R^{402}$, $R^{403}$, $R^{404}$, $R^{405}$, and $R^{406}$ may have some or all of hydrogen atoms substituted with a hydroxy group, a carboxy group, a halogen atom, a cyano group, a nitro group, a mercapto group, a sultone group, a sulfone group, or a sulfonium salt-containing group, and may have some of carbon atoms substituted with an ether bond, an ester bond, a carbonyl group, an amide bond, a carbonate group, or a sulfonic acid ester bond. Alternatively, $R^{402}$ and $R^{403}$ may bond to each other to form a ring together with a sulfur atom bonded thereto. In this event, examples of the ring include those given as examples of the ring that can be formed by $R^{101}$ and $R^{102}$ being bonded with each other together with the sulfur atom bonded to $R^{101}$ and $R^{102}$ in the description of the formula (2-1).

Examples of the cation of the sulfonium salt represented by the formula (4-1) include those given as examples of the cation of the sulfonium salt represented by the formula (2-1). Meanwhile, examples of the cation of the iodonium salt represented by the formula (4-2) include those given as examples of the cation of the iodonium salt represented by the formula (2-2).

Examples of the anions of the onium salts shown by the formula (4-1) or (4-2) include ones shown below, but are not limited thereto. Note that, in the following formulae, $X^{BI}$ is as defined above.

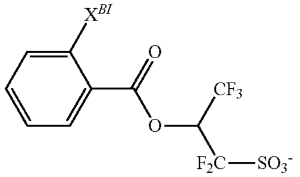

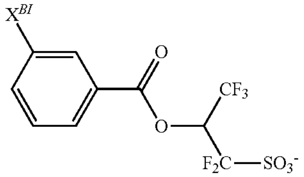

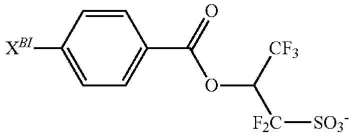

-continued

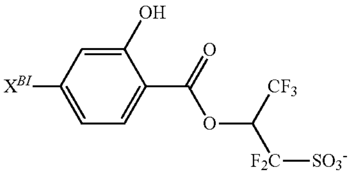

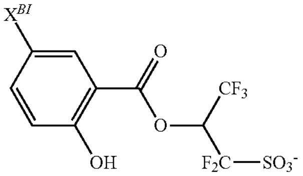

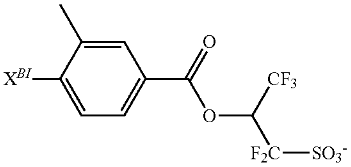

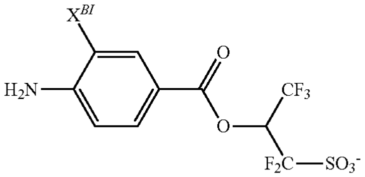

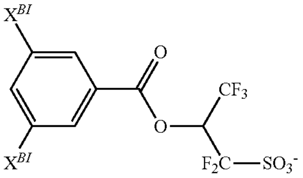

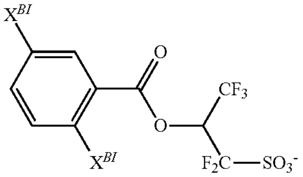

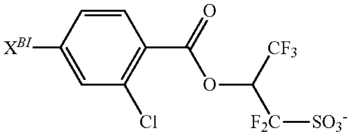

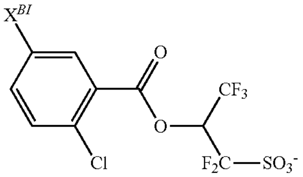

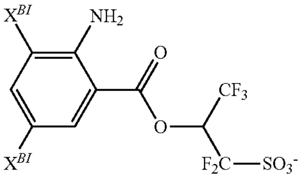

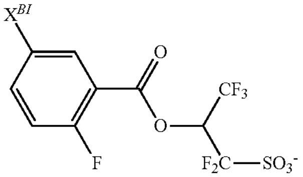

-continued
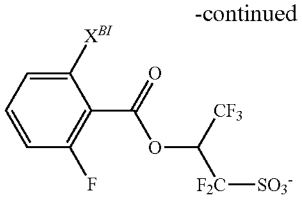
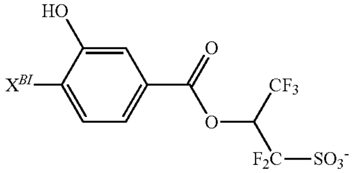
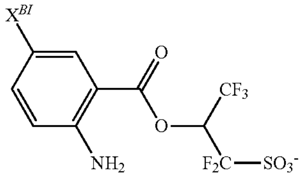
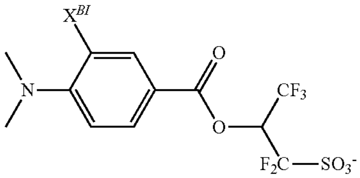
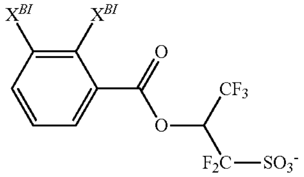
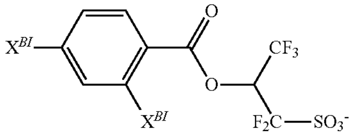
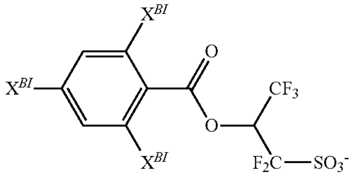
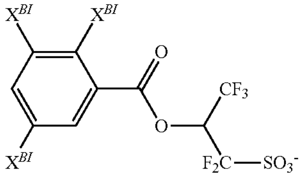
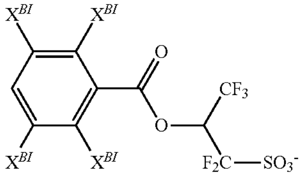
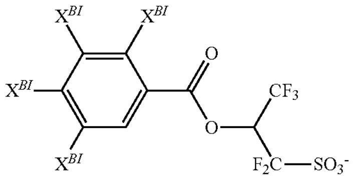
-continued
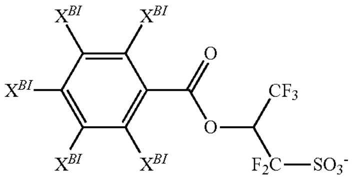
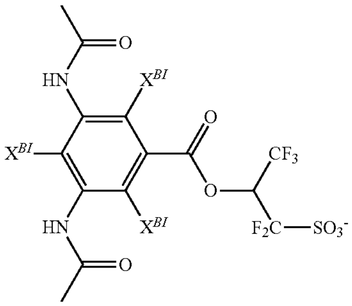
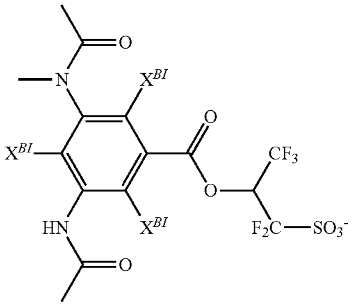
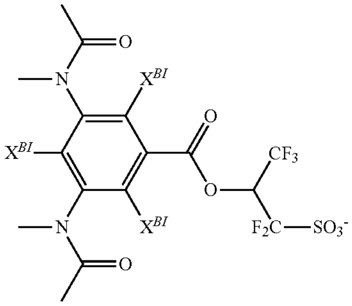
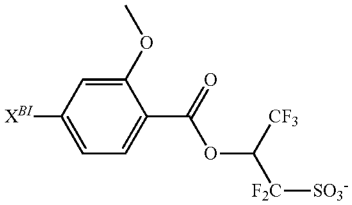
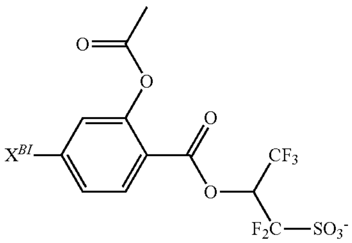

-continued
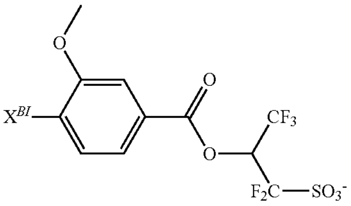
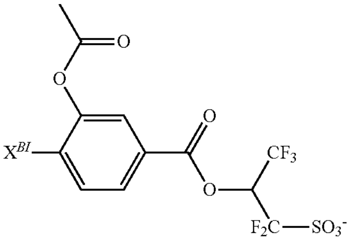
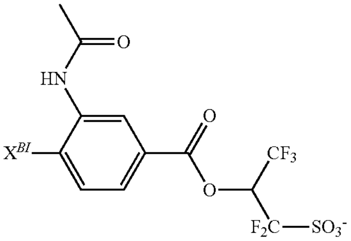
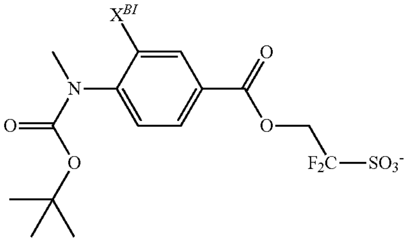
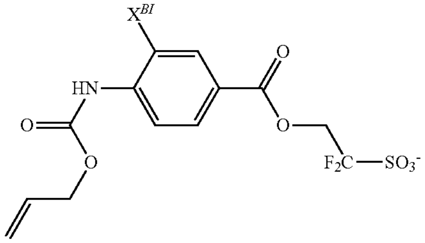
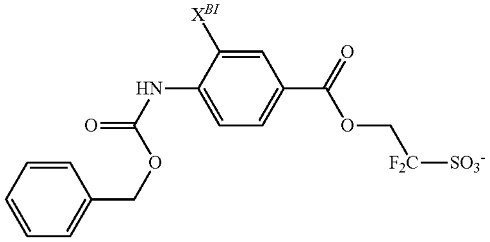
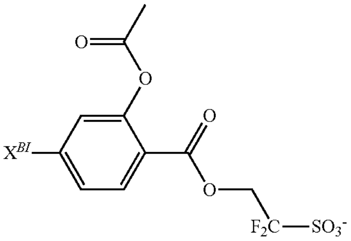
-continued
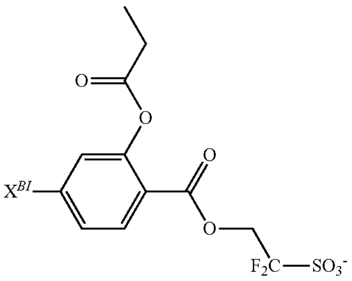
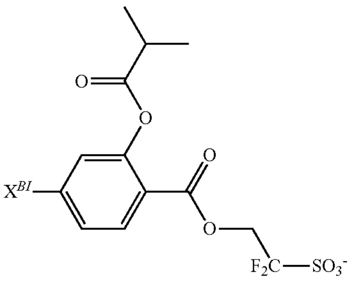
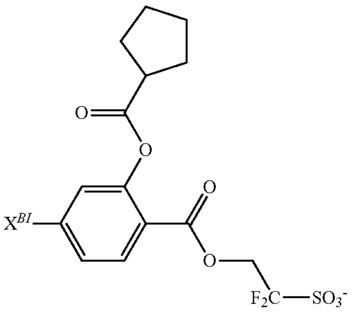
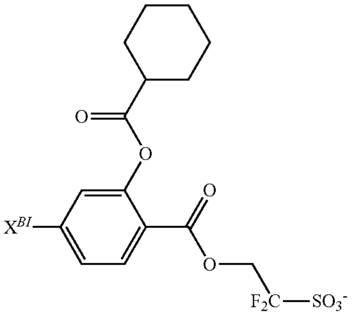
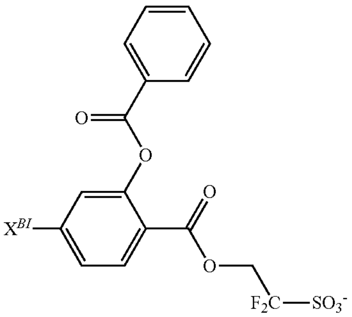

-continued
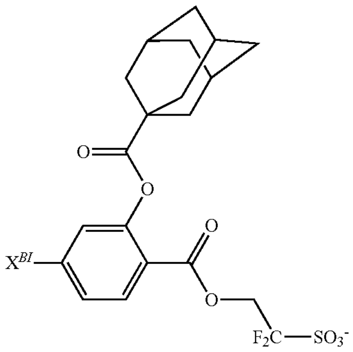
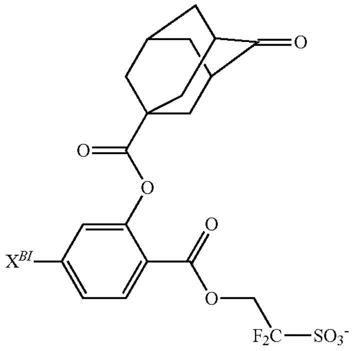
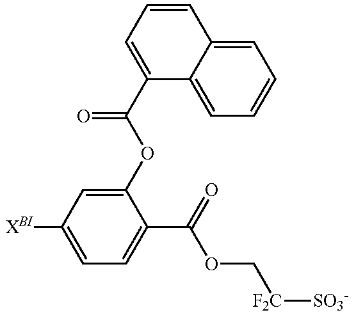
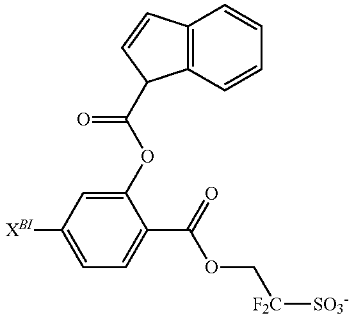
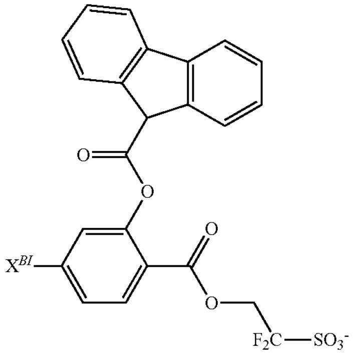
-continued
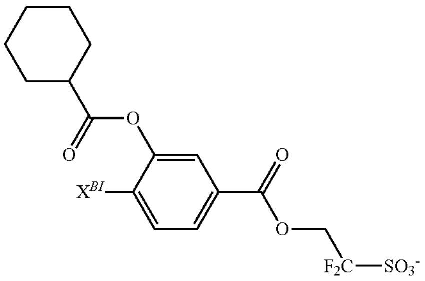
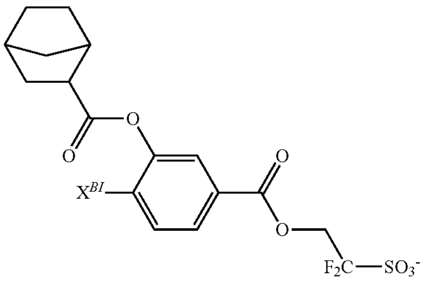
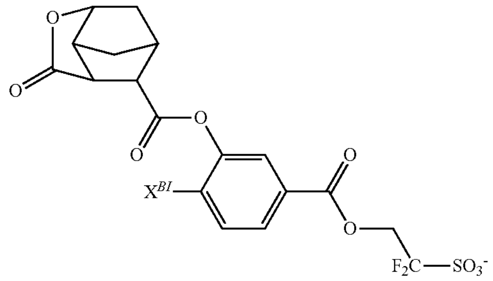
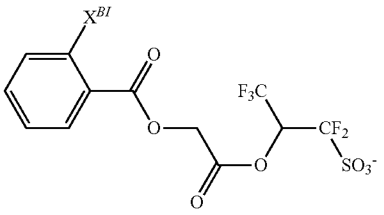
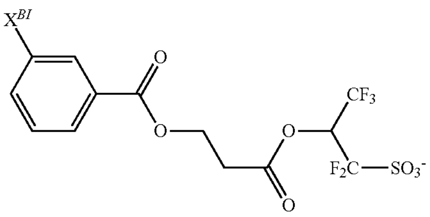
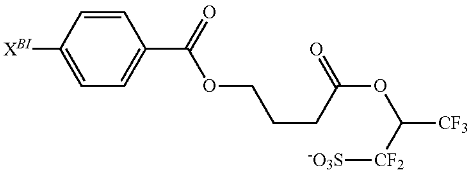
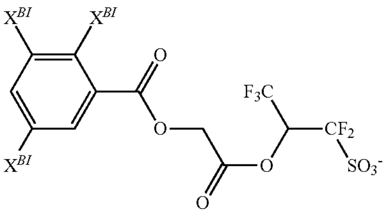

-continued
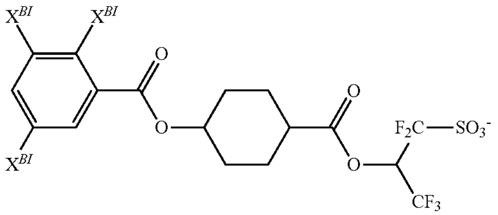
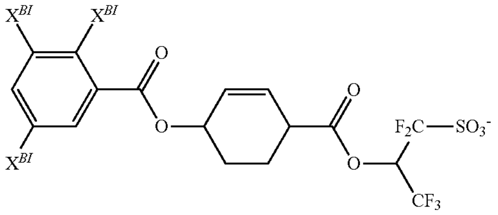
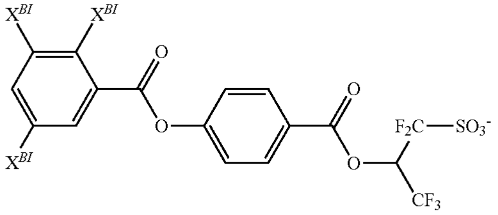
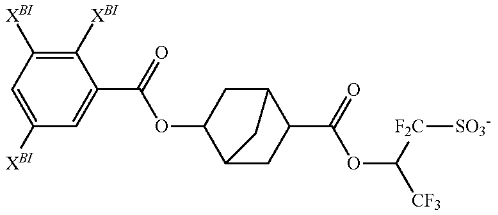
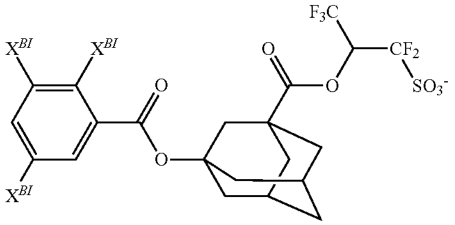
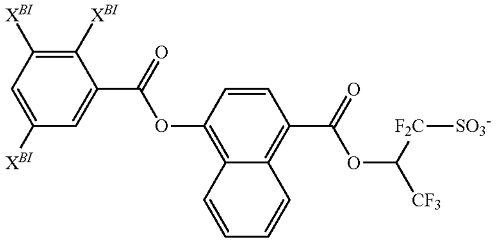
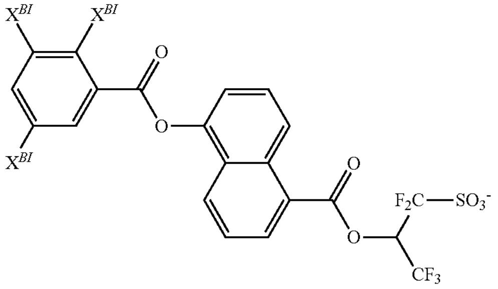
-continued
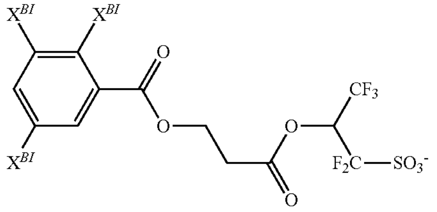
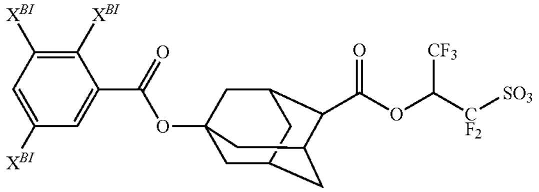
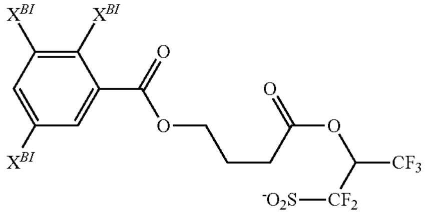
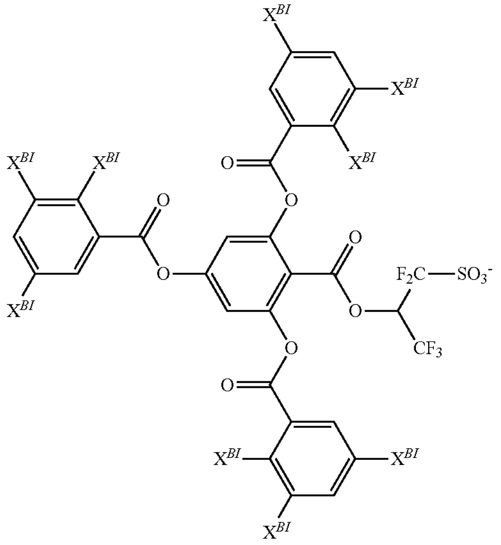
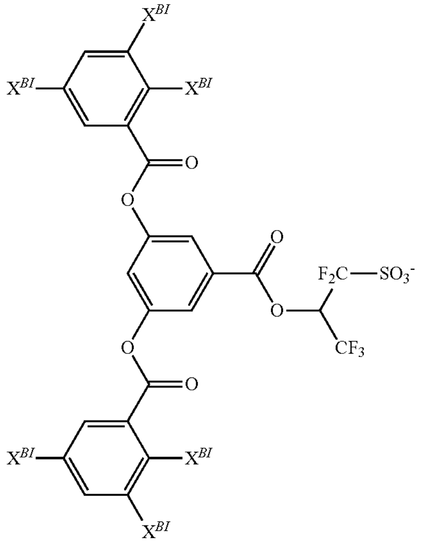

-continued
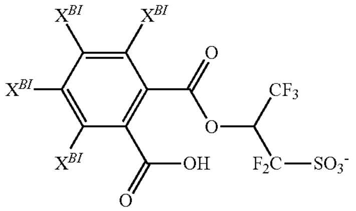
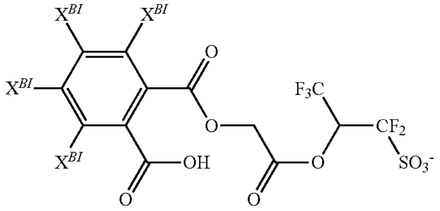
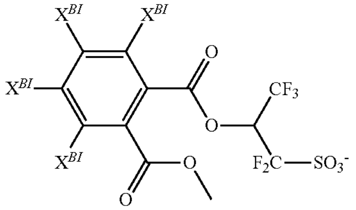
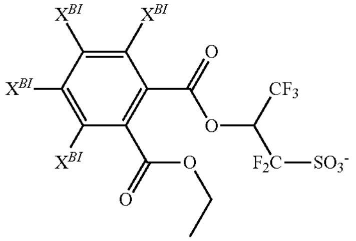
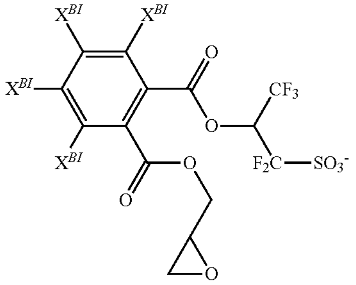
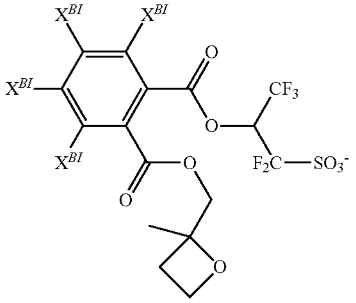
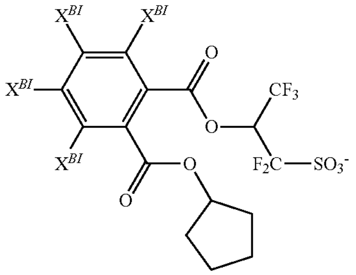
-continued
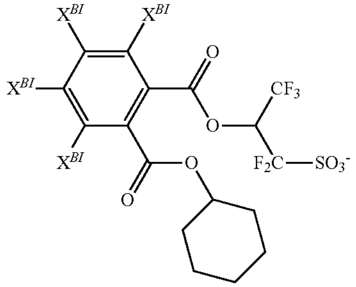
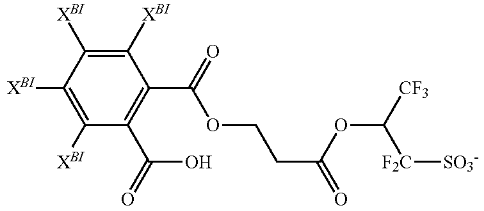
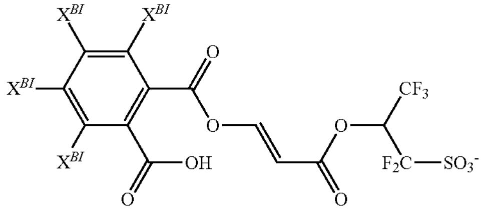
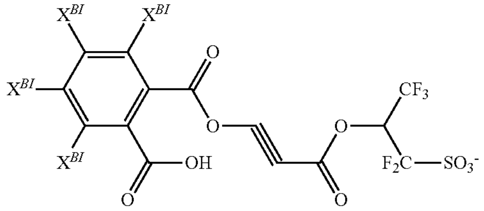
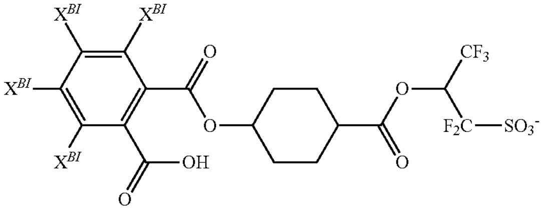
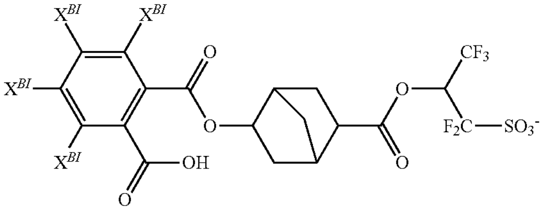
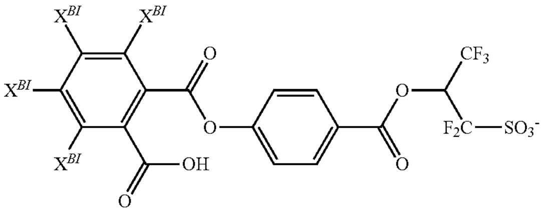

-continued
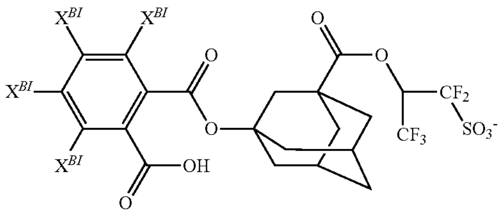
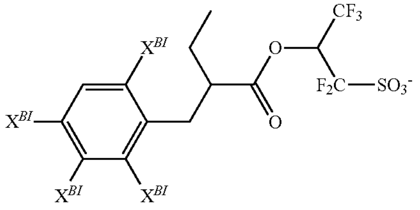
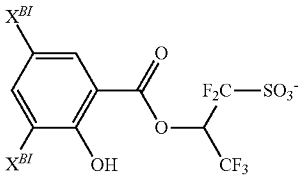
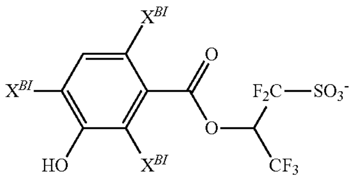
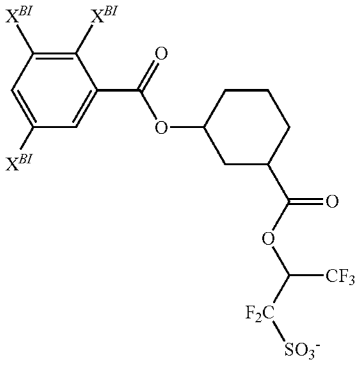
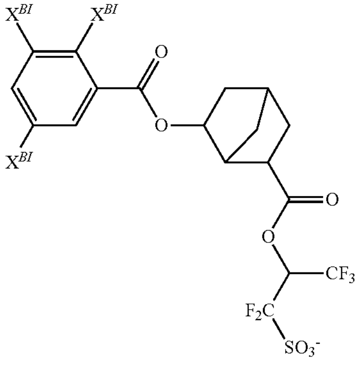
-continued
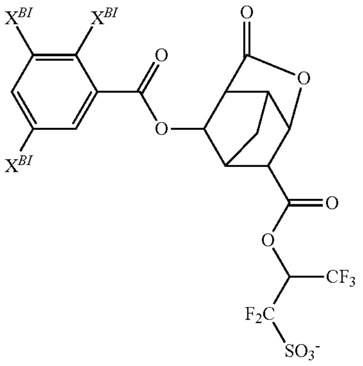
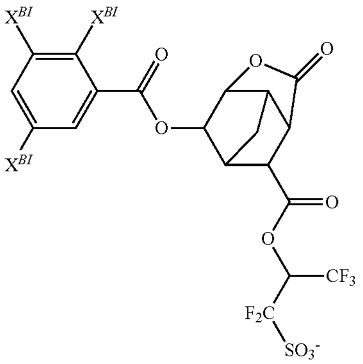
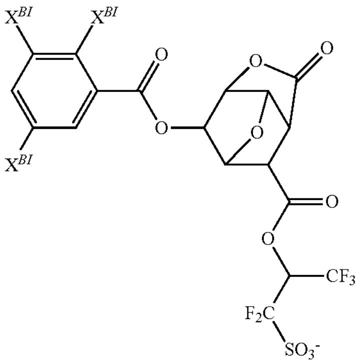
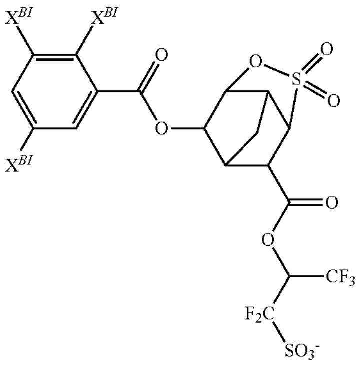

-continued
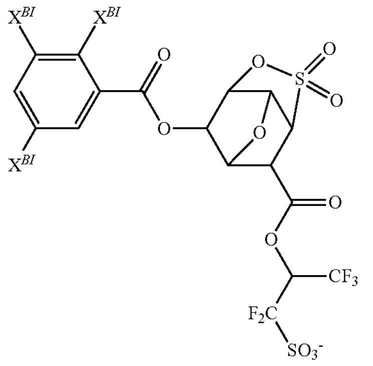
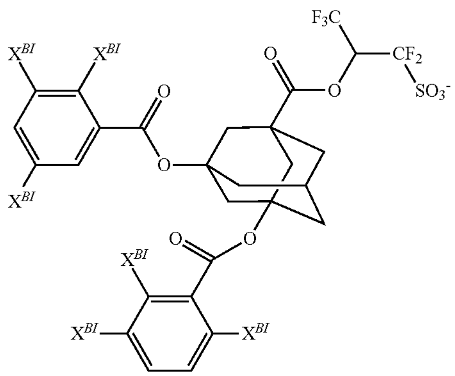
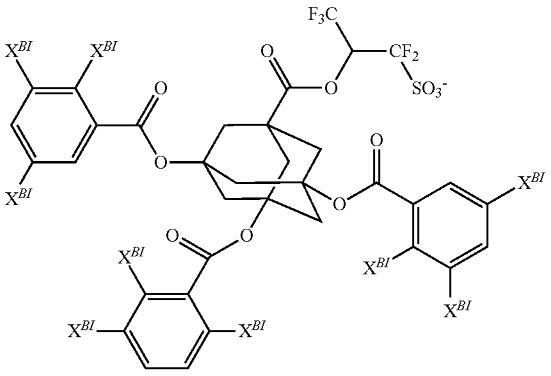
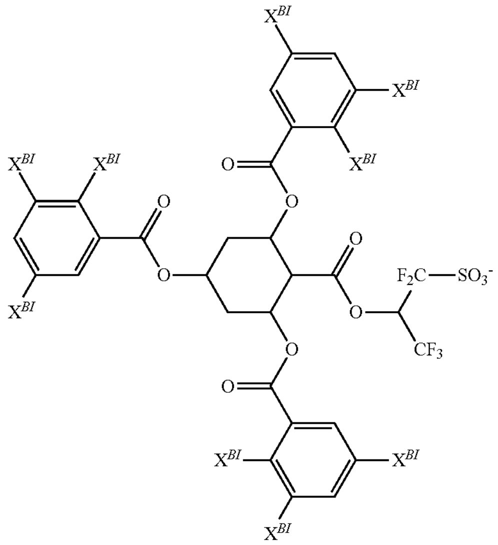
-continued
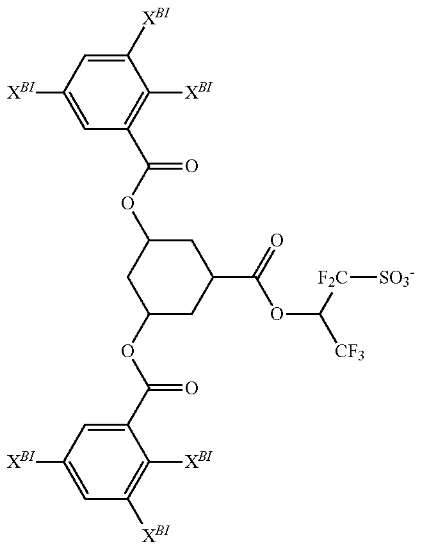
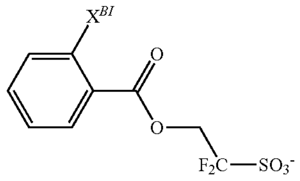
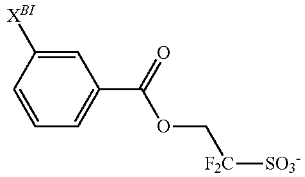
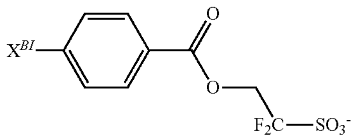
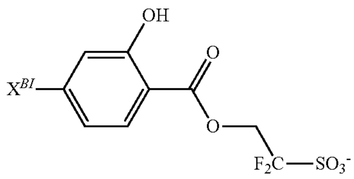
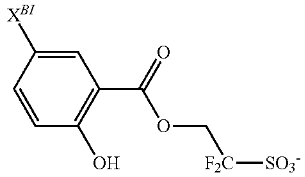
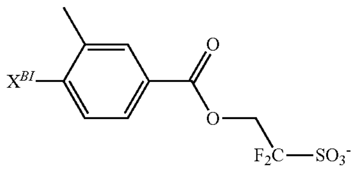

-continued
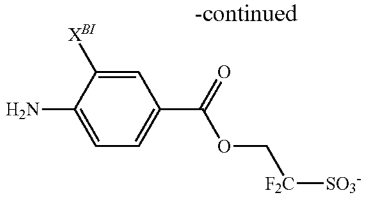
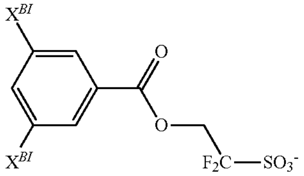
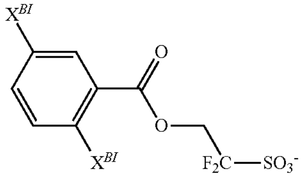
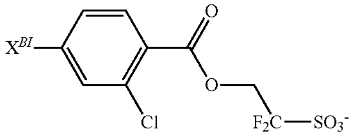
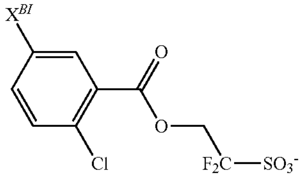
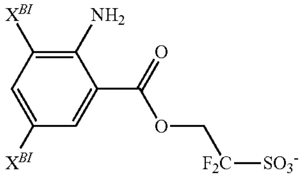
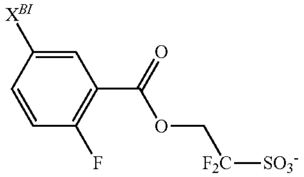
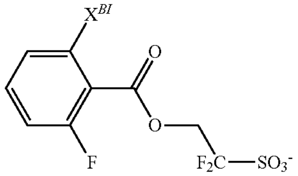
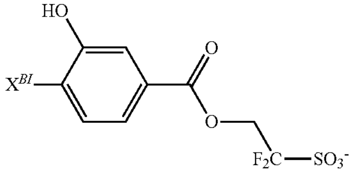
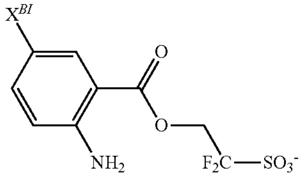
-continued
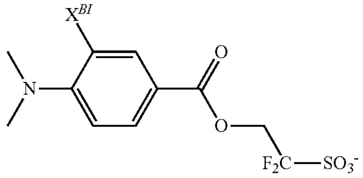
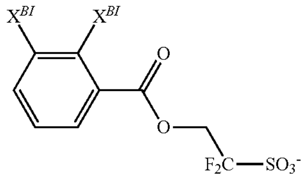
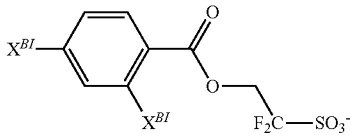
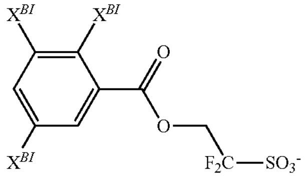
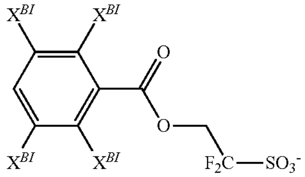
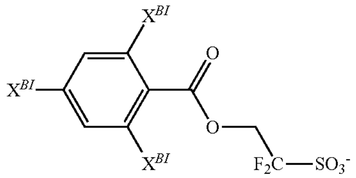
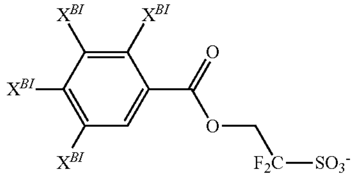
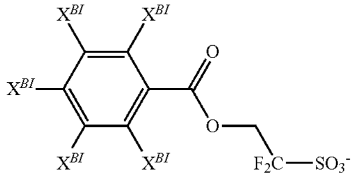
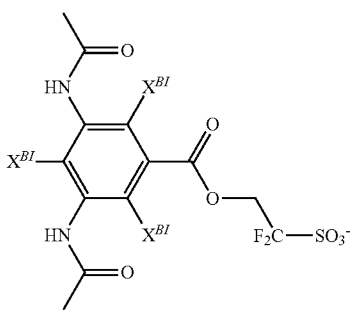

-continued
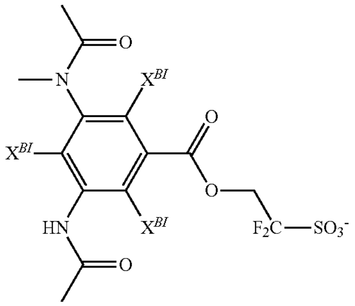
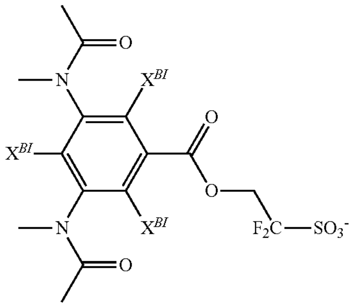
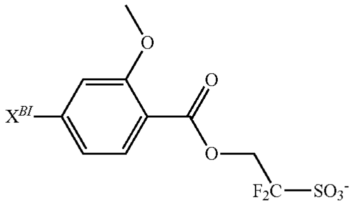
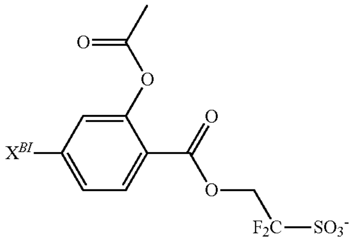
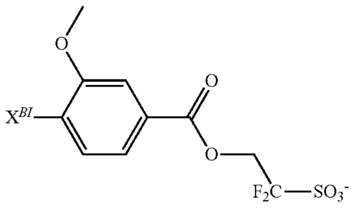
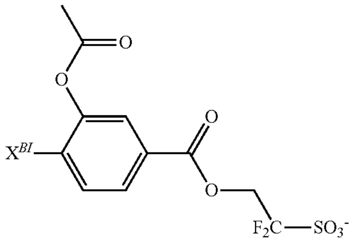
-continued
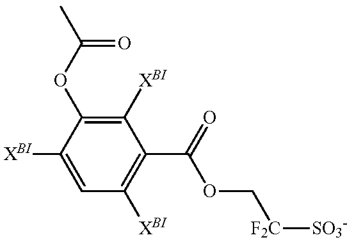
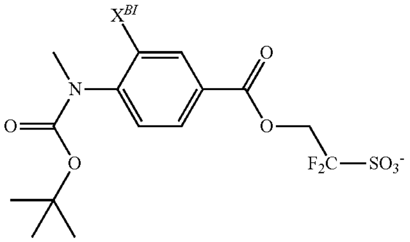
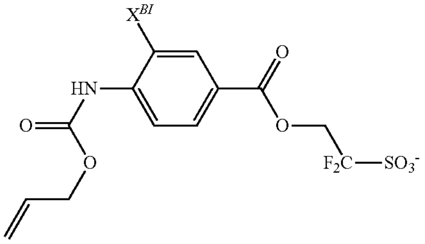
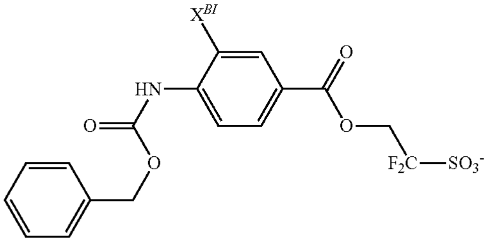
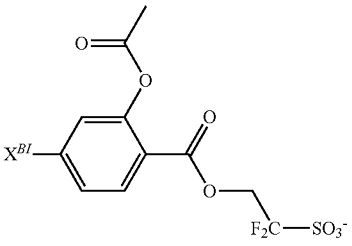
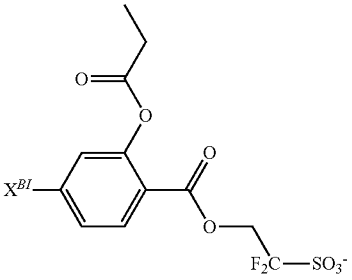

-continued
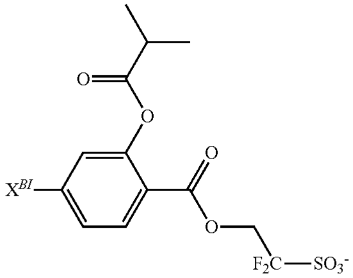
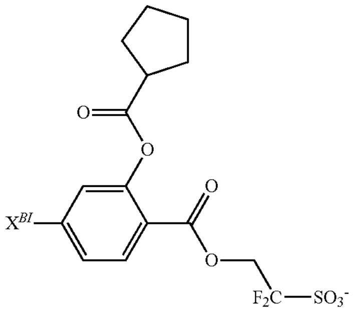
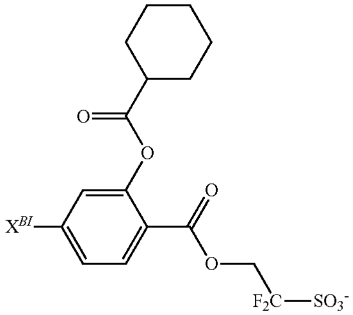
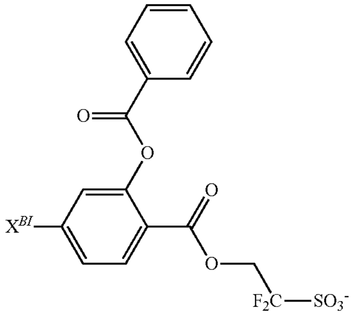
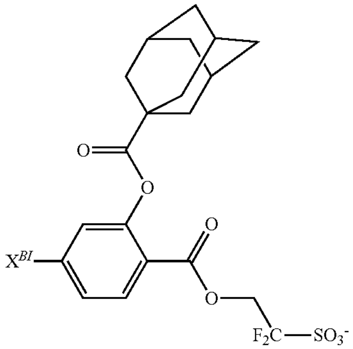
-continued
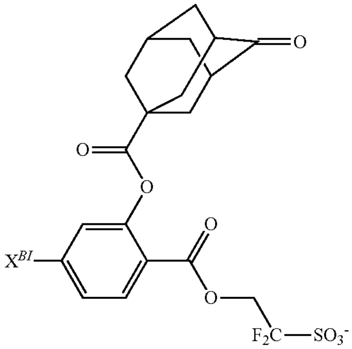
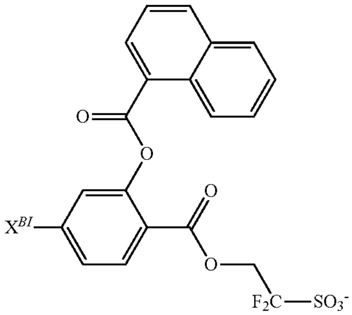
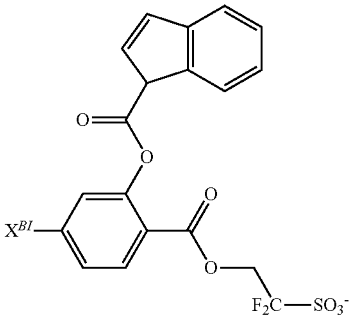
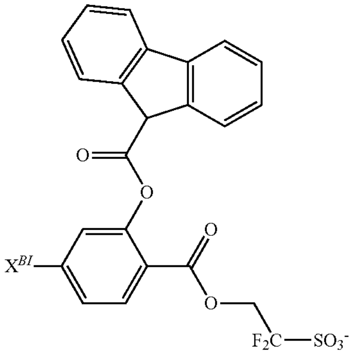
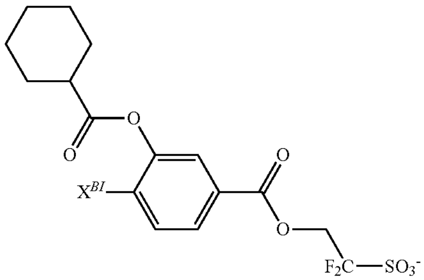

-continued
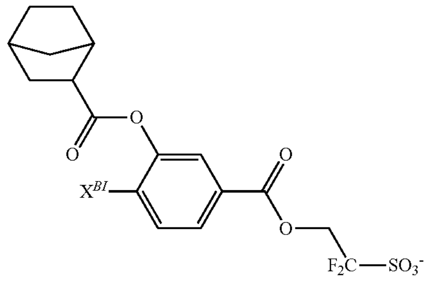
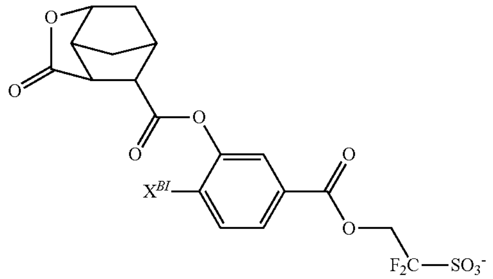
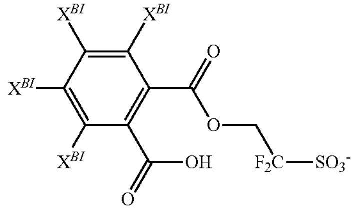
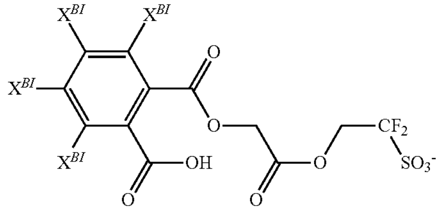
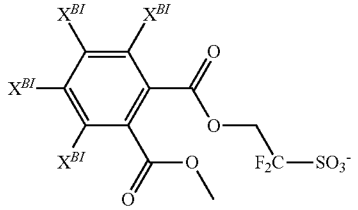
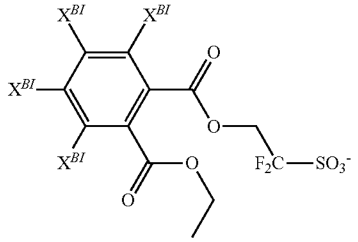
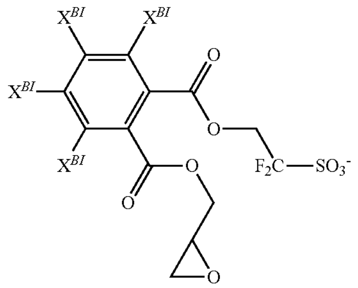
-continued
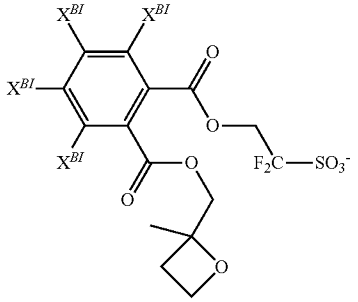
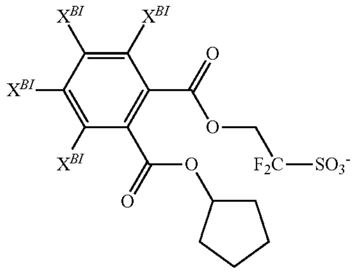
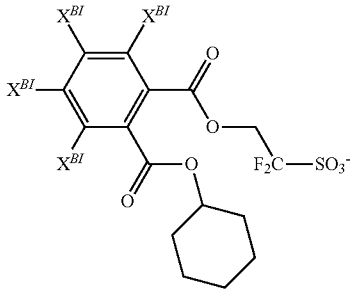
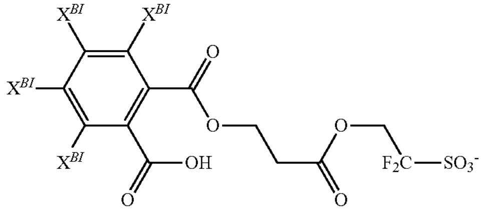
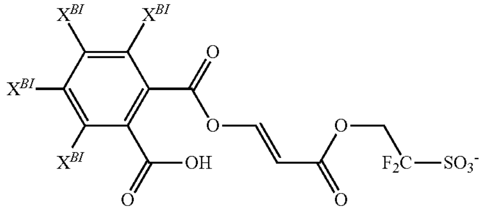
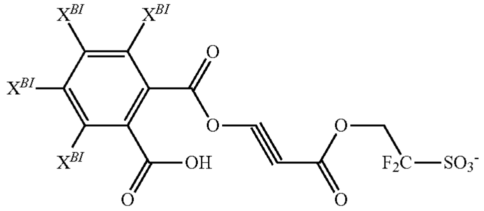
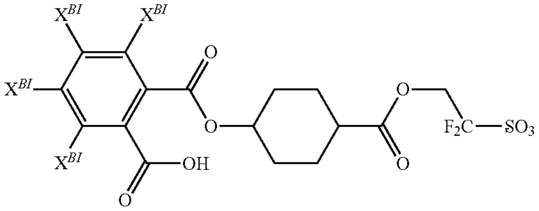

-continued
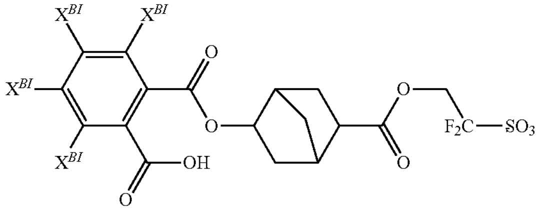
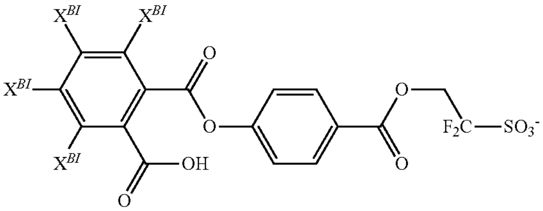
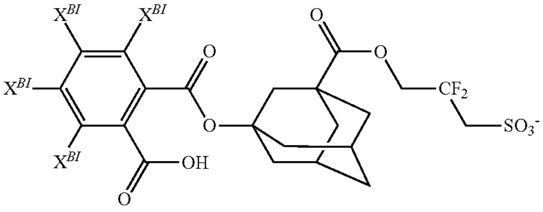
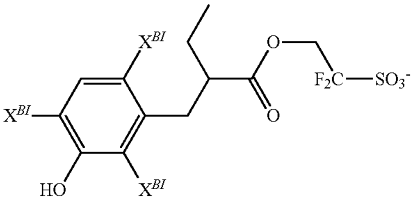
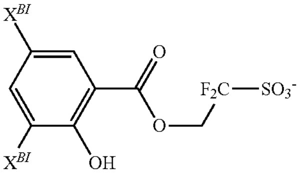
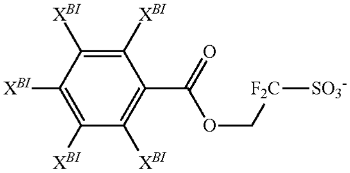
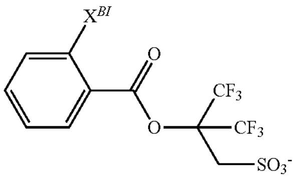
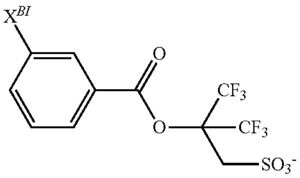
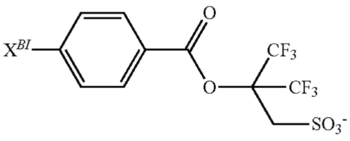
-continued
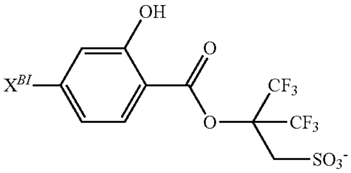
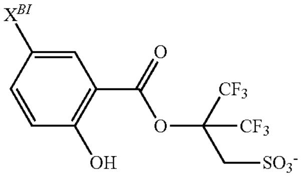
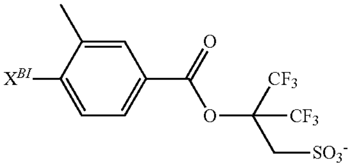
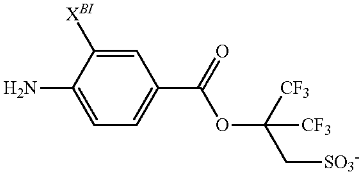
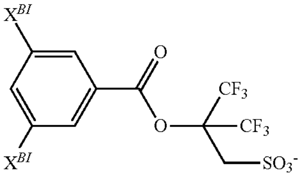
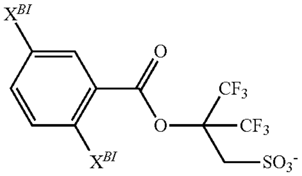
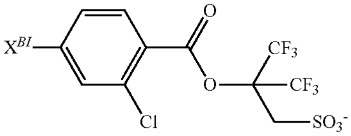
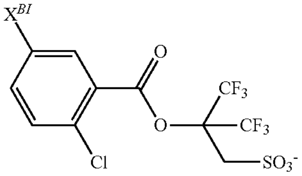
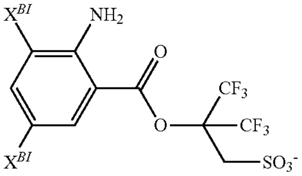
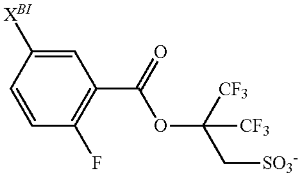

-continued
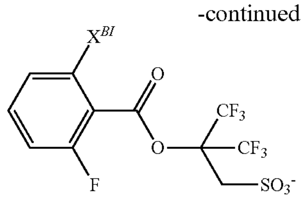
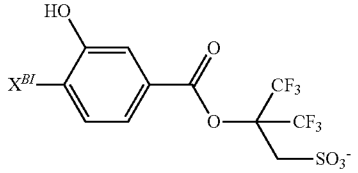
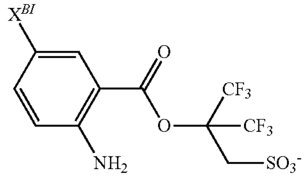
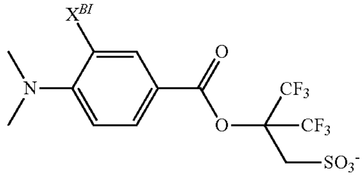
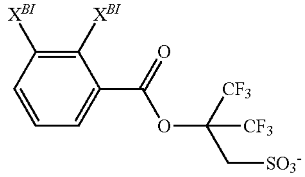
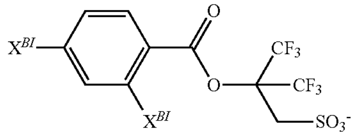
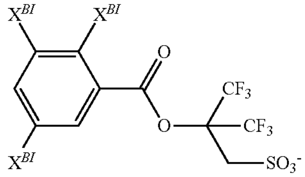
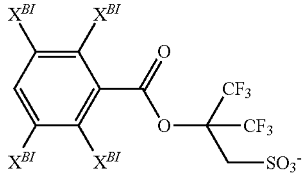
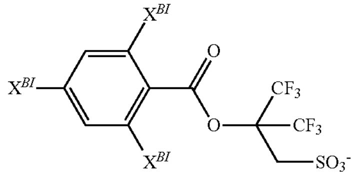
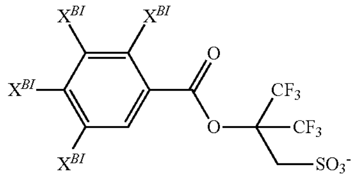
-continued
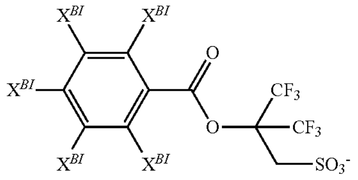
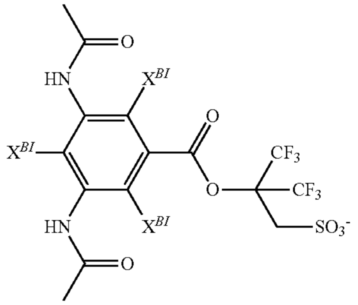
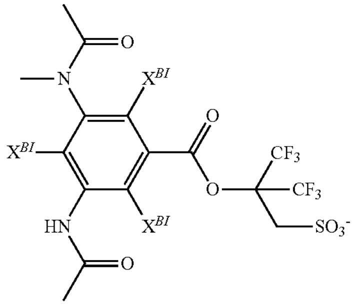
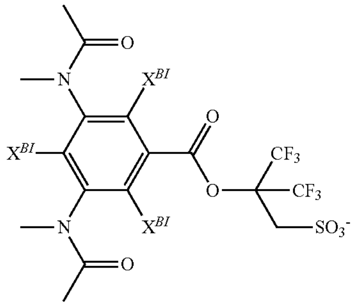
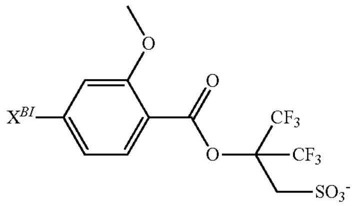
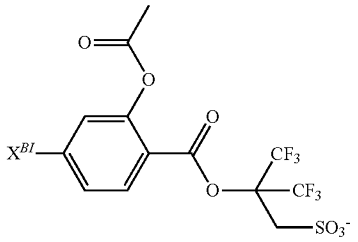

-continued
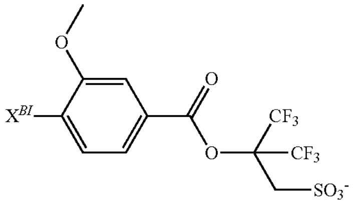
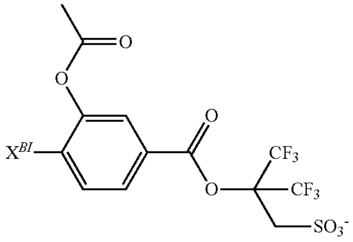
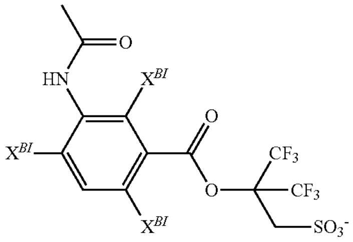
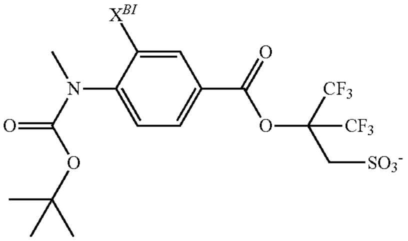
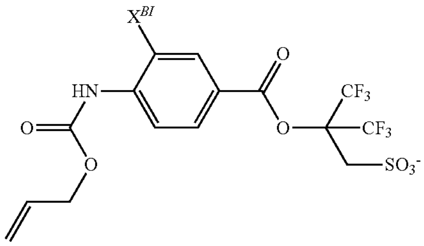
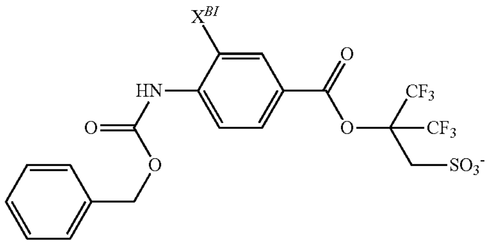
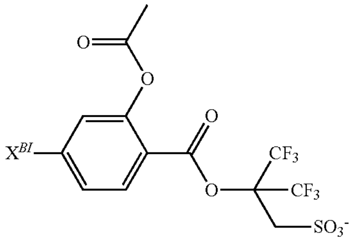
-continued
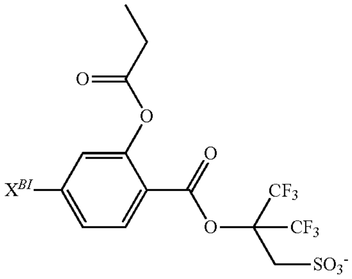
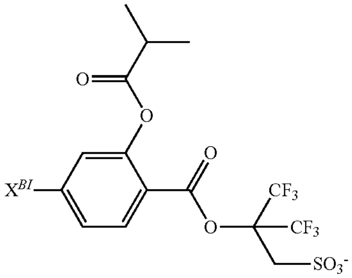
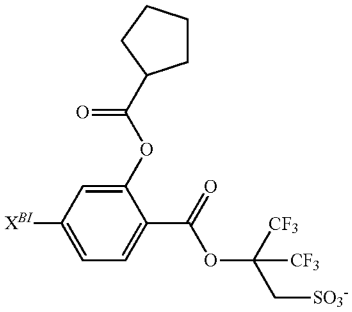
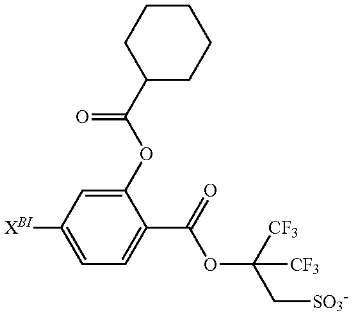
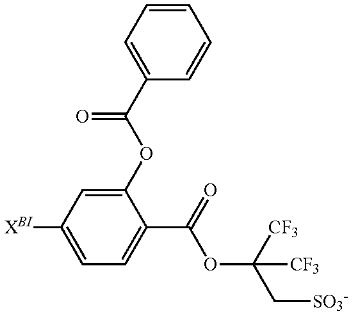

-continued
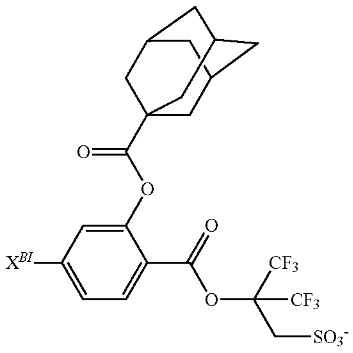
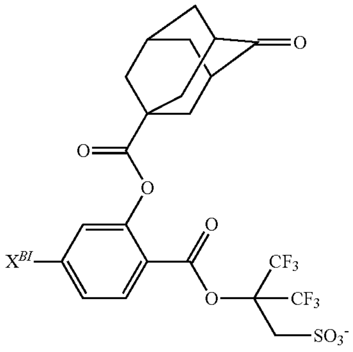
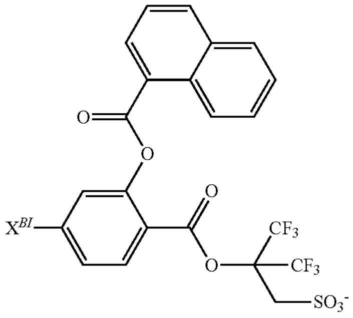
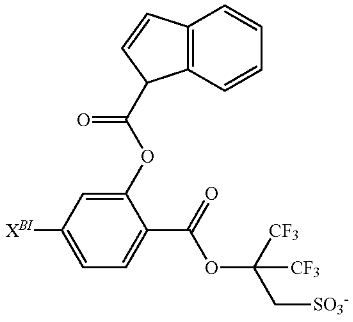
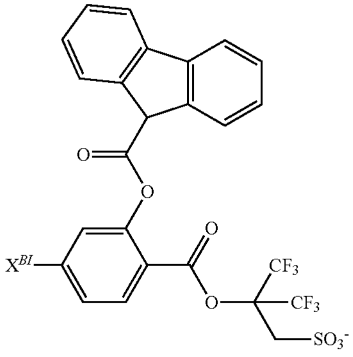
-continued
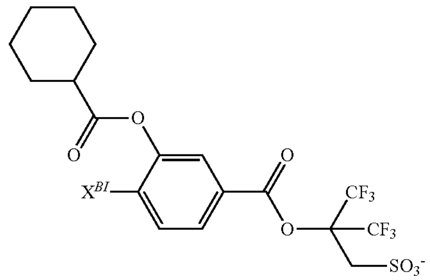
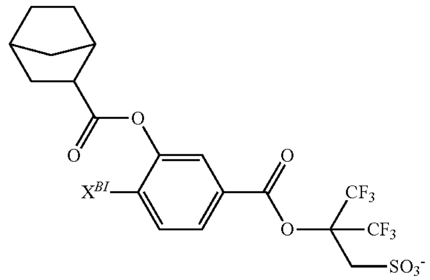
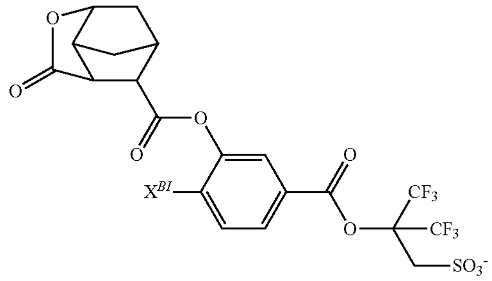
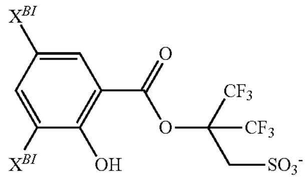
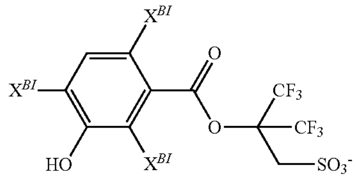
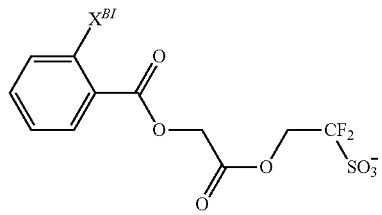
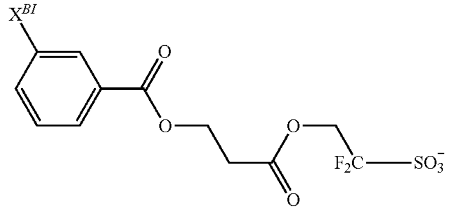

-continued
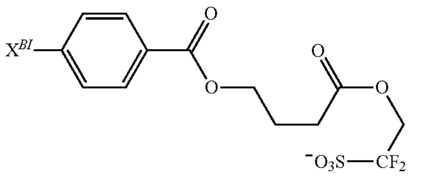
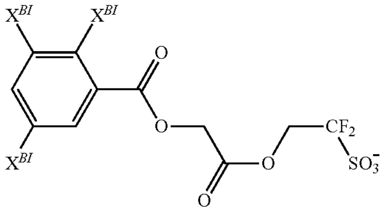
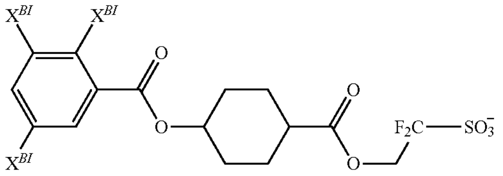
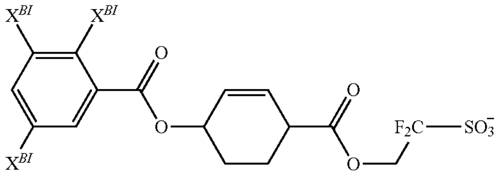
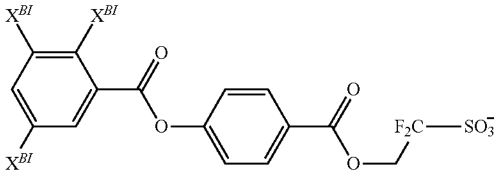
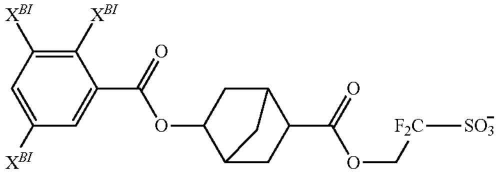
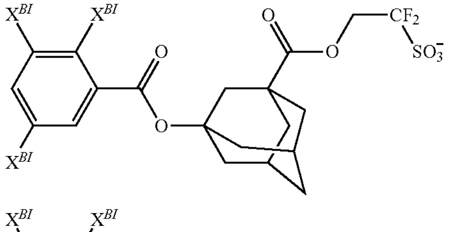
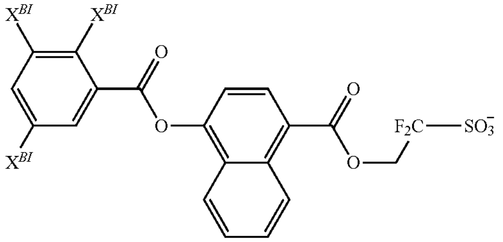
-continued
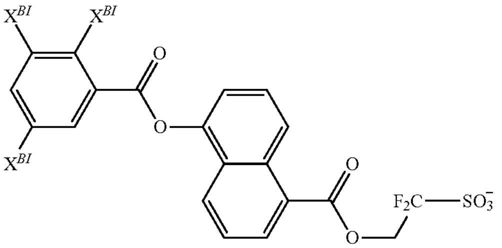
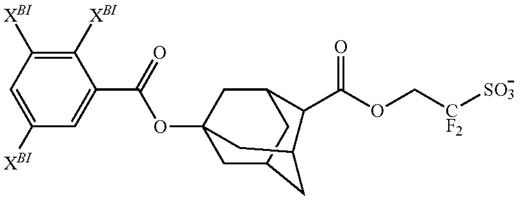
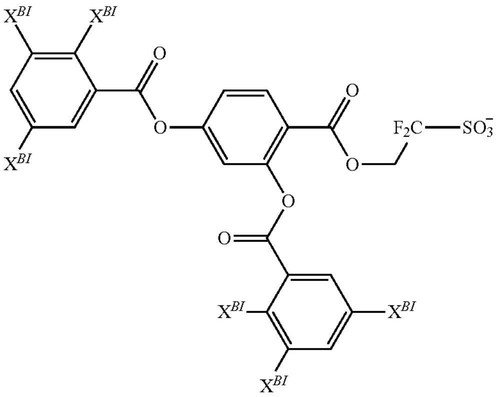
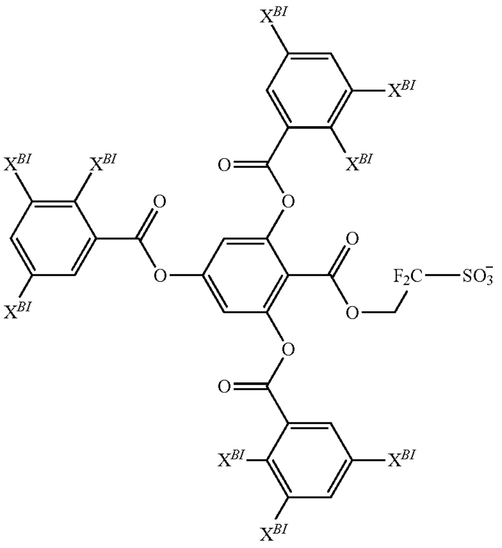

-continued
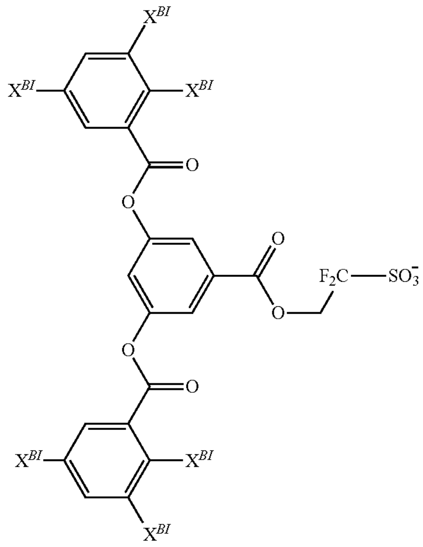
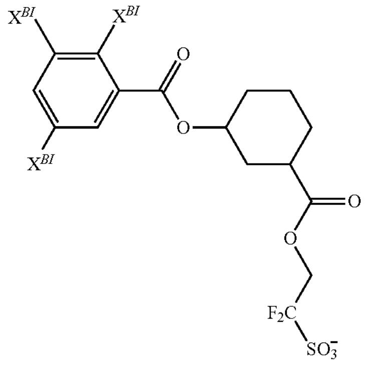
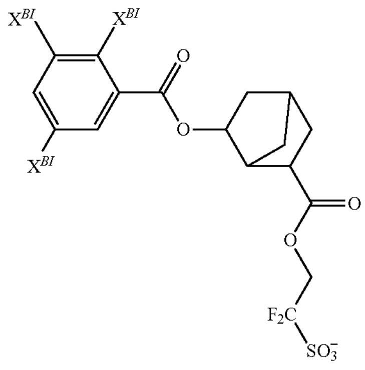
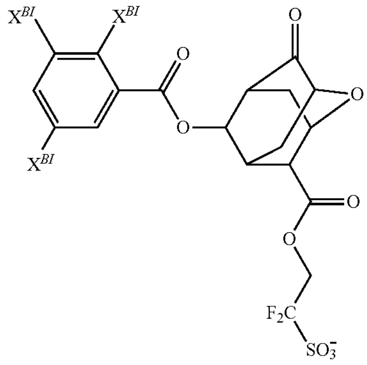
-continued
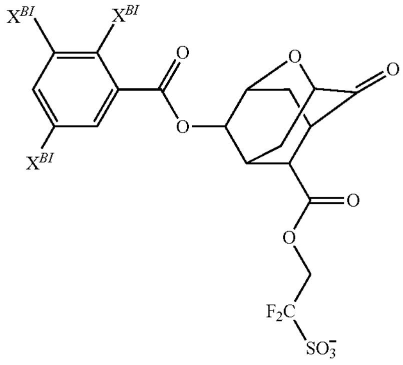
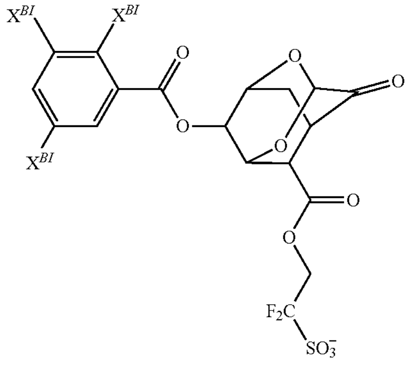
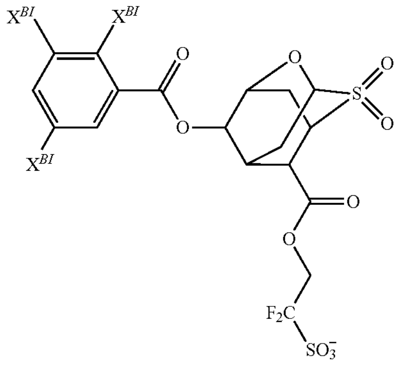
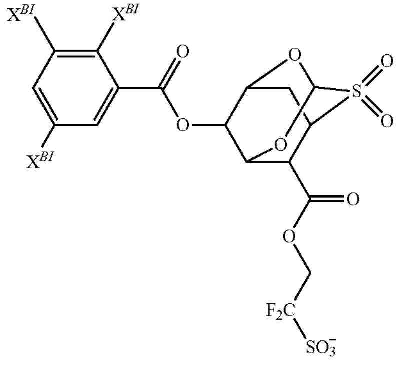

-continued
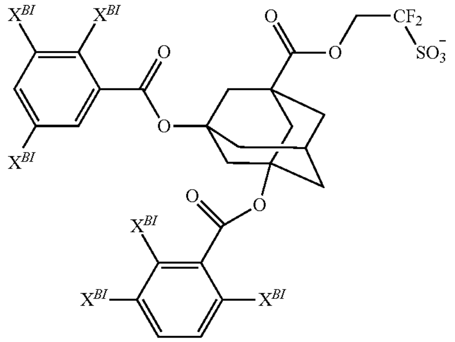
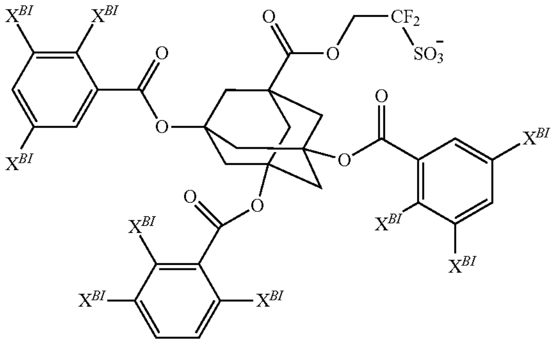
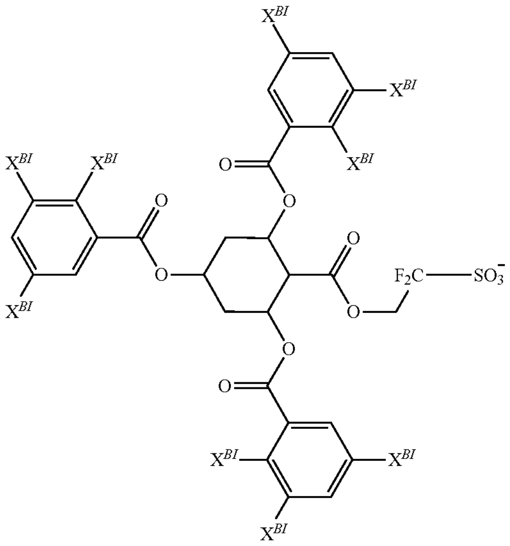
-continued
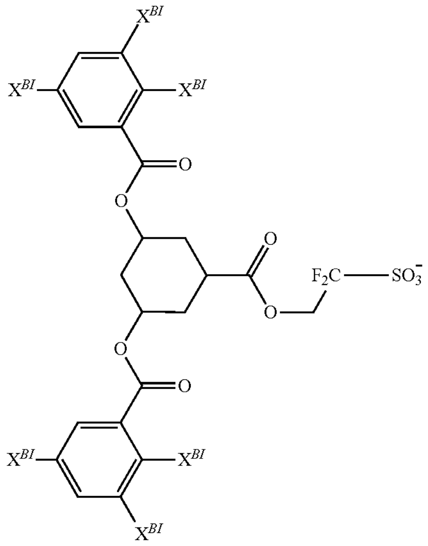
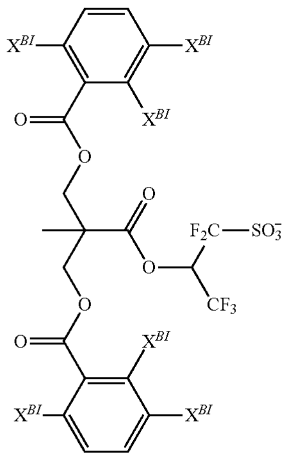
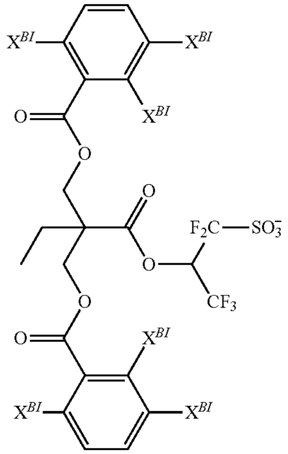

-continued
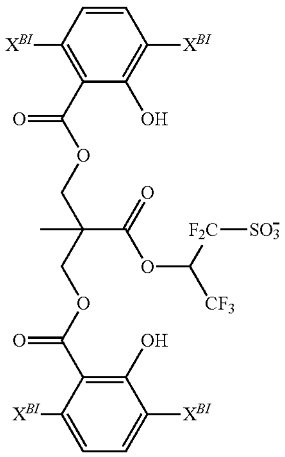
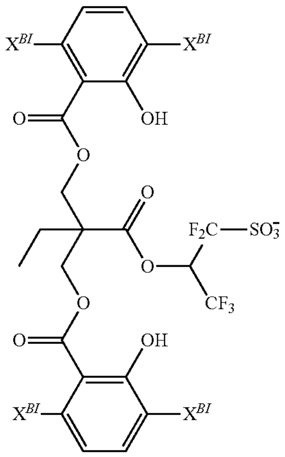
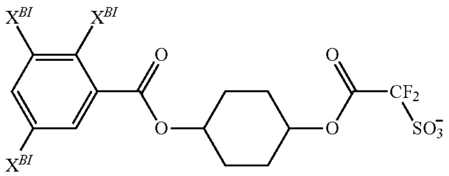
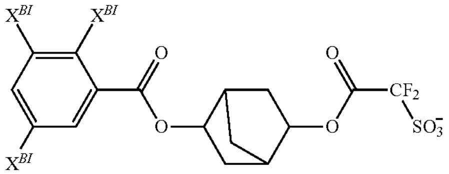
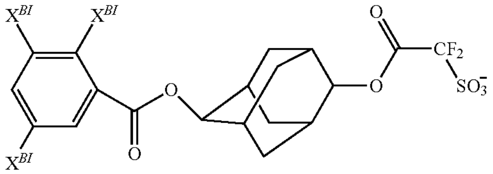
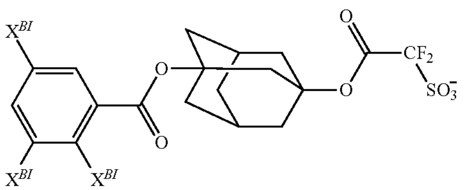
-continued
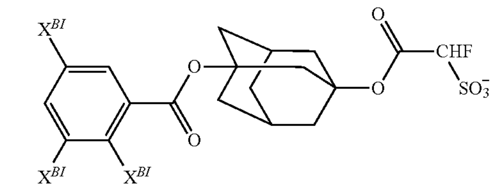
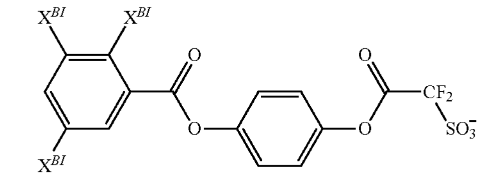
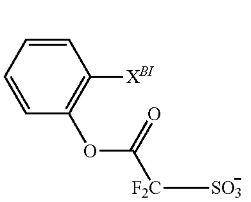
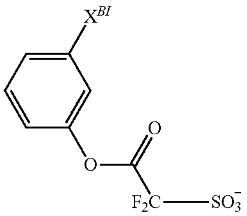
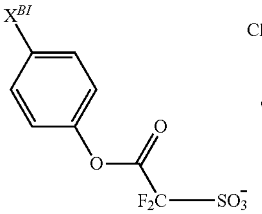
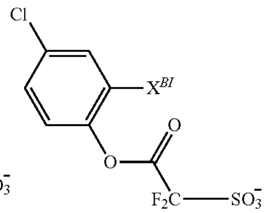
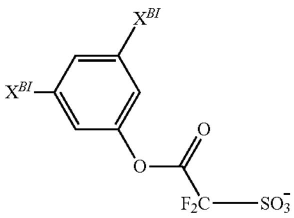
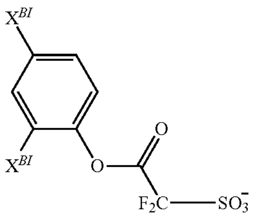
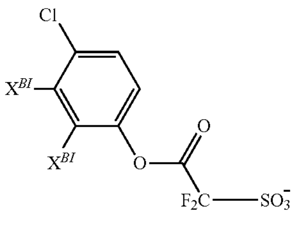
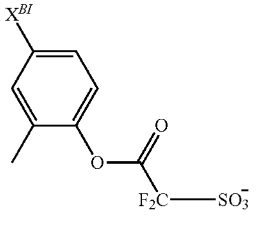
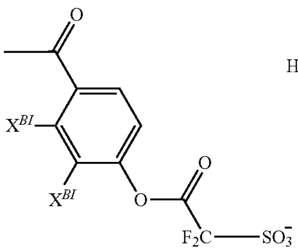
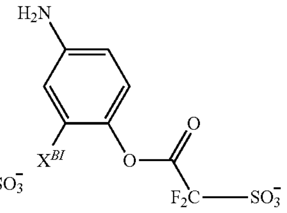

-continued
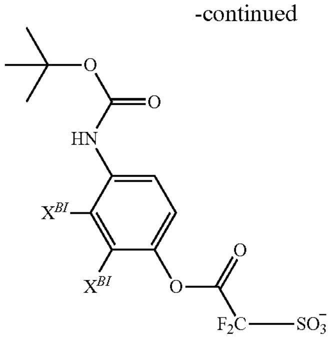
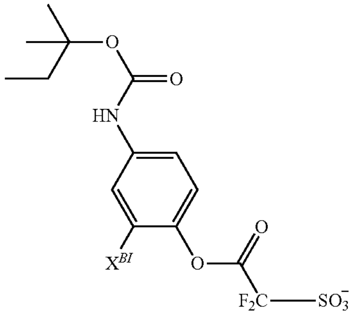
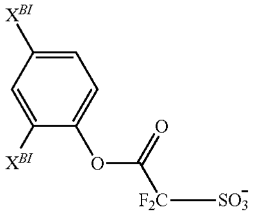
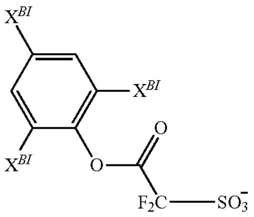
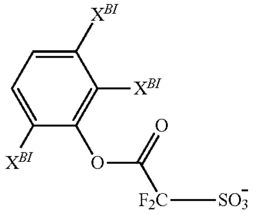
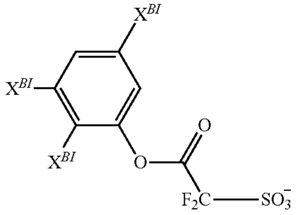
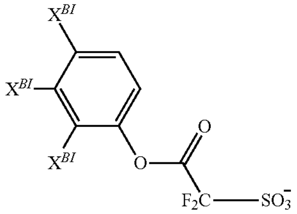
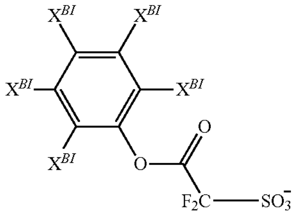
-continued
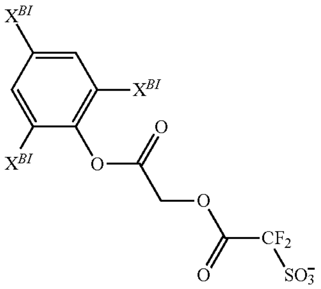
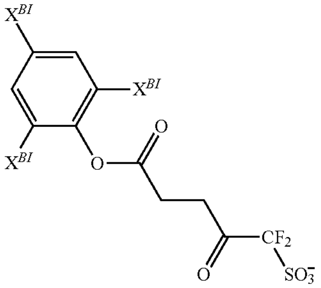
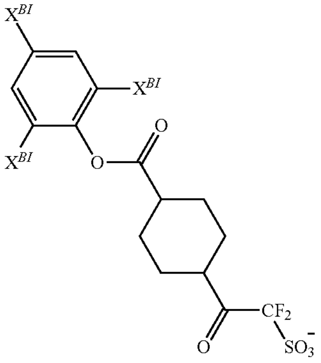
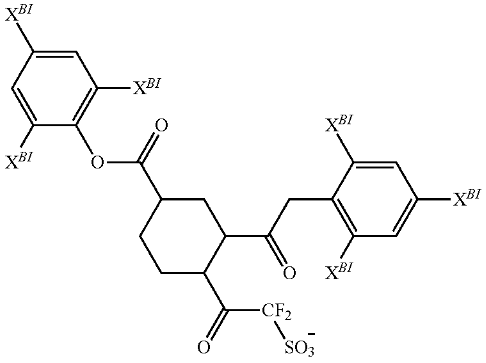
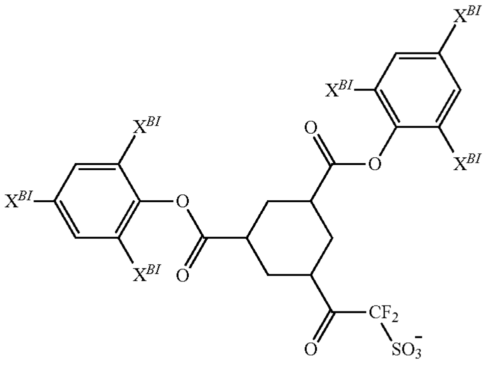

-continued
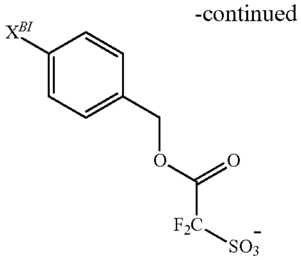
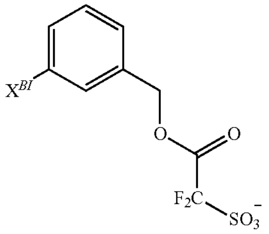
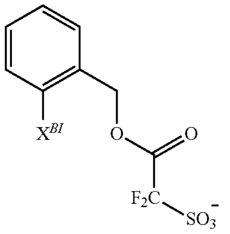
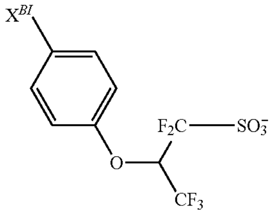
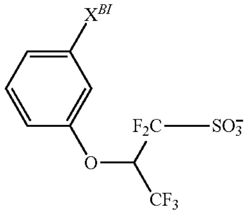
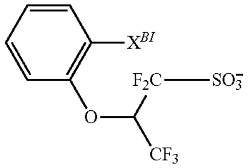
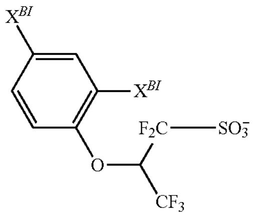
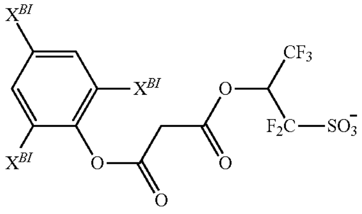
-continued
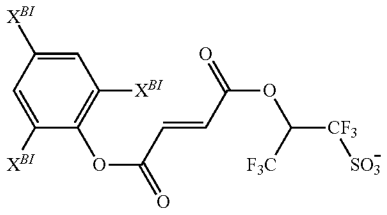
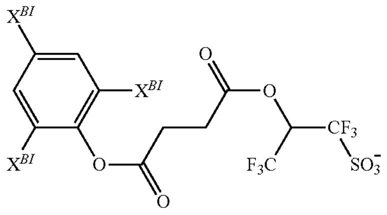
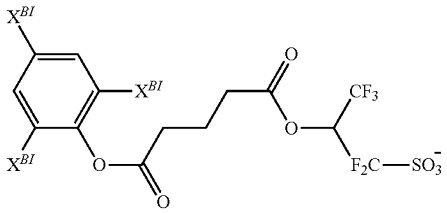
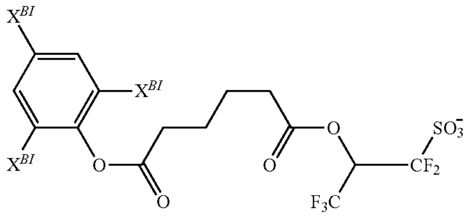
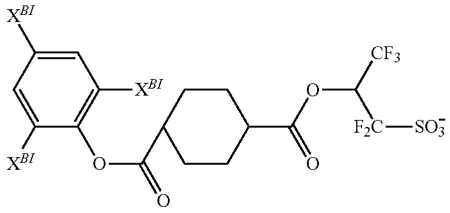
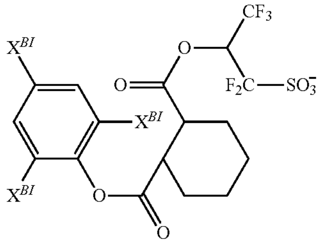
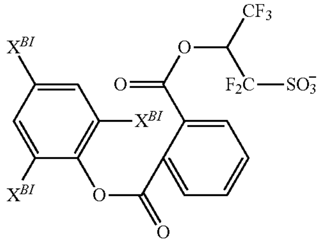

-continued
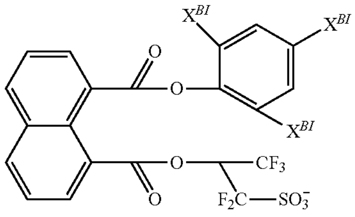
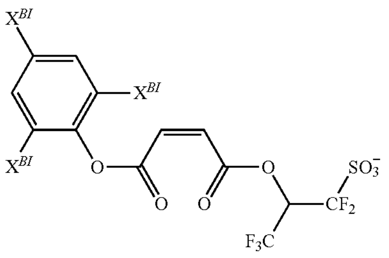
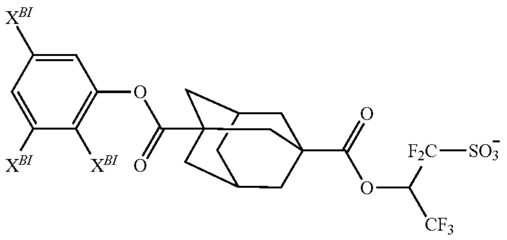
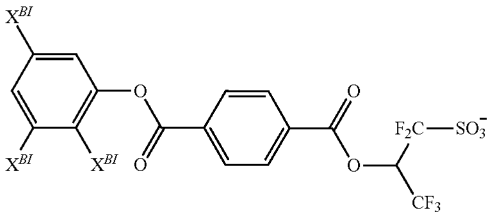
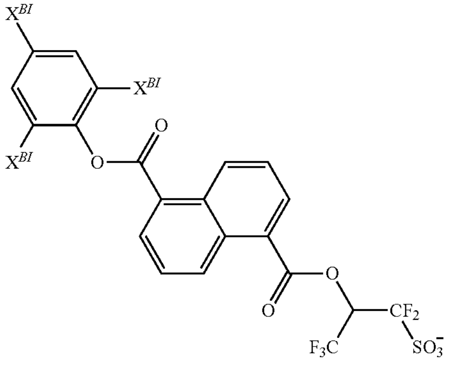
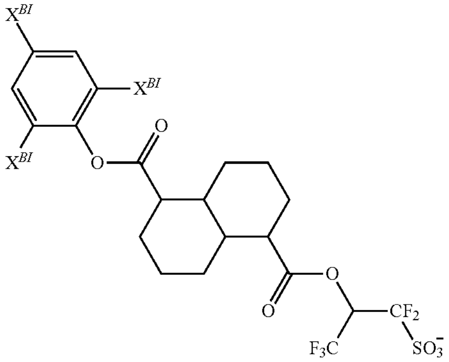
-continued
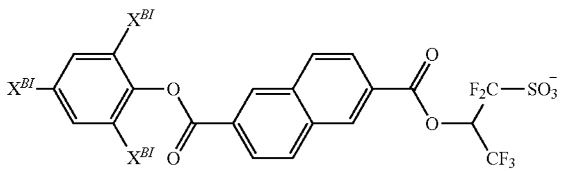
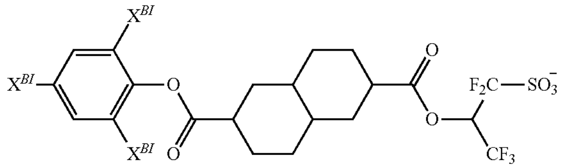
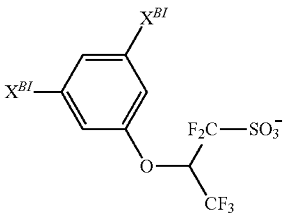
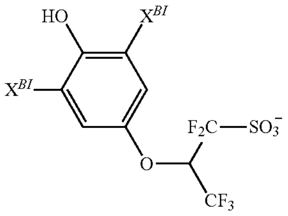
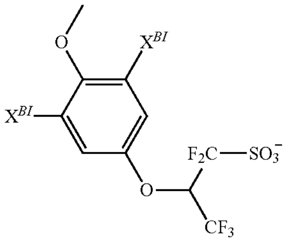
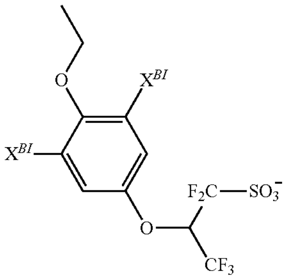
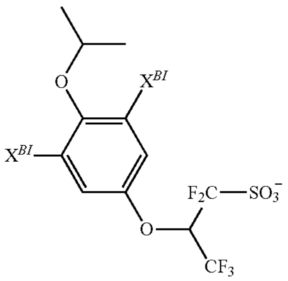

-continued
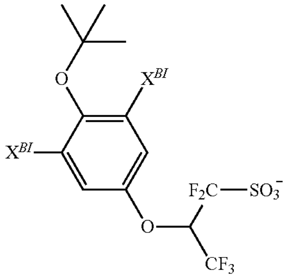
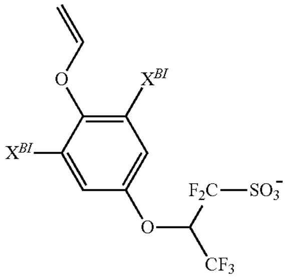
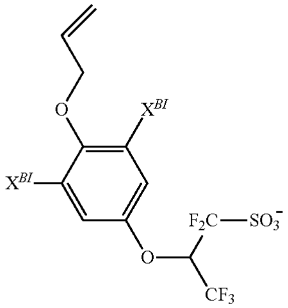
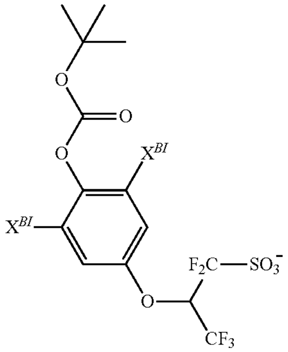
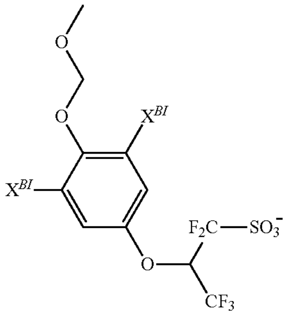
-continued
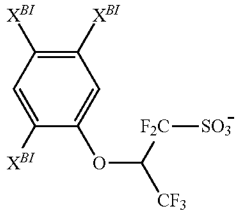
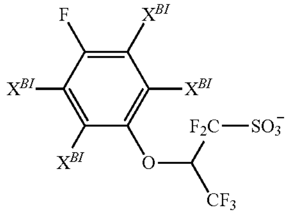
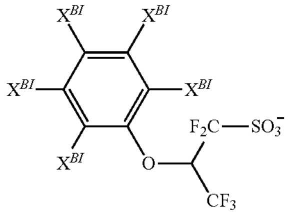
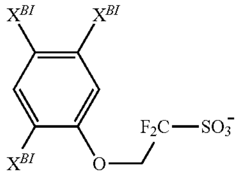
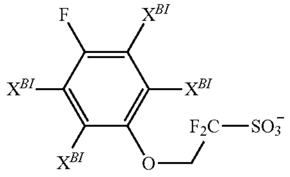
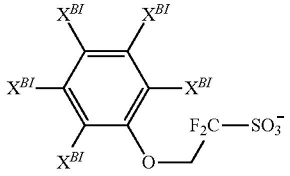
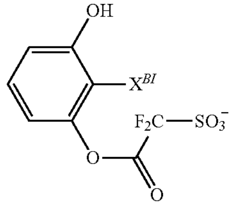
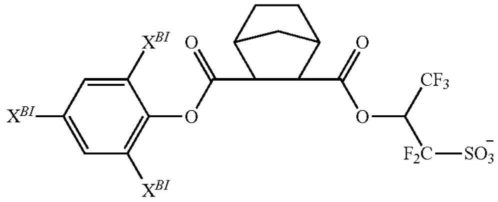

-continued
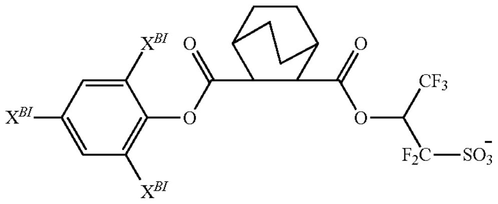
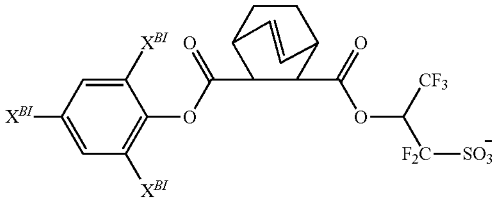
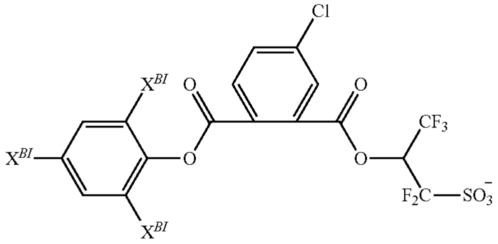
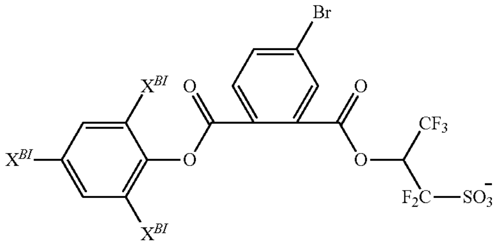
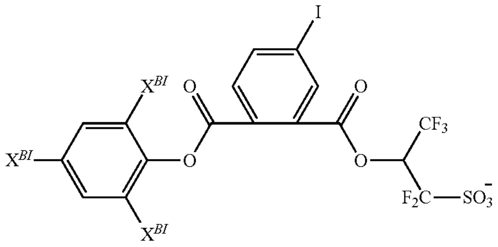
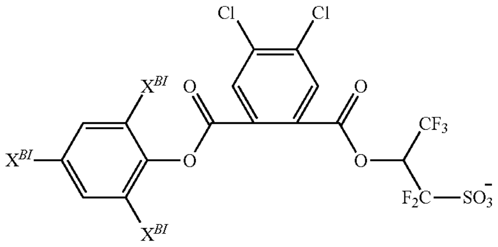
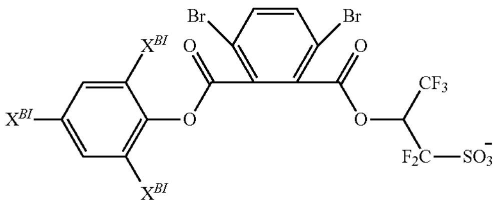
-continued
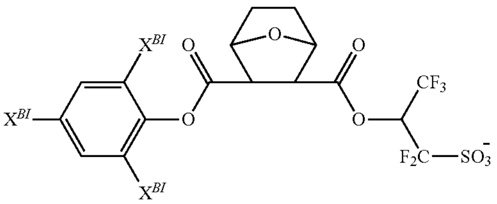
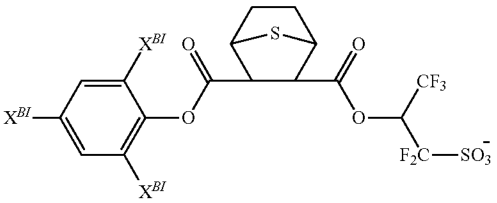
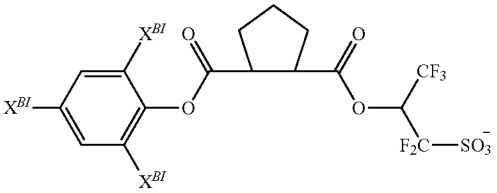
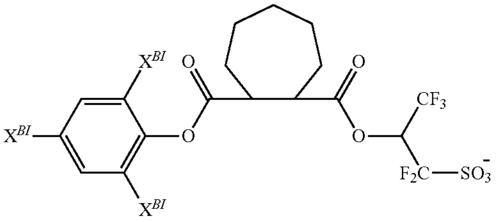
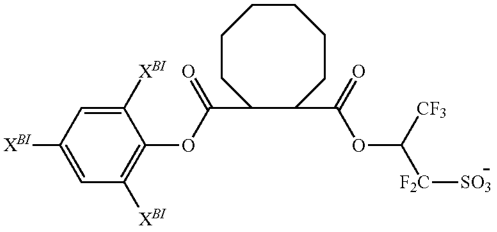
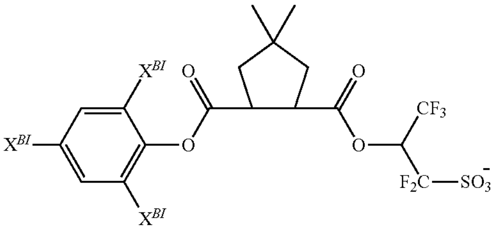
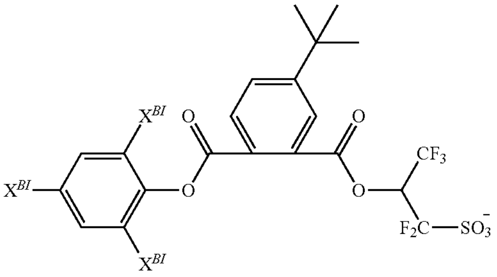

-continued
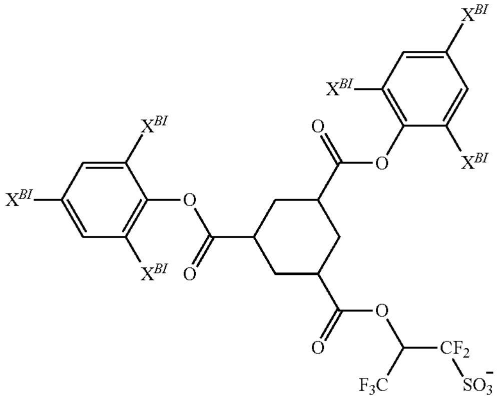
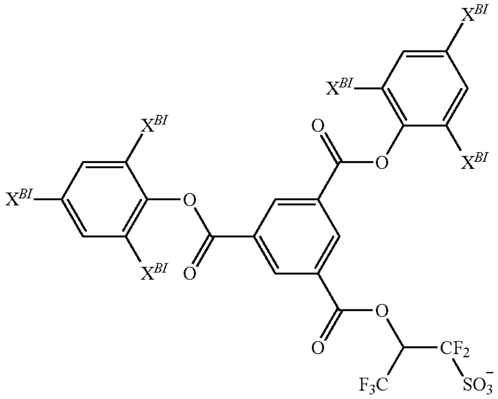
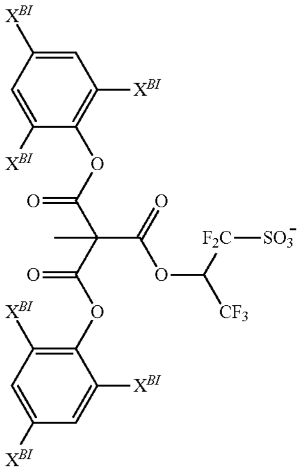
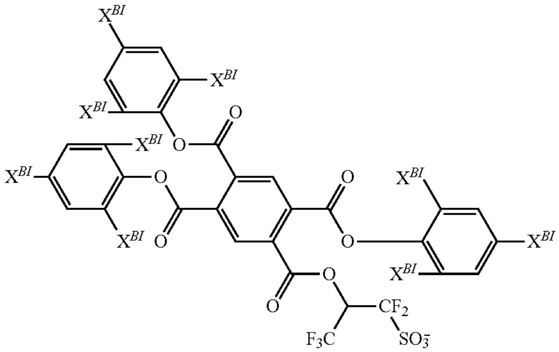
-continued
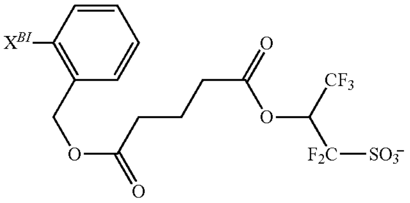
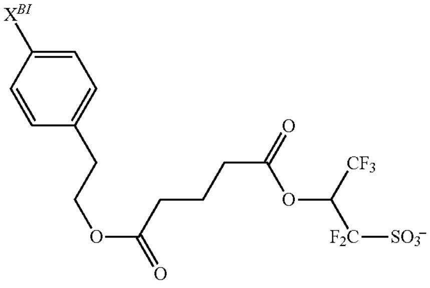
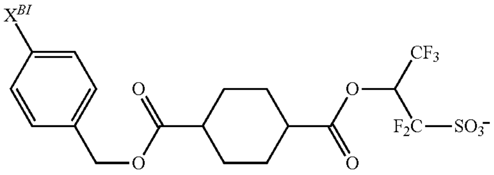
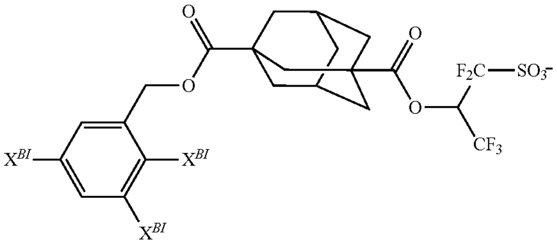
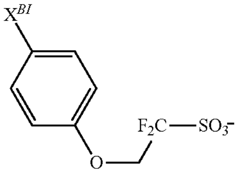
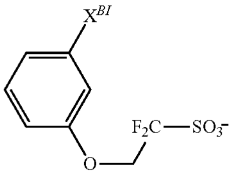
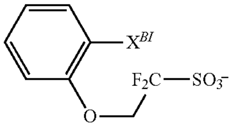
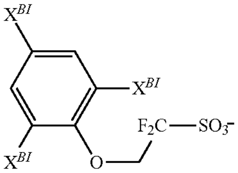

-continued
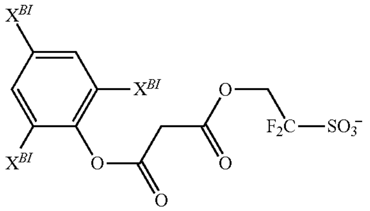
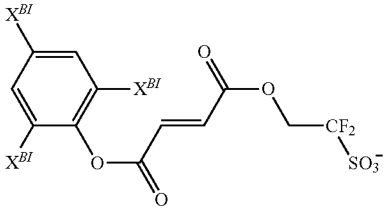
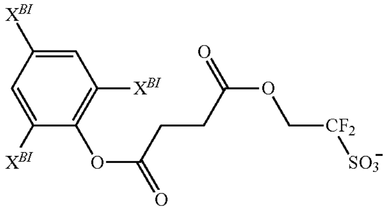
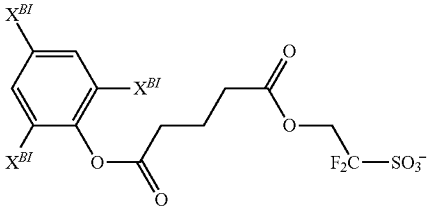
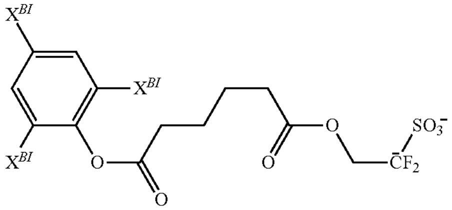
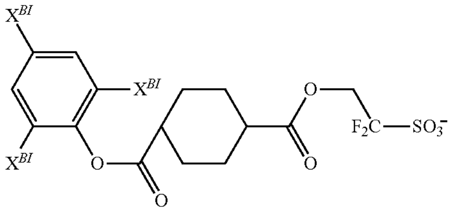
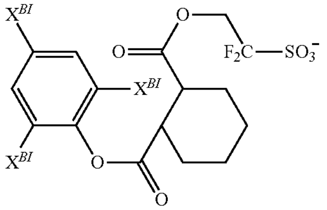
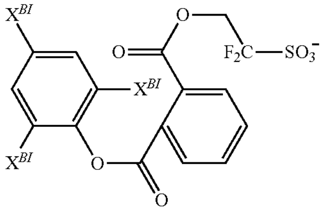
-continued
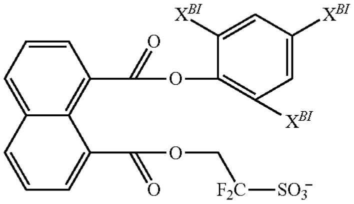
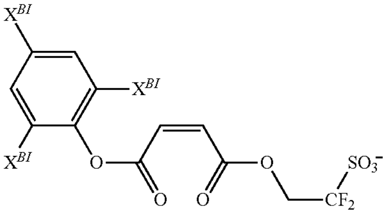
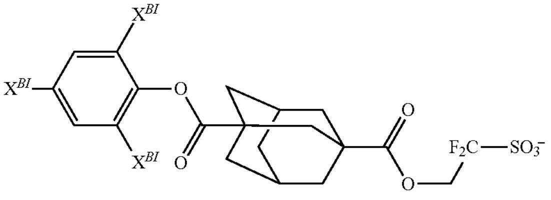
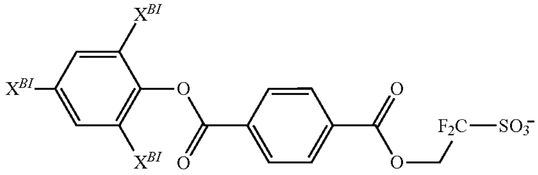
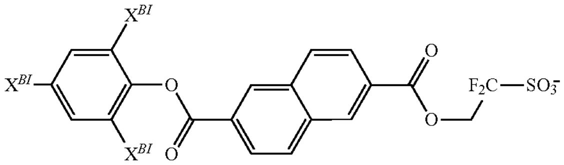
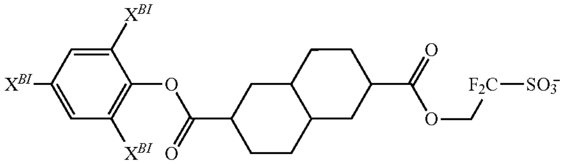
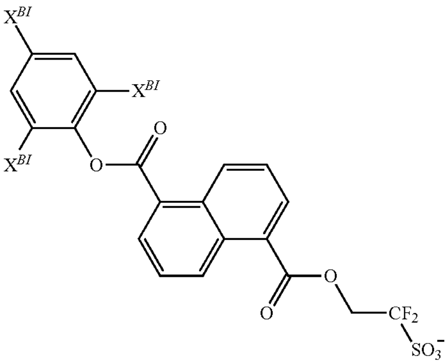

-continued
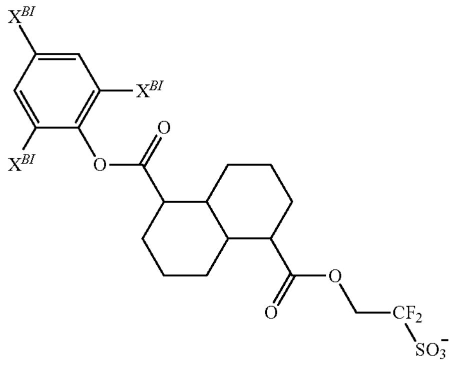
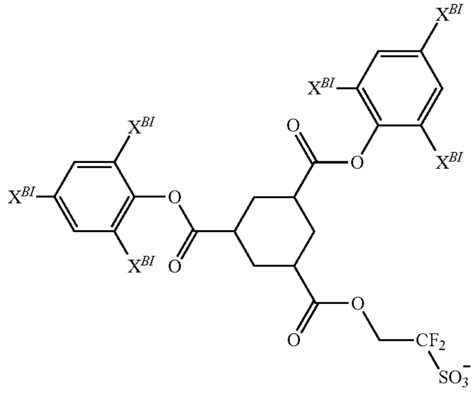
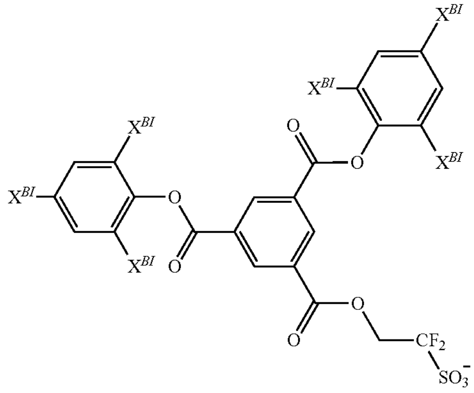
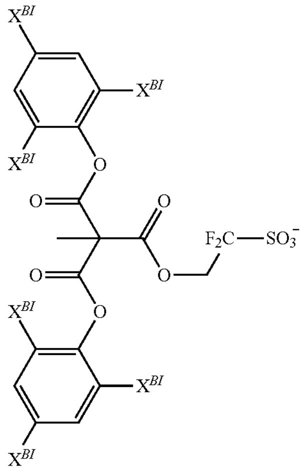
-continued
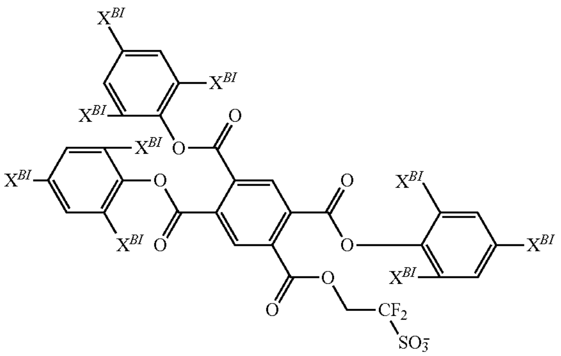
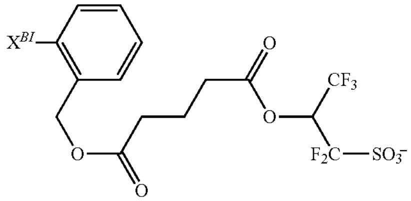
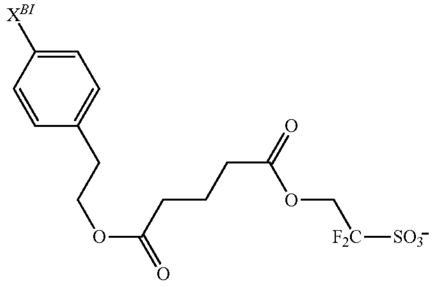
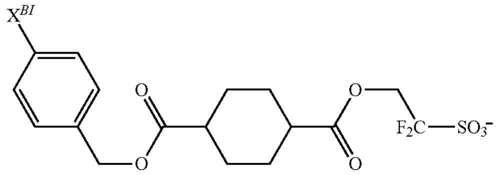
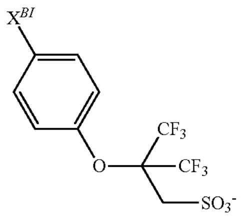
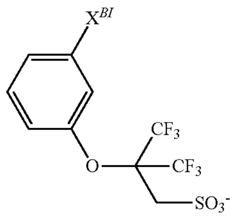
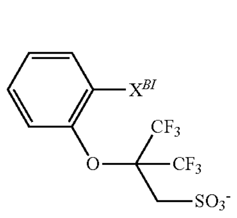
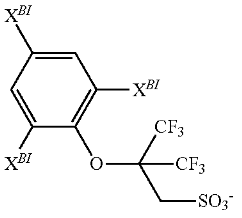

-continued
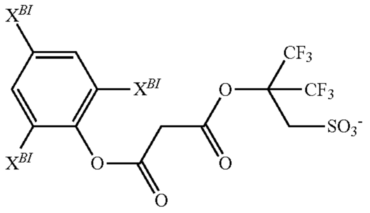
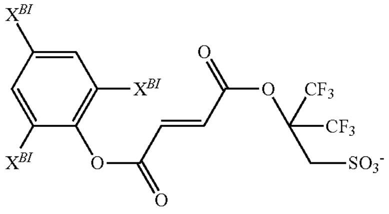
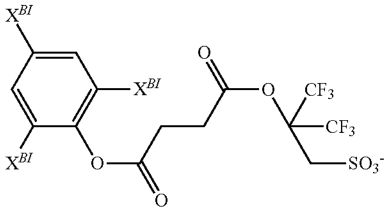
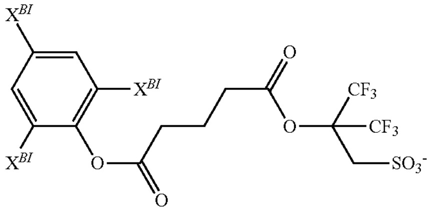
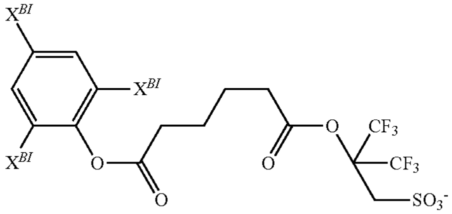
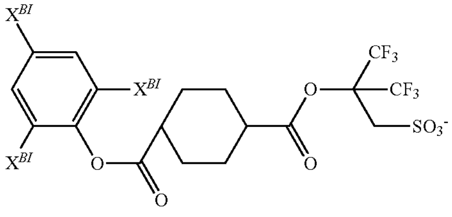
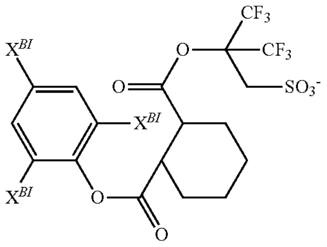
-continued
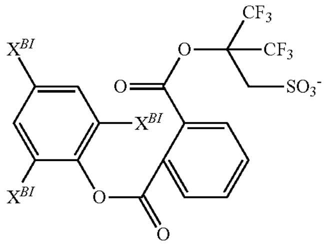
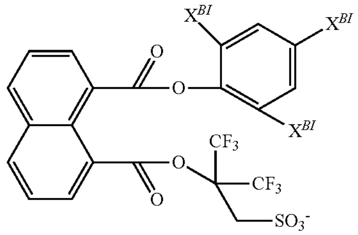
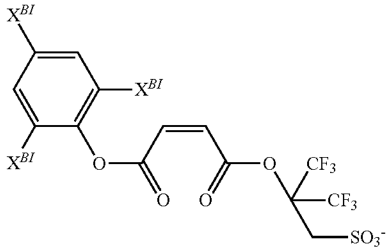
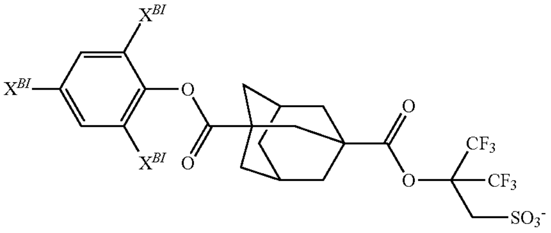
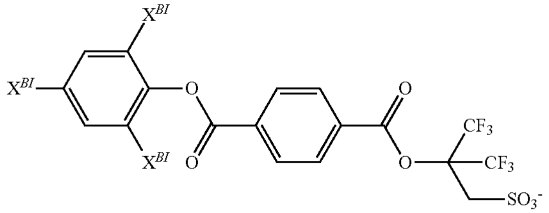
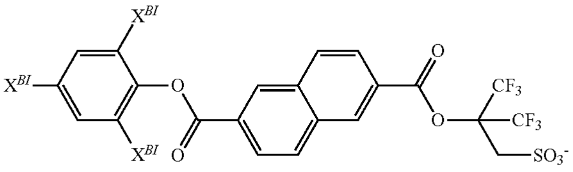
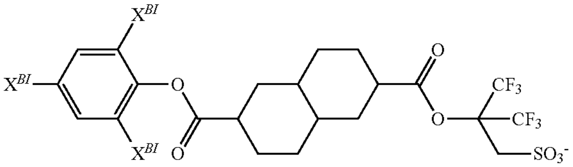

-continued

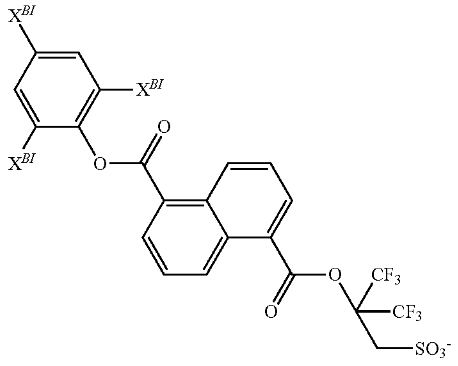

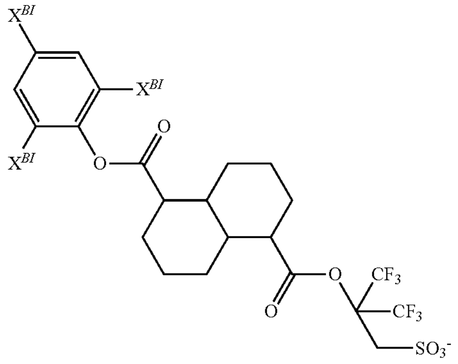

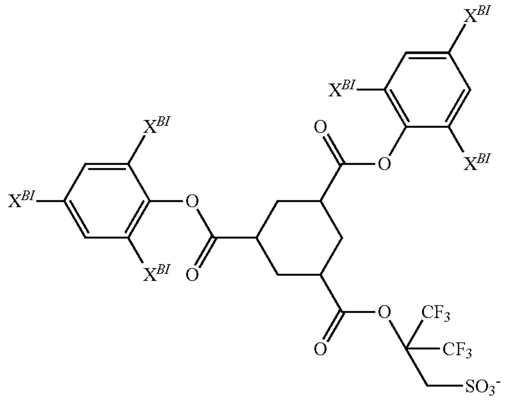

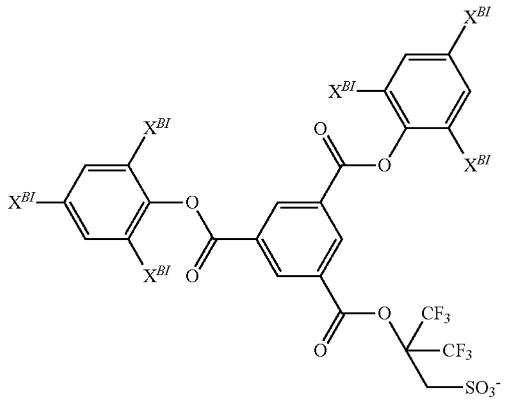

-continued

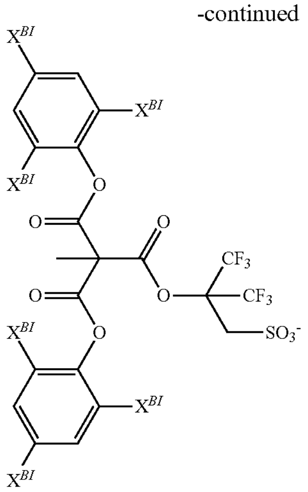

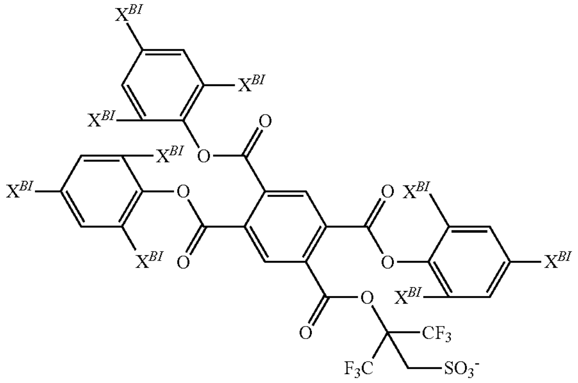

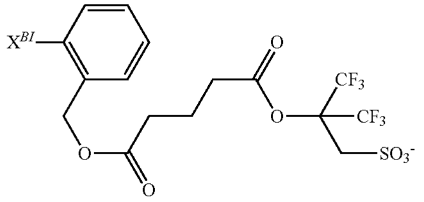

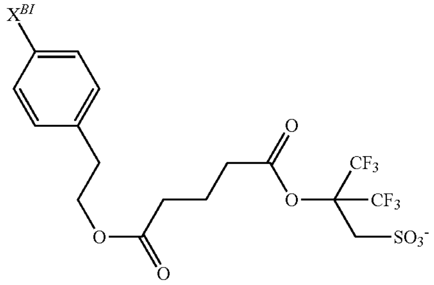

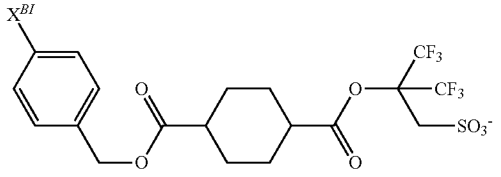

When the inventive positive resist material does not contain a base polymer, the additive-type acid generator is preferably added in an amount of 0.1 to 50 parts by mass, more preferably 1 to 40 parts by mass based on 100 parts by mass of the above-described compound. When the inventive positive resist material contains a base polymer, the additive-type acid generator is preferably contained in an amount of 0.1 to 50 parts by mass, more preferably 1 to 40 parts by mass based on a total of 100 parts by mass of the compound and the base polymer. When the base polymer contains the repeating units-c1 to -c3 and/or the inventive positive resist material contains the additive-type acid generator, the inventive positive resist material can function as a chemically amplified positive resist material.

[Organic Solvent]

The inventive positive resist material may be blended with an organic solvent. This organic solvent is not particularly limited, as long as it is capable of dissolving the above-described components and components described below. Examples of such an organic solvent include ones disclosed in paragraphs [0144] and [0145] of JP 2008-111103 A: ketones, such as cyclohexanone, cyclopentanone, methyl-2-n-pentyl ketone, and 2-heptanone; alcohols, such as 3-methoxybutanol, 3-methyl-3-methoxybutanol, 1-methoxy-2-propanol, 1-ethoxy-2-propanol, and diacetone alcohol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones, such as γ-butyrolactone; and mixed solvents thereof.

When the inventive positive resist material does not contain a base polymer, the organic solvent is preferably contained in an amount of 100 to 10,000 parts by mass, more preferably 200 to 8,000 parts by mass based on 100 parts by mass of the above-described compound. When the inventive positive resist material contains a base polymer, the organic solvent is preferably contained in an amount of 100 to 10,000 parts by mass, more preferably 200 to 8,000 parts by mass based on a total of 100 parts by mass of the compound and the base polymer.

[Quencher]

The inventive positive resist material may be blended with a quencher. Examples of the quencher include conventional basic compounds. Examples of the conventional basic compounds include primary, secondary, and tertiary aliphatic amines, mixed amines, aromatic amines, heterocyclic amines, nitrogen-containing compounds having a carboxy group, nitrogen-containing compounds having a sulfonyl group, nitrogen-containing compounds having a hydroxy group, nitrogen-containing compounds having a hydroxyphenyl group, alcoholic nitrogen-containing compounds, amides, imides, carbamates, etc. Particularly preferable are primary, secondary, and tertiary amine compounds disclosed in paragraphs [0146] to [0164] of JP 2008-111103 A; especially amine compounds having a hydroxy group, an ether bond, an ester bond, a lactone ring, a cyano group, or a sulfonic acid ester bond; compounds having a carbamate group disclosed in JP 3790649 B2; etc. Adding such a basic compound can, for example, further suppress the acid diffusion rate in the resist film and correct the shape.

Other examples of the quencher include onium salts, such as sulfonium salts, iodonium salts, and ammonium salts of carboxylic acids and sulfonic acids which are not fluorinated at α position as disclosed in JP 2008-158339 A. While α-fluorinated sulfonic acid, imide acid, or methide acid is necessary to deprotect the acid-labile group of carboxylic acid ester, a carboxylic acid or sulfonic acid not fluorinated at α position is released by salt exchange with the onium salt not fluorinated at α position. Such carboxylic acid and sulfonic acid not fluorinated at α position hardly induce deprotection reaction, and thus function as quenchers.

Examples of such quenchers include a compound shown by the following formula (5) (onium salt of sulfonic acid not fluorinated at α position) and a compound shown by the following formula (6) (onium salt of carboxylic acid).

$$R^{q1}—SO_3^- \quad Mq^+ \tag{5}$$

$$R^{q2}—CO_2^- \quad Mq^+ \tag{6}$$

In the formula (5), $R^{501}$ represents a hydrogen atom or a hydrocarbyl group having 1 to 40 carbon atoms and optionally containing a heteroatom, but excludes groups in which a hydrogen atom bonded to the carbon atom at a position of the sulfo group is substituted with a fluorine atom or a fluoroalkyl group.

The hydrocarbyl group may be saturated or unsaturated, and may be linear, branched, or cyclic. Specific examples thereof include: alkyl groups, such as a methyl group, an ethyl group, a propyl group, an isopropyl group, an n-butyl group, a sec-butyl group, a tert-butyl group, a tert-pentyl group, an n-pentyl group, an n-hexyl group, an n-octyl group, a 2-ethylhexyl group, an n-nonyl group, and an n-decyl group; cyclic saturated hydrocarbyl groups, such as a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.$0^{2,6}$]decanyl group, an adamantyl group, and an adamantylmethyl group; alkenyl groups, such as a vinyl group, an allyl group, a propenyl group, a butenyl group, and a hexenyl group; cyclic unsaturated aliphatic hydrocarbyl groups, such as a cyclohexenyl group; aryl groups, such as a phenyl group, a naphthyl group, alkylphenyl groups (such as a 2-methylphenyl group, a 3-methylphenyl group, a 4-methylphenyl group, a 4-ethylphenyl group, a 4-tert-butylphenyl group, and a 4-n-butylphenyl group), dialkylphenyl groups (such as a 2,4-dimethylphenyl group and a 2,4,6-triisopropylphenyl group), alkylnaphthyl groups (such as a methylnaphthyl group and an ethylnaphthyl group), and dialkylnaphthyl groups (such as a dimethylnaphthyl group and a diethylnaphthyl group); heteroaryl groups, such as a thienyl group; aralkyl groups, such as a benzyl group, a 1-phenylethyl group, and a 2-phenylethyl group; etc.

Moreover, these groups may have some of hydrogen atoms substituted with a group containing a heteroatom, such as an oxygen atom, a sulfur atom, a nitrogen atom, or a halogen atom, while these groups may have some of carbon atoms substituted with a group containing a heteroatom, such as an oxygen atom, a sulfur atom, or a nitrogen atom. Thus, the resulting hydrocarbyl group may contain a hydroxy group, a cyano group, a carbonyl group, an ether bond, an ester bond, a sulfonic acid ester group, a carbonate bond, a lactone ring, a sultone ring, carboxylic anhydride, a haloalkyl group, etc. Examples of the hydrocarbyl group containing a heteroatom include: alkoxyphenyl groups, such as a 4-hydroxyphenyl group, a 4-methoxyphenyl group, a 3-methoxyphenyl group, a 2-methoxyphenyl group, a 4-ethoxyphenyl group, a 4-tert-butoxyphenyl group, and a 3-tert-butoxyphenyl group; alkoxynaphthyl groups, such as a methoxynaphthyl group, an ethoxynaphthyl group, an n-propoxynaphthyl group, and an n-butoxynaphthyl group;

dialkoxynaphthyl groups, such as a dimethoxynaphthyl group and a diethoxynaphthyl group; aryloxoalkyl groups, such as 2-aryl-2-oxoethyl groups including a 2-phenyl-2-oxoethyl group, a 2-(1-naphthyl)-2-oxoethyl group, and a 2-(2-naphthyl)-2-oxoethyl group; etc.

In the formula (6), $R^{502}$ represents a hydrocarbyl group having 1 to 40 carbon atoms and optionally containing a heteroatom. Examples of the hydrocarbyl group represented by $R^{502}$ include those exemplified as the hydrocarbyl group represented by $R^{501}$. Other specific examples thereof include fluorine-containing alkyl groups, such as a trifluoromethyl group, a trifluoroethyl group, a 2,2,2-trifluoro-1-methyl-1-hydroxyethyl group, and a 2,2,2-trifluoro-1-(trifluoromethyl)-1-hydroxyethyl group; fluorine-containing aryl groups, such as a pentafluorophenyl group and a 4-trifluoromethylphenyl group; etc.

A sulfonium salt of a carboxylic acid containing an iodized benzene ring shown by the following formula (7) can also be used suitably as the quencher.

(7)

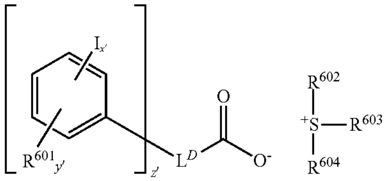

In the formula (7), $R^{601}$ represents a hydroxy group, a fluorine atom, a chlorine atom, a bromine atom, an amino group, a nitro group, a cyano group, $—NR^{601A}—C(═O)—R^{601B}$, or $—NR^{601A}—C(═O)—O—R^{601B}$; or a saturated hydrocarbyl group having 1 to 6 carbon atom, a saturated hydrocarbyloxy group having 1 to 6 carbon atoms, a saturated hydrocarbylcarbonyloxy group having 2 to 6 carbon atoms, or a saturated hydrocarbylsulfonyloxy group having 1 to 4 carbon atoms, the groups optionally having part or all of hydrogen atoms substituted with a halogen atom. $R^{601A}$ represents a hydrogen atom or a saturated hydrocarbyl group having 1 to 6 carbon atoms. $R^{601B}$ represents a saturated hydrocarbyl group having 1 to 6 carbon atoms or an unsaturated aliphatic hydrocarbyl group having 2 to 8 carbon atoms.

In the formula (7), "x'" represents an integer of 1 to 5. "y'" represents an integer of 0 to 3. x'+y' is an integer of 1 to 5. "z'" represents an integer of 1 to 3. $L^D$ represents a single bond or a linking group having a valency of z'+1 and having 1 to 20 carbon atoms, and optionally contains at least one selected from an ether bond, a carbonyl group, an ester bond, an amide bond, a sultone ring, a lactam ring, a carbonate group, a halogen atom, a hydroxy group, and a carboxy group. The saturated hydrocarbyl group, saturated hydrocarbyloxy group, saturated hydrocarbylcarbonyloxy group, and saturated hydrocarbylsulfonyloxy group may be linear, branched, or cyclic. When "y'" is 2 or more, the $R^{601}$'s may be identical to or different from one another.

In the formula (7), $R^{602}$, $R^{603}$, and $R^{604}$ each independently represent a hydrocarbyl group having 1 to 20 carbon atoms and optionally containing a fluorine atom, a chlorine atom, a bromine atom, an iodine atom, or a heteroatom. The hydrocarbyl group may be saturated or unsaturated, and may be linear, branched, or cyclic. Specific examples thereof include alkyl groups having 1 to 20 carbon atoms, alkenyl groups having 2 to 20 carbon atoms, aryl groups having 6 to 20 carbon atoms, aralkyl groups having 7 to 20 carbon atoms, etc. These groups may have part or all of hydrogen atoms substituted with a group containing a hydroxy group, a carboxy group, a halogen atom, an oxo group, a cyano group, a nitro group, a sultone group, a sulfone group, or a sulfonium salt, while these groups may have part of carbon atoms substituted with an ether bond, an ester bond, a carbonyl group, an amide bond, a carbonate group, or a sulfonic acid ester bond. $R^{602}$ and $R^{603}$ may also be bonded with each other to form a ring together with a sulfur atom bonded thereto.

Specific examples of the compound represented by the formula (7) include those disclosed in JP 2017-219836 A. Iodine greatly absorbs EUV having a wavelength of 13.5 nm, so that secondary electrons are generated during exposure. Thus, by the energy of the secondary electrons being transferred to the acid generator, decomposition of the quencher is promoted. In this manner, sensitivity can be enhanced.

When the inventive positive resist material does not contain a base polymer, the quencher is preferably contained in an amount of 0.01 to 100 parts by mass, more preferably 0.01 to 50 parts by mass based on 100 parts by mass of the above-described compound. When the inventive positive resist material contains a base polymer, the quencher is preferably contained in an amount of 0.01 to 100 parts by mass, more preferably 0.01 to 50 parts by mass based on a total of 100 parts by mass of the compound and the base polymer.

[Other Components]

In addition to the above-described components, a surfactant, a dissolution inhibitor, and so forth can be blended in appropriate combination depending on the purpose to formulate a positive resist material. Thereby, in an exposed area of the base polymer, the dissolution rate to a developer is accelerated by the catalytic reaction, so that the positive resist material successfully has very high sensitivity. In this case, the resist film has high dissolution contrast and resolution, exposure latitude, excellent process adaptability, and favorable pattern profile after exposure. Particularly, the positive resist material is capable of suppressing acid diffusion, resulting in a small difference in profile between isolated and nested. Because of these advantages, the inventive positive resist material is highly practical and very effective resist material for VLSI.

Examples of the surfactant include ones disclosed in paragraphs [0165] and [0166] of JP 2008-111103 A. Adding a surfactant can further enhance or control the coatability of the resist material. When the inventive positive resist material does not contain a base polymer, the surfactant is preferably contained in an amount of 0.0001 to 10 parts by mass based on 100 parts by mass of the above-described compound. When the inventive positive resist material contains a base polymer, the surfactant is preferably contained in an amount of 0.0001 to 10 parts by mass based on a total of 100 parts by mass of the compound and the base polymer. One kind of the surfactant may be used, or two or more kinds thereof may be used in combination.

Blending a dissolution inhibitor can further increase the difference in dissolution rate between exposed and unexposed areas, and further enhance the resolution. Examples of the dissolution inhibitor include a compound which contains two or more phenolic hydroxy groups per molecule, and in which 0 to 100 mol % of all the hydrogen atoms of the phenolic hydroxy groups are substituted with acid-labile groups; and a compound which contains a carboxy group in a molecule, and in which 50 to 100 mol % of all the hydrogen atoms of such carboxy groups are substituted with acid-labile groups on average. The compounds each have a molecular weight of preferably 100 to 1,000, more preferably 150 to 800. Specific examples include compounds obtained by substituting acid-labile groups for hydrogen atoms of hydroxy groups or carboxy groups of bisphenol A, trisphenol, phenolphthalein, cresol novolak, naphthalenecarboxylic acid, adamantanecarboxylic acid, or cholic acid; etc. Examples of such compounds are disclosed in paragraphs [0155] to [0178] of JP 2008-122932 A. When the inventive positive resist material does not contain a base polymer, the dissolution inhibitor is preferably contained in an amount of 0 to 50 parts by mass, more preferably 5 to 40 parts by mass based on 100 parts by mass of the above-described compound. When the inventive positive resist material contains a base polymer, the dissolution inhibitor is preferably contained in an amount of 0 to 50 parts by mass, more preferably 5 to 40 parts by mass based on a total of 100 parts by mass of the compound and the base polymer. One kind of the dissolution inhibitor can be used, or two or more kinds thereof can be used in combination.

The inventive positive resist material may be blended with a water-repellency enhancer for enhancing the water repellency on the resist surface after spin-coating. The water-repellency enhancer can be employed in immersion lithography with no top coat. The water-repellency enhancer is preferably a polymer compound containing a fluorinated alkyl group, a polymer compound containing a 1,1,1,3,3,3-hexafluoro-2-propanol residue with a particular structure, etc., more preferably ones exemplified in JP 2007-297590 A, JP 2008-111103 A, etc. The water-repellency enhancer needs to be dissolved in an alkali developer or an organic solvent developer. The water-repellency enhancer having a particular 1,1,1,3,3,3-hexafluoro-2-propanol residue mentioned above has favorable solubility to developers. A polymer compound containing a repeating unit with an amino group or amine salt as a water-repellency enhancer exhibits high effects of preventing acid evaporation during post-exposure baking (PEB) and opening failure of a hole pattern after development. When the inventive positive resist material does not contain a base polymer, the water-repellency enhancer is preferably contained in an amount of 0 to 20 parts by mass, more preferably 0.5 to 10 parts by mass based on 100 parts by mass of the above-described compound. When the inventive positive resist material contains a base polymer, the water-repellency enhancer is preferably contained in an amount of 0 to 20 parts by mass, more preferably 0.5 to 10 parts by mass based on a total of 100 parts by mass of the compound and the base polymer. One kind of the water-repellency enhancer can be used, or two or more kinds thereof can be used in combination.

The inventive positive resist material may be blended with an acetylene alcohol. Examples of the acetylene alcohol include ones disclosed in paragraphs [0179] to [0182] of JP 2008-122932 A. When the inventive positive resist material does not contain a base polymer, the acetylene alcohol is preferably contained in an amount of 0 to 5 parts by mass based on 100 parts by mass of the above-described compound. When the inventive positive resist material contains a base polymer, the acetylene alcohol is preferably contained in an amount of 0 to 5 parts by mass based on a total of 100 parts by mass of the compound and the base polymer.

[Patterning Process]

When the inventive positive resist material is used for manufacturing various integrated circuits, known lithography techniques are applicable. An exemplary patterning process includes the steps of:

forming a resist film on a substrate by using the above-described resist material;

exposing the resist film to a high-energy beam; and developing the exposed resist film by using a developer.

First, the inventive positive resist material is applied onto a substrate (such as Si, $SiO_2$, SiN, SiON, TiN, WSi, BPSG, SOG, or organic antireflective film) for manufacturing an integrated circuit or a substrate (such as Cr, CrO, CrON, $MoSi_2$, or $SiO_2$) for manufacturing a mask circuit by an appropriate coating process such as spin coating, roll coating, flow coating, dip coating, spray coating, or doctor coating so that the coating film has a thickness of 0.01 to 2 μm. The resultant is prebaked on a hot plate preferably at 60 to 150° C. for 10 seconds to 30 minutes, more preferably at 80 to 120° C. for 30 seconds to 20 minutes. In this manner, a resist film is formed.

Then, the resist film is exposed using a high-energy beam. Examples of the high-energy beam include ultraviolet ray, deep ultraviolet ray, electron beam (EB), EUV, X-ray, soft X-ray, excimer laser beam, γ-ray, synchrotron radiation, extreme ultraviolet ray having a wavelength of 3 to 15 nm, etc. When ultraviolet ray, deep ultraviolet ray, EUV, X-ray, soft X-ray, excimer laser beam, γ-ray, synchrotron radiation, or the like is employed as the high-energy beam, the irradiation is performed using a mask for forming a target pattern at an exposure dose of preferably about 1 to 200 $mJ/cm^2$, more preferably about 10 to 100 $mJ/cm^2$. When EB is employed as the high-energy beam, the exposure dose is preferably about 0.1 to 100 $\mu C/cm^2$, more preferably about 0.5 to 50 $\mu C/cm^2$, and the writing is performed directly or using a mask for forming a target pattern. Note that the inventive positive resist material is particularly suitable for fine patterning with an i-line beam having a wavelength of 365 nm, a KrF excimer laser beam, an ArF excimer laser beam, an electron beam (EB), EUV, X-ray, soft X-ray, γ-ray, synchrotron radiation, or an extreme ultraviolet ray having a wavelength of 3 to 15 nm among the high-energy beams, and is especially suitable for fine patterning with EB or EUV.

The exposure may be followed by PEB on a hot plate or in an oven preferably at 50 to 150° C. for 10 seconds to 30 minutes, more preferably at 60 to 120° C. for 30 seconds to 20 minutes. The deprotection reaction of acid-labile groups also progresses by exposure alone in a high-energy radiation such as EB or EUV. Deprotection reaction during exposure is promoted when a high-absorption element, such as iodine, is contained in the compound. In such a case, a pattern can be formed without performing PEB without adding an acid generator.

After the exposure or PEB, development is performed using a developer of 0.1 to 10 mass %, preferably 2 to 5 mass %, aqueous alkaline solution, such as tetramethylammonium hydroxide (TMAH), tetraethylammonium hydroxide (TEAH), tetrapropylammonium hydroxide (TPAH), or tetrabutylammonium hydroxide (TBAH), for 3 seconds to 3 minutes, preferably 5 seconds to 2 minutes, by a conventional technique, such as a dip, puddle, or spray method. Thereby, the portion irradiated with the light is dissolved by the developer, while the unexposed portion remains undissolved. In this way, the target positive pattern is formed on the substrate.

After the development, a hole pattern or trench pattern can be shrunk by thermal flow, RELACS process, or DSA process. A shrink agent is applied onto the hole pattern, and the shrink agent undergoes crosslinking on the resist surface by diffusion of the acid catalyst from the resist layer during baking, so that the shrink agent is attached to sidewalls of the hole pattern. The baking temperature is preferably 70 to 180° C., more preferably 80 to 170° C. The baking time is preferably 10 to 300 seconds. The extra shrink agent is removed, and thus the hole pattern is shrunk.

EXAMPLE

Hereinafter, the present invention will be specifically described with reference to Synthesis Examples, Examples, and Comparative Examples. However, the present invention is not limited to the following Examples.

[1] Synthesis of Compound Having Two or More Urethane Groups and Having Two or More Carboxy Groups that are Each Substituted with Acid-Labile Group and are Bonded to Urethane Groups Via Linking Group.

In a PGMEA solution, an isocyanate compound was allowed to react with a compound having both a hydroxy group and a carboxy group substituted with an acid-labile group in the presence of 1 mass % of a bismuth salt XK-640 available from Kusumoto Chemicals, Ltd. The bismuth salt was removed by liquid-liquid separation and washing with pure water. Thus, urethane compounds 1 to 29 were synthesized.

Urethane compound 1

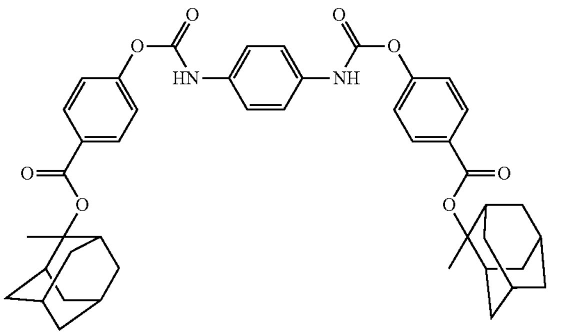

Urethane compound 2

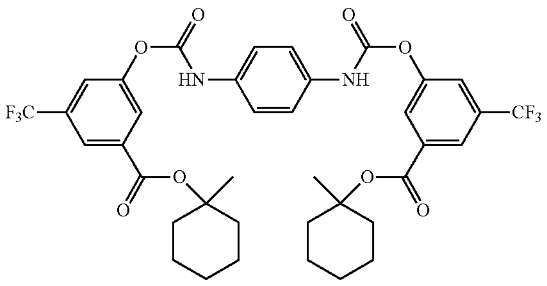

Urethane compound 3

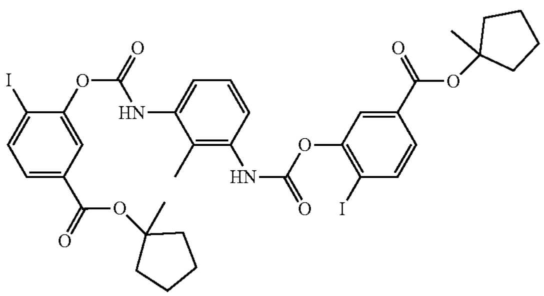

Urethane compound 4

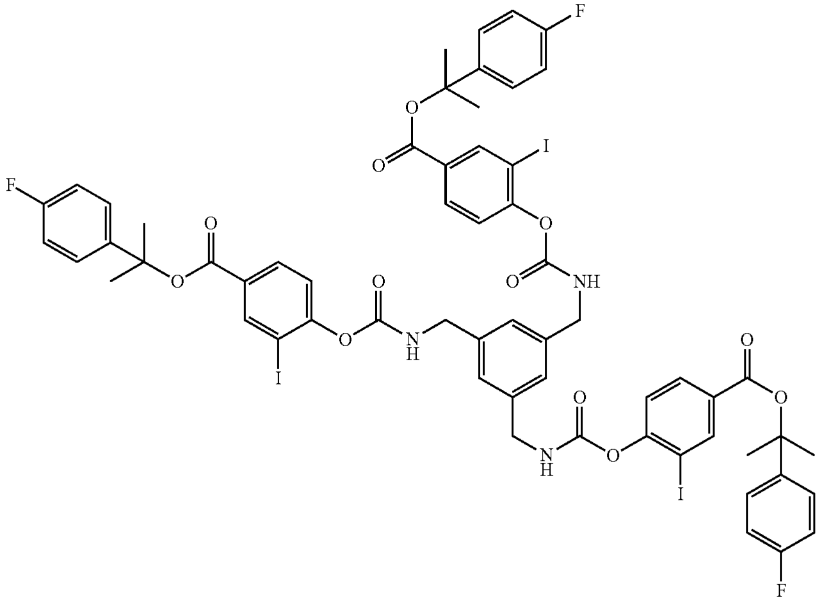

-continued
Urethane compound 5
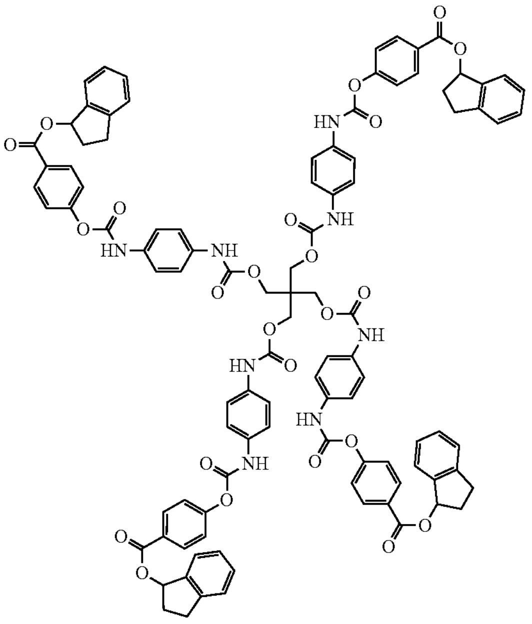
Urethane compound 6
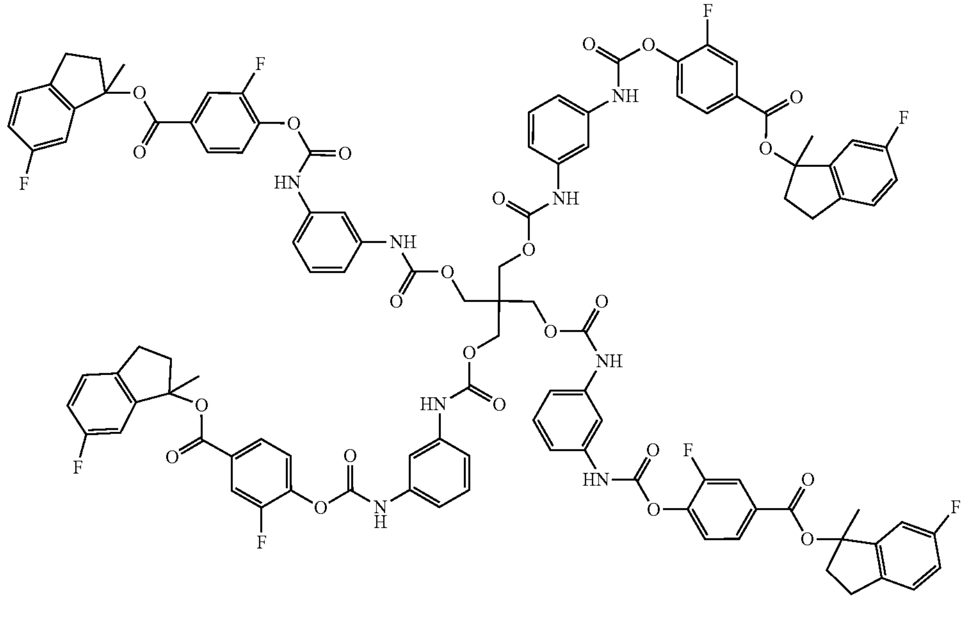

-continued
Urethane compound 7
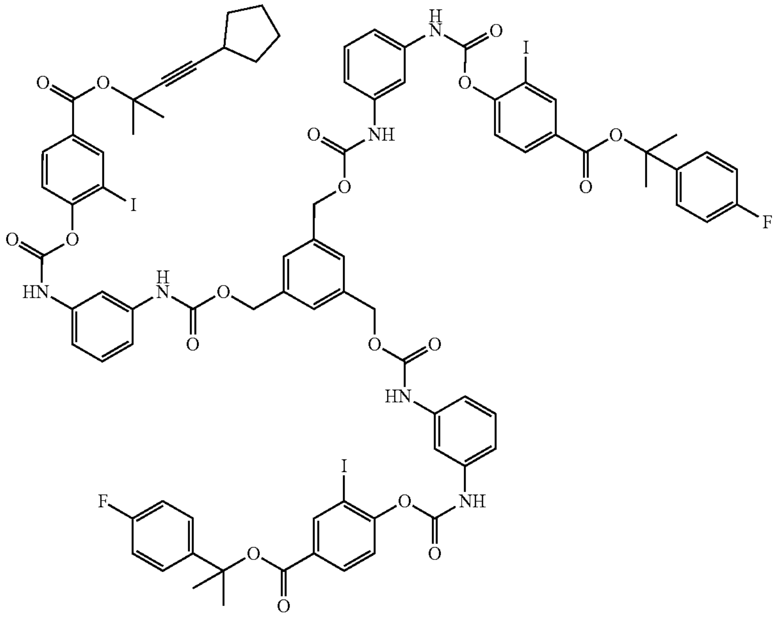
Urethane compound 8
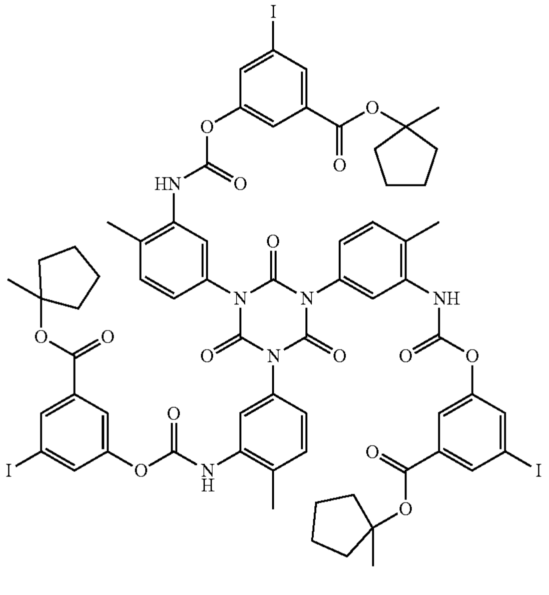
Urethane compound 9
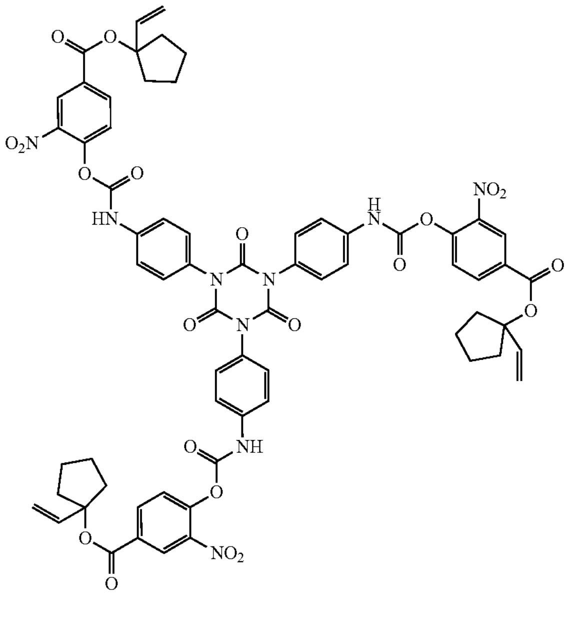

-continued
Urethane compound 10
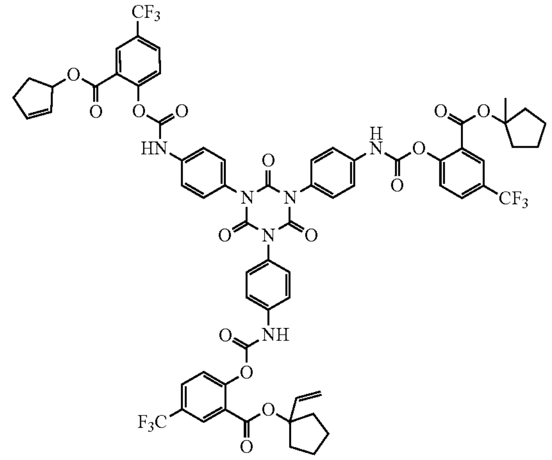
Urethane compound 11
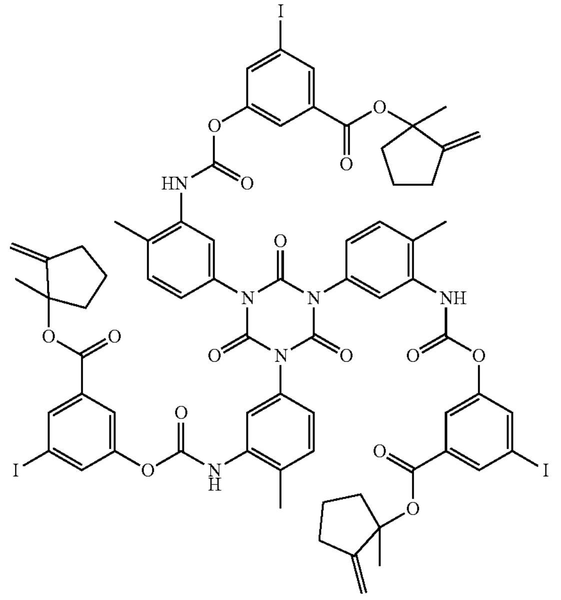
Urethane compound 12
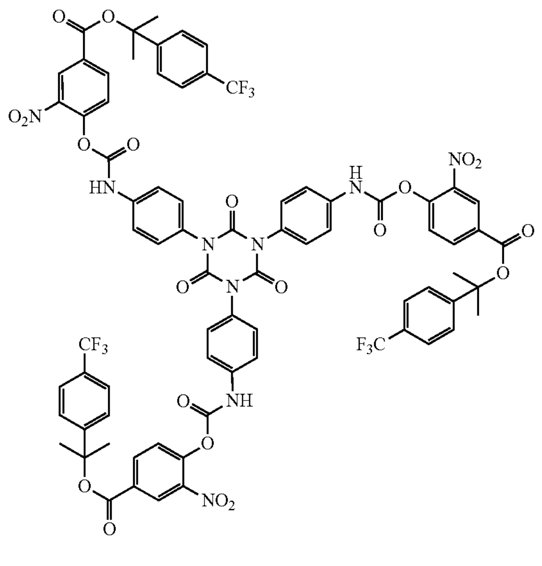

-continued
Urethane compound 13
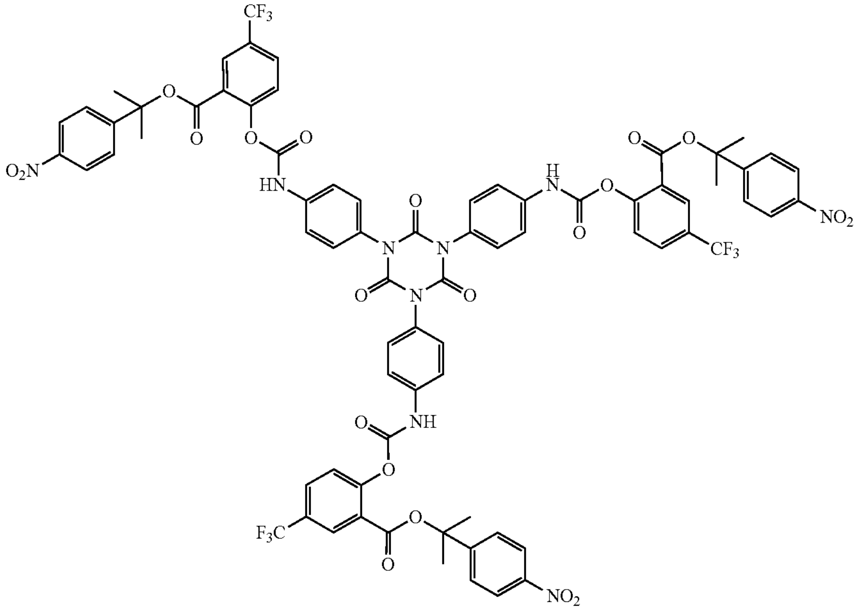
Urethane compound 14
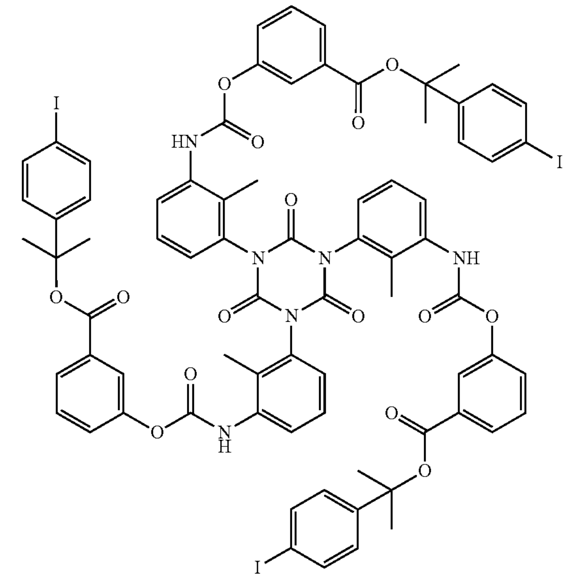
Urethane compound 15
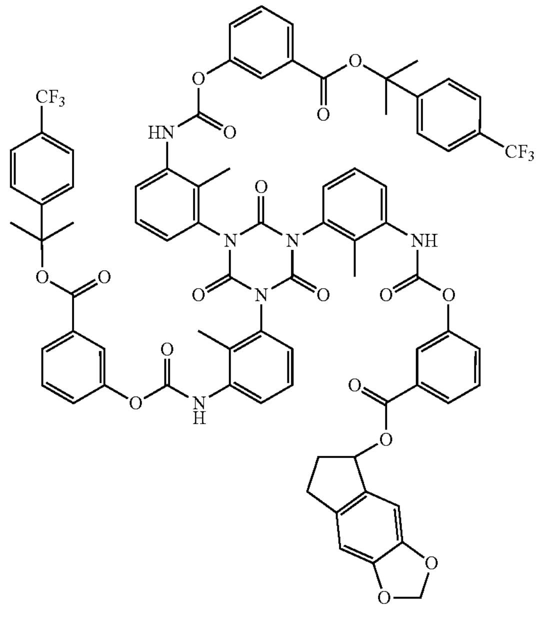

-continued
Urethane compound 16
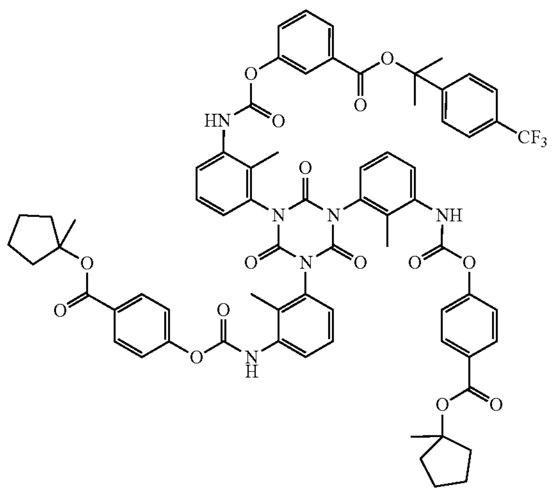
Urethane compound 17
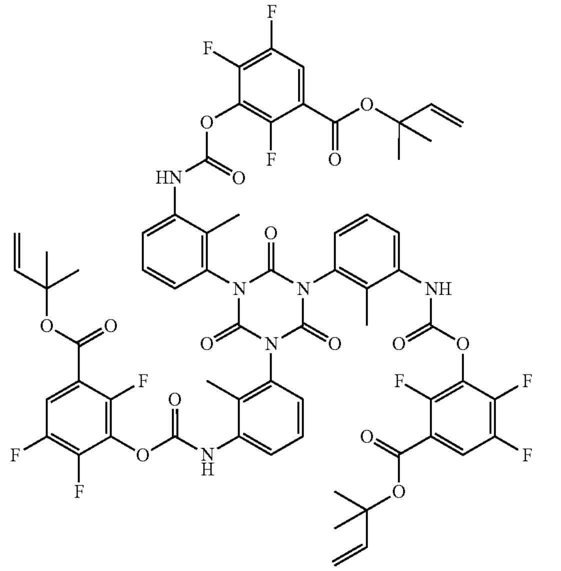
Urethane compound 18
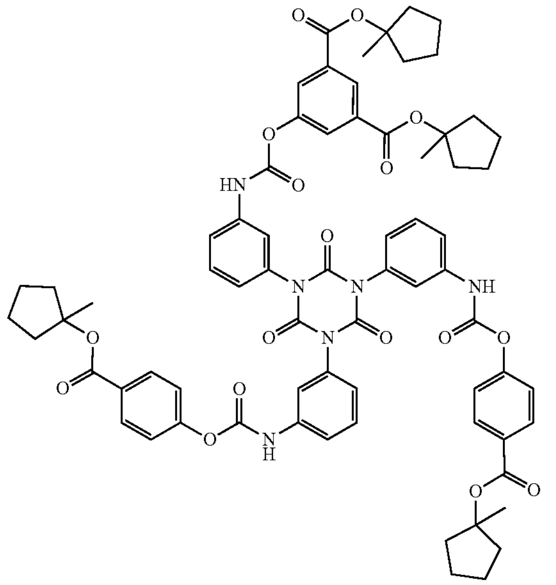
Urethane compound 19
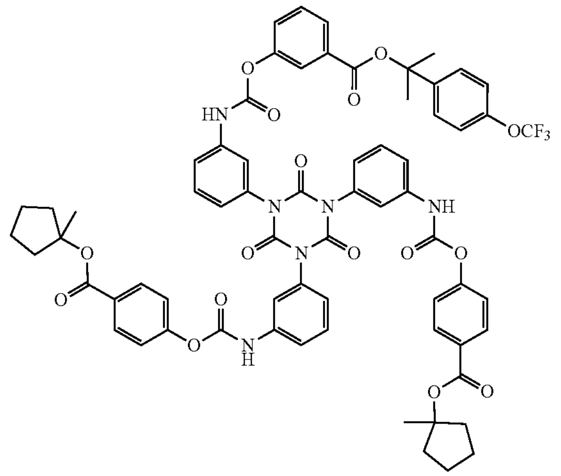

-continued
Urethane compound 20
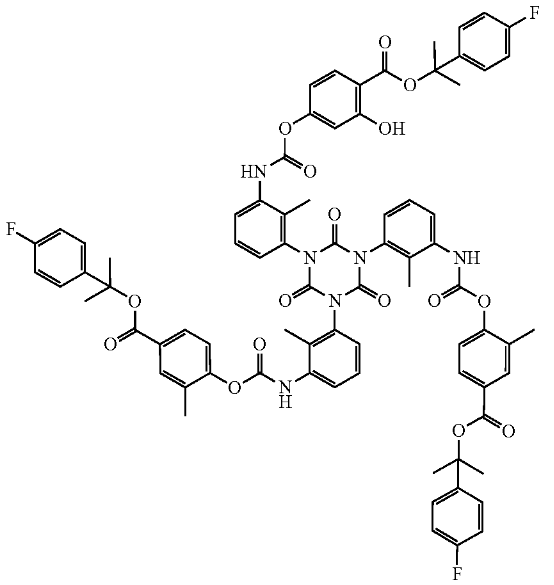
Urethane compound 21
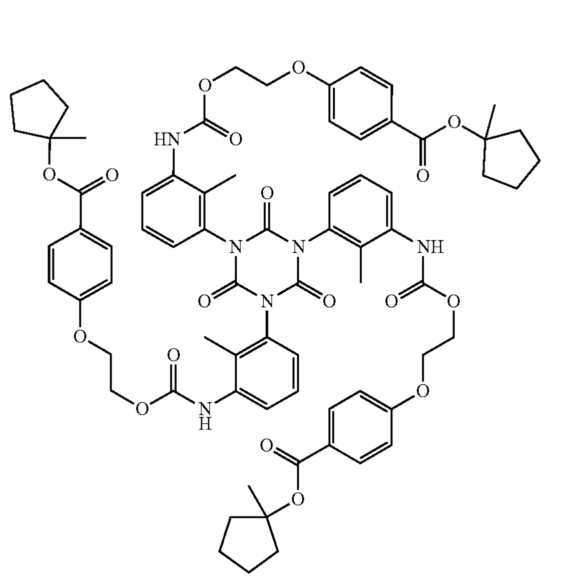
Urethane compound 22
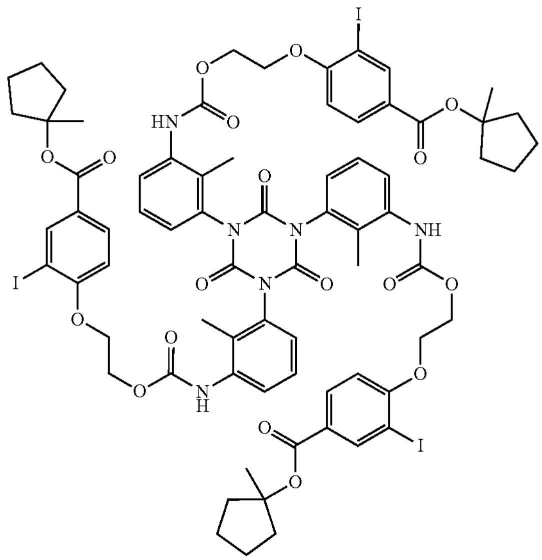
Urethane compound 23
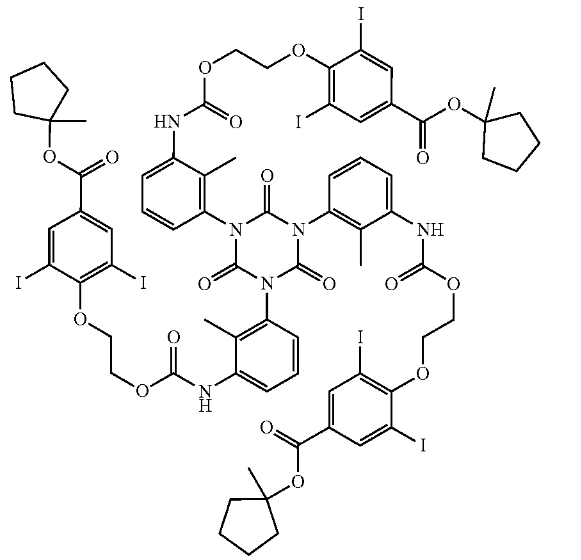

-continued
Urethane compound 24
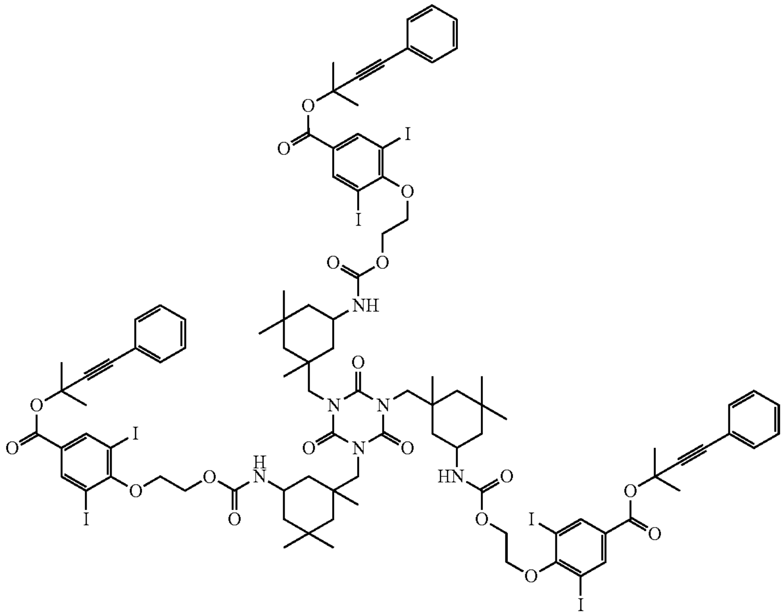
Urethane compound 25
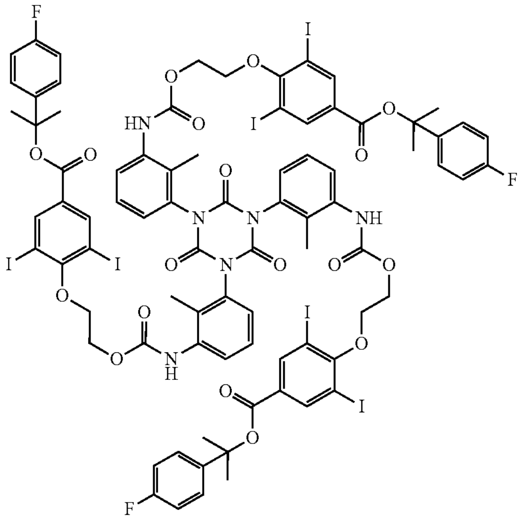
Urethane compound 26
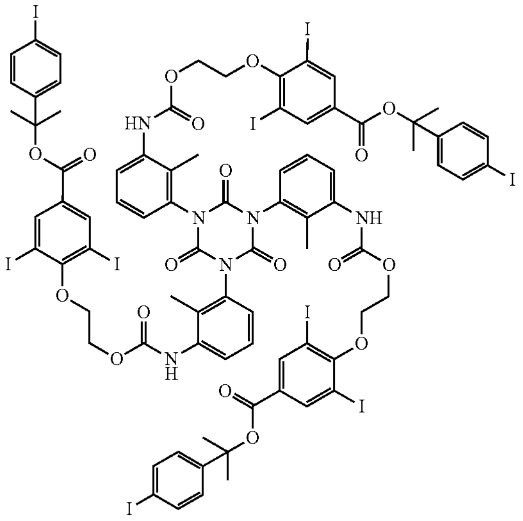
Urethane compound 27
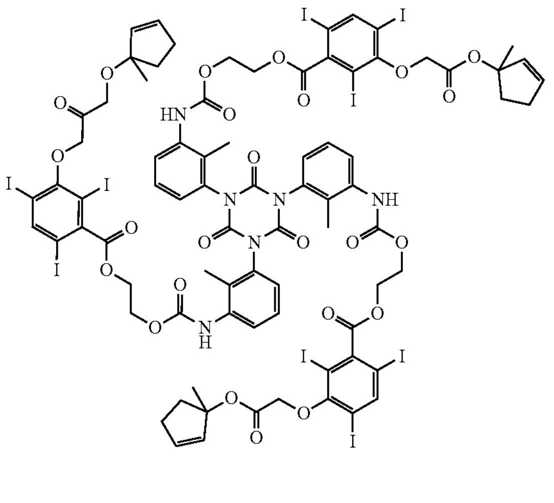
Urethane compound 28
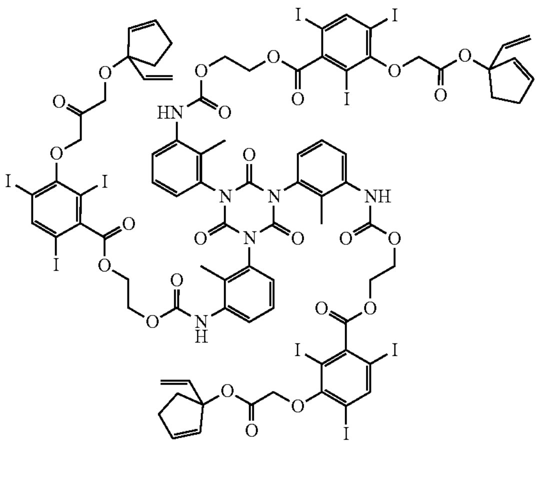

-continued

Urethane compound 29

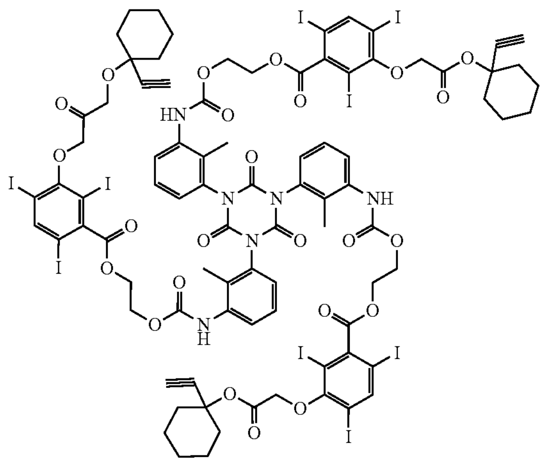

[2] Synthesis of Base Polymer

[Synthesis Examples 2-1 to 2-3] Syntheses of Polymers 1 to 3

A combination of monomers was subjected to a copolymerization reaction in THF. A crystal was precipitated in methanol. The crystal was then washed repeatedly with hexane, and then isolated and dried to obtain a base polymer (polymers 1 to 3) having the composition shown below. The composition of the obtained base polymer was identified by $^1$H-NMR, and the Mw and Mw/Mn of the base polymer was determined by GPC (eluent: THF, standard: polystyrene).

Polymer 1

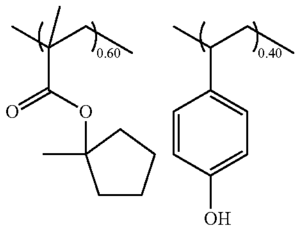

Mw = 8,600
Mw/Mn = 1.73

Polymer 2

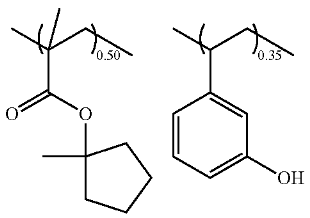

-continued

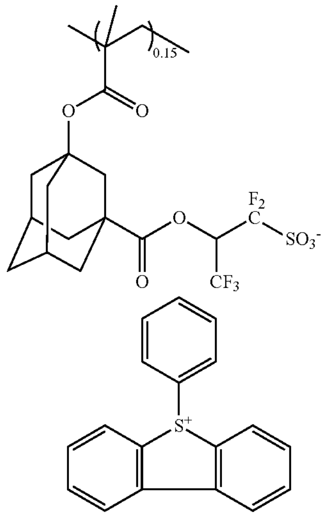

Mw = 9,900
Mw/Mn = 1.99

Polymer 3

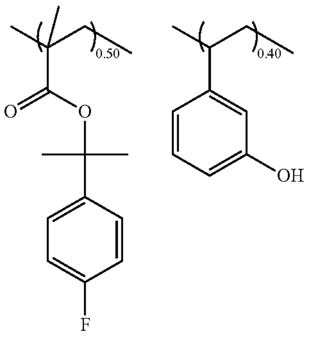

-continued

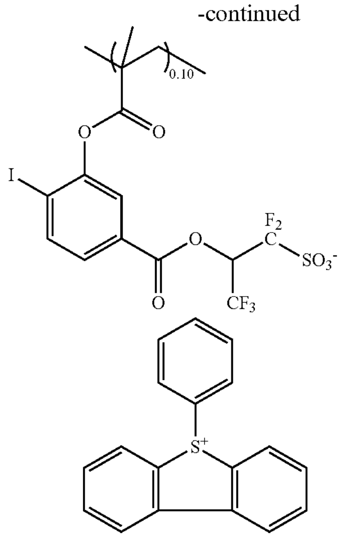

Mw = 9,800
Mw/Mn = 1.82

[3] Preparation and Evaluation of Positive Resist Materials

Examples 1 to 27 and Comparative Example 1

(1) Preparation of Positive Resist Materials

According to the composition shown in Tables 1 and 2, components were dissolved in a solvent in which 30 ppm of a surfactant PolyFox PF-636, manufactured by OMNOVA Solutions Inc., had been dissolved. The resulting solution was filtered through a filter having a pore size of 0.2 μm. In this manner, positive resist materials were prepared.

The components in Tables 1 and 2 are as follows.

Organic solvents:

PGMEA (propylene glycol monomethyl ether acetate)

DAA (diacetone alcohol)

EL (ethyl lactate)

Acid generators: PAG-1 to -3

PAG-1

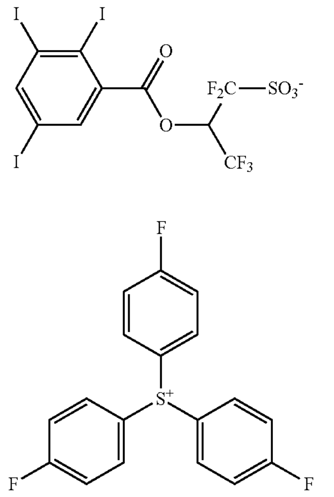

-continued

PAG-2

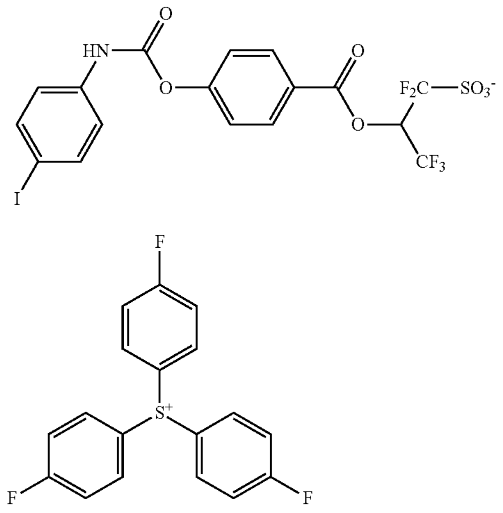

PAG-3

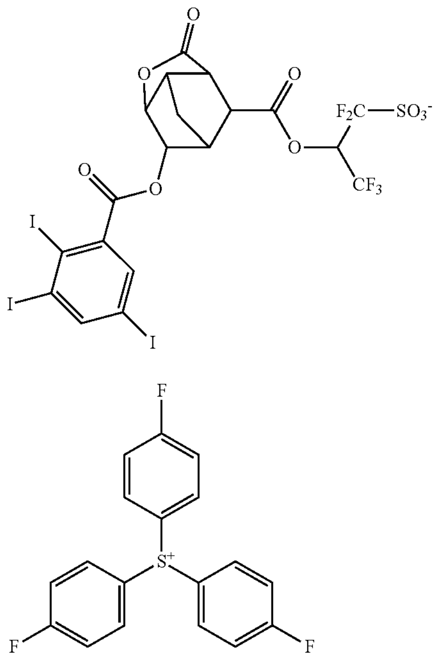

Quenchers: Q-1 and -2

Q-1

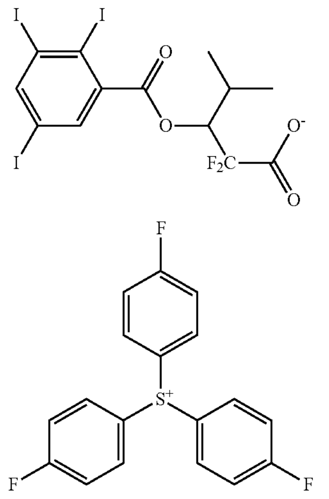

Q-2

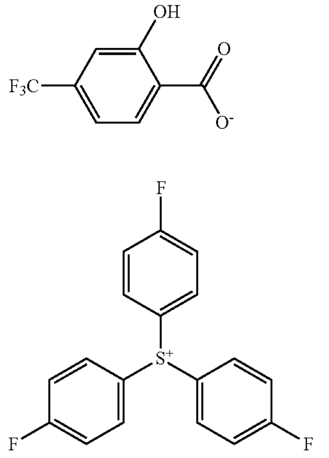

(2) EUV Exposure Evaluation

A Si substrate with a silicon-containing spin-on hard mask SHB-A940 (manufactured by Shin-Etsu Chemical CO., Ltd., silicon content: 43 mass %) formed to have a film thickness of 20 nm was spin-coated with one of the resist materials shown in Tables 1 and 2. The resultant was prebaked using a hot plate at 100° C. for 60 seconds to prepare a resist film having a film thickness of 50 nm. The resist film was exposed using an EUV scanner NXE3400 (manufactured by ASML, NA: 0.33, σ: 0.9/0.6, quadrupole illumination, with a mask having a hole pattern with a pitch of 46 nm and +20% bias (on-wafer size)), followed by PEB on the hot plate at a temperature shown in Tables 1 and 2 for 60 seconds, and development with a 2.38 mass % aqueous TMAH solution for 30 seconds to obtain a hole pattern with a size of 23 nm.

An exposure dose at which the hole size of 23 nm was formed was measured and determined as sensitivity. Moreover, the dimensions of 50 holes were measured using a CD-SEM (CG6300) manufactured by Hitachi High-Technologies Corporation. Thus, CDU (size variation 3σ) was determined.

The results are shown together in Tables 1 and 2.

TABLE 1

| | Compound (parts by mass) | Polymer (parts by mass) | Acid generator (parts by mass) | Quencher (parts by mass) | Organic solvent (parts by mass) | PEB temperature (° C.) | Sensitivity ($mJ/cm^2$) | CDU (nm) |
|---|---|---|---|---|---|---|---|---|
| Example 1 | Urethane compound 1 (40) | Polymer 1 (60) | PAG-1 (25.7) | Q-1 (9.70) | PGMEA (2,500) | 80 | 29 | 2.8 |
| Example 2 | Urethane compound 2 (40) | Polymer 1 (60) | PAG-1 (25.7) | Q-1 (9.70) | PGMEA (2,500) | 80 | 29 | 2.8 |
| Example 3 | Urethane compound 3 (40) | Polymer 2 (60) | — | Q-1 (9.70) | PGMEA (2,000) DAA (500) | 80 | 29 | 2.7 |
| Example 4 | Urethane compound 4 (40) | Polymer 3 (60) | — | Q-2 (5.22) | PGMEA (2,000) DAA (500) | 85 | 28 | 2.7 |
| Example 5 | Urethane compound 5 (50) Urethane compound 7 (50) | — | PAG- 2 (22.8) | Q-2 (5.22) | PGMEA (2,500) | 85 | 27 | 2.4 |
| Example 6 | Urethane compound 6 (40) Urethane compound 8 (60) | — | PAG- 2 (22.8) | Q-2 (5.22) | PGMEA (2,500) | 80 | 28 | 2.4 |
| Example 7 | Urethane compound 9 (100) | — | PAG-2 (22.8) | Q-2 (5.22) | PGMEA (2,000) EL (500) | 80 | 28 | 2.5 |
| Example 8 | Urethane compound 10 (100) | — | PAG-2 (22.8) | Q-2 (5.22) | PGMEA (2,000) EL (500) | 90 | 27 | 2.6 |
| Example 9 | Urethane compound 11 (100) | — | PAG-2 (22.8) | Q-2 (5.22) | PGMEA (2,000) EL (500) | 80 | 25 | 2.7 |

TABLE 1-continued

| | Compound (parts by mass) | Polymer (parts by mass) | Acid generator (parts by mass) | Quencher (parts by mass) | Organic solvent (parts by mass) | PEB temperature (° C.) | Sensitivity (mJ/cm$^2$) | CDU (nm) |
|---|---|---|---|---|---|---|---|---|
| Example 10 | Urethane compound 12 (100) | — | PAG-2 (22.8) | Q-2 (5.22) | PGMEA (2,000) EL (500) | 80 | 25 | 2.4 |
| Example 11 | Urethane compound 13 (100) | — | PAG-2 (22.8) | Q-2 (5.22) | PGMEA (2,000) EL (500) | 80 | 28 | 2.5 |
| Example 12 | Urethane compound 14 (100) | — | PAG-2 (22.8) | Q-2 (5.22) | PGMEA (2,000) EL (500) | 80 | 28 | 2.6 |
| Example 13 | Urethane compound 15 (100) | — | PAG-2 (22.8) | Q-2 (5.22) | PGMEA (2,000) EL (500) | 80 | 26 | 2.7 |
| Example 14 | Urethane compound 16 (100) | — | PAG-3 (30.2) | Q-2 (5.22) | PGMEA (2,000) EL (500) | 80 | 24 | 2.6 |
| Example 15 | Urethane compound 17 (100) | — | PAG-3 (30.2) | Q-2 (5.22) | PGMEA (2,000) EL (500) | 80 | 23 | 2.5 |
| Example 16 | Urethane compound 18 (100) | — | PAG-3 (30.2) | Q-2 (5.22) | PGMEA (2,000) EL (500) | 80 | 26 | 2.4 |
| Example 17 | Urethane compound 19 (100) | — | PAG-3 (30.2) | Q-2 (5.22) | PGMEA (2,000) EL (500) | 80 | 25 | 2.5 |
| Example 18 | Urethane compound 20 (100) | — | PAG-3 (30.2) | Q-2 (5.22) | PGMEA (2,000) EL (500) | 80 | 23 | 2.6 |
| Example 19 | Urethane compound 21 (100) | — | PAG-3 (30.2) | Q-2 (5.22) | PGMEA (2,000) EL (500) | 75 | 27 | 2.4 |
| Example 20 | Urethane compound 22 (100) | — | PAG-3 (30.2) | Q-2 (5.22) | PGMEA (2,000) EL (500) | 75 | 26 | 2.5 |
| Example 21 | Urethane compound 23 (100) | — | PAG-3 (30.2) | Q-2 (5.22) | PGMEA (2,000) EL (500) | 75 | 24 | 2.6 |
| Example 22 | Urethane compound 24 (100) | — | PAG-3 (30.2) | Q-2 (5.22) | PGMEA (2,000) EL (500) | 75 | 25 | 2.5 |

TABLE 2

| | Compound (parts by mass) | Polymer (parts by mass) | Acid generator (parts by mass) | Quencher (parts by mass) | Organic solvent (parts by mass) | PEB temperature (° C.) | Sensitivity (mJ/cm$^2$) | CDU (nm) |
|---|---|---|---|---|---|---|---|---|
| Example 23 | Urethane compound 25 (100) | — | PAG-3 (30.2) | Q-2 (5.22) | PGMEA (2,000) EL (500) | 75 | 26 | 2.4 |
| Example 24 | Urethane compound 26 (100) | — | — | — | PGMEA (2,000) EL (500) | — | 78 | 2.0 |
| Example 25 | Urethane compound 27 (100) | — | — | — | PGMEA (2,000) EL (500) | — | 72 | 1.9 |
| Example 26 | Urethane compound 28 (100) | — | — | — | PGMEA (2,000) EL (500) | — | 68 | 2.4 |
| Example 27 | Urethane compound 29 (100) | — | PAG-3 (30.2) | Q-2 (5.22) | PGMEA (2,000) EL (500) | 70 | 33 | 2.6 |
| Comparative Example 1 | Polymer 1 (100) | — | PAG-1 (25.7) | Q-1 (9.70) | PGMEA (2,500) | 80 | 31 | 3.1 |

From the results of Tables 1 and 2, the inventive positive resist material had high sensitivity and excellent CDU, the inventive positive resist material containing a compound having two or more urethane groups and having two or more carboxy groups that are each substituted with an acid-labile group and are bonded to the urethane groups via a linking group.

The present description includes the following embodiments.

[1]: A positive resist material comprising a compound having two or more urethane groups and having two or more carboxy groups that are each substituted with an acid-labile group and are bonded to the urethane groups via a linking group.

[2]: The positive resist material of the above [1], wherein the compound is represented by the following formula (1), (1)

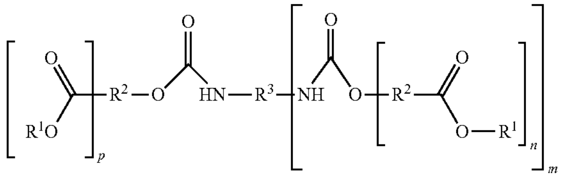

wherein $R^1$'s are identical to or different from each other and each represent an acid-labile group; $R^2$'s each represent a linking group, are identical to or different from each other, and represent a hydrocarbylene group having 1 to 20 carbon atoms, having a valency of n+1 or p+1, and optionally containing an oxygen atom, a sulfur atom, a nitrogen atom, or a halogen atom; $R^3$ represents a hydrocarbylene group having 2 to 33 carbon atoms, having a valency of m+1, and optionally containing an oxygen atom, a sulfur atom, a nitrogen atom, or a halogen atom; "m" represents an integer satisfying 1≤m≤6; and "n" and "p" represent 1 or 2.

[3]: The positive resist material of the above [2], wherein the $R^1$ satisfies one of the following 1) to 3):

1) a carbon atom bonded to an ester group is a tertiary carbon atom, and an alkyl group bonded to the tertiary carbon atom does not contain a halogen atom, a cyano group, or a nitro group;
2) a carbon atom bonded to an ester group is a secondary carbon atom and has a cyclic structure, does not contain a heteroatom, and has a double bond, a triple bond, or an aromatic group on a carbon atom other than the secondary carbon atom bonded to the ester group;
3) an acetal group having an ether group adjacent to a carbon atom bonded to an ester group.

[4]: The positive resist material of any one of the above [1] to [3], further comprising a base polymer.

[5]: The positive resist material of the above [4], wherein the base polymer comprises: a repeating unit having an acid-labile group substituting a hydrogen atom of a carboxy group; and/or a repeating unit having an acid-labile group substituting a hydrogen atom of a phenolic hydroxy group.

[6]: The positive resist material of the above [5], wherein the repeating unit having an acid-labile group substituting a hydrogen atom of a carboxy group and the repeating unit having an acid-labile group substituting a hydrogen atom of a phenolic hydroxy group are respectively a repeating unit represented by the following formula (a1) and a repeating unit represented by the following formula (a2), (a1)

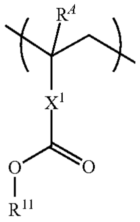

(a2)

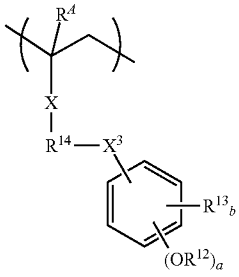

wherein each $R^A$ independently represents a hydrogen atom or a methyl group; $X^1$ represents a single bond or a linking group having 1 to 14 carbon atoms and containing a phenylene group, a naphthylene group, an ester bond, an ether bond, or a lactone ring; $X^2$ represents a single bond, an ester bond, or an amide bond; $X^3$ represents a single bond, an ether bond, or an ester bond; $R^{11}$ and $R^{12}$ represent an acid-labile group; $R^{13}$ represents a fluorine atom, a trifluoromethyl group, a cyano group, or a saturated hydrocarbyl group having 1 to 6 carbon atoms; $R^{14}$ represents a single bond or a saturated hydrocarbylene group having 1 to 6 carbon atoms, part of the carbon atoms optionally being substituted with an ether bond or an ester bond; and "a" represents 1 or 2 and "b" represents an integer of 0 to 4, provided that 1≤a+b≤5.

[7]: The positive resist material of any one of the above [4] to [6], wherein the base polymer further comprises a repeating unit-b having an adhesive group selected from a hydroxy group, a carboxy group, a lactone ring, a carbonate group, a thiocarbonate group, a carbonyl group, a cyclic acetal group, an ether bond, an ester bond, a sulfonic acid ester bond, a cyano group, an amide bond, —O—C(═O)—S—, and —O—C(═O)—NH—.

[8]: The positive resist material of any one of the above [4] to [7], wherein the base polymer further comprises a repeating unit-c represented by one or more of the following formulae (c1) to (c3), (c1)

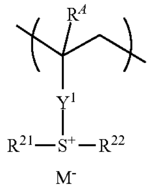

(c2)

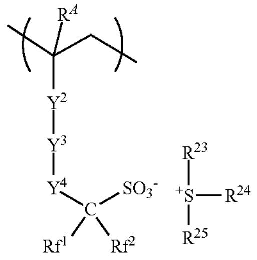

(c3)

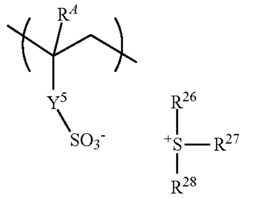

wherein each $R^A$ independently represents a hydrogen atom or a methyl group; $Y^1$ represents a single bond, a phenylene group, a naphthylene group, —O—$Y^{11}$—, —C(═O)—O—$Y^{11}$—, or —C(═O)—NH—$Y^{11}$—; $Y^{11}$ represents an aliphatic hydrocarbylene group having 1 to 6 carbon atoms, a phenylene group, a naphthylene group, or a group having 7 to 18 carbon atoms derived from a combination of these groups, $Y^{11}$ optionally containing a carbonyl group, an ester bond, an ether bond, or a hydroxy group; $Y^2$ represents a single bond or an ester bond; $Y^3$ represents a single bond, —$Y^{31}$—C(═O)—O—, —$Y^{31}$—O—, or —$Y^{31}$—O—C(═O)—; $Y^{31}$ represents a hydrocarbylene group having 1 to 12 carbon atoms, a phenylene group, or a group having 7 to 18 carbon atoms derived from a combination of these groups, $Y^{31}$ optionally containing a carbonyl group, an ester bond, an ether bond, an iodine atom, or a bromine atom; $Y^4$ represents a single bond, a methylene group, or a 2,2,2-trifluoro-1,1-ethanediyl group; $Y^5$ represents a single bond, a methylene group, an ethylene group, a phenylene group, a fluorinated phenylene group, —O—$Y^{51}$—, —C(═O)—O—$Y^{51}$—, or —C(═O)—NH—$Y^{51}$—; $Y^{51}$ represents an aliphatic hydrocarbylene group having 1 to 6 carbon atoms, a phenylene group, or a group having 7 to 18 carbon atoms derived from a combination of these groups, $Y^{51}$ optionally containing a carbonyl group, an ester bond, an ether bond, or a hydroxy group; $Rf^1$ and $Rf^2$ each independently represent a hydrogen atom, a fluorine atom, or a trifluoromethyl group, provided that at least one of $Rf^1$ and $Rf^2$ is a fluorine atom; $R^{21}$ to $R^{28}$ each independently represent a hydrocarbyl group having 1 to 20 carbon atoms and optionally containing a fluorine atom, a chlorine atom, a bromine atom, an iodine atom, or a heteroatom; $R^{23}$ and $R^{24}$ or $R^{26}$ and $R^{27}$ are optionally bonded with each other to form a ring together with a sulfur atom bonded to $R^{23}$ and $R^{24}$ or $R^{26}$ and $R^{27}$; and $M^-$ represents a non-nucleophilic counter ion.

[9]: The positive resist material of any one of the above [1] to [8], further comprising an acid generator.

[10]: The positive resist material of any one of the above [1] to [9], further comprising an organic solvent.

[11]: The positive resist material of any one of the above [1] to [10], further comprising a quencher.

[12]: The positive resist material of any one of the above [1] to [11], further comprising a surfactant.

[13]: A patterning process comprising the steps of:

forming a resist film on a substrate by using the positive resist material of any one of the above [1] to [12];

exposing the resist film to a high-energy beam; and developing the exposed resist film by using a developer.

[14]: The patterning process of the above [13], wherein the high-energy beam is an i-line beam, a KrF excimer laser beam, an ArF excimer laser beam, an electron beam, or an extreme ultraviolet ray having a wavelength of 3 to 15 nm.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A positive resist material comprising a compound having two or more urethane groups and having two or more carboxy groups that are each substituted with an acid-labile group and are bonded to the urethane groups via a linking group.

2. The positive resist material according to claim 1, wherein the compound is represented by the following formula (1), (1)

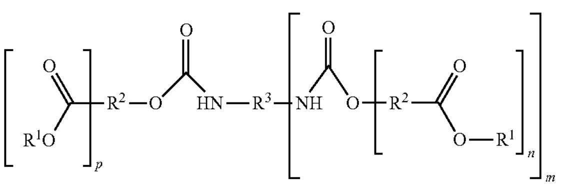

wherein $R^1$'s are identical to or different from each other and each represent an acid-labile group; $R^2$'s each represent a linking group, are identical to or different from each other, and represent a hydrocarbylene group having 1 to 20 carbon atoms, having a valency of n+1 or p+1, and optionally containing an oxygen atom, a sulfur atom, a nitrogen atom, or a halogen atom; $R^3$ represents a hydrocarbylene group having 2 to 33 carbon atoms, having a valency of m+1, and optionally containing an oxygen atom, a sulfur atom, a nitrogen atom, or a halogen atom; "m" represents an integer satisfying $1 \leq m \leq 6$; and "n" and "p" represent 1 or 2.

3. The positive resist material according to claim 2, wherein the $R^1$ satisfies one of the following 1) to 3):

1) a carbon atom bonded to an ester group is a tertiary carbon atom, and an alkyl group bonded to the tertiary carbon atom does not contain a halogen atom, a cyano group, or a nitro group;
2) a carbon atom bonded to an ester group is a secondary carbon atom and has a cyclic structure, does not contain a heteroatom, and has a double bond, a triple bond, or an aromatic group on a carbon atom other than the secondary carbon atom bonded to the ester group;
3) an acetal group having an ether group adjacent to a carbon atom bonded to an ester group.

4. The positive resist material according to claim 1, further comprising a base polymer.

5. The positive resist material according to claim 4, wherein the base polymer comprises: a repeating unit having an acid-labile group substituting a hydrogen atom of a carboxy group; and/or a repeating unit having an acid-labile group substituting a hydrogen atom of a phenolic hydroxy group.

6. The positive resist material according to claim 5, wherein the repeating unit having an acid-labile group substituting a hydrogen atom of a carboxy group and the repeating unit having an acid-labile group substituting a hydrogen atom of a phenolic hydroxy group are respectively a repeating unit represented by the following formula (a1) and a repeating unit represented by the following formula (a2), (a1)

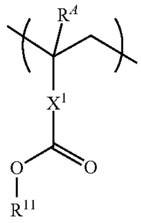

(a2)

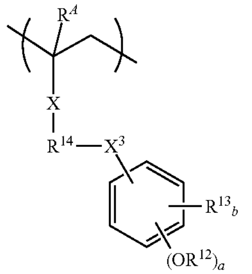

wherein each $R^A$ independently represents a hydrogen atom or a methyl group; $X^1$ represents a single bond or a linking group having 1 to 14 carbon atoms and containing a phenylene group, a naphthylene group, an ester bond, an ether bond, or a lactone ring; $X^2$ represents a single bond, an ester bond, or an amide bond; $X^3$ represents a single bond, an ether bond, or an ester bond; $R^{11}$ and $R^{12}$ represent an acid-labile group; $R^{13}$ represents a fluorine atom, a trifluoromethyl group, a cyano group, or a saturated hydrocarbyl group having 1 to 6 carbon atoms; $R^{14}$ represents a single bond or a saturated hydrocarbylene group having 1 to 6 carbon atoms, part of the carbon atoms optionally being substituted with an ether bond or an ester bond; and "a" represents 1 or 2 and "b" represents an integer of 0 to 4, provided that 1≤a+b≤5.

7. The positive resist material according to claim 4, wherein the base polymer further comprises a repeating unit-b having an adhesive group selected from a hydroxy group, a carboxy group, a lactone ring, a carbonate group, a thiocarbonate group, a carbonyl group, a cyclic acetal group, an ether bond, an ester bond, a sulfonic acid ester bond, a cyano group, an amide bond, —O—C(=O)—S—, and —O—C(=O)—NH—.

8. The positive resist material according to claim 4, wherein the base polymer further comprises a repeating unit-c represented by one or more of the following formulae (c1) to (c3), (c1)

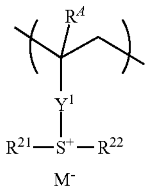

(c2)

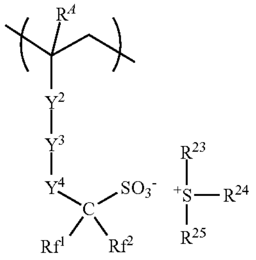

(c3)

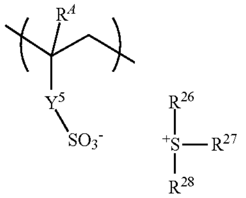

wherein each $R^A$ independently represents a hydrogen atom or a methyl group; $Y^1$ represents a single bond, a phenylene group, a naphthylene group, —O—$Y^{11}$—, —C(=O)—O—$Y^{11}$—, or —C(=O)—NH—$Y^{11}$—; $Y^{11}$ represents an aliphatic hydrocarbylene group having 1 to 6 carbon atoms, a phenylene group, a naphthylene group, or a group having 7 to 18 carbon atoms derived from a combination of these groups, $Y^{11}$ optionally containing a carbonyl group, an ester bond, an ether bond, or a hydroxy group; $Y^2$ represents a single bond or an ester bond; $Y^3$ represents a single bond, —$Y^{31}$—C(=O)—O—, —$Y^{31}$—O—, or —$Y^{31}$—O—C(=O)—; $Y^{31}$ represents a hydrocarbylene group having 1 to 12 carbon atoms, a phenylene group, or a group having 7 to 18 carbon atoms derived from a combination of these groups, $Y^{31}$ optionally containing a carbonyl group, an ester bond, an ether bond, an iodine atom, or a bromine atom; $Y^4$ represents a single bond, a methylene group, or a 2,2,2-trifluoro-1,1-ethanediyl group; $Y^5$ represents a single bond, a methylene group, an ethylene group, a phenylene group, a fluorinated phenylene group, —O—$Y^{51}$—, —C(=O)—O—$Y^{51}$—, or —C(=O)—NH—$Y^{51}$—; $Y^{51}$ represents an aliphatic hydrocarbylene group having 1 to 6 carbon atoms, a phenylene group, or a group having 7 to 18 carbon atoms derived from a combination of these groups, $Y^{51}$ optionally containing a carbonyl group, an ester bond, an ether bond, or a hydroxy group; $Rf^1$ and $Rf^2$ each independently represent a hydrogen atom, a fluorine atom, or a trifluoromethyl group, provided that at least one of $Rf^1$ and $Rf^2$ is a fluorine atom; $R^{21}$ to $R^{28}$ each independently represent a hydrocarbyl group having 1 to 20 carbon atoms and optionally containing a fluorine atom, a chlorine atom, a bromine atom, an iodine atom, or a heteroatom; $R^{23}$ and $R^{24}$ or $R^{26}$ and $R^{27}$ are optionally bonded with each other to form a ring together with a sulfur atom bonded to $R^{23}$ and $R^{24}$ or $R^{26}$ and $R^{27}$; and $M^-$ represents a non-nucleophilic counter ion.

9. The positive resist material according to claim 1, further comprising an acid generator.

10. The positive resist material according to claim 1, further comprising an organic solvent.

11. The positive resist material according to claim 1, further comprising a quencher.

12. The positive resist material according to claim 1, further comprising a surfactant.

13. A patterning process comprising the steps of:

forming a resist film on a substrate by using the positive resist material according to claim 1;

exposing the resist film to a high-energy beam; and developing the exposed resist film by using a developer.

14. The patterning process according to claim 13, wherein the high-energy beam is an i-line beam, a KrF excimer laser beam, an ArF excimer laser beam, an electron beam, or an extreme ultraviolet ray having a wavelength of 3 to 15 nm.

* * * * *